United States Patent
Chapdelaine et al.

(10) Patent No.: US 7,425,556 B2
(45) Date of Patent: Sep. 16, 2008

(54) COMPOUNDS AND USES THEREOF

(75) Inventors: Marc J. Chapdelaine, Wilmington, DE (US); Cyrus J. Ohnmacht, Wilmington, DE (US); Christopher Becker, West Chester, PA (US); Hui-Fang Chang, Wilmington, DE (US); Bruce T. Dembofsky, Wallingford, PA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/611,936

(22) Filed: Dec. 18, 2006

(65) Prior Publication Data

US 2007/0142328 A1 Jun. 21, 2007

Related U.S. Application Data

(60) Provisional application No. 60/823,693, filed on Aug. 28, 2006, provisional application No. 60/752,137, filed on Dec. 20, 2005.

(51) Int. Cl.
*A61K 31/502* (2006.01)
*A61K 31/498* (2006.01)
*C07D 237/28* (2006.01)
*A61P 25/22* (2006.01)

(52) U.S. Cl. .................................. 514/248; 544/235
(58) Field of Classification Search ................ 514/248; 544/235
See application file for complete search history.

(56) References Cited

U.S. PATENT DOCUMENTS

| | | | |
|---|---|---|---|
| 4,230,713 A | 10/1980 | Bare | |
| 4,511,568 A | 4/1985 | Bare et al. | |
| 4,546,104 A | 10/1985 | Campbell, Jr. et al. | |
| 4,552,883 A | 11/1985 | Bare | |
| 4,563,525 A | 1/1986 | Campbell, Jr. | |
| 4,645,838 A | 2/1987 | Bare et al. | |
| 4,705,793 A | 11/1987 | Resch | |
| 4,745,121 A | 5/1988 | Bare | |
| 4,886,800 A | 12/1989 | Resch | |
| 4,925,844 A | 5/1990 | Resch | |
| 4,975,435 A | 12/1990 | Campbell et al. | |
| 5,118,688 A | 6/1992 | Campbell | |
| 5,190,951 A | 3/1993 | Hasegawa et al. | |
| 5,240,934 A | 8/1993 | Hasegawa et al. | |
| 5,300,517 A | 4/1994 | Hasegawa et al. | |
| 5,646,153 A | 7/1997 | Spada et al. | |
| 5,756,804 A | 5/1998 | Haber et al. | |
| 5,801,263 A | 9/1998 | Seitz et al. | |
| 6,015,904 A | 1/2000 | Sworin et al. | |
| 6,057,320 A | 5/2000 | Spada et al. | |
| 6,140,265 A | 10/2000 | Haber et al. | |
| 6,362,216 B1 | 3/2002 | Burgess et al. | |
| 6,417,357 B1 | 7/2002 | Tinkl et al. | |
| 6,566,571 B1 | 5/2003 | Riermeier et al. | |
| 6,800,784 B1 | 10/2004 | Schlama et al. | |
| 6,984,756 B2 | 1/2006 | Gardner et al. | |
| 2004/0097485 A1 | 5/2004 | Burkitt et al. | |
| 2004/0102360 A1 | 5/2004 | Barnett et al. | |
| 2004/0167165 A1 | 8/2004 | Shankar et al. | |
| 2004/0186148 A1 | 9/2004 | Shankar et al. | |
| 2005/0113283 A1 | 5/2005 | Solow-Cordero et al. | |
| 2006/0264439 A1* | 11/2006 | Bearss et al. ............... | 514/248 |

FOREIGN PATENT DOCUMENTS

| | | |
|---|---|---|
| DE | 249011 A5 | 8/1987 |
| EP | 0328282 A2 | 8/1989 |
| EP | 0205272 B1 | 8/1991 |
| EP | 0987262 A1 | 3/2000 |
| EP | 0842145 B1 | 7/2000 |
| EP | 0842183 B1 | 10/2001 |
| EP | 1064243 B1 | 10/2002 |
| EP | 1171406 B1 | 4/2004 |
| EP | 1294683 B1 | 11/2005 |
| PL | 189894 * | 10/2005 |
| WO | 9216497 A1 | 10/1992 |
| WO | 9220642 A1 | 11/1992 |
| WO | 9515758 A1 | 6/1995 |
| WO | 9737989 A1 | 10/1997 |
| WO | 9946268 A1 | 9/1999 |
| WO | 0114377 A1 | 3/2001 |
| WO | 0118000 A1 | 3/2001 |
| WO | 0118001 A1 | 3/2001 |
| WO | 0138326 A2 | 5/2001 |
| WO | 0144244 A1 | 6/2001 |
| WO | 0144249 A1 | 6/2001 |
| WO | 0181318 A1 | 11/2001 |
| WO | 0190108 A1 | 11/2001 |

(Continued)

OTHER PUBLICATIONS

Haider, et al., Science of Synthesis (2004), 16, 251-313.*

(Continued)

*Primary Examiner*—Mark L. Berch
*Assistant Examiner*—Cecilia M Jaisle
(74) *Attorney, Agent, or Firm*—Jianzhong Shen

(57) ABSTRACT

This invention relates to novel compounds having the structural formula I below:

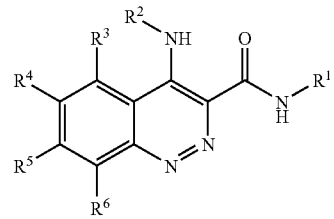

and their pharmaceutically acceptable salts, tautomers or in vivo-hydrolysable precursors, compositions and methods of use thereof. These novel compounds provide a treatment or prophylaxis of anxiety disorders, cognitive disorders, and/or mood disorders.

5 Claims, No Drawings

FOREIGN PATENT DOCUMENTS

| | | | |
|---|---|---|---|
| WO | 0200622 | A3 | 1/2002 |
| WO | 0210170 | A1 | 2/2002 |
| WO | 0238568 | A1 | 5/2002 |
| WO | 0238569 | A1 | 5/2002 |
| WO | 02090359 | A1 | 11/2002 |
| WO | 03003009 | A1 | 1/2003 |
| WO | 03006464 | A1 | 1/2003 |
| WO | 03016311 | A1 | 2/2003 |
| WO | 03018536 | A1 | 3/2003 |
| WO | 03018546 | A3 | 3/2003 |
| WO | 03024964 | A1 | 3/2003 |
| WO | 03024968 | A1 | 3/2003 |
| WO | 03062392 | A3 | 7/2003 |
| WO | 03086406 | A1 | 10/2003 |
| WO | 03093272 | A1 | 11/2003 |
| WO | 03093273 | A1 | 11/2003 |
| WO | 03099816 | A1 | 12/2003 |
| WO | 03099817 | A1 | 12/2003 |
| WO | 2004007025 | A1 | 1/2004 |
| WO | 2004014865 | A1 | 2/2004 |
| WO | 2004014891 | A1 | 2/2004 |
| WO | WO 2004016615 | * | 2/2004 |
| WO | 2004031161 | A1 | 4/2004 |
| WO | 2004039802 | A1 | 5/2004 |
| WO | 2004043930 | A1 | 5/2004 |
| WO | 2004065388 | A1 | 8/2004 |
| WO | 2004076452 | A1 | 9/2004 |
| WO | 2005024416 | A1 | 3/2005 |
| WO | 2005026148 | A1 | 3/2005 |
| WO | WO 2006124996 | * | 5/2005 |
| WO | 2005051302 | A3 | 6/2005 |
| WO | 2002063766 | A3 | 7/2005 |

OTHER PUBLICATIONS

Hipparagi, et al., Indian Journal of Heterocyclic Chemistry (2003), 13(2), 123-126.*
Purushothaman, et al., Indian Journal of Heterocyclic Chemistry (1999), 9(1), 43-46.*
Stanczak, et al., Pharmazie (1998), 53(3), 156-161.*
Stanczak, et al., Pharmazie (1997), 52(11), 838-843.*
Manohara, et al., Synthesis and Reactivity in Inorganic and Metal-Organic Chemistry (1997), 27(4), 589-599.*
Stanczak, et al., Pharmazie (1997), 52 (2), 91-97.*
Menon, et al., Indian Journal of Chemistry, Section B: Organic Chemistry Including Medicinal Chemistry (1996), 35B(11), 1185-1189.*
Stanczak, et al., Pharmazie (1994), 49(12), 884-9.*
Gewald, et al., Liebigs Annalen der Chemie (1984), (7), 1390-4.*
Patel, J.B. et al., "A Novel Potent Non-Benzodiazepine Anxioselective Agent with Reduced Dependence Liability: ICI 198,256", Progress in Clinical and Biological Research, 1990, vol. 361, pp. 483-488.
Non-Final Office Action issued for U.S. Appl. No. 11/611,943 on Nov. 14, 2007; AstraZeneca Ref.
Non-final Office Action issued for U.S. Appl. No. 11/611,943 on Mar. 19, 2008; AZ Ref.

* cited by examiner

COMPOUNDS AND USES THEREOF

The present application claims the benefit of U.S. Provisional Applications 60/752,137, filed Dec. 20, 2005 and 60/823,693, filed Aug. 28, 2006 under 35 U.S.C. § 119(e), the entireties of which are incorporated herein by reference.

FIELD OF THE INVENTION

The present invention relates to novel cinnoline compounds, their pharmaceutical compositions, methods of use and processes to make such compounds. In addition, the present invention relates to therapeutic methods for the treatment and/or prevention of anxiety disorders, cognitive disorders, and/or mood disorders.

BACKGROUND OF THE INVENTION

The present invention comprises, inter alia, cinnoline compounds, their use as central nervous system (CNS) depressants (especially anxiolytics), and pharmacological tools, methods for their preparation, pharmaceutical compositions containing the same, and intermediates used in their preparation.

Some cinnoline compounds including selected 4-amino- and 4-oxo-cinnoline-3-carboxamides are disclosed in East German Patent 123525 (Verfahren zur Herstellung von substituierten 4-Aminocinnolinen); U.S. Pat. No. 4,379,929 to Conrad et al; U.S. Pat. Nos. 4,886,800 and 4,925,844 to Resch; Daunis et al., "Preparation et proprietes de cinnolones-3 et cinnolones-4," Bull. de la Societe Chimique de France, 8:3198-3202 (1972); Lunt et al. "A New Cinnoline Synthesis," J. Chem. Soc. (C), 687-695 (1968); Gewald, et al., "Synthese von 4-Aminocinnolinen aus (Arylhydrazono) (cyan)-essigsaurederivaten," Liebigs Ann. Chem., 1390-1394 (1984); and U.S. Pat. No. 3,657,241 to Kurihara. Additionally, selected cinnoline compounds, including 3-acyl-4-substituted cinnoline derivatives are disclosed in Liebigs Ann. Chem. 1390-1394 (1984) supra and Sandison, et al., "A New Heterocyclisation Reaction Leading to Cinnolin-4(1H)-one Derivatives," J. Chem. Soc. Chem. Comm., 752-753 (1974). Additionally, cinnoline compounds are also disclosed in EP205272 and EP328282. However, none of the foregoing discloses or suggests the novel compounds of the present invention or suggests their use as CNS depressants.

gamma-Aminobutyric acid (GABA) is a common inhibitory neurotransmitter in the mammalian brain and is estimated to be present at about one third of all synapses. When GABA binds to a GABA receptor, it affects the ability of neurons expressing the receptors to conduct neural impulses. In the adult mammalian nervous system, GABA typically inhibits neuron firing (depolarization). Neurons in the brain express three main types of GABA receptors: GABA type A receptors (GABAA), GABA type B receptors (GABAB), and GABA type C receptors (GABAC). GABAA receptors function as ligand-gated ion channels to mediate fast inhibitory synaptic transmissions that regulate neuronal excitability involved in such responses as seizure threshold, skeletal muscle tone, and emotional status. GABAA receptors are targets of many sedating drugs, such as benzodiazepines, barbiturates and neurosteroids.

The intrinsic inhibitory signal of GABA is transduced principally by GABAA receptors. GABAA receptors are pentameric, ligand-gated chloride ion ($Cl^-$) channels belonging to a superfamily of ligand-gated ionotropic receptors that includes the nicotinic acetylcholine receptor. GABAA receptors are very heterogeneous, with at least 16 different subunits producing potentially thousands of different receptor types.

GABAA receptor subunits aggregate into complexes that form chloride ion selective channels and contain sites that bind GABA along with a variety of pharmacologically active substances. When GABA binds to this receptor, the anion channel is activated, causing it to open and allowing chloride ions ($Cl^-$) to enter the neuron. This influx of $Cl^-$ ions hyperpolarizes the neuron, making it less excitable. The resultant decrease in neuronal activity following activation of the GABAA receptor complex can rapidly alter brain function, to such an extent that consciousness and motor control may be impaired.

The numerous possible combinations of GABAA receptor subunits and the widespread distribution of these receptors in the nervous system likely contributes to the diverse and variable physiological functions of GABAA receptors, which have been implicated in many neurological and psychiatric disorders, and related conditions, including: stroke, head trauma, epilepsy, pain, migraine, mood disorders, anxiety, post traumatic stress disorder, obsessive compulsive disorders, schizophrenia, seizures, convulsions, tinnitus, neurodegenerative disorders including Alzheimer's disease, amyotrophic lateral sclerosis, Huntington's Chorea, Parkinson's disease, depression, bipolar disorders, mania, trigeminal and other neuralgia, neuropathic pain, hypertension, cerebral ischemia, cardiac arrhythmia, myotonia, substance abuse, myoclonus, essential tremor, dyskinesia and other movement disorders, neonatal cerebral hemorrhage, and spasticity. GABAA receptors are also believed to play a role in cognition, consciousness, and sleep.

Currently available drugs for modulating GABAA receptor activity include barbiturates, such as pentobarbital and secobarbital, and benzodiazepines such as diazepam, chlordiazepoxide and midazolam. Barbiturates can directly activate GABAA receptors, significantly increasing $Cl^-$ currents in the absence of further intervention by GABA itself and can also indirectly augment GABAergic neural transmission. In contrast, benzodiazepines act as indirect allosteric modulators, and are largely incapable of increasing $Cl^-$ currents in the absence of GABA, but enhance GABA-activated increases in $Cl^-$ conductance. This latter property is thought to be responsible for the usefulness of benzodiazepines for treating a number of disorders, including generalized anxiety disorder, panic disorder, seizures, movement disorders, epilepsy, psychosis, mood disorders, and muscle spasms, as well as the relative safety of benzodiazepines compared to barbiturates.

Both barbiturates and benzodiazepines are addictive and can cause drowsiness, poor concentration, ataxia, dysarthria, motor incoordination, diplopia, muscle weakness, vertigo and mental confusion. These side effects can interfere with an individual's ability to perform daily routines such as driving, operating heavy machinery or performing other complex motor tasks while under therapy, making barbiturates and benzodiazepines less than optimal for treating chronic disorders involving GABA and GABAA receptors.

GABAA receptors and GABAergic neural transmissions are implicated as targets for therapeutic intervention in a myriad of neurological and psychiatric disorders. Adverse side effects, including addictive properties exhibited by currently available GABA and GABAA receptor modulating drugs, make these drugs unsuitable in many therapeutic contexts. Accordingly, there remains an important, unmet need in the art for alternative compositions, methods and tools that will be useful in broad clinical applications to modulate the function and activity of GABA and GABA receptors in mammalian subjects, including humans, and/or to target GABAergic neural transmission. The present invention is also, inter alia, directed toward this end.

DESCRIPTION OF EMBODIMENTS

Provided herein are novel compounds of structural formula I:

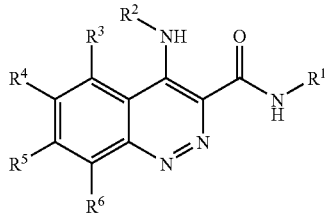

or a pharmaceutically acceptable salt, tautomer, atropisomer, or in vivo-hydrolysable precursor thereof, wherein:

$R^1$ is $C_{1-6}$ alkyl, $C_{1-6}$ haloalkyl, aryl, heteroaryl, cycloalkyl, heterocycloalkyl, arylalkyl, heteroarylalkyl, cycloalkylalkyl or heterocycloalkylalkyl, each optionally substituted by 1, 2, 3, 4 or 5 $R^7$;

$R^2$ is H, $C(=O)R^b$, $C(=O)NR^cR^d$, $C(=O)OR^a$, $S(=O)_2R^b$, $C_{1-6}$ alkyl, $C_{1-6}$ haloalkyl, aryl, heteroaryl, cycloalkyl, heterocycloalkyl, arylalkyl, heteroarylalkyl, cycloalkylalkyl or heterocycloalkylalkyl, wherein each of the $C_{1-6}$ alkyl, aryl, heteroaryl, cycloalkyl, heterocycloalkyl, arylalkyl, heteroarylalkyl, cycloalkylalkyl or heterocycloalkylalkyl is optionally substituted by 1, 2, 3, 4 or 5 $R^8$;

$R^3$, $R^4$ and $R^5$ are each, independently, H, halo, $Si(C_{1-10}$ alkyl)$_3$, CN, $NO_2$, $OR^a$, $SR^a$, $OC(=O)R^a$, $OC(=O)OR^b$, $OC(=O)NR^cR^d$, $C(=O)R^a$, $C(=O)OR^b$, $C(=O)NR^cR^d$, $NR^cR^d$, $NR^cC(=O)R^a$, $NR^cC(=O)OR^b$, $NR^cS(=O)_2R^b$, $S(=O)R^a$, $S(=O)NR^cR^d$, $S(=O)_2R^a$, $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2 or 3 $R^9$;

$R^6$ is aryl, cycloalkyl, heteroaryl or heterocycloalkyl, each optionally substituted by 1, 2, 3, 4 or 5 $A^1$;

$R^7$, $R^8$ and $R^9$ are each, independently, halo, $C_{1-4}$ alkyl, $C_{1-4}$ haloalkyl, aryl, cycloalkyl, heteroaryl, heterocycloalkyl, CN, $NO_2$, $OR^{a'}$, $SR^{a'}$, $C(=O)R^{b'}$, $C(=O)NR^{c'}R^{d'}$, $C(=O)OR^{a'}$, $OC(=O)R^{b'}$, $OC(=O)NR^{c'}R^{d'}$, $NR^{c'}R^{d'}$, $NR^{c'}C(=O)R^{b'}$, $NR^{c'}C(=O)OR^{a'}$, $NR^{c'}S(=O)_2R^{b'}$, $S(=O)R^{b'}$, $S(=O)NR^{c'}R^{d'}$, $S(=O)_2R^{b'}$, or $S(=O)_2NR^{c'}R^{d'}$;

$A^1$ is halo, CN, $NO_2$, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^d$, $NR^cC(=O)OR^a$, $NR^cS(=O)R^b$, $NR^cS(=O)_2R^b$, $S(=O)R^b$, $S(=O)NR^cR^d$, $S(=O)_2R^b$, $S(=O)_2NR^cR^d$, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, arylalkyl, cycloalkylalkyl, heteroarylalkyl, heterocycloalkylalkyl, aryl, cycloalkyl, heteroaryl or heterocycloalkyl, wherein each of the $C_{1-6}$ alkyl, $C_{2-6}$ alkenyl, $C_{2-6}$ alkynyl, arylalkyl, cycloalkylalkyl, heteroarylalkyl, heterocycloalkylalkyl, aryl, cycloalkyl, heteroaryl or heterocycloalkyl is optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^{a'}$, $SR^{a'}$, $C(=O)R^{b'}$, $C(=O)NR^{c'}R^{d'}$, $C(=O)OR^{a'}$, $OC(=O)R^{b'}$, $OC(=O)NR^{c'}R^{d'}$, $NR^{c'}R^{d'}$, $NR^{c'}C(=O)R^{b'}$, $NR^{c'}C(=O)OR^{a'}$, $NR^{c'}S(=O)_2R^{b'}$, $S(=O)R^{b'}$, $S(=O)NR^{c'}R^{d'}$, $S(=O)_2R^{b'}$, or $S(=O)_2NR^{c'}R^{d'}$;

$R^a$ and $R^{a'}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

$R^b$ and $R^{b'}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

$R^c$ and $R^d$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein the $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, 6- or 7-membered heterocycloalkyl group; and $R^{c'}$ and $R^{d'}$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein the $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^{c'}$ and $R^{d'}$ together with the N atom to which they are attached form a 4-, 5-, 6- or 7-membered heterocycloalkyl group.

In some embodiments, when $R^2$, $R^3$, $R^4$ and $R^5$ are each H, then $R^6$ is other than unsubstituted phenyl or unsubstituted cycloalkyl.

In some embodiments, $R^1$ is $C_{1-6}$ alkyl, $C_{1-6}$ haloalkyl, arylalkyl, heteroarylalkyl, cycloalkylalkyl or heterocycloalkylalkyl, each optionally substituted by 1, 2, 3, 4 or 5 $R^7$.

In some embodiments, $R^1$ is $C_{1-6}$ alkyl, $C_{1-6}$ haloalkyl, arylalkyl, heteroarylalkyl, cycloalkylalkyl or heterocycloalkylalkyl, each optionally substituted by 1, 2, 3, 4 or 5 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, $SR^{a'}$, $C(=O)R^{b'}$, $C(=O)NR^{c'}R^{d'}$, $C(=O)OR^{a'}$, $OC(=O)R^{b'}$, $OC(=O)NR^{c'}R^{d'}$, $NR^{c'}C(=O)R^{b'}$, $NR^{c'}C(=O)OR^{a'}$, $NR^{c'}S(=O)_2R^{b'}$, $S(=O)R^{b'}$, $S(=O)NR^{c'}R^{d'}$, $S(=O)_2R^{b'}$, or $S(=O)_2NR^{c'}R^{d'}$.

In some embodiments, $R^1$ is $C_{1-6}$ alkyl, $C_{1-6}$ haloalkyl, arylalkyl, heteroarylalkyl, cycloalkylalkyl or heterocycloalkylalkyl, each optionally substituted by 1, 2, 3, 4 or 5 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, SH, —S—($C_{1-4}$ alkyl), C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl) and S(=O)$_2$NH(arylalkyl).

In some embodiments, $R^1$ is $C_{1-6}$ alkyl, $C_{1-6}$ haloalkyl, arylalkyl, heteroarylalkyl, cycloalkylalkyl or heterocycloalkylalkyl, each optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, SH, —S—($C_{1-4}$ alkyl), C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl) and S(=O)$_2$NH(arylalkyl).

In some embodiments, $R^1$ is $C_{1-6}$ alkyl, $C_{1-6}$ haloalkyl, arylalkyl, heteroarylalkyl, cycloalkylalkyl or heterocycloalkylalkyl, each optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)—($C_{1-4}$ alkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl) and S(=O)$_2$NH(arylalkyl).

In some embodiments, $R^1$ is $C_{1-6}$ alkyl, $C_{1-6}$ haloalkyl, arylalkyl, heteroarylalkyl, cycloalkylalkyl or heterocycloalkylalkyl.

In some embodiments, $R^1$ is $C_{1-6}$ alkyl or $C_{1-6}$ haloalkyl.

In some embodiments, $R^1$ is $C_{1-6}$ alkyl.

In some embodiments, $R^1$ is n-propyl.

In some embodiments, $R^2$ is H, C(=O)—($C_{1-4}$ alkyl), C(=O)-(arylalkyl), C(=O)O—($C_{1-4}$ alkyl), C(=O)O-(arylalkyl), C(=O)$NH_2$, C(=O)NH($C_{1-4}$ alkyl), C(=O)N($C_{1-4}$ alkyl)$_2$, $C_{1-6}$ alkyl, $C_{1-6}$ haloalkyl, arylalkyl, heteroarylalkyl, cycloalkylalkyl or heterocycloalkylalkyl, wherein each of the $C_{1-6}$ alkyl, arylalkyl, heteroarylalkyl, cycloalkylalkyl or heterocycloalkylalkyl is optionally substituted by 1, 2, 3, 4 or 5 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, SH, —S—($C_{1-4}$ alkyl), C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl) and S(=O)$_2$NH(arylalkyl).

In some embodiments, $R^2$ is H, C(=O)—($C_{1-4}$ alkyl), C(=O)-(arylalkyl), C(=O)O—($C_{1-4}$ alkyl), C(=O)O-(arylalkyl), C(=O)$NH_2$, C(=O)NH($C_{1-4}$ alkyl), C(=O)N($C_{1-4}$ alkyl)$_2$, $C_{1-6}$ alkyl, $C_{1-6}$ haloalkyl, arylalkyl, heteroarylalkyl, cycloalkylalkyl or heterocycloalkylalkyl, wherein each of the $C_{1-6}$ alkyl, arylalkyl, heteroarylalkyl, cycloalkylalkyl or heterocycloalkylalkyl is optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, SH, —S—($C_{1-4}$ alkyl), C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl) and S(=O)$_2$NH(arylalkyl).

In some embodiments, $R^2$ is H, C(=O)—($C_{1-4}$ alkyl), C(=O)-(arylalkyl), C(=O)O—($C_{1-4}$ alkyl), C(=O)O-(arylalkyl), C(=O)$NH_2$, C(=O)NH($C_{1-4}$ alkyl), C(=O)N($C_{1-4}$ alkyl)$_2$, $C_{1-6}$ alkyl, $C_{1-6}$ haloalkyl, arylalkyl, heteroarylalkyl, cycloalkylalkyl or heterocycloalkylalkyl.

In some embodiments, $R^2$ is H, C(=O)—($C_{1-4}$ alkyl), C(=O)-(arylalkyl), C(=O)O—($C_{1-4}$ alkyl), C(=O)O-(arylalkyl), C(=O)$NH_2$, C(=O)NH($C_{1-4}$ alkyl), C(=O)N($C_{1-4}$ alkyl)$_2$ or $C_{1-6}$ alkyl.

In some embodiments, $R^2$ is H, C(=O)—($C_{1-4}$ alkyl), C(=O)-(arylalkyl), C(=O)O—($C_{1-4}$ alkyl), C(=O)O-(arylalkyl), C(=O)$NH_2$, C(=O)NH($C_{1-4}$ alkyl), C(=O)N($C_{1-4}$ alkyl)$_2$, or $C_{1-3}$ alkyl.

In some embodiments, $R^2$ is H.

In some embodiments, $R^3$, $R^4$ and $R^5$ are each, independently, H, halo, CN, $NO_2$, $OR^a$, $SR^a$, OC(=O)$R^a$, OC(=O)$OR^b$, OC(=O)$NR^cR^d$, C(=O)$R^a$, C(=O)$OR^b$, C(=O)$NR^cR^d$, $NR^cR^d$, $NR^cC(=O)R^a$, $NR^cC(=O)OR^b$, $NR^cS(=O)_2R^b$, S(=O)$R^a$, S(=O)$NR^cR^d$, S(=O)$_2R^a$, S(=O)$_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, SH, —S—($C_{1-4}$ alkyl), C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS $(=O)_2$—$(C_{1-4}$ alkyl), $NHS(=O)_2$-(arylalkyl), $S(=O)_2$—$(C_{1-4}$ alkyl), $S(=O)_2$-(arylalkyl), $S(=O)_2NH(C_{1-4}$ alkyl) and $S(=O)_2NH$(arylalkyl).

In some embodiments, $R^3$, $R^4$ and $R^5$ are each, independently, H, halo, CN, $NO_2$, OH, $C_{1-4}$ alkoxy, $C_{1-4}$ haloalkoxy, amino, $C_{1-4}$ alkylamino, $C_{2-8}$ dialkylamino, SH, —S—$(C_{1-4}$ alkyl), $C(=O)H$, $C(=O)$—$(C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)OH$, $C(=O)O$—$(C_{1-4}$ alkyl), $C(=O)O$-(arylalkyl), $OC(=O)H$, $OC(=O)$—$(C_{1-4}$ alkyl), $OC(=O)$-(arylalkyl), $OC(=O)NH_2$, $OC(=O)NH(C_{1-4}$ alkyl), $OC(=O)NH$-(arylalkyl), $OC(=O)N(C_{1-4}$ alkyl)$_2$, $NHC(=O)$—$(C_{1-4}$ alkyl), $NHC(=O)O$-(arylalkyl), $NHC(=O)O$—$(C_{1-4}$ alkyl), $NHC(=O)O$-(arylalkyl), $NHS(=O)_2$—$(C_{1-4}$ alkyl), $NHS(=O)_2$-(arylalkyl), $S(=O)_2$—$(C_{1-4}$ alkyl), $S(=O)_2$-(arylalkyl), $S(=O)_2NH(C_{1-4}$ alkyl), $S(=O)_2NH$(arylalkyl), $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, SH, —S—$(C_{1-4}$ alkyl), $C(=O)H$, $C(=O)$—$(C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)OH$, $C(=O)O$—$(C_{1-4}$ alkyl), $C(=O)O$-(arylalkyl), $OC(=O)H$, $OC(=O)$—$(C_{1-4}$ alkyl), $OC(=O)$-(arylalkyl), $OC(=O)NH_2$, $OC(=O)NH(C_{1-4}$ alkyl), $OC(=O)NH$-(arylalkyl), $OC(=O)N(C_{1-4}$ alkyl)$_2$, $NHC(=O)$—$(C_{1-4}$ alkyl), $NHC(=O)O$-(arylalkyl), $NHC(=O)O$—$(C_{1-4}$ alkyl), $NHC(=O)O$-(arylalkyl), $NHS(=O)_2$—$(C_{1-4}$ alkyl), $NHS(=O)_2$-(arylalkyl), $S(=O)_2$—$(C_{1-4}$ alkyl), $S(=O)_2$-(arylalkyl), $S(=O)_2NH(C_{1-4}$ alkyl) and $S(=O)_2NH$(arylalkyl).

In some embodiments, $R^3$, $R^4$ and $R^5$ are each, independently, H, halo, CN, $NO_2$, OH, $C_{1-4}$ alkoxy, $C_{1-4}$ haloalkoxy, amino, $C_{1-4}$ alkylamino, $C_{2-8}$ dialkylamino, $C(=O)H$, $C(=O)$—$(C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)OH$, $C(=O)O$—$(C_{1-4}$ alkyl), $C(=O)O$-(arylalkyl), $OC(=O)H$, $OC(=O)$—$(C_{1-4}$ alkyl), $NHC(=O)$—$(C_{1-4}$ alkyl), $NHC(=O)O$-(arylalkyl), $NHC(=O)O$—$(C_{1-4}$ alkyl), $NHC(=O)O$-(arylalkyl), $NHS(=O)_2$—$(C_{1-4}$ alkyl), $NHS(=O)_2$-(arylalkyl), $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, $C(=O)H$, $C(=O)$—$(C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)OH$, $C(=O)O$—$(C_{1-4}$ alkyl), $C(=O)O$-(arylalkyl), $OC(=O)H$, $OC(=O)$—$(C_{1-4}$ alkyl), $OC(=O)$-(arylalkyl), $OC(=O)NH_2$, $OC(=O)NH(C_{1-4}$ alkyl), $OC(=O)NH$-(arylalkyl), $OC(=O)N(C_{1-4}$ alkyl)$_2$, $NHC(=O)$—$(C_{1-4}$ alkyl), $NHC(=O)O$-(arylalkyl), $NHC(=O)O$—$(C_{1-4}$ alkyl), $NHC(=O)O$-(arylalkyl), $NHS(=O)_2$—$(C_{1-4}$ alkyl), $NHS(=O)_2$-(arylalkyl), $S(=O)_2$—$(C_{1-4}$ alkyl), $S(=O)_2$-(arylalkyl), $S(=O)_2NH(C_{1-4}$ alkyl) and $S(=O)_2NH$(arylalkyl).

In some embodiments, $R_3$, $R^4$ and $R^5$ are each, independently, H, $C_{1-4}$ alkoxy, halo, $C_{1-6}$ alkyl or $C_{1-6}$ haloalkyl.

In some embodiments, $R^3$, $R^4$ and $R^5$ are each, independently, H, $C_{1-4}$ alkoxy, halo or $C_{1-3}$ haloalkyl.

In some embodiments, $R^3$, $R^4$ and $R^5$ are each, independently, H, $C_{1-4}$ alkoxy, or halo.

In some embodiments, $R^6$ is aryl or heteroaryl, each optionally substituted by 1, 2, 3, 4 or 5 $A^1$.

In some embodiments, $R^6$ is aryl optionally substituted by 1, 2, 3, 4 or 5 $A^1$.

In some embodiments, $R^6$ is aryl substituted by 1, 2, 3, 4 or 5 $A^1$.

In some embodiments, $R^6$ is heteroaryl optionally substituted by 1, 2, 3, 4 or 5 $A^1$.

In some embodiments, $R^6$ is phenyl, naphthyl, pyridyl, pyrimidinyl, pyrazinyl, pyrazolyl, quinolyl or indolyl, each optionally substituted by 1, 2, 3, 4 or 5 $A^1$.

In some embodiments, $R^6$ is phenyl, 2-naphthyl, 3-pyridyl, 4-pyridyl, pyrimidin-5-yl, pyrazin-2-yl, pyrazol-3-yl, pyrazol-4-yl, 3-quinolyl, 6-quinolyl, or indol-5-yl, each optionally substituted by 1, 2, 3, 4 or 5 $A^1$.

In some embodiments, $R^6$ is phenyl, naphthyl, pyridyl, pyrimidinyl, pyrazinyl, pyrazolyl, quinolyl or indolyl, each optionally substituted by 1, 2, 3, 4 or 5 halo, CN, $NO_2$, OH, $C_{1-4}$ alkoxy, $C_{1-4}$ haloalkoxy, amino, $C_{1-4}$ alkylamino, $C_{2-8}$ dialkylamino, $NR^cR^d$, SH, —S—$(C_{1-4}$ alkyl), $C(=O)H$, $C(=O)$—$(C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)NR^cR^d$, $C(=O)OH$, $C(=O)O$—$(C_{1-4}$ alkyl), $C(=O)O$-(arylalkyl), $OC(=O)H$, $OC(=O)$—$(C_{1-4}$ alkyl), $OC(=O)$-(arylalkyl), $OC(=O)NH_2$, $OC(=O)NH(C_{1-4}$ alkyl), $OC(=O)NH$-(arylalkyl), $OC(=O)N(C_{1-4}$ alkyl)$_2$, $NHC(=O)$—$(C_{1-4}$ alkyl), $NHC(=O)O$-(arylalkyl), $NHC(=O)O$—$(C_{1-4}$ alkyl), $NHC(=O)O$-(arylalkyl), $NHS(=O)_2$—$(C_{1-4}$ alkyl), $NHS(=O)_2$-(arylalkyl), $S(=O)_2$—$(C_{1-4}$ alkyl), $S(=O)_2$-(arylalkyl), $S(=O)_2NH(C_{1-4}$ alkyl), $S(=O)_2NH$(arylalkyl), $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, $R^{c'}R^{d'}$, SH, —S—$(C_{1-4}$ alkyl), $C(=O)H$, $C(=O)$—$(C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)R^{c'}R^{d'}$, $C(=O)OH$, $C(=O)O$—$(C_{1-4}$ alkyl), $C(=O)O$-(arylalkyl), $OC(=O)H$, $OC(=O)$—$(C_{1-4}$ alkyl), $OC(=O)$-(arylalkyl), $OC(=O)NH_2$, $OC(=O)NH(C_{1-4}$ alkyl), $OC(=O)NH$-(arylalkyl), $OC(=O)N(C_{1-4}$ alkyl)$_2$, $NHC(=O)$—$(C_{1-4}$ alkyl), $NHC(=O)O$-(arylalkyl), $NHC(=O)O$—$(C_{1-4}$ alkyl), $NHC(=O)O$-(arylalkyl), $NHS(=O)_2$—$(C_{1-4}$ alkyl), $NHS(=O)_2$-(arylalkyl), $S(=O)_2$—$(C_{1-4}$ alkyl), $S(=O)_2$-(arylalkyl), $S(=O)_2NH(C_{1-4}$ alkyl), $S(=O)_2NH$(arylalkyl) and $S(=O)_2NR^{c'}R^{d'}$;

$R^c$ and $R^d$ together with the N atom to which they are attached form a 4-, 5-, 6- or 7-membered heterocycloalkyl group; and $R^{c'}$ and $R^{d'}$ together with the N atom to which they are attached form a 4-, 5-, 6- or 7-membered heterocycloalkyl group.

In some embodiments, $R^6$ is phenyl, naphthyl, pyridyl, pyrimidinyl, pyrazinyl, pyrazolyl, quinolyl or indolyl, each optionally substituted by 1, 2, 3, 4 or 5 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, $C(=O)H$, $C(=O)-(C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)NR^cR^d$, $C(=O)OH$, $C(=O)O-(C_{1-4}$ alkyl), $C(=O)O$-(arylalkyl), $OC(=O)H$, $OC(=O)-(C_{1-4}$ alkyl), $OC(=O)$-(arylalkyl), $OC(=O)NH_2$, $OC(=O)NH(C_{1-4}$ alkyl), $OC(=O)NH$-(arylalkyl), $OC(=O)N(C_{1-4}$ alkyl)$_2$, $NHC(=O)-(C_{1-4}$ alkyl), $NHC(=O)O$-(arylalkyl), $NHC(=O)O-(C_{1-4}$ alkyl), $NHC(=O)O$-(arylalkyl), $NHS(=O)_2-(C_{1-4}$ alkyl), $NHS(=O)_2$-(arylalkyl), $S(=O)_2-(C_{1-4}$ alkyl), $S(=O)_2$-(arylalkyl), $S(=O)_2NH(C_{1-4}$ alkyl), $S(=O)_2NH$(arylalkyl), $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl; and $R^c$ and $R^d$ together with the N atom to which they are attached form a 4-, 5-, 6- or 7-membered heterocycloalkyl group.

In some embodiments, $R^6$ is phenyl, naphthyl, pyridyl, pyrimidinyl, pyrazinyl, pyrazolyl, quinolyl or indolyl, each optionally substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, $C(=O)H$, $C(=O)-(C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)NR^cR^d$, $C(=O)OH$, $C(=O)O-(C_{1-4}$ alkyl), $C(=O)O$-(arylalkyl), $OC(=O)H$, $OC(=O)-(C_{1-4}$ alkyl), $OC(=O)$-(arylalkyl), $OC(=O)NH_2$, $OC(=O)NH(C_{1-4}$ alkyl), $OC(=O)NH$-(arylalkyl), $OC(=O)N(C_{1-4}$ alkyl)$_2$, $NHC(=O)-(C_{1-4}$ alkyl), $NHC(=O)O$-(arylalkyl), $NHC(=O)O-(C_{1-4}$ alkyl), $NHC(=O)O$-(arylalkyl), $NHS(=O)_2-(C_{1-4}$ alkyl), $NHS(=O)_2$-(arylalkyl), $S(=O)_2-(C_{1-4}$ alkyl), $S(=O)_2$-(arylalkyl), $S(=O)_2NH(C_{1-4}$ alkyl), $S(=O)_2NH$(arylalkyl), $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl; and $R^c$ and $R^d$ together with the N atom to which they are attached form a 4-, 5-, 6- or 7-membered heterocycloalkyl group.

In some embodiments, $R^6$ is phenyl, naphthyl, pyridyl, pyrimidinyl, pyrazinyl, pyrazolyl, quinolyl or indolyl, each optionally substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, $C(=O)H$, $C(=O)-(C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)NR^cR^d$, $C(=O)OH$, $C(=O)O-(C_{1-4}$ alkyl), $C(=O)O$-(arylalkyl), $S(=O)_2-(C_{1-4}$ alkyl), $S(=O)_2$-(arylalkyl), $S(=O)_2NH(C_{1-4}$ alkyl), $S(=O)_2NH$(arylalkyl), $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl; and $R^c$ and $R^d$ together with the N atom to which they are attached form a 4-, 5-, 6- or 7-membered heterocycloalkyl group.

In some embodiments, $R^6$ is phenyl substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, $C(=O)H$, $C(=O)-(C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)NR^cR^d$, $C(=O)OH$, $C(=O)O-(C_{1-4}$ alkyl), $C(=O)O$-(arylalkyl), $S(=O)_2-(C_{1-4}$ alkyl), $S(=O)_2$-(arylalkyl), $S(=O)_2NH(C_{1-4}$ alkyl), $S(=O)_2NH$(arylalkyl), $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl; and $R^c$ and $R^d$ together with the N atom to which they are attached form a 4-, 5-, 6- or 7-membered heterocycloalkyl group.

In some embodiments, $R^6$ is naphthyl, pyridyl, pyrimidinyl, pyrazinyl, pyrazolyl, quinolyl or indolyl, each optionally substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, $C(=O)H$, $C(=O)-(C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)NR^cR^d$, $C(=O)OH$, $C(=O)O-(C_{1-4}$ alkyl), $C(=O)O$-(arylalkyl), $S(=O)_2-(C_{1-4}$ alkyl), $S(=O)_2$-(arylalkyl), $S(=O)_2NH(C_{1-4}$ alkyl), $S(=O)_2NH$(arylalkyl), $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl; and $R^c$ and $R^d$ together with the N atom to which they are attached form a 4-, 5-, 6- or 7-membered heterocycloalkyl group.

Also provided herein are novel compounds of structural formula II:

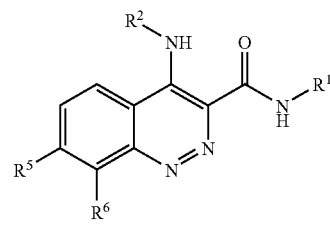

II or a pharmaceutically acceptable salt, tautomer, atropisomer, or in vivo-hydrolysable precursor thereof, wherein:

$R^1$ is $C_{1-6}$ alkyl or $C_{1-6}$ haloalkyl;

$R^2$ is H, $C(=O)-(C_{1-4}$ alkyl), $C(=O)$-(arylalkyl), $C(=O)O-(C_{1-4}$ alkyl), $C(=O)O$-(arylalkyl), $C(=O)NH_2$, $C(=O)NH(C_{1-4}$ alkyl), $C(=O)N(C_{1-4}$ alkyl)$_2$ or $C_{1-6}$ alkyl;

$R^5$ is H, $C_{1-4}$ alkoxy, halo, $C_{1-6}$ alkyl or $C_{1-6}$ haloalkyl;

$R^6$ is phenyl, naphthyl, pyridyl, pyrimidinyl, pyrazinyl, pyrazolyl, quinolyl or indolyl, each optionally substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, $C(=O)H$, $C(=O)-(C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)NR^cR^d$, $C(=O)OH$, $C(=O)O-(C_{1-4}$ alkyl), $C(=O)O$-(arylalkyl), $OC(=O)H$, $OC(=O)-(C_{1-4}$ alkyl), $OC(=O)$-(arylalkyl), $OC(=O)NH_2$, $OC(=O)NH(C_{1-4}$ alkyl), $OC(=O)NH$-(arylalkyl), $OC(=O)N(C_{1-4}$ alkyl)$_2$, $NHC(=O)-(C_{1-4}$ alkyl), $NHC(=O)O$-(arylalkyl), $NHC(=O)O-(C_{1-4}$ alkyl), $NHC(=O)O$-(arylalkyl), $NHS(=O)_2-(C_{1-4}$ alkyl), $NHS(=O)_2$-(arylalkyl), $S(=O)_2-(C_{1-4}$ alkyl), $S(=O)_2$-(arylalkyl), $S(=O)_2NH(C_{1-4}$ alkyl), $S(=O)_2NH$(arylalkyl), $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl; and $R^c$ and $R^d$ together with the N atom to which they are attached form a 4-, 5-, 6- or 7-membered heterocycloalkyl group.

In some embodiments, when $R^2$ and $R^5$ are each H, then $R^6$ is other than unsubstituted phenyl.

In some embodiments, $R^1$ is $C_{1-6}$ alkyl.

In some embodiments, $R^1$ is n-propyl.

In some embodiments, $R^2$ is H, C(=O)—($C_{1-4}$ alkyl), C(=O)O—($C_{1-4}$ alkyl), C(=O)O-(arylalkyl) or $C_{1-6}$ alkyl.

In some embodiments, $R^2$ is H.

In some embodiments, $R^5$ is H, $C_{1-4}$ alkoxy or halo.

In some embodiments, $R^6$ is phenyl substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)$NR^cR^d$, C(=O)OH, C(=O)O—($C_{1-4}$ alkyl), C(=O)O-(arylalkyl), S(=O)$_2$—($C_{1-4}$ alkyl), S(=O)$_2$-(arylalkyl), S(=O)$_2$NH($C_{1-4}$ alkyl), S(=O)$_2$NH(arylalkyl), S(=O)$_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl; and $R^c$ and $R^d$ together with the N atom to which they are attached form a 4-, 5-, 6- or 7-membered heterocycloalkyl group.

In some embodiments, $R^6$ is phenyl, naphthyl, pyridyl, pyrimidinyl, pyrazinyl, pyrazolyl, quinolyl or indolyl, each substituted by 1, 2 or 3 $C_{1-4}$ alkoxy or $C_{1-4}$ alkyl.

In some embodiments, $R^6$ is phenyl, naphthyl, pyridyl, pyrimidinyl, pyrazinyl, pyrazolyl, quinolyl or indolyl, each substituted by 2 $C_{1-4}$ alkoxy or $C_{1-4}$ alkyl.

In some embodiments, $R^1$ is n-propyl and $R^2$ is H.

The present invention further provides compositions comprising a compound of any of the formulas described herein, or a pharmaceutically acceptable salt, tautomer, atropisomer, or in vivo-hydrolysable precursor thereof, and at least one pharmaceutically acceptable carrier, diluent or excipient.

The present invention further provides methods of treating or preventing an anxiety disorder in a patient, comprising administering to the patient a therapeutically effective amount of a compound of any of the formulas described herein, or a pharmaceutically acceptable salt, tautomer, atropisomer, or in vivo-hydrolysable precursor thereof.

The present invention further provides methods of treating or preventing a cognitive disorder in a patient, comprising administering to the patient a therapeutically effective amount of a compound of any of the formulas described herein, or a pharmaceutically acceptable salt, tautomer, atropisomer, or in vivo-hydrolysable precursor thereof.

The present invention further provides methods of treating or preventing a mood disorder in a patient, comprising administering to the patient a therapeutically effective amount of a compound of any of the formulas described herein, or a pharmaceutically acceptable salt, tautomer, atropisomer, or in vivo-hydrolysable precursor thereof.

The present invention further provides a compound of any of the formulas described herein, or a pharmaceutically acceptable salt, tautomer, atropisomer, or in vivo-hydrolysable precursor thereof, described herein for use as a medicament.

The present invention further provides a compound of any of the formulas described herein, or a pharmaceutically acceptable salt, tautomer, atropisomer, or in vivo-hydrolysable precursor thereof, described herein for the manufacture of a medicament.

The present invention further provides methods of modulating activity of GABAA receptor comprising contacting the GABAA receptor with a compound of any of the formulas described herein, or a pharmaceutically acceptable salt, tautomer, atropisomer, or in vivo-hydrolysable precursor thereof.

The present invention further provides synthetic methods of making a compound of any of the formulas described herein, or a pharmaceutically acceptable salt, tautomer, atropisomer, or in vivo-hydrolysable precursor thereof.

Provided herein are novel compounds of structural formula I:

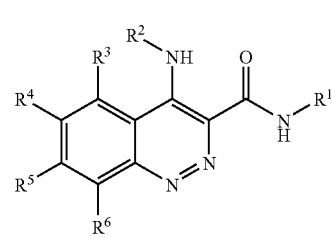

or a pharmaceutically acceptable salt, tautomer, atropisomer, or in vivo-hydrolysable precursor thereof, wherein:

$R^1$ is $C_{1-6}$ alkyl, $C_{1-6}$ haloalkyl, aryl, heteroaryl, cycloalkyl, heterocycloalkyl, arylalkyl, heteroarylalkyl, cycloalkylalkyl or heterocycloalkylalkyl, each optionally substituted by 1, 2, 3, 4 or 5 $R^7$;

$R^2$ is H, C(=O)$R^b$, C(=O)$NR^cR^d$, C(=O)$OR^a$, S(=O)$_2R^b$, $C_{1-6}$ alkyl, $C_{1-6}$ haloalkyl, aryl, heteroaryl, cycloalkyl, heterocycloalkyl, arylalkyl, heteroarylalkyl, cycloalkylalkyl or heterocycloalkylalkyl, wherein each of the $C_{1-6}$ alkyl, aryl, heteroaryl, cycloalkyl, heterocycloalkyl, arylalkyl, heteroarylalkyl, cycloalkylalkyl or heterocycloalkylalkyl is optionally substituted by 1, 2, 3, 4 or 5 $R^8$;

$R^3$, $R^4$ and $R^5$ are each, independently, H, halo, Si($C_{1-10}$ alkyl)$_3$, CN, $NO_2$, $OR^a$, $SR^a$, OC(=O)$R^a$, OC(=O)$OR^b$, OC(=O)$NR^cR^d$, C(=O)$R^a$, C(=O)$OR^b$, C(=O)$NR^cR^d$, $NR^cR^d$, $NR^cC(=O)R^a$, $NR^cC(=O)OR^b$, $NR^cS(=O)_2R^b$, S(=O)$R^a$, S(=O)$NR^cR^d$, S(=O)$_2R^a$, S(=O)$_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2 or 3 $R^9$;

$R^6$ is aryl, cycloalkyl, heteroaryl or heterocycloalkyl, each optionally substituted by 1, 2, 3, 4 or 5 $A^1$;

$R^7$, $R^8$ and $R^9$ are each, independently, halo, $C_{1-4}$ alkyl, $C_{1-4}$ haloalkyl, aryl, cycloalkyl, heteroaryl, heterocycloalkyl, CN, $NO_2$, $OR^{a'}$, $SR^{a'}$, C(=O)$R^{b'}$, C(=O)$NR^{c'}R^{d'}$, C(=O)$OR^{a'}$, OC(=O)$R^{b'}$, OC(=O)$NR^{c'}R^{d'}$, $NR^{c'}R^{d'}$, $NR^{c'}C(=O)R^{b'}$, $NR^{c'}C(=O)OR^{a'}$, $NR^{c'}S(=O)_2R^{b'}$, S(=O)$R^{b'}$, S(=O)$NR^{c'}R^{d'}$, S(=O)$_2R^{b'}$, or S(=O)$_2NR^{c'}R^{d'}$;

$A^1$ is halo, CN, $NO_2$, $OR^a$, $SR^a$, C(=O)$R^b$, C(=O)$NR^cR^d$, C(=O)$OR^a$, OC(=O)$R^b$, OC(=O)$NR^cR^d$, $NR^cR^d$, $NR^cC(=O)R^d$, $NR^cC(=O)OR^a$, $NR^cS(=O)R^b$, $NR^cS(=O)_2R^b$, S(=O)$R^b$, S(=O)$NR^cR^d$, S(=O)$_2R^b$, S(=O)$_2NR^cR^d$, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, arylalkyl, cycloalkylalkyl, heteroarylalkyl, heterocycloalkylalkyl, aryl, cycloalkyl, heteroaryl or heterocycloalkyl, wherein each of the $C_{1-6}$ alkyl, $C_{2-6}$ alkenyl, $C_{2-6}$ alkynyl, arylalkyl, cycloalkylalkyl, heteroarylalkyl, heterocycloalkylalkyl, aryl, cycloalkyl, heteroaryl or heterocycloalkyl is optionally substituted by 1, 2, 3, 4 or 5 substituents independently selected from halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^{a'}$, $SR^{a'}$, C(=O)$R^{b'}$, C(=O)$NR^{c'}R^{d'}$, C(=O)$OR^{a'}$, OC(=O)$R^{b'}$, OC(=O)$NR^{c'}R^{d'}$, $NR^{c'}R^{d'}$, $NR^{c'}C(=O)R^{b'}$, $NR^cC(=O)OR^{a'}$, $NR^cS(=O)R^{b'}$, $NR^cS(=O)_2R^{b'}$, $S(=O)R^{b'}$, $S(=O)NR^cR^{d'}$, $S(=O)_2R^{b'}$, or $S(=O)_2NR^cR^{d'}$;

$R^a$ and $R^{a'}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

$R^b$ and $R^{b'}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

$R^c$ and $R^d$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein the $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, 6- or 7-membered heterocycloalkyl group; and $R^{c'}$ and $R^{d'}$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein the $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^{c'}$ and $R^{d'}$ together with the N atom to which they are attached form a 4-, 5-, 6- or 7-membered heterocycloalkyl group.

In some embodiments, when $R^2$, $R^3$, $R^4$ and $R^5$ are each H, then $R^6$ is other than unsubstituted phenyl or unsubstituted cycloalkyl.

In some embodiments, $R^1$ is $C_{1-6}$ alkyl, $C_{1-6}$ haloalkyl, aryl, heteroaryl, cycloalkyl, heterocycloalkyl, arylalkyl, heteroarylalkyl, cycloalkylalkyl or heterocycloalkylalkyl, each optionally substituted by 1, 2, 3, 4 or 5 $R^7$, or any subgroup thereof In some embodiments, $R^1$ is $C_{1-6}$ alkyl, $C_{1-6}$ haloalkyl, arylalkyl, heteroarylalkyl, cycloalkylalkyl or heterocycloalkylalkyl, each optionally substituted by 1, 2, 3, 4 or 5 $R^7$. In some embodiments, $R^1$ is $C_{1-6}$ alkyl, $C_{1-6}$ haloalkyl, arylalkyl, heteroarylalkyl, cycloalkylalkyl or heterocycloalkylalkyl, each optionally substituted by 1, 2, 3, 4 or 5 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, $SR^{a'}$, $C(=O)R^{b'}$, $C(=O)NR^cR^{d'}$, $C(=O)OR^{a'}$, $OC(=O)R^{b'}$, $OC(=O)NR^cR^{d'}$, $NR^cC(=O)R^{b'}$, $NR^cC(=O)OR^{a'}$, $NR^cS(=O)_2R^{b'}$, $S(=O)R^{b'}$, $S(=O)NR^cR^{d'}$, $S(=O)_2R^{b'}$, or $S(=O)_2NR^cR^{d'}$. In some embodiments, $R^1$ is $C_{1-6}$ alkyl, $C_{1-6}$ haloalkyl, arylalkyl, heteroarylalkyl, cycloalkylalkyl or heterocycloalkylalkyl, each optionally substituted by 1, 2, 3, 4 or 5 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, SH, —S—($C_{1-4}$ alkyl), $C(=O)H$, $C(=O)$—($C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)OH$, $C(=O)O$—($C_{1-4}$ alkyl), $C(=O)O$-(arylalkyl), $OC(=O)H$, $OC(=O)$—($C_{1-4}$ alkyl), $OC(=O)$-(arylalkyl), $OC(=O)NH_2$, $OC(=O)NH(C_{1-4}$ alkyl), $OC(=O)NH$-(arylalkyl), $OC(=O)N(C_{1-4}$ alkyl)$_2$, $NHC(=O)$—($C_{1-4}$ alkyl), $NHC(=O)O$-(arylalkyl), $NHC(=O)O$—($C_{1-4}$ alkyl), $NHC(=O)O$-(arylalkyl), $NHS(=O)_2$—($C_{1-4}$ alkyl), $NHS(=O)_2$-(arylalkyl), $S(=O)_2$—($C_{1-4}$ alkyl), $S(=O)_2$-(arylalkyl), $S(=O)_2NH(C_{1-4}$ alkyl) and $S(=O)_2NH$(arylalkyl). In some embodiments, $R^1$ is $C_{1-6}$ alkyl, $C_{1-6}$ haloalkyl, arylalkyl, heteroarylalkyl, cycloalkylalkyl or heterocycloalkylalkyl, each optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, SH, —S—($C_{1-4}$ alkyl), $C(=O)H$, $C(=O)$—($C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)OH$, $C(=O)O$—($C_{1-4}$ alkyl), $C(=O)O$-(arylalkyl), $OC(=O)H$, $OC(=O)$—($C_{1-4}$ alkyl), $OC(=O)$-(arylalkyl), $OC(=O)NH_2$, $OC(=O)NH(C_{1-4}$ alkyl), $OC(=O)NH$-(arylalkyl), $OC(=O)N(C_{1-4}$ alkyl)$_2$, $NHC(=O)$—($C_{1-4}$ alkyl), $NHC(=O)O$-(arylalkyl), $NHC(=O)O$—($C_{1-4}$ alkyl), $NHC(=O)O$-(arylalkyl), $NHS(=O)_2$—($C_{1-4}$ alkyl), $NHS(=O)_2$-(arylalkyl), $S(=O)_2$—($C_{1-4}$ alkyl), $S(=O)_2$-(arylalkyl), $S(=O)_2NH(C_{1-4}$ alkyl) and $S(=O)_2NH$(arylalkyl). In some embodiments, $R^1$ is $C_{1-6}$ alkyl, $C_{1-6}$ haloalkyl, arylalkyl, heteroarylalkyl, cycloalkylalkyl or heterocycloalkylalkyl, each optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, $C(=O)H$, $C(=O)$—($C_{1-4}$ alkyl), $C(=O)$-(arylalkyl), $C(=O)NH_2$, $C(=O)NH(C_{1-4}$ alkyl), $C(=O)N(C_{1-4}$ alkyl)$_2$, $C(=O)OH$, $C(=O)O$—($C_{1-4}$ alkyl), $C(=O)O$-(arylalkyl), $OC(=O)$—($C_{1-4}$ alkyl), $OC(=O)NH_2$, $OC(=O)NH$ ($C_{1-4}$ alkyl), $OC(=O)NH$-(arylalkyl), $OC(=O)N(C_{1-4}$ alkyl)$_2$, $NHC(=O)$—($C_{1-4}$ alkyl), $NHC(=O)O$-(arylalkyl), $NHS(=O)_2$—($C_{1-4}$ alkyl), $NHS(=O)_2$-(arylalkyl), $S(=O)_2$—($C_{1-4}$ alkyl), $S(=O)_2$-(arylalkyl), $S(=O)_2NH(C_{1-4}$ alkyl) and $S(=O)_2NH$(arylalkyl). In some embodiments, $R^1$ is $C_{1-6}$ alkyl, $C_{1-6}$ haloalkyl, arylalkyl, heteroarylalkyl, cycloalkylalkyl or heterocycloalkylalkyl. In some embodiments, $R^1$ is $C_{1-6}$ alkyl or $C_{1-6}$ haloalkyl. In some embodiments, $R^1$ is $C_{1-6}$ alkyl. In some embodiments, $R^1$ is n-propyl.

In some embodiments, $R^2$ is H, $C(=O)R^b$, $C(=O)NR^cR^d$, $C(=O)OR^a$, $S(=O)_2R^b$, $C_{1-6}$ alkyl, $C_{1-6}$ haloalkyl, aryl, heteroaryl, cycloalkyl, heterocycloalkyl, arylalkyl, heteroarylalkyl, cycloalkylalkyl or heterocycloalkylalkyl, or any subgroup thereof, wherein each of the $C_{1-6}$ alkyl, aryl, heteroaryl, cycloalkyl, heterocycloalkyl, arylalkyl, heteroarylalkyl, cycloalkylalkyl or heterocycloalkylalkyl is optionally substituted by 1, 2, 3, 4 or 5 $R^8$, or any subgroup thereof. In some embodiments, $R^2$ is H, $C(=O)$—($C_{1-4}$ alkyl), $C(=O)$-(arylalkyl), $C(=O)O$—($C_{1-4}$ alkyl), $C(=O)O$-(arylalkyl), $C(=O)NH_2$, $C(=O)NH(C_{1-4}$ alkyl), $C(=O)N(C_{1-4}$ alkyl)$_2$, $C_{1-6}$ alkyl, $C_{1-6}$ haloalkyl, arylalkyl, heteroarylalkyl, cycloalkylalkyl or heterocycloalkylalkyl, wherein each of the $C_{1-6}$ alkyl, arylalkyl, heteroarylalkyl, cycloalkylalkyl or heterocycloalkylalkyl is optionally substituted by 1, 2, 3, 4 or 5 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, SH, —S—($C_{1-4}$ alkyl), C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl) and S(=O)$_2$NH(arylalkyl). In some embodiments, $R^2$ is H, C(=O)—($C_{1-4}$ alkyl), C(=O)-(arylalkyl), C(=O)O—($C_{1-4}$ alkyl), C(=O)O-(arylalkyl), C(=O)$NH_2$, C(=O)NH($C_{1-4}$ alkyl), C(=O)N($C_{1-4}$ alkyl)$_2$, $C_{1-6}$ alkyl, $C_{1-6}$ haloalkyl, arylalkyl, heteroarylalkyl, cycloalkylalkyl or heterocycloalkylalkyl, wherein each of the $C_{1-6}$ alkyl, arylalkyl, heteroarylalkyl, cycloalkylalkyl or heterocycloalkylalkyl is optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, SH, —S—($C_{1-4}$ alkyl), C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl) and S(=O)$_2$NH(arylalkyl). In some embodiments, $R^2$ is H, C(=O)—($C_{1-4}$ alkyl), C(=O)-(arylalkyl), C(=O)O—($C_{1-4}$ alkyl), C(=O)O-(arylalkyl), C(=O)$NH_2$, C(=O)NH($C_{1-4}$ alkyl), C(=O)N($C_{1-4}$ alkyl)$_2$, $C_{1-6}$ alkyl, $C_{1-6}$ haloalkyl, arylalkyl, heteroarylalkyl, cycloalkylalkyl or heterocycloalkylalkyl. In some embodiments, $R^2$ is H, C(=O)—($C_{1-4}$ alkyl), C(=O)-(arylalkyl), C(=O)O—($C_{1-4}$ alkyl), C(=O)O-(arylalkyl), C(=O)$NH_2$, C(=O)NH($C_{1-4}$ alkyl), C(=O)N($C_{1-4}$ alkyl)$_2$ or $C_{1-6}$ alkyl. In some embodiments, $R^2$ is H, C(=O)—($C_{1-4}$ alkyl), C(=O)-(arylalkyl), C(=O)O—($C_{1-4}$ alkyl), C(=O)O-(arylalkyl), C(=O)$NH_2$, C(=O)NH($C_{1-4}$ alkyl), C(=O)N($C_{1-4}$ alkyl)$_2$, or $C_{1-3}$ alkyl. In some embodiments, $R^2$ is H.

In some embodiments, $R^3$, $R^4$ and $R^5$ are each, independently, H, halo, Si($C_{1-10}$ alkyl)$_3$, CN, $NO_2$, $OR^a$, $SR^a$, $OC(=O)R^a$, $OC(=O)OR^b$, $OC(=O)NR^cR^d$, $C(=O)R^a$, $C(=O)OR^b$, $C(=O)NR^cR^d$, $NR^cR^d$, $NR^cC(=O)R^a$, $NR^cC(=O)OR^b$, $NR^cS(=O)_2R^b$, $S(=O)R^a$, $S(=O)NR^cR^d$, $S(=O)_2R^a$, $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, or any subgroup thereof, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2 or 3 $R^9$, or any subgroup thereof. In some embodiments, $R^3$, $R^4$ and $R^5$ are each, independently, H, halo, CN, $NO_2$, OH, $OR^a$, $SR^a$, $OC(=O)R^a$, $OC(=O)OR^b$, $OC(=O)NR^cR^d$, $C(=O)R^a$, $C(=O)OR^b$, $C(=O)NR^cR^d$, $NR^cR^d$, $NR^cC(=O)R^a$, $NR^cC(=O)OR^b$, $NR^cS(=O)_2R^b$, $S(=O)R^a$, $S(=O)NR^cR^d$, $S(=O)_2R^a$, $S(=O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, SH, —S—($C_{1-4}$ alkyl), C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl) and S(=O)$_2$NH(arylalkyl). In some embodiments, $R^3$, $R^4$ and $R^5$ are each, independently, H, halo, CN, $NO_2$, OH, $C_{1-4}$ alkoxy, $C_{1-4}$ haloalkoxy, amino, $C_{1-4}$ alkylamino, $C_{2-8}$ dialkylamino, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl) and S(=O)$_2$NH(arylalkyl). In some embodiments, $R^3$, $R^4$ and $R^5$ are each, independently, H, $C_{1-4}$ alkoxy, halo, $C_{1-6}$ alkyl or $C_{1-6}$ haloalkyl. In some embodiments, $R^3$, $R^4$ and $R^5$ are each, independently, H, $C_{1-4}$ alkoxy, halo or $C_{1-3}$ haloalkyl. In some embodiments, $R^3$, $R^4$ and $R^5$ are each, independently, H, $C_{1-4}$ alkoxy, or halo.

In some embodiments, $R^6$ is aryl, cycloalkyl, heteroaryl or heterocycloalkyl, or any subgroup thereof, each optionally substituted by 1, 2, 3, 4 or 5 $A^1$, or any subgroup thereof In some embodiments, $R^6$ is aryl or heteroaryl, each optionally substituted by 1, 2, 3, 4 or 5 $A^1$. In some embodiments, $R^6$ is aryl optionally substituted by 1, 2, 3, 4 or 5 $A^1$. In some embodiments, $R^6$ is aryl substituted by 1, 2, 3, 4 or 5 $A^1$. In some embodiments, $R^6$ is heteroaryl optionally substituted by 1, 2, 3, 4 or 5 $A^1$. In some embodiments, $R^6$ is phenyl, naphthyl, pyridyl, pyrimidinyl, pyrazinyl, pyrazolyl, quinolyl or indolyl, each optionally substituted by 1, 2, 3, 4 or 5 $A^1$. In some embodiments, $R^6$ is phenyl, 2-naphthyl, 3-pyridyl, 4-pyridyl, pyrimidin-5-yl, pyrazin-2-yl, pyrazol-3-yl, pyrazol-4-yl, 3-quinolyl, 6-quinolyl, or indol-5-yl, each optionally substituted by 1, 2, 3, 4 or 5 $A^1$. In some embodiments, $R^6$ is phenyl, naphthyl, pyridyl, pyrimidinyl, pyrazinyl, pyrazolyl, quinolyl or indolyl, each optionally substituted by 1, 2, 3, 4 or 5 halo, CN, $NO_2$, OH, $C_{1-4}$ alkoxy, $C_{1-4}$ haloalkoxy, amino, $C_{1-4}$ alkylamino, $C_{2-8}$ dialkylamino, $NR^cR^d$, SH, —S—($C_{1-4}$ alkyl), C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)$NR^cR^d$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl), S(=O)$_2$NH(arylalkyl), S(=O)$_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2 or 3 substituents independently selected from halo, $C_{1-4}$ alkyl, $C_{1-4}$ haloalkyl, aryl, cycloalkyl, heteroaryl, heterocycloalkyl, CN, $NO_2$, OH, $C_{1-4}$ alkoxy, $C_{1-4}$ haloalkoxy, amino, $C_{1-4}$ alkylamino, $C_{2-8}$ dialkylamino, $R^cR^{d'}$, SH, —S—($C_{1-4}$ alkyl), C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)$NR^{c'}R^{d'}$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl), S(=O)$_2$NH(arylalkyl) and S(=O)$_2NR^{c'}R^{d'}$.

In some embodiments, $R^6$ is phenyl, naphthyl, pyridyl, pyrimidinyl, pyrazinyl, pyrazolyl, quinolyl or indolyl, each optionally substituted by 1, 2, 3, 4 or 5 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)$NR^cR^d$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl), S(=O)$_2$NH(arylalkyl), S(=O)$_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl. In some embodiments, $R^6$ is phenyl substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)$NR^cR^d$, C(=O)OH, C(=O)O—($C_{1-4}$ alkyl), C(=O)O-(arylalkyl), S(=O)$_2$—($C_{1-4}$ alkyl), S(=O)$_2$-(arylalkyl), S(=O)$_2$NH($C_{1-4}$ alkyl), S(=O)$_2$NH(arylalkyl), S(=O)$_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl. In some embodiments, $R^6$ is naphthyl, pyridyl, pyrimidinyl, pyrazinyl, pyrazolyl, quinolyl or indolyl, each optionally substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)$NR^cR^d$, C(=O)OH, C(=O)O—($C_{1-4}$ alkyl), C(=O)O-(arylalkyl), S(=O)$_2$—($C_{1-4}$ alkyl), S(=O)$_2$-(arylalkyl), S(=O)$_2$NH($C_{1-4}$ alkyl), S(=O)$_2$NH(arylalkyl), S(=O)$_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl.

In some embodiments, $R^7$, $R^8$ and $R^9$ are each, independently, halo, $C_{1-4}$ alkyl, $C_{1-4}$ haloalkyl, aryl, cycloalkyl, heteroaryl, heterocycloalkyl, CN, $NO_2$, $OR^{a'}$, $SR^{a'}$, C(=O)$R^{b'}$, C(=O)$NR^{c'}R^{d'}$, C(=O)$OR^{a'}$, OC(=O)$R^{b'}$, OC(=O)$NR^{c'}R^{d'}$, $NR^{c'}R^{d'}$, $NR^{c'}$C(=O)$R^{b'}$, $NR^{c'}$C(=O)$OR^{a'}$, $NR^{c'}$S(=O)$_2R^{b'}$, S(=O)$R^{b'}$, S(=O)$NR^{c'}R^{d'}$, S(=O)$_2R^{b'}$, or S(=O)$_2NR^{c'}R^{d'}$, or any subgroup thereof.

In some embodiments, $A^1$ is halo, CN, $NO_2$, $OR^a$, $SR^a$, C(=O)$R^b$, C(=O)$NR^cR^d$, C(=O)$OR^a$, OC(=O)$R^b$, OC(=O)NR$^c$R$^d$, NR$^c$R$^d$, NR$^c$C(=O)R$^d$, NR$^c$C(=O)OR$^a$, NR$^c$S(=O)R$^b$, NR$^c$S(=O)$_2$R$^b$, S(=O)R$^b$, S(=O)NR$^c$R$^d$, S(=O)$_2$R$^b$, S(=O)$_2$NR$^c$R$^d$, C$_{1-4}$ alkoxy, C$_{1-4}$ haloalkoxy, amino, C$_{1-4}$ alkylamino, C$_{2-8}$ dialkylamino, C$_{1-6}$ alkyl, C$_{2-6}$ alkenyl, C$_{2-6}$ alkynyl, arylalkyl, cycloalkylalkyl, heteroarylalkyl, heterocycloalkylalkyl, aryl, cycloalkyl, heteroaryl or heterocycloalkyl, or any subgroup thereof, wherein each of the C$_{1-6}$ alkyl, C$_{2-6}$ alkenyl, C$_{2-6}$ alkynyl, arylalkyl, cycloalkylalkyl, heteroarylalkyl, heterocycloalkylalkyl, aryl, cycloalkyl, heteroaryl or heterocycloalkyl is optionally substituted by 1, 2, 3, 4 or 5 substituents independently selected from halo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, CN, NO$_2$, OR$^{a'}$, SR$^{a'}$, C(=O)R$^{b'}$, C(=O)NR$^{c'}$R$^{d'}$, C(=O)OR$^{a'}$, OC(=O)R$^{b'}$, OC(=O)NR$^{c'}$R$^{d'}$, NR$^{c'}$R$^{d'}$, NR$^{c'}$C(=O)R$^{b'}$, NR$^{c'}$C(=O)OR$^{a'}$, NR$^{c'}$S(=O)R$^{b'}$, NR$^{c'}$S(=O)$_2$R$^{b'}$, S(=O)R$^{b'}$, S(=O)NR$^{c'}$R$^{d'}$, S(=O)$_2$R$^{b'}$, or S(=O)$_2$NR$^{c'}$R$^{d'}$, or any subgroup thereof.

In some embodiments, R$^a$ and R$^{a'}$ are each, independently, H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl, or any subgroup thereof, wherein the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ haloalkyl, aryl, arylalkyl, heteroaryl, heteroarylalkyl, cycloalkyl or heterocycloalkyl, or any subgroup thereof.

In some embodiments, R$^b$ and R$^{b'}$ are each, independently, H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl, or any subgroup thereof, wherein the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ haloalkyl, C$_{1-6}$ haloalkyl, aryl, arylalkyl, heteroaryl, heteroarylalkyl, cycloalkyl or heterocycloalkyl, or any subgroup thereof.

In some embodiments, R$^c$ and R$^d$ are each, independently, H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl, or any subgroup thereof, wherein the C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ halo alkyl, C$_{1-6}$ halo alkyl, aryl, arylalkyl, heteroaryl, heteroarylalkyl, cycloalkyl or heterocycloalkyl, or any subgroup thereof.

In some embodiments, R$^c$ and R$^d$ together with the N atom to which they are attached form a 4-, 5-, 6- or 7-membered heterocycloalkyl group, or any subgroup thereof.

In some embodiments, R$^{c'}$ and R$^{d'}$ are each, independently, H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl, or any subgroup thereof, wherein the C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ halo alkyl, C$_{1-6}$ halo alkyl, aryl, arylalkyl, heteroaryl, heteroarylalkyl, cycloalkyl or heterocycloalkyl, or any subgroup thereof.

In some embodiments, R$^{c'}$ and R$^{d'}$ together with the N atom to which they are attached form a 4-, 5-, 6- or 7-membered heterocycloalkyl group, or any subgroup thereof.

In some embodiments, when R$^2$, R$^3$, R$^4$ and R$^5$ are each H, then R$^6$ is other than unsubstituted phenyl or unsubstituted cycloalkyl.

In some embodiments, R$^6$ is phenyl, naphthyl, pyridyl, pyrimidinyl, pyrazinyl, pyrazolyl, quinolyl or indolyl, each optionally substituted by 1, 2, 3, 4 or 5 halo, CN, NO$_2$, OH, C$_{1-4}$ alkoxy, C$_{1-4}$ haloalkoxy, amino, C$_{1-4}$ alkylamino, C$_{2-8}$ dialkylamino, NR$^c$R$^d$, SH, —S—(C$_{1-4}$ alkyl), C(=O)H, C(=O)—(C$_{1-4}$ alkyl), C(=O)-(arylalkyl), C(=O)NH$_2$, C(=O)NH(C$_{1-4}$ alkyl), C(=O)N(C$_{1-4}$ alkyl)$_2$, C(=O)NR$^c$R$^d$, C(=O)OH, C(=O)O—(C$_{1-4}$ alkyl), C(=O)O-(arylalkyl), OC(=O)H, OC(=O)—(C$_{1-4}$ alkyl), OC(=O)-(arylalkyl), OC(=O)NH$_2$, OC(=O)NH(C$_{1-4}$ alkyl), OC(=O)NH-(arylalkyl), OC(=O)N(C$_{1-4}$ alkyl)$_2$, NHC(=O)—(C$_{1-4}$ alkyl), NHC(=O)O-(arylalkyl), NHC(=O)O—(C$_{1-4}$ alkyl), NHC(=O)O-(arylalkyl), NHS(=O)$_2$—(C$_{1-4}$ alkyl), NHS(=O)$_2$-(arylalkyl), S(=O)$_2$—(C$_{1-4}$ alkyl), S(=O)$_2$-(arylalkyl), S(=O)$_2$NH(C$_{1-4}$ alkyl), S(=O)$_2$NH(arylalkyl), S(=O)$_2$NR$^c$R$^d$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2 or 3 substituents independently selected from halo, C$_{1-4}$ alkyl, C$_{1-4}$ haloalkyl, aryl, cycloalkyl, heteroaryl, heterocycloalkyl, CN, NO$_2$, OH, C$_{1-4}$ alkoxy, C$_{1-4}$ haloalkoxy, amino, C$_{1-4}$ alkylamino, C$_{2-8}$ dialkylamino, R$^c$R$^{d'}$, SH, —S—(C$_{1-4}$ alkyl), C(=O)H, C(=O)—(C$_{1-4}$ alkyl), C(=O)-(arylalkyl), C(=O)NH$_2$, C(=O)NH(C$_{1-4}$ alkyl), C(=O)N(C$_{1-4}$ alkyl)$_2$, C(=O)R$^{c'}$R$^{d'}$, C(=O)OH, C(=O)O—(C$_{1-4}$ alkyl), C(=O)O-(arylalkyl), OC(=O)H, OC(=O)—(C$_{1-4}$ alkyl), OC(=O)-(arylalkyl), OC(=O)NH$_2$, OC(=O)NH(C$_{1-4}$ alkyl), OC(=O)NH-(arylalkyl), OC(=O)N(C$_{1-4}$ alkyl)$_2$, NHC(=O)—(C$_{1-4}$ alkyl), NHC(=O)O-(arylalkyl), NHC(=O)O—(C$_{1-4}$ alkyl), NHC(=O)O-(arylalkyl), NHS(=O)$_2$—(C$_{1-4}$ alkyl), NHS(=O)$_2$-(arylalkyl), S(=O)$_2$—(C$_{1-4}$ alkyl), S(=O)$_2$-(arylalkyl), S(=O)$_2$NH(C$_{1-4}$ alkyl), S(=O)$_2$NH(arylalkyl) and S(=O)$_2$NR$^{c'}$R$^{d'}$; R$^c$ and R$^d$ together with the N atom to which they are attached form a 4-, 5-, 6- or 7-membered heterocycloalkyl group; and R$^{c'}$ and R$^{d'}$ together with the N atom to which they are attached form a 4-, 5-, 6- or 7-membered heterocycloalkyl group.

In some embodiments, R$^6$ is phenyl, naphthyl, pyridyl, pyrimidinyl, pyrazinyl, pyrazolyl, quinolyl or indolyl, each optionally substituted by 1, 2, 3, 4 or 5 halo, CN, OH, C$_{1-4}$ alkoxy, C$_{1-4}$ haloalkoxy, amino, C$_{1-4}$ alkylamino, C$_{2-8}$ dialkylamino, NR$^c$R$^d$, C(=O)H, C(=O)—(C$_{1-4}$ alkyl), C(=O)-(arylalkyl), C(=O)NH$_2$, C(=O)NH(C$_{1-4}$ alkyl), C(=O)N(C$_{1-4}$ alkyl)$_2$, C(=O)NR$^c$R$^d$, C(=O)OH, C(=O)O—(C$_{1-4}$ alkyl), C(=O)O-(arylalkyl), OC(=O)H, OC(=O)—(C$_{1-4}$ alkyl), OC(=O)-(arylalkyl), OC(=O)NH$_2$, OC(=O)NH(C$_{1-4}$ alkyl), OC(=O)NH-(arylalkyl), OC(=O)N(C$_{1-4}$ alkyl)$_2$, NHC(=O)—(C$_{1-4}$ alkyl), NHC(=O)O-(arylalkyl), NHC(=O)O—(C$_{1-4}$ alkyl), NHC(=O)O-(arylalkyl), NHS(=O)$_2$—(C$_{1-4}$ alkyl), NHS(=O)$_2$-(arylalkyl), S(=O)$_2$—(C$_{1-4}$ alkyl), S(=O)$_2$-(arylalkyl), S(=O)$_2$NH(C$_{1-4}$ alkyl), S(=O)$_2$NH(arylalkyl), S(=O)$_2$NR$^c$R$^d$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl; and R$^c$ and R$^d$ together with the N atom to which they are attached form a 4-, 5-, 6- or 7-membered heterocycloalkyl group.

In some embodiments, $R^6$ is phenyl, naphthyl, pyridyl, pyrimidinyl, pyrazinyl, pyrazolyl, quinolyl or indolyl, each optionally substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)$NR^cR^d$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl), S(=O)$_2$NH(arylalkyl), S(=O)$_2$$NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl; and $R^c$ and $R^d$ together with the N atom to which they are attached form a 4-, 5-, 6- or 7-membered heterocycloalkyl group.

In some embodiments, $R^6$ is phenyl, naphthyl, pyridyl, pyrimidinyl, pyrazinyl, pyrazolyl, quinolyl or indolyl, each optionally substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)$NR^cR^d$, C(=O)OH, C(=O)O—($C_{1-4}$ alkyl), C(=O)O-(arylalkyl), S(=O)$_2$—($C_{1-4}$ alkyl), S(=O)$_2$-(arylalkyl), S(=O)$_2$NH($C_{1-4}$ alkyl), S(=O)$_2$NH(arylalkyl), S(=O)$_2$$NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl; and $R^c$ and $R^d$ together with the N atom to which they are attached form a 4-, 5-, 6- or 7-membered heterocycloalkyl group.

In some embodiments, $R^6$ is phenyl substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)$NR^cR^d$, C(=O)OH, C(=O)O—($C_{1-4}$ alkyl), C(=O)O-(arylalkyl), S(=O)$_2$—($C_{1-4}$ alkyl), S(=O)$_2$-(arylalkyl), S(=O)$_2$NH($C_{1-4}$ alkyl), S(=O)$_2$NH(arylalkyl), S(=O)$_2$$NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl; and $R^c$ and $R^d$ together with the N atom to which they are attached form a 4-, 5-, 6- or 7-membered heterocycloalkyl group.

In some embodiments, $R^6$ is naphthyl, pyridyl, pyrimidinyl, pyrazinyl, pyrazolyl, quinolyl or indolyl, each optionally substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)$NR^cR^d$, C(=O)OH, C(=O)O—($C_{1-4}$ alkyl), C(=O)O-(arylalkyl), S(=O)$_2$—($C_{1-4}$ alkyl), S(=O)$_2$-(arylalkyl), S(=O)$_2$NH($C_{1-4}$ alkyl), S(=O)$_2$NH(arylalkyl), S(=O)$_2$$NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl; and $R^c$ and $R^d$ together with the N atom to which they are attached form a 4-, 5-, 6- or 7-membered heterocycloalkyl group.

Also provided herein are novel compounds of structural formula II:

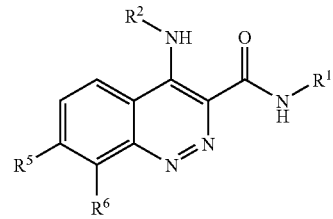

or a pharmaceutically acceptable salt, tautomer, or in vivo-hydrolysable precursor thereof, wherein:

$R^1$ is $C_{1-6}$ alkyl or $C_{1-6}$ haloalkyl;

$R^2$ is H, C(=O)—($C_{1-4}$ alkyl), C(=O)-(arylalkyl), C(=O)O—($C_{1-4}$ alkyl), C(=O)O-(arylalkyl), C(=O)$NH_2$, C(=O)NH($C_{1-4}$ alkyl), C(=O)N($C_{1-4}$ alkyl)$_2$ or $C_{1-6}$ alkyl;

$R^5$ is H, $C_{1-4}$ alkoxy, halo, $C_{1-6}$ alkyl or $C_{1-6}$ haloalkyl;

$R^6$ is phenyl, naphthyl, pyridyl, pyrimidinyl, pyrazinyl, pyrazolyl, quinolyl or indolyl, each optionally substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)$NR^cR^d$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), S(=O)$_2$—($C_{1-4}$ alkyl), S(=O)$_2$-(arylalkyl), S(=O)$_2$NH($C_{1-4}$ alkyl), S(=O)$_2$NH(arylalkyl), S(=O)$_2$$NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl; and $R^c$ and $R^d$ together with the N atom to which they are attached form a 4-, 5-, 6- or 7-membered heterocycloalkyl group.

In some embodiments, when $R^2$ and $R^5$ are each H, then $R^6$ is other than unsubstituted phenyl.

In some embodiments, $R^1$ is $C_{1-6}$ alkyl or $C_{1-6}$ haloalkyl, or any subgroup thereof.

In some embodiments, $R^1$ is $C_{1-6}$ alkyl. In some embodiments, $R^1$ is n-propyl.

In some embodiments, $R^2$ is H, C(=O)—($C_{1-4}$ alkyl), C(=O)-(arylalkyl), C(=O)O—($C_{1-4}$ alkyl), C(=O)O-(arylalkyl), C(=O)$NH_2$, C(=O)NH($C_{1-4}$ alkyl), C(=O)N($C_{1-4}$ alkyl)$_2$ or $C_{1-6}$ alkyl, or any subgroup thereof. In some embodiments, $R^2$ is H, C(=O)—($C_{1-4}$ alkyl), C(=O)O—($C_{1-4}$ alkyl), C(=O)O-(arylalkyl) or $C_{1-6}$ alkyl. In some embodiments, $R^2$ is H.

In some embodiments, $R^5$ is H, $C_{1-4}$ alkoxy, halo, $C_{1-6}$ alkyl or $C_{1-6}$ haloalkyl, or any subgroup thereof. In some embodiments, $R^5$ is H, $C_{1-4}$ alkoxy or halo.

In some embodiments, $R^6$ is phenyl, naphthyl, pyridyl, pyrimidinyl, pyrazinyl, pyrazolyl, quinolyl or indolyl, or any subgroup thereof, each optionally substituted by 1, 2 or 3 halo, CN, OH, $C_{1-4}$ alkoxy, $C_{1-4}$ haloalkoxy, amino, $C_{1-4}$ alkylamino, $C_{2-8}$ dialkylamino, $NR^cR^d$, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)$NR^cR^d$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N(C$_{1-4}$ alkyl)$_2$, NHC(=O)—(C$_{1-4}$ alkyl), NHC(=O)O-(arylalkyl), NHC(=O)O—(C$_{1-4}$ alkyl), NHC(=O)O-(arylalkyl), NHS(=O)$_2$—(C$_{1-4}$ alkyl), NHS(=O)$_2$-(arylalkyl), S(=O)$_2$—(C$_{1-4}$ alkyl), S(=O)$_2$-(arylalkyl), S(=O)$_2$NH(C$_{1-4}$ alkyl), S(=O)$_2$NH(arylalkyl), S(=O)$_2$NR$^c$R$^d$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl, or any subgroup thereof. In some embodiments, R$^6$ is phenyl substituted by 1, 2 or 3 halo, CN, OH, C$_{1-4}$ alkoxy, C$_{1-4}$ haloalkoxy, amino, C$_{1-4}$ alkylamino, C$_{2-8}$ dialkylamino, NR$^c$R$^d$, C(=O)H, C(=O)—(C$_{1-4}$ alkyl), C(=O)-(arylalkyl), C(=O)NH$_2$, C(=O)NH(C$_{1-4}$ alkyl), C(=O)N(C$_{1-4}$ alkyl)$_2$, C(=O)NR$^c$R$^d$, C(=O)OH, C(=O)O—(C$_{1-4}$ alkyl), C(=O)O-(arylalkyl), S(=O)$_2$—(C$_{1-4}$ alkyl), S(=O)$_2$-(arylalkyl), S(=O)$_2$NH(C$_{1-4}$ alkyl), S(=O)$_2$NH(arylalkyl), S(=O)$_2$NR$^c$R$^d$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl. In some embodiments, R$^6$ is phenyl, naphthyl, pyridyl, pyrimidinyl, pyrazinyl, pyrazolyl, quinolyl or indolyl, each substituted by 1, 2 or 3 C$_{1-4}$ alkoxy or C$_{1-4}$ alkyl. In some embodiments, R$^6$ is phenyl, naphthyl, pyridyl, pyrimidinyl, pyrazinyl, pyrazolyl, quinolyl or indolyl, each substituted by 2 C$_{1-4}$ alkoxy or C$_{1-4}$ alkyl.

In some embodiments, R$^c$ and R$^d$ together with the N atom to which they are attached form a 4-, 5-, 6- or 7-membered heterocycloalkyl group, or any subgroup thereof.

In some embodiments, R$^6$ is phenyl substituted by 1, 2 or 3 halo, CN, OH, C$_{1-4}$ alkoxy, C$_{1-4}$ haloalkoxy, amino, C$_{1-4}$ alkylamino, C$_{2-8}$ dialkylamino, NR$^c$R$^d$, C(=O)H, C(=O)—(C$_{1-4}$ alkyl), C(=O)-(arylalkyl), C(=O)NH$_2$, C(=O)NH(C$_{1-4}$ alkyl), C(=O)N(C$_{1-4}$ alkyl)$_2$, C(=O)NR$^c$R$^d$, C(=O)OH, C(=O)O—(C$_{1-4}$ alkyl), C(=O)O-(arylalkyl), S(=O)$_2$—(C$_{1-4}$ alkyl), S(=O)$_2$-(arylalkyl), S(=O)$_2$NH(C$_{1-4}$ alkyl), S(=O)$_2$NH(arylalkyl), S(=O)$_2$NR$^c$R$^d$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl; and R$^c$ and R$^d$ together with the N atom to which they are attached form a 4-, 5-, 6- or 7-membered heterocycloalkyl group.

In some embodiments, R$^1$ is n-propyl and R$^2$ is H.

In some embodiments, the present invention provides the following compounds:

4-amino-7-fluoro-8-phenyl-N-propyl-cinnoline-3-carboxamide;
4-amino-7-chloro-8-phenyl-N-propyl-cinnoline-3-carboxamide;
4-amino-7-methoxy-8-phenyl-N-propyl-cinnoline-3-carboxamide;
4-amino-7-chloro-8-(2,5-dimethylphenyl)-N-propyl-cinnoline-3-carboxamide;
4-amino-8-(2,4-dimethoxypyrimidin-5-yl)-N-propyl-cinnoline-3-carboxamide;
4-amino-8-(5-methoxy-3-pyridyl)-N-propyl-cinnoline-3-carboxamide;
4-amino-8-(2-methoxypyrimidin-5-yl)-N-propyl-cinnoline-3-carboxamide;
4-amino-8-(3-fluoro-2-methoxy-phenyl)-N-propyl-cinnoline-3-carboxamide;
4-amino-8-[4-methoxy-2-(trifluoromethyl)phenyl]-N-propyl-cinnoline-3-carboxamide;
4-amino-8-(2,5-difluoro-4-methoxy-phenyl)-N-propyl-cinnoline-3-carboxamide;
4-amino-8-(5-fluoro-6-methoxy-3-pyridyl)-N-propyl-cinnoline-3-carboxamide;
4-amino-8-(5-chloro-6-methoxy-3-pyridyl)-N-propyl-cinnoline-3-carboxamide;
4-amino-8-(3,5-dichlorophenyl)-N-propyl-cinnoline-3-carboxamide;
4-amino-8-(3,5-difluorophenyl)-N-propyl-cinnoline-3-carboxamide;
4-amino-8-(5-azetidin-1-ylcarbonyl-3-pyridyl)-N-propyl-cinnoline-3-carboxamide;
4-amino-8-(2,3-dimethoxyphenyl)-N-propyl-cinnoline-3-carboxamide;
4-amino-8-(4-dimethylaminophenyl)-N-propyl-cinnoline-3-carboxamide;
4-amino-8-(3-methoxyphenyl)-N-propyl-cinnoline-3-carboxamide;
4-amino-8-(3,4-dimethoxyphenyl)-N-propyl-cinnoline-3-carboxamide;
4-amino-8-(2,5-dimethoxyphenyl)-N-propyl-cinnoline-3-carboxamide;
4-amino-8-(3,5-dimethoxyphenyl)-N-propyl-cinnoline-3-carboxamide;
4-amino-8-(2,4-dimethoxyphenyl)-N-propyl-cinnoline-3-carboxamide;
4-amino-8-(2-fluoro-3-pyridyl)-N-propyl-cinnoline-3-carboxamide;
4-amino-8-(2,3-difluorophenyl)-N-propyl-cinnoline-3-carboxamide;
4-amino-8-(2,3-dichlorophenyl)-N-propyl-cinnoline-3-carboxamide;
4-amino-N-propyl-8-(6-quinolyl)cinnoline-3-carboxamide;
4-amino-N-propyl-8-(3-quinolyl)cinnoline-3-carboxamide;
4-amino-8-(2-naphthyl)-N-propyl-cinnoline-3-carboxamide;
4-amino-8-(1H-indol-5-yl)-N-propyl-cinnoline-3-carboxamide;
4-amino-8-(4-methoxy-3-pyridyl)-N-propyl-cinnoline-3-carboxamide;
4-amino-8-(3-dimethylaminophenyl)-N-propyl-cinnoline-3-carboxamide;
4-amino-N-propyl-8-(3,4,5-trimethoxyphenyl)-cinnoline-3-carboxamide;
4-amino-8-(2,4-difluorophenyl)-N-propyl-cinnoline-3-carboxamide;
4-amino-8-(3,4-difluorophenyl)-N-propyl-cinnoline-3-carboxamide;
4-amino-N-propyl-8-(2,3,4-trimethoxyphenyl)-cinnoline-3-carboxamide;
4-amino-8-(2-methoxy-3-pyridyl)-N-propyl-cinnoline-3-carboxamide;
4-amino-8-(2,6-dimethoxy-3-pyridyl)-N-propyl-cinnoline-3-carboxamide;
4-amino-8-(2,5-dimethylphenyl)-N-propyl-cinnoline-3-carboxamide;
3-[4-amino-3-(propylcarbamoyl)cinnolin-8-yl]benzoic acid;
4-amino-8-(3-azetidin-1-ylcarbonylphenyl)-N-propyl-cinnoline-3-carboxamide;
4-amino-N-propyl-8-pyrazin-2-yl-cinnoline-3-carboxamide;
4-amino-N-propyl-8-(3-pyridyl)cinnoline-3-carboxamide;
4-amino-8-(3-methylsulfonylphenyl)-N-propyl-cinnoline-3-carboxamide;
4-amino-8-(3-cyanophenyl)-N-propyl-cinnoline-3-carboxamide;
4-amino-N-propyl-8-(2-pyridyl)cinnoline-3-carboxamide;
4-amino-8-[3,5-bis(trifluoromethyl)phenyl]-N-propyl-cinnoline-3-carboxamide;
4-amino-N-propyl-8-(1H-pyrazol-4-yl)cinnoline-3-carboxamide;

4-amino-8-[2-chloro-5-(trifluoromethyl)phenyl]-N-propyl-cinnoline-3-carboxamide;
4-amino-8-(2-methoxy-5-methyl-phenyl)-N-propyl-cinnoline-3-carboxamide;
4-amino-N-propyl-8-[2-(trifluoromethyl)phenyl]-cinnoline-3-carboxamide;
4-amino-8-(5-chloro-2-methoxy-phenyl)-N-propyl-cinnoline-3-carboxamide;
4-amino-N-propyl-8-(4-pyridyl)cinnoline-3-carboxamide;
4-amino-8-(2,5-dichlorophenyl)-N-propyl-cinnoline-3-carboxamide;
4-amino-8-(2,5-difluorophenyl)-N-propyl-cinnoline-3-carboxamide;
4-amino-8-(1-methyl-1H-pyrazol-4-yl)-N-propyl-cinnoline-3-carboxamide;
4-amino-8-(2-fluoro-3-methoxy-phenyl)-N-propyl-cinnoline-3-carboxamide;
4-amino-8-(2,5-dimethyl-2H-pyrazol-3-yl)-N-propyl-cinnoline-3-carboxamide;
4-amino-8-[2-fluoro-5-(trifluoromethyl)phenyl]-N-propyl-cinnoline-3-carboxamide;
4-amino-8-(2-fluoro-5-methyl-phenyl)-N-propyl-cinnoline-3-carboxamide;
4-amino-8-(2-fluoro-4-methyl-phenyl)-N-propyl-cinnoline-3-carboxamide;
4-amino-8-(5-fluoro-2-methyl-phenyl)-N-propyl-cinnoline-3-carboxamide;
4-amino-8-(4-fluoro-2-methoxy-phenyl)-N-propyl-cinnoline-3-carboxamide;
4-amino-8-(3-fluoro-4-methoxy-phenyl)-N-propyl-cinnoline-3-carboxamide;
4-amino-8-(2-fluoro-6-methoxy-phenyl)-N-propyl-cinnoline-3-carboxamide;
4-amino-8-(2-fluoro-5-methoxy-phenyl)-N-propyl-cinnoline-3-carboxamide;
4-amino-8-(5-fluoro-2-methoxy-phenyl)-N-propyl-cinnoline-3-carboxamide;
4-amino-8-(4-methoxyphenyl)-N-propyl-cinnoline-3-carboxamide;
4-amino-8-(4-fluorophenyl)-N-propyl-cinnoline-3-carboxamide;
4-amino-N-propyl-8-[4-(trifluoromethoxy)phenyl]-cinnoline-3-carboxamide;
4-amino-N-propyl-8-[3-(trifluoromethoxy)phenyl]-cinnoline-3-carboxamide;
4-amino-8-(6-methoxy-3-pyridyl)-N-propyl-cinnoline-3-carboxamide;
4-amino-8-(4-methoxy-3,5-dimethyl-phenyl)-N-propyl-cinnoline-3-carboxamide;
4-amino-8-(4-methoxy-3-methyl-phenyl)-N-propyl-cinnoline-3-carboxamide;
4-amino-8-(2-fluoro-4-methoxy-phenyl)-N-propyl-cinnoline-3-carboxamide;
4-amino-8-(6-methylpyridin-3-yl)-N-propylcinnoline-3-carboxamide;
4-amino-8-(4-methylpyridin-3-yl)-N-propylcinnoline-3-carboxamide;
4-amino-8-(5-methoxy-2-methylphenyl)-N-propylcinnoline-3-carboxamide; and
4-Amino-8-(2,4-dimethoxyphenyl)-7-fluoro-N-propylcinnoline-3-carboxamide;

or a pharmaceutically acceptable salt thereof, or any subgroup thereof

In some embodiments, the present invention provides the following compounds: 4-amino-8-(2,4-dimethoxypyrimidin-5-yl)-N-propyl-cinnoline-3-carboxamide; 4-amino-8-(2,5-dimethoxyphenyl)-N-propyl-cinnoline-3-carboxamide;
4-amino-8-(4-methoxy-3-pyridyl)-N-propyl-cinnoline-3-carboxamide; and 4-amino-8-(2-methoxy-5-methyl-phenyl)-N-propyl-cinnoline-3-carboxamide; or a pharmaceutically acceptable salt thereof, or any subgroup thereof.

In some embodiments, the present invention provides 4-amino-8-(2,4-dimethoxypyrimidin-5-yl)-N-propyl-cinnoline-3-carboxamide, or a pharmaceutically acceptable salt thereof, or any subgroup thereof.

In some embodiments, the present invention provides the following compounds:
4-amino-8-(3,5-dimethyl-1H-pyrazol-4-yl)-N-propyl-cinnoline-3-carboxamide;
4-amino-8-(3,5-difluoro-2-methoxyphenyl)-N-propylcinnoline-3-carboxamide;
4-amino-8-[5-(azetidin-1-ylcarbonyl)-2-methoxyphenyl]-N-propylcinnoline-3-carboxamide;
4-amino-8-(6-methoxy-2-methylpyridin-3-yl)-N-propylcinnoline-3-carboxamide;
4-amino-N-propyl-8-(1,3,5-trimethyl-1H-pyrazol-4-yl)cinnoline-3-carboxamide;
4-amino-N-propyl-8-(2,4,6-trifluoro-3-methoxyphenyl)cinnoline-3-carboxamide;
4-amino-8-(2-fluoro-5-methylpyridin-3-yl)-N-propylcinnoline-3-carboxamide;
4-amino-8-(1,3-dimethyl-1H-pyrazol-5-yl)-N-propylcinnoline-3-carboxamide;
4-amino-8-(2-fluoro-4,6-dimethoxyphenyl)-N-propylcinnoline-3-carboxamide;
4-amino-8-(3,5-difluoro-2-methoxyphenyl)-N-propylcinnoline-3-carboxamide;
4-amino-8-(2,3-dihydro-1,4-benzodioxin-6-yl)-N-propyl-cinnoline-3-carboxamide;
4-amino-8-(4,5-difluoro-2-methoxyphenyl)-N-propylcinnoline-3-carboxamide;
4-amino-8-(1,3-benzodioxol-4-yl)-N-propylcinnoline-3-carboxamide;
4-amino-8-[5-(azetidin-1-ylcarbonyl)-2-methylphenyl]-N-propylcinnoline-3-carboxamide;
4-amino-8-(6-methoxy-4-methylpyridin-3-yl)-N-propylcinnoline-3-carboxamide;
4-amino-7-chloro-8-(4-methoxypyridin-3-yl)-N-propylcinnoline-3-carboxamide;
4-amino-7-fluoro-8-(4-methoxypyridin-3-yl)-N-propylcinnoline-3-carboxamide;
4-amino-7-chloro-8-(2-methoxy-5-methylphenyl)-N-propylcinnoline-3-carboxamide;
4-amino-7-fluoro-8-(2-methoxy-5-methylphenyl)-N-propylcinnoline-3-carboxamide;
4-amino-8-(2,5-dimethoxyphenyl)-7-chloro-N-propylcinnoline-3-carboxamide;
4-amino-8-(2,5-dimethoxyphenyl)-7-fluoro-N-propylcinnoline-3-carboxamide;
4-amino-8-(2,4-dimethoxypyrimidin-5-yl)-7-chloro-N-propylcinnoline-3-carboxamide;
4-amino-8-(2,4-dimethoxypyrimidin-5-yl)-7-fluoro-N-propylcinnoline-3-carboxamide;
4-amino-N-butyl-8-(4-methoxypyridin-3-yl)cinnoline-3-carboxamide;
4-amino-N-ethyl-8-(4-methoxypyridin-3-yl)cinnoline-3-carboxamide;
4-amino-8-(4-methoxypyridin-3-yl)-N-methylcinnoline-3-carboxamide;
4-amino-N-butyl-8-(2-methoxy-5-methylphenyl)cinnoline-3-carboxamide;
4-amino-N-ethyl-8-(2-methoxy-5-methylphenyl)cinnoline-3-carboxamide;

4-amino-8-(2-methoxy-5-methylphenyl)-N-methylcinnoline-3-carboxamide;
4-amino-N-butyl-8-(2,5-dimethoxyphenyl)cinnoline-3-carboxamide;
4-amino-8-(2,5-dimethoxyphenyl)-N-ethylcinnoline-3-carboxamide;
4-amino-8-(2,5-dimethoxyphenyl)-N-methylcinnoline-3-carboxamide;
4-amino-N-butyl-8-(2,4-dimethoxypyrimidin-5-yl)cinnoline-3-carboxamide;
4-amino-8-(2,4-dimethoxypyrimidin-5-yl)-N-ethylcinnoline-3-carboxamide;
4-amino-8-(2,4-dimethoxypyrimidin-5-yl)-N-methylcinnoline-3-carboxamide;
4-amino-8-(4-methoxypyridin-3-yl)-N-(tetrahydrofuran-2-ylmethyl)cinnoline-3-carboxamide;
4-amino-N-isobutyl-8-(4-methoxypyridin-3-yl)cinnoline-3-carboxamide;
4-amino-N-(2-hydroxypropyl)-8-(4-methoxypyridin-3-yl)cinnoline-3-carboxamide;
4-amino-8-(2-methoxy-5-methylphenyl)-N-(tetrahydrofuran-2-ylmethyl)cinnoline-3-carboxamide;
4-amino-N-isobutyl-8-(2-methoxy-5-methylphenyl)cinnoline-3-carboxamide;
4-amino-N-(2-hydroxypropyl)-8-(2-methoxy-5-methylphenyl)cinnoline-3-carboxamide;
4-amino-8-(2,5-dimethoxyphenyl)-N-(tetrahydrofuran-2-ylmethyl)cinnoline-3-carboxamide;
4-amino-8-(2,5-dimethoxyphenyl)-N-isobutylcinnoline-3-carboxamide;
4-amino-8-(2,5-dimethoxyphenyl)-N-(2-hydroxypropyl)cinnoline-3-carboxamide;
4-amino-8-(2,4-dimethoxypyrimidin-5-yl)-N-(tetrahydrofuran-2-ylmethyl)cinnoline-3-carboxamide;
4-amino-8-(2,4-dimethoxypyrimidin-5-yl)-N-isobutylcinnoline-3-carboxamide; and
4-amino-8-(2,4-dimethoxypyrimidin-5-yl)-N-(2-hydroxypropyl)cinnoline-3-carboxamide;

or a pharmaceutically acceptable salt thereof, or any subgroup thereof

In some embodiments, the present invention provides the following compounds:
4-amino-8-(2,3-dimethylphenyl)-N-propyl-cinnoline-3-carboxamide;
4-amino-8-(3,5-dimethylphenyl)-N-propyl-cinnoline-3-carboxamide;
4-amino-8-(2,4-dimethylphenyl)-N-propyl-cinnoline-3-carboxamide;
4-amino-8-(3,4-dimethylphenyl)-N-propyl-cinnoline-3-carboxamide;
4-amino-N-(cyclopropylmethyl)-8-phenyl-cinnoline-3-carboxamide;
4-amino-N-propyl-8-(p-tolyl)cinnoline-3-carboxamide;
4-amino-8-(3-chlorophenyl)-N-propyl-cinnoline-3-carboxamide;
4-amino-8-(4-chlorophenyl)-N-propyl-cinnoline-3-carboxamide;
4-amino-8-(o-tolyl)-N-propyl-cinnoline-3-carboxamide;
4-amino-8-(m-tolyl)-N-propyl-cinnoline-3-carboxamide;
4-amino-N-propyl-8-(3-thienyl)cinnoline-3-carboxamide; and
4-amino-8-(2,6-dimethylphenyl)-N-propyl-cinnoline-3-carboxamide;

or a pharmaceutically acceptable salt thereof, or any subgroup thereof.

Compounds of the present invention also include pharmaceutically acceptable salts, tautomers and in vivo-hydrolysable precursors of the compounds of any of the formulas described herein. Compounds of the invention further include hydrates and solvates.

Compounds of the invention can be used as medicaments. In some embodiments, the present invention provides compounds of any of the formulas described herein, or pharmaceutically acceptable salts, tautomers or in vivo-hydrolysable precursors thereof, for use as medicaments. In some embodiments, the present invention provides compounds described herein for use as medicaments for treating or preventing an anxiety disorder, cognitive disorder, or mood disorder.

In some embodiments, the present invention provides compounds of any of the formulas described herein, or pharmaceutically acceptable salts, tautomers or in vivo-hydrolysable precursors thereof, in the manufacture of a medicament for the treatment or prophylaxis of an anxiety disorder, cognitive disorder, or mood disorder.

In some embodiments, the present invention provides a method for the treatment or prophylaxis of an anxiety disorder comprising administering to a mammal (including a human) a therapeutically effective amount of a compound of any of the formulas described herein, or a pharmaceutically acceptable salt, tautomer or in vivo-hydrolysable precursor thereof As used herein, the phrase "anxiety disorder" includes, but is not limited to, one or more of the following: panic disorder, panic disorder without agoraphobia, panic disorder with agoraphobia, agoraphobia without history of panic disorder, specific phobia, social phobia, social anxiety disorder, obsessive-compulsive disorder, posttraumatic stress disorder, acute stress disorder, generalized anxiety disorder, generalized anxiety disorder due to a general medical condition, and the like.

In some embodiments, the present invention provides a method for the treatment or prophylaxis of a cognitive disorder comprising administering to a mammal (including a human) a therapeutically effective amount of a compound of any of the formulas described herein, or a pharmaceutically acceptable salt, tautomer or in vivo-hydrolysable precursor thereof As used herein, the phrase "cognitive disorder" includes, but is not limited to, one or more of the following: Alzheimer's disease, dementia, dementia due to Alzheimer's disease, dementia due to Parkinson's disease, and the like.

In some embodiments, the present invention provides a method for the treatment or prophylaxis of a mood disorder comprising administering to a mammal (including a human) a therapeutically effective amount of a compound of any of the formulas described herein, or a pharmaceutically acceptable salt, tautomer or in vivo-hydrolysable precursor thereof As used herein, the phrase "mood disorder" is a depressive disorder including, but not limited to, one or more of the following: major depressive disorder, dysthymic disorder, bipolar depression and/or bipolar mania, bipolar I with or without manic, depressive or mixed episodes, bipolar II, cyclothymic disorder, mood disorder due to a general medical condition, manic episodes associated with bipolar disorder, mixed episodes associated with bipolar disorder, and the like.

Anxiety disorders, cognitive disorders, and mood disorders are defined, for example, in the American Psychiatric Association: Diagnostic and Statistical Manual of Mental Disorders, Fourth Edition, Text Revision, Washington, D.C., American Psychiatric Association, 2000.

In some embodiments, the present invention provides a method of treating or preventing an anxiety disorder, cognitive disorder, or mood disorder (such as any of those described herein), by administering to a mammal (including a human) a compound of any of the formulas described herein or a pharmaceutically acceptable salt, tautomer or in vivo-hydrolysable precursors and a cognitive and/or memory enhancing agent.

In some embodiments, the present invention provides a method of treating or preventing an anxiety disorder, cognitive disorder, or mood disorder (such as any of those described herein), by administering to a mammal (including a human) a compound of any of the formulas described herein or a pharmaceutically acceptable salt, tautomer or in vivo-hydrolysable precursors thereof wherein constituent members are provided herein, and a choline esterase inhibitor or anti-inflammatory agent.

In some embodiments, the present invention provides a method of treating or preventing an anxiety disorder, cognitive disorder, or mood disorder (such as any of those described herein), by administering to a mammal (including human) a compound of the present invention, and an atypical antipsychotic agent. Atypical antipsychotic agents include, but are not limited to, Olanzapine (marketed as Zyprexa), Aripiprazole (marketed as Abilify), Risperidone (marketed as Risperdal), Quetiapine (marketed as Seroquel), Clozapine (marketed as Clozaril), Ziprasidone (marketed as Geodon) and Olanzapine/Fluoxetine (marketed as Symbyax).

In some embodiments, the mammal or human being treated with a compound of the present invention, has been diagnosed with a particular disease or disorder, such as those described herein. In these cases, the mammal or human being treated is in need of such treatment. Diagnosis, however, need not be previously performed.

The present invention also includes pharmaceutical compositions which contain, as the active ingredient, one or more of the compounds of the invention herein together with at least one pharmaceutically acceptable carrier, diluent or excipient.

When used for pharmaceutical compositions, medicaments, manufacture of a medicament, or treating or preventing an anxiety disorder, cognitive disorder, or mood disorder (such as any of those described herein), compounds of the present invention include the compounds of any of the formulas described herein, and pharmaceutically acceptable salts, tautomers and in vivo-hydrolysable precursors thereof Compounds of the present invention further include hydrates and solvates.

The definitions set forth in this application are intended to clarify terms used throughout this application. The term "herein" means the entire application.

As used in this application, the term "optionally substituted," as used herein, means that substitution is optional and therefore it is possible for the designated atom or moiety to be unsubstituted. In the event a substitution is desired then such substitution means that any number of hydrogens on the designated atom or moiety is replaced with a selection from the indicated group, provided that the normal valency of the designated atom or moiety is not exceeded, and that the substitution results in a stable compound. For example, if a methyl group (i.e., $CH_3$) is optionally substituted, then 3 hydrogens on the carbon atom can be replaced. Examples of suitable substituents include, but are not limited to: halogen, CN, $NH_2$, OH, SO, $SO_2$, COOH, $OC_{1-6}$alkyl, $CH_2OH$, $SO_2H$, $C_{1-6}$alkyl, $OC_{1-6}$alkyl, $C(=O)C_{1-6}$alkyl, $C(=O)OC_{1-6}$alkyl, $C(=O)NH_2$, $C(=O)NHC_{1-6}$alkyl, $C(=O)N(C_{1-6}$alkyl$)_2$, $SO_2C_{1-6}$alkyl, $SO_2NHC_{1-6}$alkyl, $SO_2N(C_{1-6}$alkyl$)_2$, $NH(C_{1-6}$alkyl), $N(C_{1-6}$alkyl$)_2$, $NHC(=O)C_{1-6}$alkyl, $NC(=O)(C_{1-6}$alkyl$)_2$, $C_{5-6}$aryl, $OC_{5-6}$aryl, $C(=O)C_{5-6}$aryl, $C(=O)OC_{5-6}$aryl, $C(=O)NHC_{5-6}$aryl, $C(=O)N(C_{5-6}$aryl$)_2$, $SO_2C_{5-6}$aryl, $SO_2NHC_{5-6}$aryl, $SO_2N(C_{5-6}$aryl$)_2$, $NH(C_{5-6}$aryl), $N(C_{5-6}$aryl$)_2$, $NC(=O)C_{5-6}$aryl, $NC(=O)(C_{5-6}$aryl$)_2$, $C_{5-6}$heterocyclyl, $OC_{5-6}$heterocyclyl, $C(=O)C_{5-6}$heterocyclyl, $C(=O)OC_{5-6}$heterocyclyl, $C(=O)NHC_{5-6}$heterocyclyl, $C(=O)N(C_{5-6}$heterocyclyl$)_2$, $SO_2C_{5-6}$heterocyclyl, $SO_2NHC_{5-6}$heterocyclyl, $SO_2N(C_{5-6}$heterocyclyl$)_2$, $NH(C_{5-6}$heterocyclyl), $N(C_{5-6}$heterocyclyl$)_2$, $NC(=O)C_{5-6}$heterocyclyl, $NC(=O)(C_{5-6}$heterocyclyl$)_2$.

A variety of compounds in the present invention may exist in particular stereoisomeric forms. The present invention takes into account all such compounds, including cis- and trans isomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. When required, separation of the racemic material can be achieved by methods known in the art. Many stereoisomers of olefins, C=N double bonds, and the like can also be present in the compounds described herein, and all such stable isomers are contemplated in the present invention. Cis and trans isomers of the compounds of the present invention are described and may be isolated as a mixture of isomers or as separated isomeric forms. All chiral, diastereomeric, racemic forms and all stereoisomeric forms of a structure are intended, unless the specific stereochemistry or isomeric form is specifically indicated.

The compounds of the invention may form isolable atropisomers in certain solvents (e.g. supercritical $CO_2$ containing 25-35% methanol) at room temperature. The atropisomers of the compounds may be isolated using chiral LC. All atropisomers of a structure are intended, unless the specific atropisomer is specifically indicated.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The term "$C_{m-n}$" or "$C_{m-n}$ group" used alone or as a prefix, refers to any group having m to n carbon atoms.

The term "alkyl" used alone or as a suffix or prefix, refers to a saturated monovalent straight or branched chain hydrocarbon radical comprising 1 to about 12 carbon atoms. Illustrative examples of alkyls include, but are not limited to, $C_{1-6}$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl.

The term "alkylene" used alone or as suffix or prefix, refers to divalent straight or branched chain hydrocarbon radicals comprising 1 to about 12 carbon atoms, which serves to links two structures together.

As used herein, "alkenyl" refers to an alkyl group having one or more double carbon-carbon bonds. Example alkenyl groups include ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include ethynyl, propynyl, and the like. The term "alkynylenyl" refers to a divalent linking alkynyl group.

As used herein, "aromatic" refers to hydrocarbyl groups having one or more polyunsaturated carbon rings having aromatic characters, (e.g., 4n+2 delocalized electrons) and comprising up to about 14 carbon atoms.

As used herein, the term "aryl" refers to an aromatic ring structure made up of from 5 to 14 carbon atoms. Ring structures containing 5, 6, 7 and 8 carbon atoms would be single-ring aromatic groups, for example, phenyl. Ring structures containing 8, 9, 10, 11, 12, 13, or 14 would be a polycyclic moiety in which at least one carbon is common to any two adjoining rings therein (for example, the rings are "fused rings"), for example naphthyl. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls or cycloalkynyls. The terms ortho, meta and para apply to 1,2-, 1,3- and 1,4-disubstituted benzenes, respectively. For example, the names 1,2-dimethylbenzene and ortho-dimethylbenzene are synonymous.

The term "cycloalkyl," used alone or as suffix or prefix, refers to a saturated monovalent ring-containing hydrocarbon radical comprising at least 3 up to about 12 carbon atoms. Examples of cycloalkyls include, but are not limited to, $C_{3-7}$cycloalkyl groups, such as cyclopropyl, cyclobutyl, cyclopentyl, cyclohexyl, and cycloheptyl, and saturated cyclic and bicyclic terpenes. A cycloalkyl can be unsubstituted or substituted by one or two suitable substituents. Preferably, the cycloalkyl is a monocyclic ring or bicyclic ring.

As used herein, "cycloalkenyl" refers to ring-containing hydrocarbyl groups having at least one carbon-carbon double bond in the ring, and having from 3 to 12 carbons atoms.

As used herein, "halo" or "halogen" refers to fluoro, chloro, bromo, and iodo. "Counterion" is used to represent a small, negatively or positively charged species such as chloride ($Cl^-$), bromide ($Br^-$), hydroxide ($OH^-$), acetate ($CH_3COO^-$), sulfate ($SO_4^{2-}$), tosylate ($CH_3$-phenyl-$SO_3^-$), benezensulfonate (phenyl-$SO_3^-$), sodium ion ($Na^+$), potassium ($K^+$), ammonium ($NH_4^+$), and the like.

The term "heterocycle" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heteroaromatic" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s), wherein the ring-containing structure or molecule has an aromatic character (e.g., 4n+2 delocalized electrons).

The term "heterocyclic group," "heterocyclic moiety," "heterocyclic," or "heterocyclo" used alone or as a suffix or prefix, refers to a radical derived from a heterocycle by removing one or more hydrogens therefrom.

The term "heterocyclyl" used alone or as a suffix or prefix, refers a monovalent radical derived from a heterocycle by removing one hydrogen therefrom.

The term "heterocyclylene" used alone or as a suffix or prefix, refers to a divalent radical derived from a heterocycle by removing two hydrogens therefrom, which serves to links two structures together.

The term "heteroaryl" used alone or as a suffix or prefix, refers to a heterocyclyl having aromatic character.

The term "heterocylcoalkyl" used alone or as a suffix or prefix, refers to a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 6 carbon atoms and form 1 to 3 heteroatoms, referred to herein as $C_{3-6}$ heterocycloalkyl.

The term "heteroarylene" used alone or as a suffix or prefix, refers to a heterocyclylene having aromatic character.

The term "heterocycloalkylene" used alone or as a suffix or prefix, refers to a heterocyclylene that does not have aromatic character.

The term "six-membered" used as prefix refers to a group having a ring that contains six ring atoms.

The term "five-membered" used as prefix refers to a group having a ring that contains five ring atoms.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

Examples of heterocyclyls include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azabicyclo, azetidine, azepane, aziridine, azocinyl, benzimidazolyl, benzodioxol, benzofuranyl, benzothiofuranyl, benzothiophenyl, benzoxazolyl, benzthiazolyl, benzotriazolyl, benzotetrazolyl, benzisoxazolyl, benzisothiazolyl, benzimidazalonyl, carbazolyl, 4aH-carbazolyl, b-carbolinyl, chromanyl, chromenyl, cinnolinyl, diazepane, decahydroquinolinyl, 2H,6H-1,5,2-dithiazinyl, dioxolane, furyl, 2,3-dihydrofuran, 2,5-dihydrofuran, dihydrofuro[2,3-b]tetrahydrofuran, furanyl, furazanyl, homopiperidinyl, imidazolidine, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxirane, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, purinyl, pyranyl, pyrrolidinyl, pyrroline, pyrrolidine, pyrazinyl, pyrazolidinyl, pyrazolinyl, pyrazolyl, pyridazinyl, pyridooxazole, pyridoimidazole, pyridothiazole, pyridinyl, N-oxide-pyridinyl, pyridyl, pyrimidinyl, pyrrolidinyl, pyrrolidinyl dione, pyrrolinyl, pyrrolyl, pyridine, quinazolinyl, quinolinyl, 4H-quinolizinyl, quinoxalinyl, quinuclidinyl, carbolinyl, tetrahydrofuranyl, tetramethylpiperidinyl, tetrahydroquinoline, tetrahydroisoquinolinyl, thiophane, thiotetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiopheneyl, thiirane, triazinyl, 1,2,3-triazolyl, 1,2,4-triazolyl, 1,2,5-triazolyl, 1,3,4-triazolyl, xanthenyl.

As used herein, "alkoxy" or "alkyloxy" represents an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

"Halogenated," used as a prefix of a group, means one or more hydrogens on the group is replaced with one or more halogens.

As used herein, the term "carbonyl" is art recognized and includes the —C(=O) groups of such moieties as can be represented by the general formula:

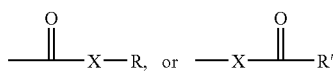

wherein X is a bond or represents an oxygen or sulfur, and R represents a hydrogen, an alkyl, an alkenyl, —$(CH_2)_m$—R" or a pharmaceutically acceptable salt, R' represents a hydrogen, an alkyl, an alkenyl or —$(CH_2)_m$—R", where m is an integer less than or equal to ten, and R" is alkyl, cycloalkyl, alkenyl, aryl, or heteroaryl. Where X is an oxygen and R and R' is not hydrogen, the formula represents an "ester". Where X is an oxygen, and R is as defined above, the moiety is referred to herein as a carboxyl group, and particularly when R' is a hydrogen, the formula represents a "carboxylic acid." Where X is oxygen, and R' is a hydrogen, the formula represents a "formate." In general, where the oxygen atom of the above formula is replaced by sulfur, the formula represents a "thiolcarbonyl" group. Where X is a sulfur and R and R' is not hydrogen, the formula represents a "thiolester." Where X is sulfur and R is hydrogen, the formula represents a "thiolcarboxylic acid." Where X is sulfur and R' is hydrogen, the formula represents a "thiolformate." On the other hand, where X is a bond, and R is not a hydrogen, the above formula represents a "ketone" group. Where X is a bond, and R is hydrogen, the above formula is represents an "aldehyde" group.

As used herein, the term "sulfonyl" refers to the —S(=O)$_2$— of a moiety that can be represented by the general formula:

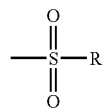

wherein R is represented by but not limited to hydrogen, alkyl, cycloalkyl, alkenyl, aryl, heteroaryl, aralkyl, or heteroaralkyl.

As used herein, some substituents are described in a combination of two or more groups. For example, the expression of "C(=O)C$_{3-9}$cycloalkylR$^d$" is meant to refer to a structure:

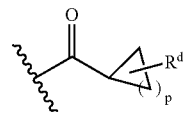

wherein p is 1, 2, 3, 4, 5, 6 or 7 (i.e., C$_{3-9}$cycloalkyl); the C$_{3-9}$cycloalkyl is substituted by R$^d$; and the point of attachment of the "C(=O)C$_{3-9}$cycloalkylR$^d$" is through the carbon atom of the carbonyl group, which is on the left of the expression.

As used herein, the phrase "protecting group" means temporary substituents which protect a potentially reactive functional group from undesired chemical transformations. Examples of such protecting groups include esters of carboxylic acids, silyl ethers of alcohols, and acetals and ketals of aldehydes and ketones respectively. The field of protecting group chemistry has been reviewed (Greene, T. W.; Wuts, P. G. M. *Protective Groups in Organic Synthesis*, 3$^{rd}$ ed.; Wiley: New York, 1999).

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof (i.e., also include counterions). Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, phosphoric, and the like; and the salts prepared from organic acids such as lactic, maleic, citric, benzoic, methanesulfonic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; nonaqueous media like ether, ethyl acetate, ethanol, isopropanol, or acetonitrile can be used.

As used herein, "in vivo hydrolysable precursors" means an in vivo hydroysable (or cleavable) ester of a compound of any of the formulas described herein that contains a carboxy or a hydroxy group. For example amino acid esters, $C_{1-6}$ alkoxymethyl esters like methoxymethyl; $C_{1-6}$ alkanoyloxymethyl esters like pivaloyloxymethyl; $C_{3-8}$cycloalkoxycarbonyloxy $C_{1-6}$alkyl esters like 1-cyclohexylcarbonyloxyethyl, acetoxymethoxy, or phosphoramidic cyclic esters.

As used herein, "tautomer" means other structural isomers that exist in equilibrium resulting from the migration of a hydrogen atom. For example, keto-enol tautomerism where the resulting compound has the properties of both a ketone and an unsaturated alcohol.

As used herein "stable compound" and "stable structure" are meant to indicate a compound that is sufficiently robust to survive isolation to a useful degree of purity from a reaction mixture, and formulation into an efficacious therapeutic agent.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radiolabeled compounds will depend on the specific application of that radio-labeled compound. For example, for in vitro receptor labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

The antidementia treatment defined herein may be applied as a sole therapy or may involve, in addition to the compound of the invention, conventional chemotherapy.

Such conjoint treatment may be achieved by way of the simultaneous, sequential or separate dosing of the individual components of the treatment. Such combination products employ the compounds of this invention.

Compounds of the present invention may be administered orally, parenteral, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of dementia is an amount sufficient to symptomatically relieve in a warm-blooded animal, particularly a human the symptoms of dementia, to slow the progression of dementia, or to reduce in patients with symptoms of dementia the risk of getting worse.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Some of the compounds of the present invention are capable of forming salts with various inorganic and organic acids and bases and such salts are also within the scope of this invention. For example, such conventional non-toxic salts include those derived from inorganic acids such as hydrochloric, phosphoric, and the like; and the salts prepared from organic acids such as lactic, maleic, citric, benzoic, methanesulfonic, trifluoroacetate and the like.

In some embodiments, the present invention provides a compound of any of the formulas described herein or a pharmaceutically acceptable salt thereof for the therapeutic treatment (including prophylactic treatment) of mammals including humans, it is normally formulated in accordance with standard pharmaceutical practice as a pharmaceutical composition.

In addition to the compounds of the present invention, the pharmaceutical composition of this invention may also contain, or be co-administered (simultaneously or sequentially) with, one or more pharmacological agents of value in treating one or more disease conditions referred to herein.

The term composition is intended to include the formulation of the active component or a pharmaceutically acceptable salt with a pharmaceutically acceptable carrier. For example this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975.

The compounds of the invention may be derivatised in various ways. As used herein "derivatives" of the compounds includes salts (e.g. pharmaceutically acceptable salts), any complexes (e.g. inclusion complexes or clathrates with compounds such as cyclodextrins, or coordination complexes with metal ions such as $Mn^{2+}$ and $Zn^{2+}$), esters such as in vivo hydrolysable esters, free acids or bases, polymorphic forms of the compounds, solvates (e.g. hydrates), prodrugs or lipids, coupling partners and protecting groups. By "prodrugs" is meant for example any compound that is converted in vivo into a biologically active compound.

Salts of the compounds of the invention are preferably physiologically well tolerated and non toxic. Many examples of salts are known to those skilled in the art. All such salts are within the scope of this invention, and references to compounds include the salt forms of the compounds.

Compounds having acidic groups, such as carboxylate, phosphates or sulfates, can form salts with alkaline or alkaline earth metals such as Na, K, Mg and Ca, and with organic amines such as triethylamine and Tris (2-hydroxyethyl) amine. Salts can be formed between compounds with basic groups, e.g. amines, with inorganic acids such as hydrochloric acid, phosphoric acid or sulfuric acid, or organic acids such as acetic acid, citric acid, benzoic acid, fumaric acid, or tartaric acid. Compounds having both acidic and basic groups can form internal salts.

Acid addition salts may be formed with a wide variety of acids, both inorganic and organic. Examples of acid addition salts include salts formed with hydrochloric, hydriodic, phosphoric, nitric, sulphuric, citric, lactic, succinic, maleic, malic, isethionic, fumaric, benzenesulphonic, toluenesulphonic, methanesulphonic, ethanesulphonic, naphthalenesulphonic, valeric, acetic, propanoic, butanoic, malonic, glucuronic and lactobionic acids.

If the compound is anionic, or has a functional group which may be anionic (e.g., COOH may be COO), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds contain an amine function, these may form quaternary ammonium salts, for example by reaction with an alkylating agent according to methods well known to the skilled person. Such quaternary ammonium compounds are within the scope of the invention.

Compounds containing an amine function may also form N-oxides. A reference herein to a compound that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, $4^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Esters can be formed between hydroxyl or carboxylic acid groups present in the compound and an appropriate carboxylic acid or alcohol reaction partner, using techniques well known in the art. Examples of esters are compounds containing the group C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, C(=O)OCH$_3$, C(=O)OCH$_2$CH$_3$, C(=O)OC(CH$_3$)$_3$, and —C(=O)OPh. Examples of acyloxy (reverse ester) groups are represented by OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, OC(=O)CH$_3$ (acetoxy), OC(=O)CH$_2$CH$_3$, OC(=O)C(CH$_3$)$_3$, OC(=O)Ph, and OC(=O)CH$_2$Ph.

Derivatives which are prodrugs of the compounds are convertible in vivo or in vitro into one of the parent compounds.

Typically, at least one of the biological activities of compound will be reduced in the prodrug form of the compound, and can be activated by conversion of the prodrug to release the compound or a metabolite of it. Some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is: $C_{1-7}$alkyl (e.g., Me, Et, -nPr, -iPr, -nBu, -sBu, -iBu, tBu); $C_{1-7}$aminoalkyl (e.g., aminoethyl; 2-(N,N-diethylamino)ethyl; 2(4morpholino)ethyl); and acyloxy-$C_{1-7}$alkyl (e.g., acyloxymethyl; acyloxyethyl; pivaloyloxymethyl; acetoxymethyl; 1acetoxyethyl; 1-(1-methoxy-1-methyl)ethyl-carbonyloxyethyl; 1-(benzoyloxy)ethyl; isopropoxy-carbonyloxymethyl; 1isopropoxy-carbonyloxyethyl; cyclohexyl-carbonyloxymethyl; 1cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1(4tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Other derivatives include coupling partners of the compounds in which the compounds is linked to a coupling partner, e.g. by being chemically coupled to the compound or physically associated with it. Examples of coupling partners include a label or reporter molecule, a supporting substrate, a carrier or transport molecule, an effector, a drug, an antibody or an inhibitor. Coupling partners can be covalently linked to compounds of the invention via an appropriate functional group on the compound such as a hydroxyl group, a carboxyl group or an amino group. Other derivatives include formulating the compounds with liposomes.

Where the compounds contain chiral centres, all individual optical forms such as enantiomers, epimers, atropisomers and diastereoisomers, as well as racemic mixtures of the compounds are within the scope of the invention.

Compounds may exist in a number of tautomeric forms and references to compounds include all such forms. For the avoidance of doubt, where a compound can exist in one of several tautomeric forms and only one is specifically described or shown, all others are nevertheless embraced by the scope of this invention.

The quantity of the compound to be administered will vary for the patient being treated and will vary from about 100 ng/kg of body weight to 100 mg/kg of body weight per day and preferably will be from 10 pg/kg to 10 mg/kg per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

In some embodiments, the compounds described herein are central nervous system depressants and may be used as tranquilizers or ataractic agents for the relief of anxiety and tension states, for example, in mice, cats, rats, dogs and other mammalian species such as humans, in the same manner as chlordiazepoxide. For this purpose a compound or mixture of compounds of any of the formulas described herein, or non-toxic physiologically acceptable salts, such as acid addition salts thereof, may be administered orally or parenterally in a conventional dosage form such as tablet, pill, capsule, injectable or the like. The dosage in mg/kg of body weight of compounds of the present invention in mammals will vary according to the size of the animal and particularly with respect to the brain/body weight ratio. In general, a higher mg/kg dosage for a small animal such as a dog will have the same effect as a lower mg/kg dosage in an adult human. A minimum effective dosage for a compound of formula (I) will be at least about 0.1 mg/kg of body weight per day for mammals with a maximum dosage for a small mammal such as a dog, of about 100 mg/kg per day. For humans, a dosage of about 0.1 to 12 mg/kg per day will be effective, for example, about 5 to 600 mg/day for an average man. The dosage can be given once daily or in divided doses, for example, 2 to 4 doses daily, and such dosage will depend on the duration and maximum level of activity of a particular compound. The dose may be conventionally formulated in an oral or parenteral dosage form by compounding about 5 to 250 mg per unit of dosage of conventional vehicle, excipient, binder, preservative, stabilizer, flavor or the like as called for by accepted pharmaceutical practice, for example, as described in U.S. Pat. No. 3,755,340. The compounds of this invention may be used in pharmaceutical compositions comprising a compound of any of the formulas described herein or can be contained in the same formulation with or co-administered with one or more known drugs.

Some example tests that can be conducted to demonstrate the anxiolytic activity of the present compounds include binding tests of GABAA receptors. In some embodiments, the binding test was directed to a subtype of GABAA receptors, such as GABAA1 receptors (i.e., those containing the $\alpha_1$ subunit), GABAA2 receptors (i.e., those containing the $\alpha_2$ subunit), GABAA3 receptors (i.e., those containing the $\alpha_3$ subunit) and GABAA5 receptors (i.e., those containing the $\alpha_5$ subunit).

Presently available GABAA modulator anxiolytics work via interactions at the classical benzodiazepine binding site. To a large degree these anxiolytics lack GABAA receptor subtype-selectivity. The subtype-selective GABAA receptor modulators may offer more advantages. For example, a growing body of work suggests that desirable anxiolytic activity is driven primarily by interactions with GABAA receptors containing the $\alpha_2$ subunit. Sedation, a side-effect common to all marketed benzodiazepines, is believed to be mediated by interactions at GABAARs containing the $\alpha_1$ subunit. To develop anxiolytics with minimal liabilities due to interactions with other subunits, an electrophysiological assay was developed to screen modulatory effects of various compounds on different GABA subunit combinations heterologously expressed in *Xenopus* oocytes.

GABAA receptors were heterologously expressed in *Xenopus* oocytes by injecting cRNA corresponding to human $\alpha_1$, $\alpha_2$, $\alpha_3$, $\alpha_5$, $\beta_2$, $\beta_3$ and $\gamma_2$ subunits of the GABAA receptor genes. The specific subunit combinations (subtypes) were as follows: $\alpha_1\beta_2\gamma_2$, $\alpha_2\beta_3\gamma_2$, $\alpha_3\beta_3\gamma_2$, and $\alpha_5\beta_3\gamma_2$. The EC10 of GABA was approximated for each cell. Stability of GABA-mediated (EC10) current was established. Modulatory effect of test compound was determined and compared across subtypes. The assay developed has reproducibility which allows discrimination of modulatory activity down to minimal effect of about 25% potentiation (prior to normalization to standard)

for all four subtypes. Thus, the assay can characterize modulatory effects and determine subtype selectivity of test compounds on major subtypes of GABAA receptors. In some embodiments, a compound can selectively bind to one subtype of GABAA receptor (by showing about 25% or more of binding comparing to another subtype of GABAA receptor).

Anxiolytic activity is indicated in the GABAA binding test by a displacement of the flunitrazepam such as is exhibited by benzodiazepines or by enhancement of the binding such as is shown by cartazolate and tracazolate.

In some embodiments, the compounds of the invention can bind to GABAA receptors. In some embodiments, the compounds of the invention can bind to GABAA receptors by displacement of benzodiazepines. Accordingly, the compounds of the invention can be used to modulate activities of GABAA receptors. In some embodiments, the compounds of the invention can selectively bind to a subtype of GABAA receptors, such as such as GABAA1 receptors (i.e., those containing the $\alpha_1$ subunit), GABAA2 receptors (i.e., those containing the $\alpha_2$ subunit), GABAA3 receptors (i.e., those containing the $\alpha_3$ subunit) or GABAA5 receptors (i.e., those containing the $\alpha_5$ subunit). In some embodiments, the compounds of the invention can selectively bind to a subtype of GABAA receptors by displacement of benzodiazepines. Accordingly, the compounds of the invention can be used to selectively modulate activities of a subtype of GABAA receptors, such as GABAA1 receptors, GABAA2 receptors, GABAA3 receptors or GABAA5 receptors.

In some embodiments, certain compounds of the invention are GABAA1 receptor antagonists and GABAA2 receptor agonists.

Because the compounds of the invention can be used to modulate activities of GABAA receptors, or to selectively modulate activities of a subtype of GABAA receptors, the compounds of the invention are envisioned to be useful for treating or preventing diseases mediated by GABAA receptors or a subtype of GABAA receptors. Such disease, include, but is not limited to, stroke, head trauma, epilepsy, pain, migraine, mood disorders, anxiety, post traumatic stress disorder, obsessive compulsive disorders, schizophrenia, seizures, convulsions, tinnitus, neurodegenerative disorders including Alzheimer's disease, amyotrophic lateral sclerosis, Huntington's Chorea, Parkinson's disease, depression, bipolar disorders, mania, trigeminal and other neuralgia, neuropathic pain, hypertension, cerebral ischemia, cardiac arrhythmia, myotonia, substance abuse, myoclonus, essential tremor, dyskinesia and other movement disorders, neonatal cerebral hemorrhage, spasticity, cognitive disorder, and sleeping disorder.

It is known that melatonin receptor agonists are effective in treating depression. We find that the compounds of the invention can selectively modulate activities of a subtype of melatonin receptors, melatonin receptor 1 (MT-1). In certain embodiments, certain compounds of the invention are MT1 agonists. As a results, the compounds of the invention may be effective in treating depression disorders such as major depressive disorder, dysthymic disorder, bipolar depression and/or bipolar mania, bipolar I with or without manic, depressive or mixed episodes, bipolar II, cyclothymic disorder, mood disorder due to a general medical condition, manic episodes associated with bipolar disorder, or mixed episodes associated with bipolar disorder. To treat depression disorders, an effective amount of one or more compounds of the invention is administered to a patient with such a need.

In another embodiment, certain compounds of the present invention may be effective in treating insomnia.

In a further embodiment, a compound of formula I or a pharmaceutically acceptable salt, solvate or in vivo hydrolysable ester thereof, or a pharmaceutical composition or formulation comprising a compound of formula I may be administered concurrently, simultaneously, sequentially or separately with one or more pharmaceutically active compound(s) selected from the following:

(i) antidepressants such as amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robalzotan, sertraline, sibutramine, thionisoxetine, tranylcypromaine, trazodone, trimipramine, venlafaxine and equivalents and pharmaceutically active isomer(s) and metabolite(s) thereof;

(ii) atypical antipsychotics including for example quetiapine and pharmaceutically active isomer(s) and metabolite(s) thereof, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, lithium, loxapine, mesoridazine, olanzapine, paliperidone, perlapine, perphenazine, phenothiazine, phenylbutlypiperidine, pimozide, prochlorperazine, risperidone, quetiapine, sertindole, sulpiride, suproclone, suriclone, thioridazine, trifluoperazine, trimetozine, valproate, valproic acid, zopiclone, zotepine, ziprasidone and equivalents thereof;

(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutlypiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof;

(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof;

(v) anticonvulsants including, for example, carbamazepine, valproate, lamotrogine, gabapentin and equivalents and pharmaceutically active isomer(s) and metabolite(s) thereof;

(vi) Alzheimer's therapies including, for example, donepezil, memantine, tacrine and equivalents and pharmaceutically active isomer(s) and metabolite(s) thereof;

(vii) Parkinson's therapies including, for example, deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof;

(viii) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof;

(ix) stroke therapies including, for example, abciximab, activase, NXY-059, citicoline, crobenetine, desmoteplase,r-epinotan, traxoprodil and equivalents and pharmaceutically active isomer(s) and metabolite(s) thereof, (x) over active bladder urinary incontinence therapies including, for example, darafenacin, falvoxate, oxybutynin, propiverine, robalzotan, solifenacin, tolterodine and and equivalents and pharmaceutically active isomer(s) and metabolite(s) thereof;

(xi) neuropathic pain therapies including, for example, gabapentin, lidoderm, pregablin and equivalents and pharmaceutically active isomer(s) and metabolite(s) thereof;

(xii) nociceptive pain therapies such as celecoxib, etoricoxib, lumiracoxib, rofecoxib, valdecoxib, diclofenac, loxoprofen, naproxen, paracetamol and equivalents and pharmaceutically active isomer(s) and metabolite(s) thereof;

(xiii) insomnia therapies including, for example, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos,secobarbital, zaleplon, zolpidem and equivalents and pharmaceutically active isomer(s) and metabolite(s) thereof; and (xiv) mood stabilizers including, for example, carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combinations employ the compounds of this invention within the dosage range described herein and the other pharmaceutically active compound or compounds within approved dosage ranges and/or the dosage described in the publication reference.

General Procedures for Making the Compounds of the Invention is as Follows:

The invention will now be illustrated by the following non-limiting examples, in which, unless stated otherwise:

In order that the invention disclosed herein may be more efficiently understood, examples are provided below. It should be understood that these examples are for illustrative purposes only and are not to be construed as limiting the invention in any manner.

Some example compounds of the invention in table 1 were made according to the methods described herein below.

TABLE 1

| Example Number | Synthesis Method | Compound Name | Structure |
|---|---|---|---|
| 1 | F | 4-amino-7-fluoro-8-phenyl-N-propyl-cinnoline-3-carboxamide | 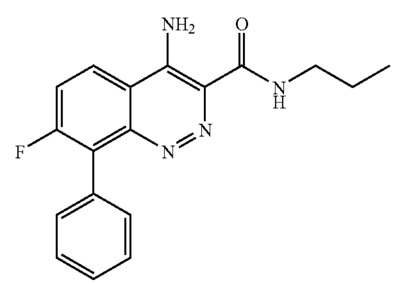 |
| 2 | F | 4-amino-7-chloro-8-phenyl-N-propyl-cinnoline-3-carboxamide | 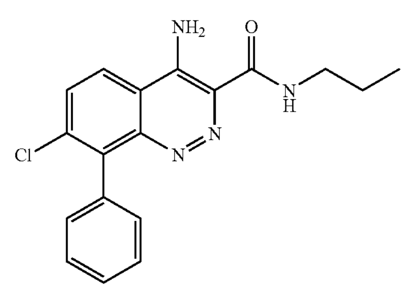 |
| 3 | F | 4-amino-7-methoxy-8-phenyl-N-propyl-cinnoline-3-carboxamide | 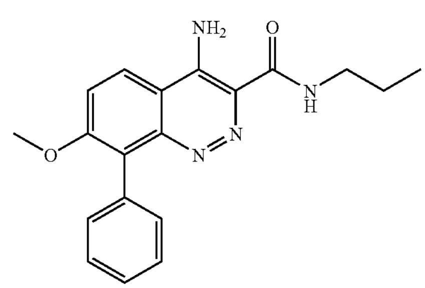 |

TABLE 1-continued

| Example Number | Synthesis Method | Compound Name | Structure |
|---|---|---|---|
| 4 | A | 4-amino-7-chloro-8-(2,5-dimethylphenyl)-N-propyl-cinnoline-3-carboxamide | 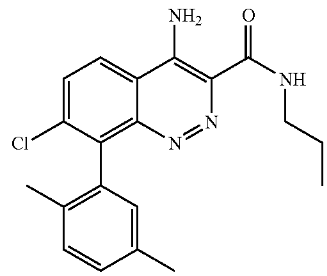 |
| 5 | A | 4-amino-8-(2,4-dimethoxy-pyrimidin-5-yl)-N-propyl-cinnoline-3-carboxamide | 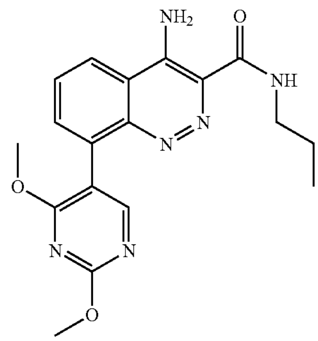 |
| 6 | A | 4-amino-8-(5-methoxy-3-pyridyl)-N-propyl-cinnoline-3-carboxamide | 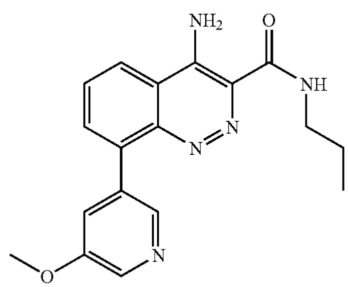 |
| 7 | A | 4-amino-8-(2-methoxy-pyrimidin-5-yl)-N-propyl-cinnoline-3-carboxamide | 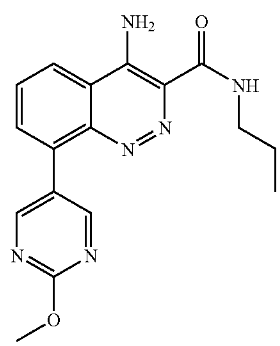 |
| 8 | A | 4-amino-8-(3-fluoro-2-methoxy-phenyl)-N-propyl-cinnoline-3-carboxamide | 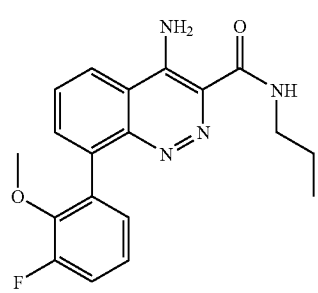 |

TABLE 1-continued

| Example Number | Synthesis Method | Compound Name | Structure |
| --- | --- | --- | --- |
| 9 | A | 4-amino-8-[4-methoxy-2-(trifluoromethyl)phenyl]-N-propyl-cinnoline-3-carboxamide | 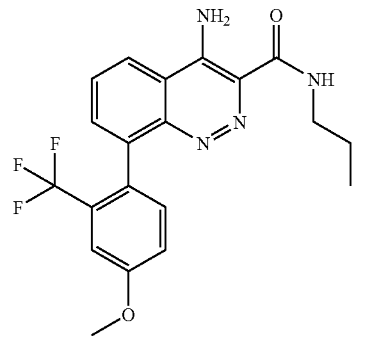 |
| 10 | A | 4-amino-8-(2,5-difluoro-4-methoxy-phenyl)-N-propyl-cinnoline-3-carboxamide | 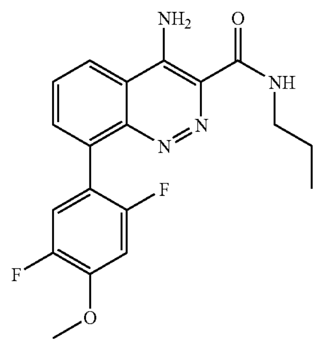 |
| 11 | A | 4-amino-8-(5-fluoro-6-methoxy-3-pyridyl)-N-propyl-cinnoline-3-carboxamide | 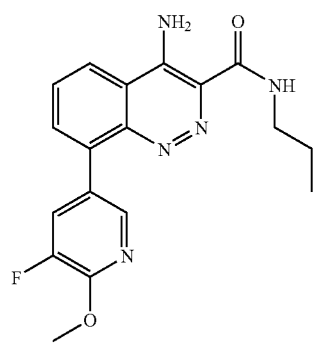 |
| 12 | A | 4-amino-8-(5-chloro-6-methoxy-3-pyridyl)-N-propyl-cinnoline-3-carboxamide | 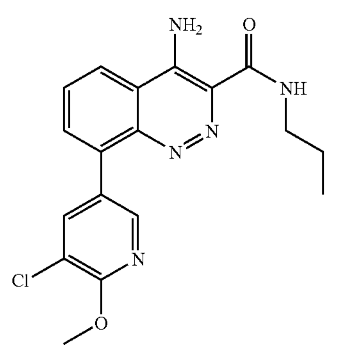 |

TABLE 1-continued

| Example Number | Synthesis Method | Compound Name | Structure |
| --- | --- | --- | --- |
| 13 | B | 4-amino-8-(3,5-dichloro-phenyl)-N-propyl-cinnoline-3-carboxamide | 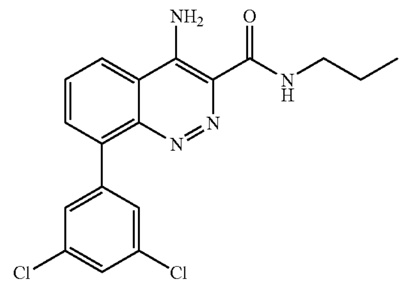 |
| 14 | B | 4-amino-8-(3,5-difluorophenyl)-N-propyl-cinnoline-3-carboxamide | 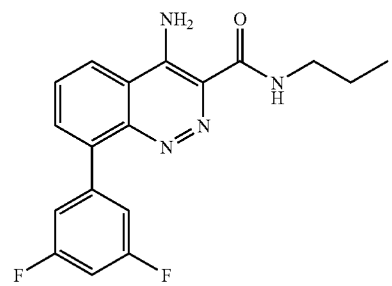 |
| 15 | D | 4-amino-8-(5-azetidin-1-ylcarbonyl-3-pyridyl)-N-propyl-cinnoline-3-carboxamide | 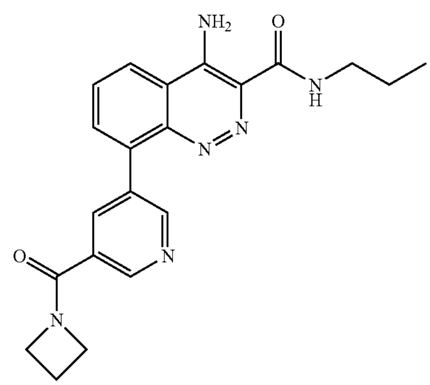 |
| 16 | A | 4-amino-8-(2,3-dimethoxyphenyl)-N-propyl-cinnoline-3-carboxamide | 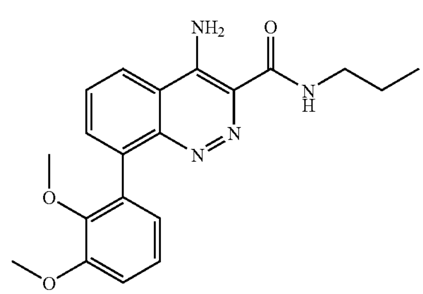 |

TABLE 1-continued

| Example Number | Synthesis Method | Compound Name | Structure |
|---|---|---|---|
| 17 | A | 4-amino-8-(4-dimethyl-aminophenyl)-N-propyl-cinnoline-3-carboxamide | 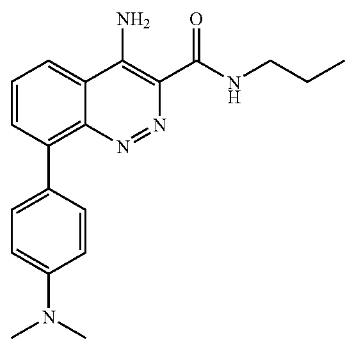 |
| 18 | A | 4-amino-8-(3-methoxy-phenyl)-N-propyl-cinnoline-3-carboxamide | 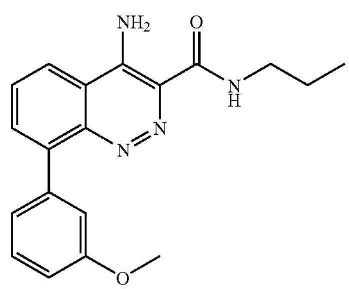 |
| 19 | A | 4-amino-8-(3,4-dimethoxy-phenyl)-N-propyl-cinnoline-3-carboxamide | 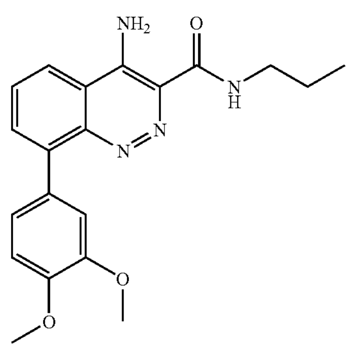 |
| 20 | B | 4-amino-8-(2,5-dimethoxyphenyl)-N-propyl-cinnoline-3-carboxamide | 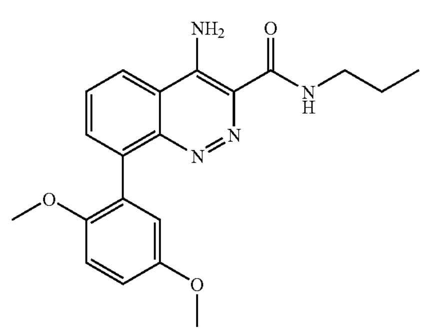 |

TABLE 1-continued

| Example Number | Synthesis Method | Compound Name | Structure |
|---|---|---|---|
| 21 | A | 4-amino-8-(3,5-dimethoxy-phenyl)-N-propyl-cinnoline-3-carboxamide | 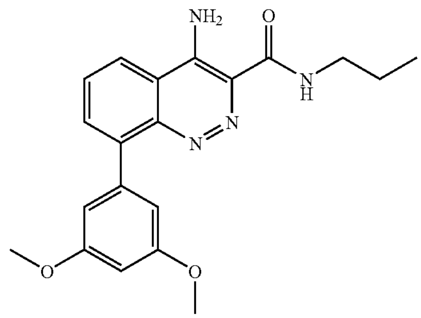 |
| 22 | A | 4-amino-8-(2,4-dimethoxyphenyl)-N-propyl-cinnoline-3-carboxamide | 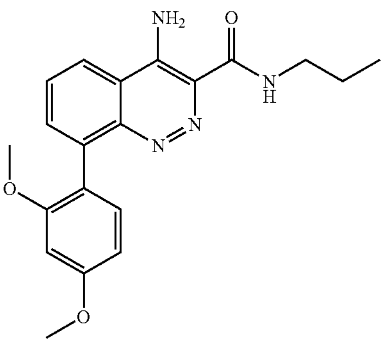 |
| 23 | E | 4-amino-8-(2-fluoro-3-pyridyl)-N-propyl-cinnoline-3-carboxamide | 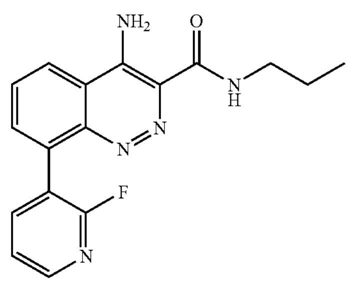 |
| 24 | A | 4-amino-8-(2,3-difluorophenyl)-N-propyl-cinnoline-3-carboxamide | 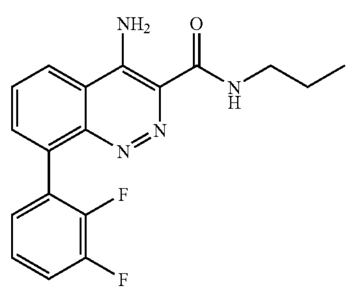 |
| 25 | A | 4-amino-8-(2,3-dichlorophenyl)-N-propyl-cinnoline-3-carboxamide | 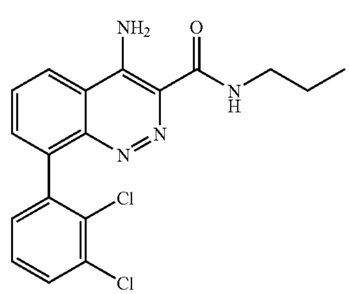 |

TABLE 1-continued

| Example Number | Synthesis Method | Compound Name | Structure |
|---|---|---|---|
| 26 | A | 4-amino-N-propyl-8-(6-quinolyl)cinnoline-3-carboxamide | 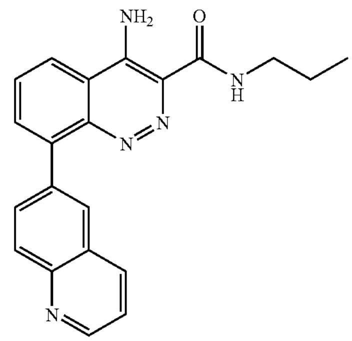 |
| 27 | A | 4-amino-N-propyl-8-(3-quinolyl)cinnoline-3-carboxamide | 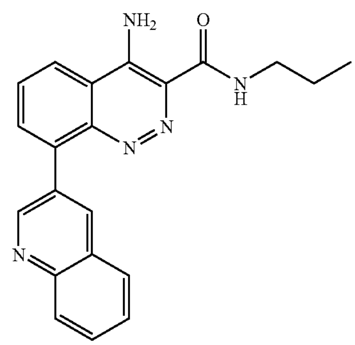 |
| 28 | A | 4-amino-8-(2-naphthyl)-N-propyl-cinnoline-3-carboxamide | 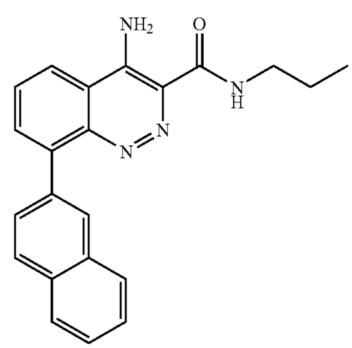 |
| 29 | A | 4-amino-8-(1H-indol-5-yl)-N-propyl-cinnoline-3-carboxamide | 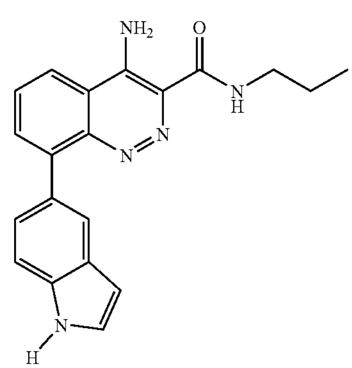 |

TABLE 1-continued

| Example Number | Synthesis Method | Compound Name | Structure |
|---|---|---|---|
| 30 | B | 4-amino-8-(4-methoxy-3-pyridyl)-N-propyl-cinnoline-3-carboxamide | 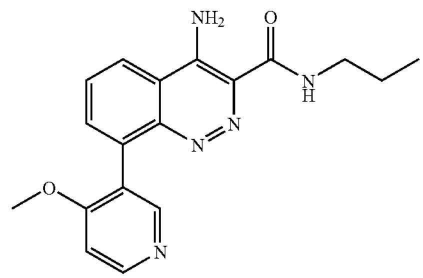 |
| 31 | A | 4-amino-8-(3-dimethyl-aminophenyl)-N-propyl-cinnoline-3-carboxamide | 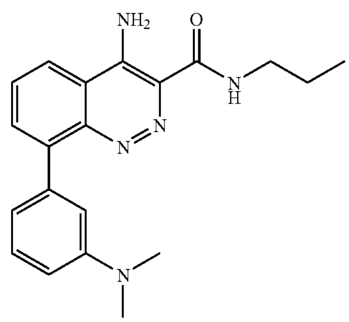 |
| 32 | A | 4-amino-N-propyl-8-(3,4,5-trimethoxyphenyl)-cinnoline-3-carboxamide | 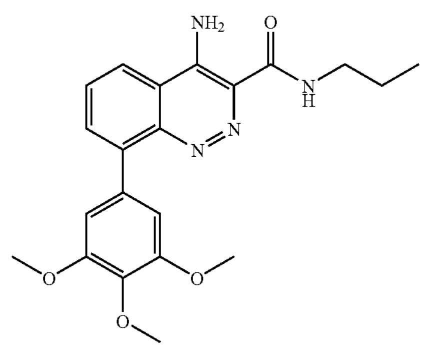 |
| 33 | A | 4-amino-8-(2,4-difluorophenyl)-N-propyl-cinnoline-3-carboxamide | 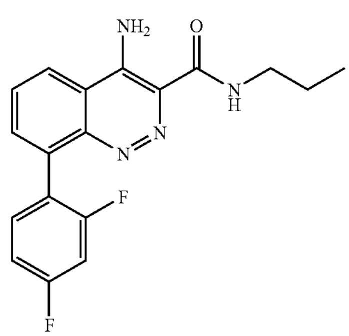 |

TABLE 1-continued

| Example Number | Synthesis Method | Compound Name | Structure |
|---|---|---|---|
| 34 | A | 4-amino-8-(3,4-difluorophenyl)-N-propyl-cinnoline-3-carboxamide | 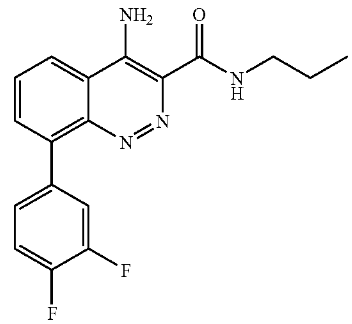 |
| 35 | A | 4-amino-N-propyl-8-(2,3,4-trimethoxyphenyl)-cinnoline-3-carboxamide | 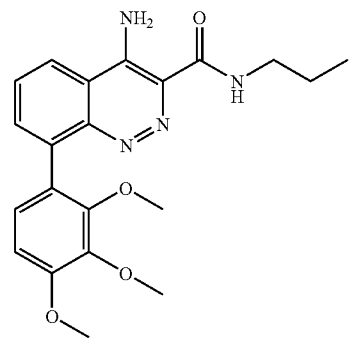 |
| 36 | A | 4-amino-8-(2-methoxy-3-pyridyl)-N-propyl-cinnoline-N-3-carboxamide | 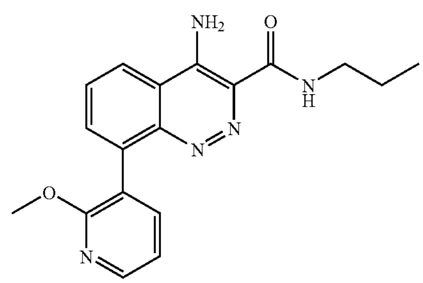 |
| 37 | A | 4-amino-8-(2,6-dimethoxy-3-pyridyl)-N-propyl-cinnoline-3-carboxamide | 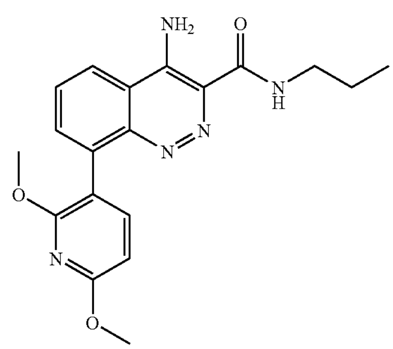 |
| 38 | B | 4-amino-8-(2,5-dimethylphenyl)-N-propyl-cinnoline-3-carboxamide | 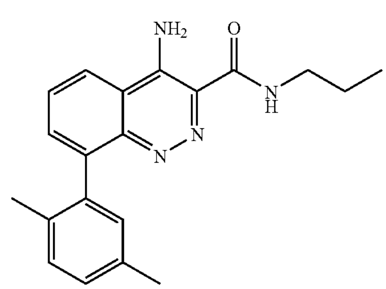 |

TABLE 1-continued

| Example Number | Synthesis Method | Compound Name | Structure |
|---|---|---|---|
| 39 | B | 3-[4-amino-3-(propylcarbamoyl)cinnolin-8-yl]benzoic acid | 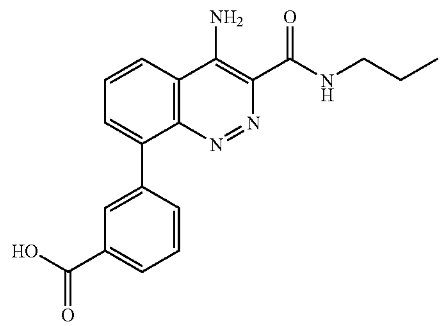 |
| 40 | | 4-amino-8-(3-azetidin-1-ylcarbonylphenyl)-N-propyl-cinnoline-3-carboxamide | 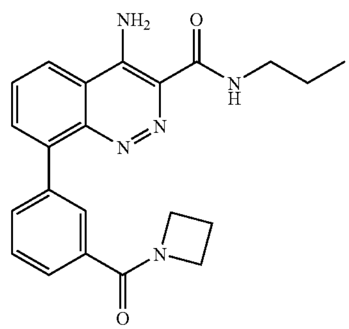 |
| 41 | C | 4-amino-N-propyl-8-pyrazin-2-yl-cinnoline-3-carboxamide | 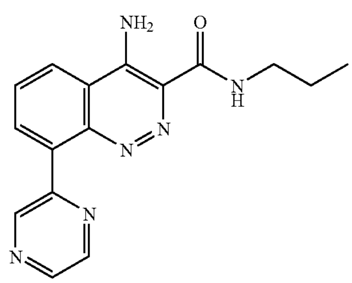 |
| 42 | A | 4-amino-N-propyl-8-(3-pyridyl)cinnoline-3-carboxamide | 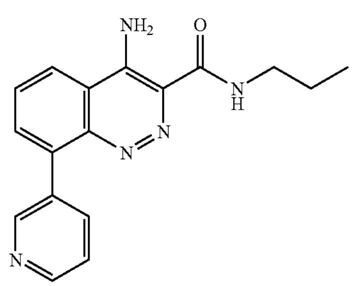 |
| 43 | A | 4-amino-8-(3-methylsulfonyl-phenyl)-N-propyl-cinnoline-3-carboxamide | 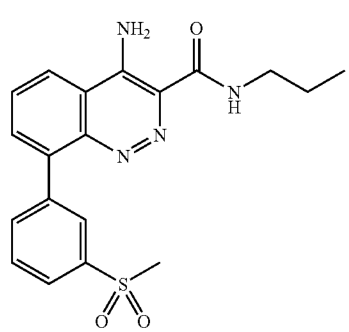 |

TABLE 1-continued

| Example Number | Synthesis Method | Compound Name | Structure |
|---|---|---|---|
| 44 | A | 4-amino-8-(3-cyanophenyl)-N-propyl-cinnoline-3-carboxamide | 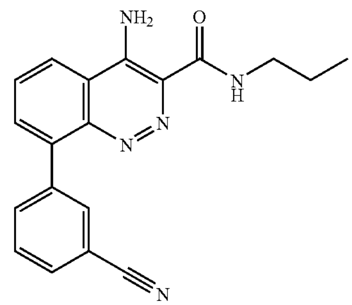 |
| 45 | C | 4-amino-N-propyl-8-(2-pyridyl)cinnoline-3-carboxamide | 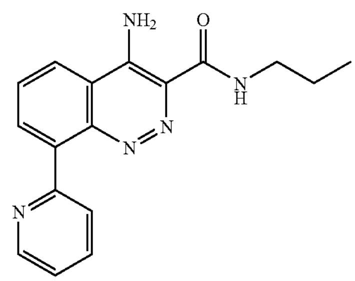 |
| 46 | A | 4-amino-8-[3,5-bis(trifluoromethyl)phenyl]-N-propyl-cinnoline-3-carboxamide | 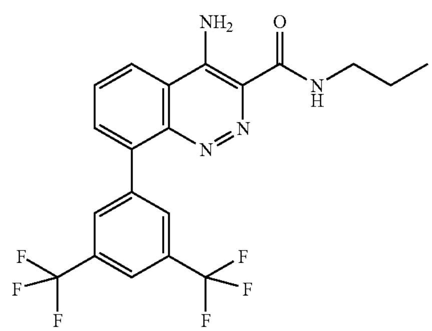 |
| 47 | A | 4-amino-N-propyl-8-(1H-pyrazol-4-yl)cinnoline-3-carboxamide | 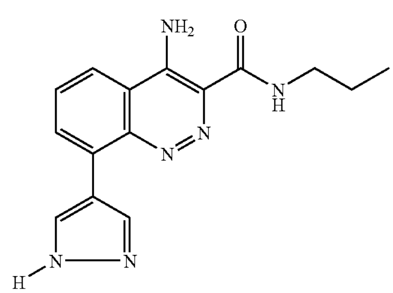 |
| 48 | A | 4-amino-8-[2-chloro-5-(trifluoromethyl)phenyl]-N-propyl-cinnoline-3-carboxamide | 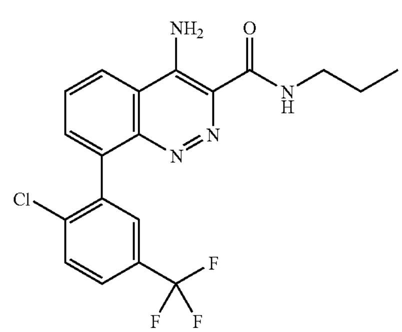 |

TABLE 1-continued

| Example Number | Synthesis Method | Compound Name | Structure |
|---|---|---|---|
| 49 | A | 4-amino-8-(2-methoxy-5-methyl-phenyl)-N-propyl-cinnoline-3-carboxamide | 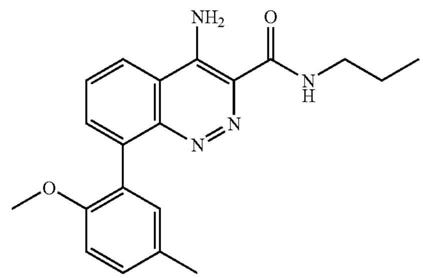 |
| 50 | A | 4-amino-N-propyl-8-[2-(trifluoromethyl)phenyl]-cinnoline-3-carboxamide | 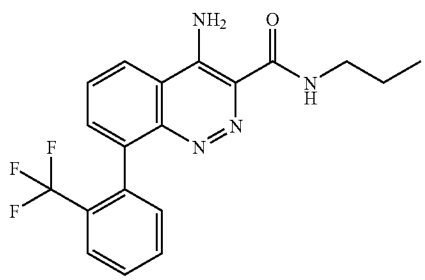 |
| 51 | A | 4-amino-8-(5-chloro-2-methoxy-phenyl)-N-propyl-cinnoline-3-carboxamide | 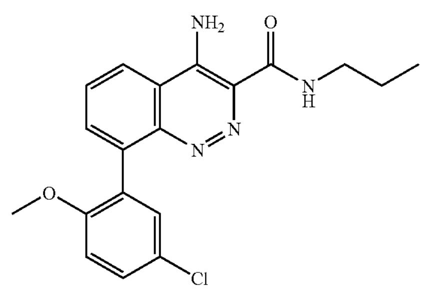 |
| 52 | C | 4-amino-N-propyl-8-(4-pyridyl)cinnoline-3-carboxamide | 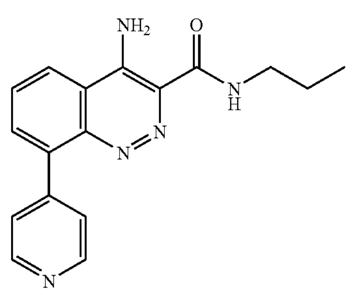 |
| 53 | A | 4-amino-8-(2,5-dichlorophenyl)-N-propyl-cinnoline-3-carboxamide | 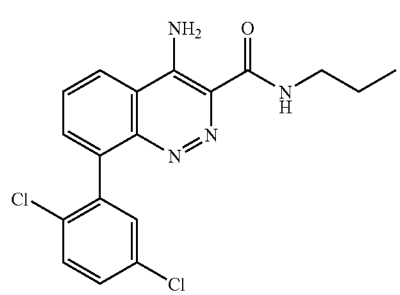 |

TABLE 1-continued

| Example Number | Synthesis Method | Compound Name | Structure |
|---|---|---|---|
| 54 | A | 4-amino-8-(2,5-difluorophenyl)-N-propyl-cinnoline-3-carboxamide | 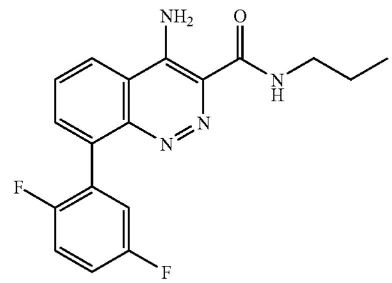 |
| 55 | A | 4-amino-8-(1-methyl-1H-pyrazol-4-yl)-N-propyl-cinnoline-3-carboxamide | 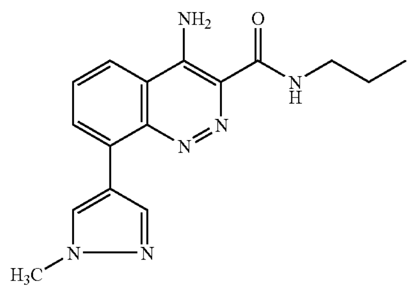 |
| 56 | A | 4-amino-8-(2-fluoro-3-methoxy-phenyl)-N-propyl-cinnoline-3-carboxamide | 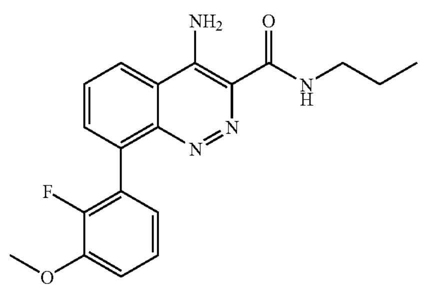 |
| 57 | A | 4-amino-8-(2,5-dimethyl-2H-pyrazol-3-yl)-N-propyl-cinnoline-3-carboxamide | 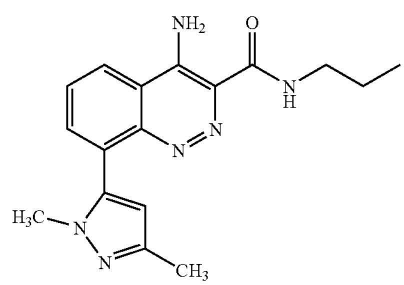 |
| 58 | A | 4-amino-8-[2-fluoro-5-(trifluoromethyl)phenyl]-N-propyl-cinnoline-3-carboxamide | 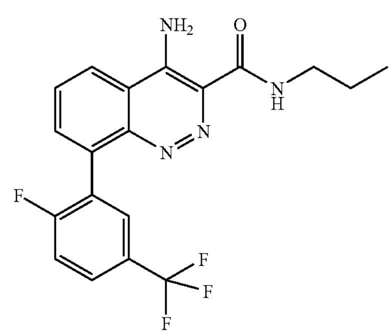 |

TABLE 1-continued

| Example Number | Synthesis Method | Compound Name | Structure |
|---|---|---|---|
| 59 | A | 4-amino-8-(2-fluoro-5-methyl-phenyl)-N-propyl-cinnoline-3-carboxamide | 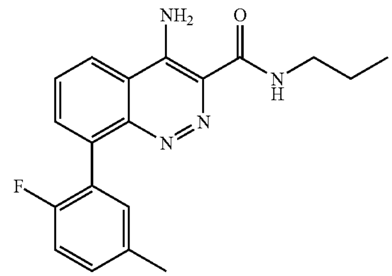 |
| 60 | A | 4-amino-8-(2-fluoro-4-methyl-phenyl)-N-propyl-cinnoline-3-carboxamide | 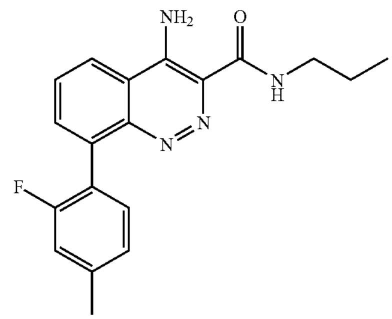 |
| 61 | A | 4-amino-8-(5-fluoro-2-methyl-phenyl)-N-propyl-cinnoline-3-carboxamide | 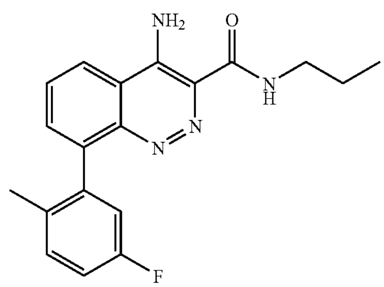 |
| 62 | A | 4-amino-8-(4-fluoro-2-methoxy-phenyl)-N-propyl-cinnoline-3-carboxamide | 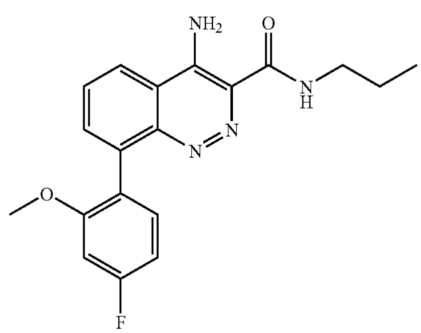 |
| 63 | A | 4-amino-8-(3-fluoro-4-methoxy-phenyl)-N-propyl-cinnoline-3-carboxamide | 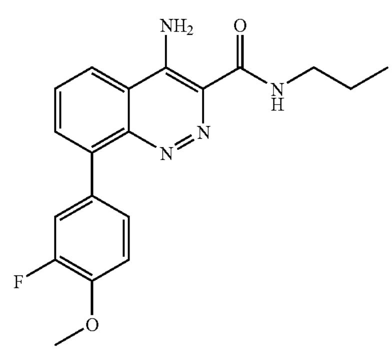 |

TABLE 1-continued

| Example Number | Synthesis Method | Compound Name | Structure |
| --- | --- | --- | --- |
| 64 | A | 4-amino-8-(2-fluoro-6-methoxy-phenyl)-N-propyl-cinnoline-3-carboxamide | 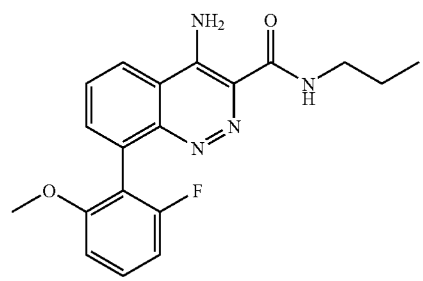 |
| 65 | A | 4-amino-8-(2-fluoro-5-methoxy-phenyl)-N-propyl-cinnoline-3-carboxamide | 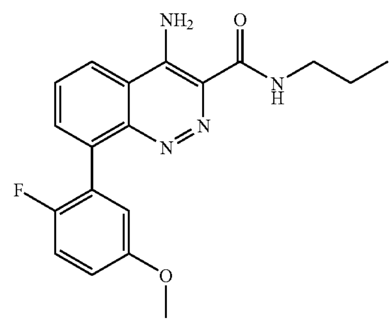 |
| 66 | A | 4-amino-8-(5-fluoro-2-methoxy-phenyl)-N-propyl-cinnoline-3-carboxamide | 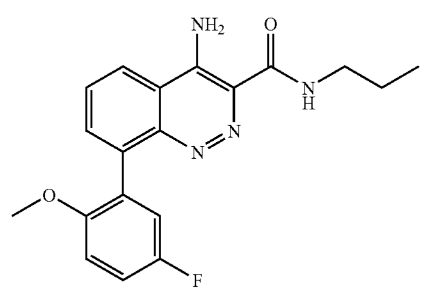 |
| 67 | F | 4-amino-8-(4-methoxyphenyl)-N-propyl-cinnoline-3-carboxamide | 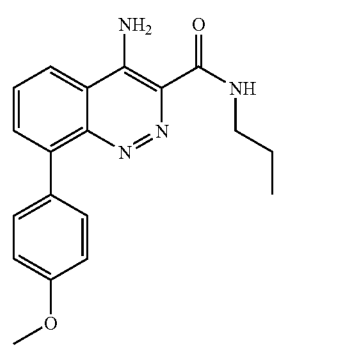 |

TABLE 1-continued
| Example Number | Synthesis Method | Compound Name | Structure |
|---|---|---|---|
| 68 | F | 4-amino-8-(4-fluorophenyl)-N-propyl-cinnoline-3-carboxamide | 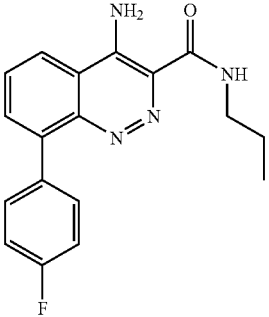 |
| 69 | F | 4-amino-N-propyl-8-[4-(trifluoromethoxy)phenyl]-cinnoline-3-carboxamide | 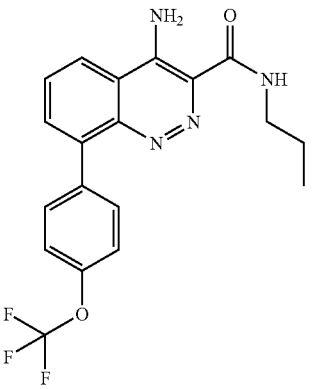 |
| 70 | F | 4-amino-N-propyl-8-[3-(trifluoromethoxy)phenyl]-cinnoline-3-carboxamide | 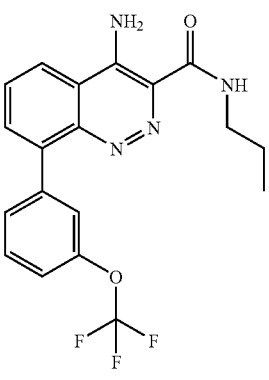 |
| 71 | A | 4-amino-8-(6-methoxy-3-pyridyl)-N-propyl-cinnoline-3-carboxamide | 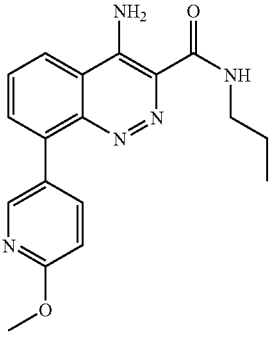 |

TABLE 1-continued

| Example Number | Synthesis Method | Compound Name | Structure |
|---|---|---|---|
| 72 | A | 4-amino-8-(4-methoxy-3,5-dimethyl-phenyl)-N-propyl-cinnoline-3-carboxamide | 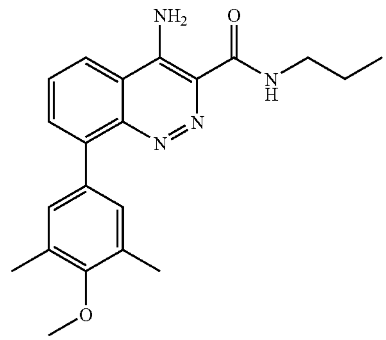 |
| 73 | A | 4-amino-8-(4-methoxy-3-methyl-phenyl)-N-propyl-cinnoline-3-carboxamide | 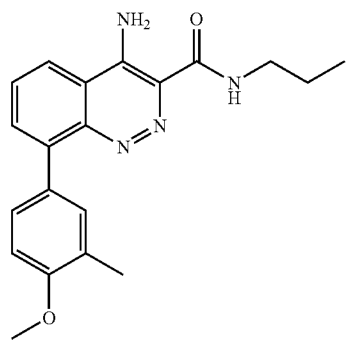 |
| 74 | A | 4-amino-8-(2-fluoro-4-methoxy-phenyl)-N-propyl-cinnoline-3-carboxamide | 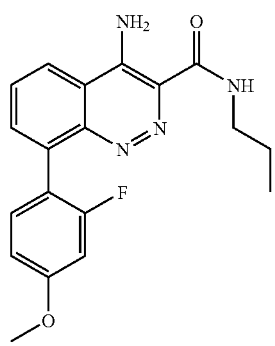 |
| 75 | C | 4-amino-8-(6-methylpyridin-3-yl)-N-propylcinnoline-3-carboxamide | 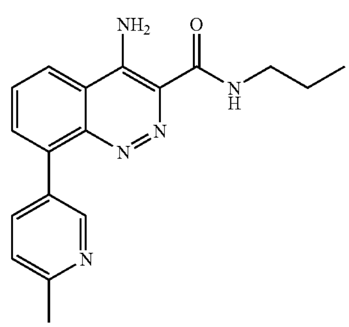 |

TABLE 1-continued

| Example Number | Synthesis Method | Compound Name | Structure |
|---|---|---|---|
| 76 | A | 4-amino-8-(4-methylpyridin-3-yl)-N-propylcinnoline-3-carboxamide | 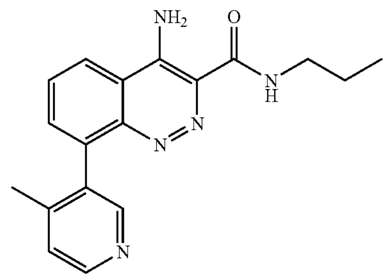 |
| 77 | A | 4-amino-8-(5-methoxy-2-methylphenyl)-N-propyl-cinnoline-3-carboxamide | 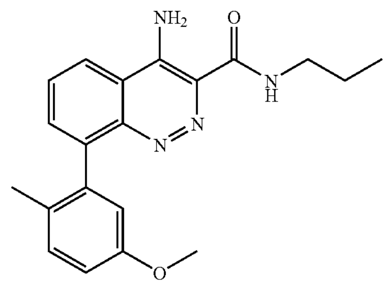 |
| 78 | A | 4-Amino-8-(2,4-dimethoxy-phenyl)-7-fluoro-N-propylcinnoline-3-carboxamide | 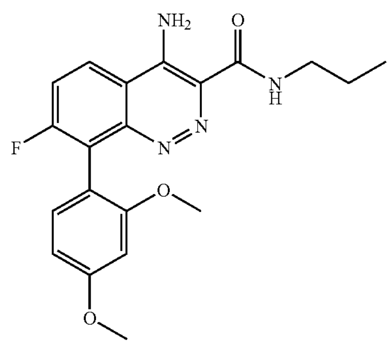 |
| 79 | A | 4-amino-8-(2,5-dimethoxy-phenyl)-7-fluoro-N-propyl-cinnoline-3-carboxamide | 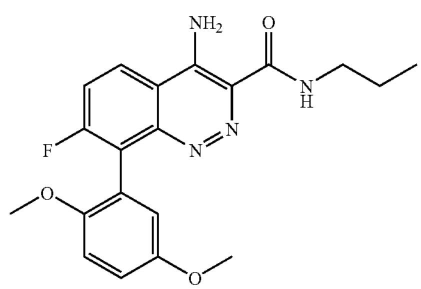 |
| 80 | A | 4-amino-8-(2,4-dimethoxy-pyrimidin-5-yl)-7-fluoro-N-propylcinnoline-3-carboxamide | 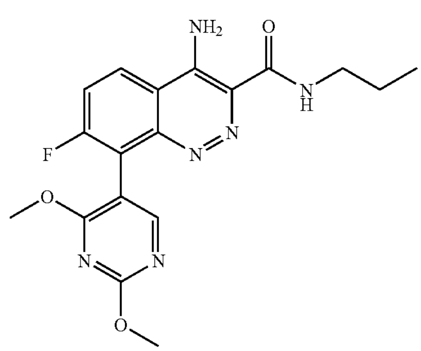 |

TABLE 1-continued

| Example Number | Synthesis Method | Compound Name | Structure |
|---|---|---|---|
| 81 | A | 4-amino-N-ethyl-8-(4-methoxypyridin-3-yl)cinnoline-3-carboxamide | 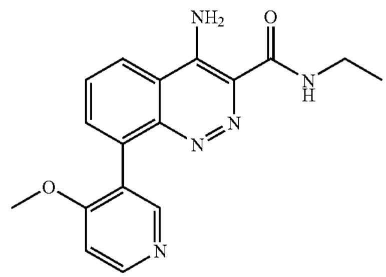 |
| 82 | A | 4-amino-N-butyl-8-(2,5-dimethoxyphenyl)cinnoline-3-carboxamide | 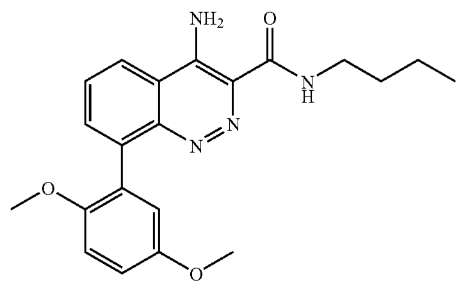 |
| 83 | A | 4-amino-8-(2,5-dimethoxyphenyl)-N-ethylcinnoline-3-carboxamide | 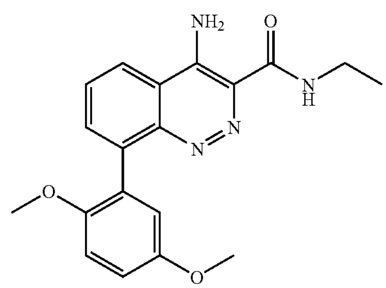 |
| 84 | B | 4-amino-8-(2,5-dimethoxyphenyl)-N-methylcinnoline-3-carboxamide | 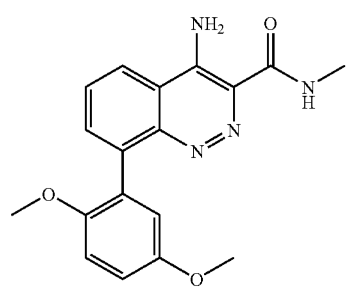 |
| 85 | B | 4-amino-N-butyl-8-(2,4-dimethoxypyrimidin-5-yl)cinnoline-3-carboxamide | 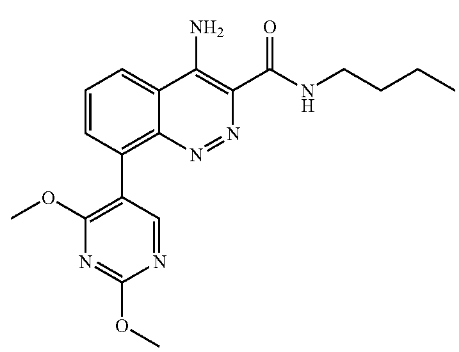 |

TABLE 1-continued

| Example Number | Synthesis Method | Compound Name | Structure |
|---|---|---|---|
| 86 | B | 4-amino-8-(2,4-dimethoxypyrimidin-5-yl)-N-ethylcinnoline-3-carboxamide | 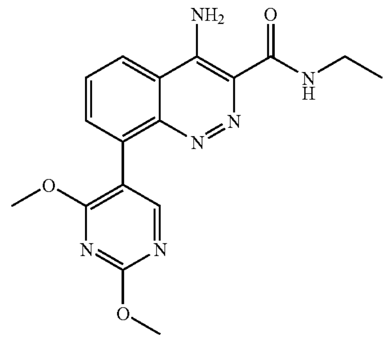 |
| 87 | A | 4-Amino-8-(2,5-dimethoxy-phenyl)-cinnoline-3-carboxylic acid allylamide | 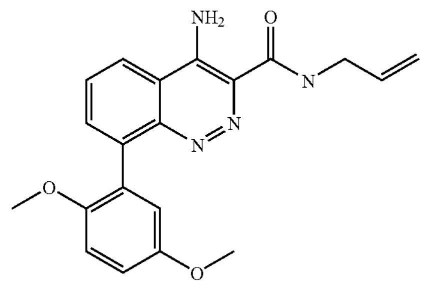 |
| 88 | | 4-amino-N-(cyclopropyl-methyl)-8-phenyl-cinnoline-3-carboxamide | 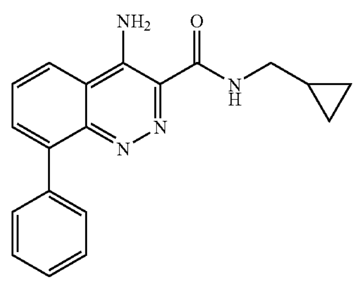 |
| 89 | A | 4-amino-8-(m-tolyl)-N-propyl-cinnoline-3-carboxamide | 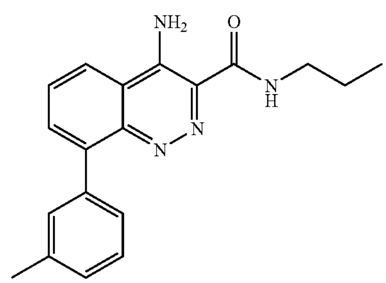 |
| 90 | A | 4-Amino-8-(2-fluoro-6-methylpyridin-3-yl)-cinnoline-3-carboxylic acid propylamide | 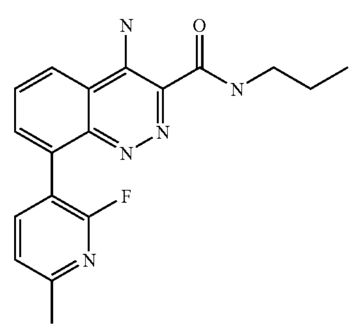 |

TABLE 1-continued

| Example Number | Synthesis Method | Compound Name | Structure |
|---|---|---|---|
| 91 | A | 4-Amino-7-fluoro-8-(5-fluoro-2-methoxyphenyl)-cinnoline-3-carboxylic acid propylamide | 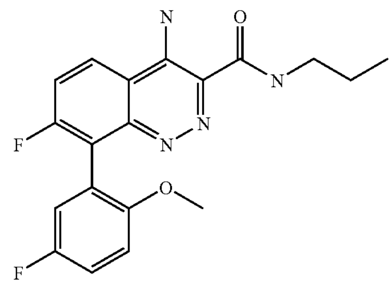 |
| 92 | A | 4-Amino-8-(2-chloro-5-methoxyphenyl)-7-fluoro-cinnoline-3-carboxylic acid propylamide | 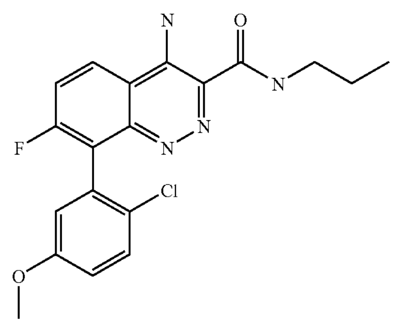 |
| 93 | A | 4-amino-N-cyclopropyl-8-(2,6-dimethoxypyridin-3-yl)cinnoline-3-carboxamide | 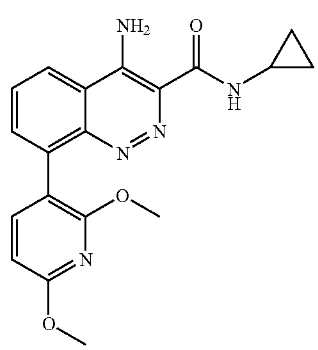 |
| 94 | A | 4-amino-N-cyclopropyl-8-(2-methoxy-5-methyl-phenyl)cinnoline-3-carboxamide | 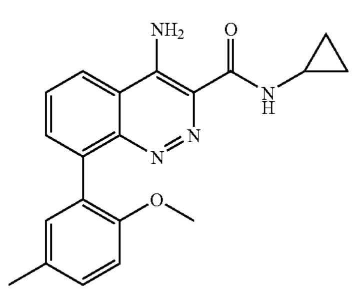 |

TABLE 1-continued

| Example Number | Synthesis Method | Compound Name | Structure |
|---|---|---|---|
| 95 | A | 4-amino-N-cyclopropyl-8-(2,4-dimethoxyphenyl)cinnoline-3-carboxamide | 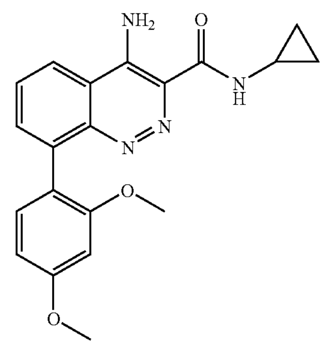 |
| 96 | A | 4-amino-N-cyclopropyl-8-(2,4-dimethoxypyrimidin-5-yl)cinnoline-3-carboxamide | 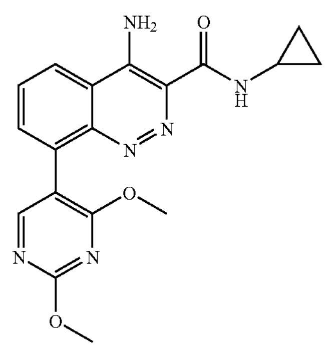 |
| 97 | A | 4-amino-N-cyclopropyl-8-(2,5-dimethoxyphenyl)cinnoline-3-carboxamide | 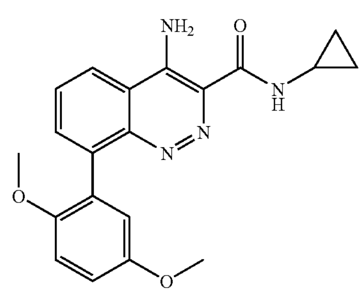 |
| 98 | A | 4-amino-N-ethyl-8-(2-fluoro-6-methoxy-phenyl)cinnoline-3-carboxamide | 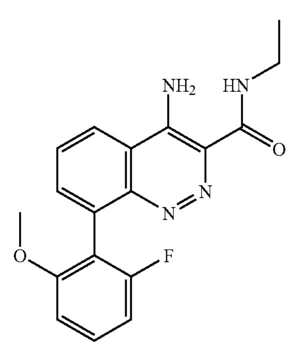 |

TABLE 1-continued

| Example Number | Synthesis Method | Compound Name | Structure |
|---|---|---|---|
| 99 | G | 4-amino-7-fluoro-8-(2-fluoro-6-methoxy-phenyl)-N-propyl-cinnoline-3-carboxamide | 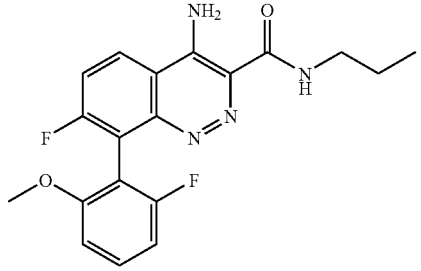 |
| 100 | G | 4-amino-7-cyano-8-(2,4-dimethoxyphenyl)-N-propyl-cinnoline-3-carboxamide | 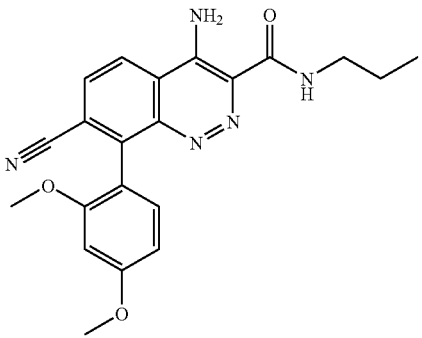 |
| 101 | H | 4-amino-N-cyclobutyl-8-(2-fluoro-6-methoxy-phenyl)cinnoline-3-carboxamide | 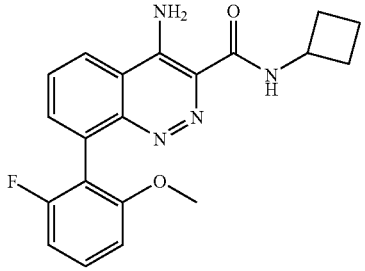 |
| 102 | H | 4-amino-N-cyclopropyl-8-(2-fluoro-6-methoxy-phenyl)cinnoline-3-carboxamide | 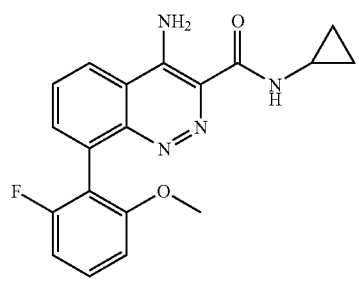 |
| 103 | H | 4-amino-8-(2-chloro-6-methoxy-phenyl)-N-propyl-cinnoline-3-carboxamide | 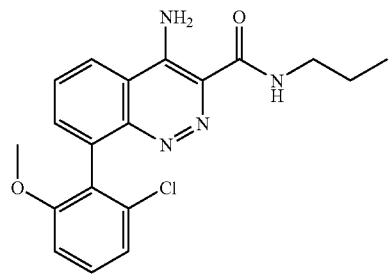 |

TABLE 1-continued
| Example Number | Synthesis Method | Compound Name | Structure |
|---|---|---|---|
| 104 | A | 4-amino-7-fluoro-8-(2-fluoro-3-methoxy-phenyl)-N-propyl-cinnoline-3-carboxamide | 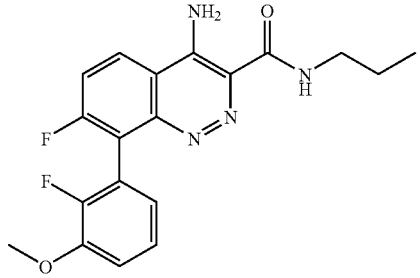 |
| 105 | A | 4-amino-7-fluoro-8-(3-fluoro-4-methoxy-phenyl)-N-propyl-cinnoline-3-carboxamide | 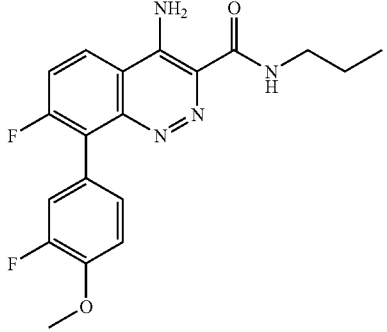 |
| 106 | A | 4-amino-8-(3,5-difluoro-2-methoxy-phenyl)-7-fluoro-N-propyl-cinnoline-3-carboxamide | 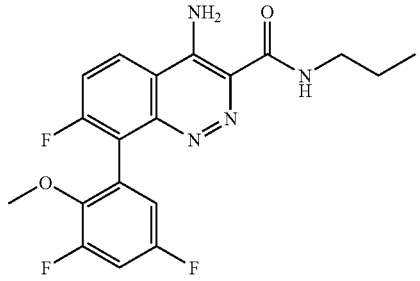 |
| 107 | A | 4-amino-7-fluoro-8-(4-fluoro-2-methoxy-phenyl)-N-propyl-cinnoline-3-carboxamide | 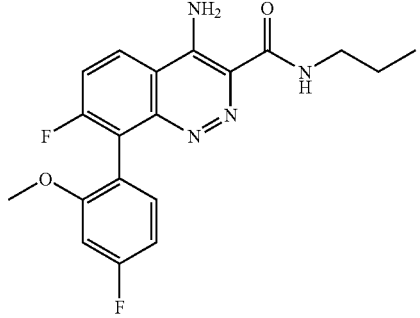 |

TABLE 1-continued

| Example Number | Synthesis Method | Compound Name | Structure |
|---|---|---|---|
| 108 | A | 4-amino-7-fluoro-8-(2-fluoro-4-methoxy-phenyl)-N-propyl-cinnoline-3-carboxamide | 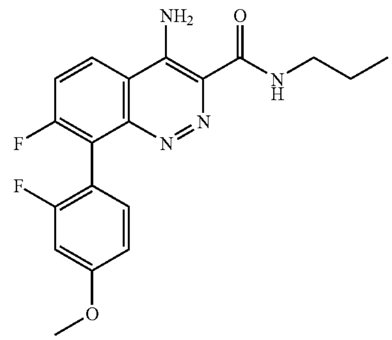 |
| 109 | A | 4-amino-8-(4-chlorophenyl)-7-fluoro-N-propyl-cinnoline-3-carboxamide | 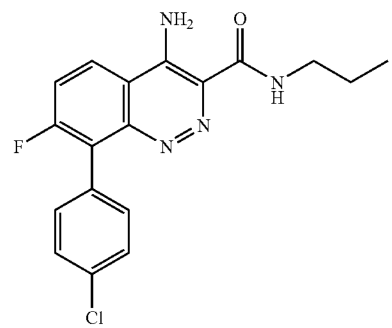 |
| 110 | A | 4-amino-7-fluoro-8-(5-fluoro-2-methyl-phenyl)-N-propyl-cinnoline-3-carboxamide | 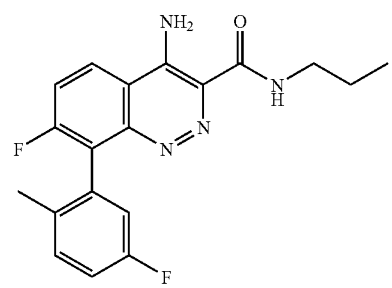 |
| 111 | A | 4-amino-8-(2,3-dimethyl-phenyl)-7-fluoro-N-propyl-cinnoline-3-carboxamide | 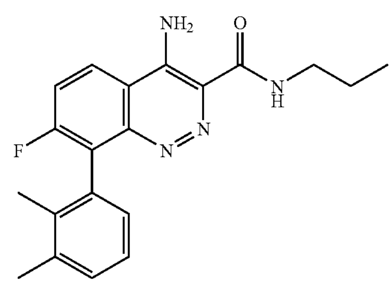 |
| 112 | A | 4-amino-8-(2,5-dimethoxy-phenyl)-N-(3,3,3-trifluoro-propyl)cinnoline-3-carboxamide | 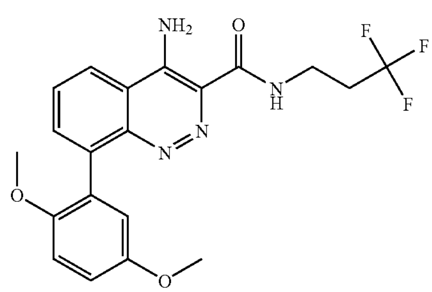 |

TABLE 1-continued

| Example Number | Synthesis Method | Compound Name | Structure |
|---|---|---|---|
| 113 | A | 4-amino-8-(2,5-difluoro-phenyl)-7-fluoro-N-propyl-cinnoline-3-carboxamide | 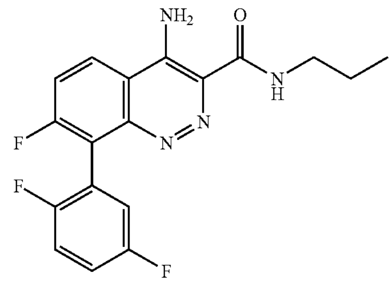 |

The compounds in Table 2 can also made according to the methods described herein below.

TABLE 2

| Synthesis Method | Compound Name | Structure |
|---|---|---|
| E | 4-amino-8-(3,5-dimethyl-1H-pyrazol-4-yl)-N-propyl-cinnoline-3-carboxamide | |
| E | 4-amino-8-(3,5-difluoro-2-methoxyphenyl)-N-propylcinnoline-3-carboxamide | |
| E | 4-amino-8-[5-(azetidin-1-ylcarbonyl)-2-methoxyphenyl]-N-propylcinnoline-3-carboxamide | |

TABLE 2-continued

| Synthesis Method | Compound Name | Structure |
|---|---|---|
| E | 4-amino-8-(6-methoxy-2-methylpyridin-3-yl)-N-propylcinnoline-3-carboxamide | |
| E | 4-amino-N-propyl-8-(1,3,5-trimethyl-1H-pyrazol-4-yl)cinnoline-3-carboxamide | |
| A | 4-amino-N-propyl-8-(2,4,6-trifluoro-3-methoxyphenyl)cinnoline-3-carboxamide | 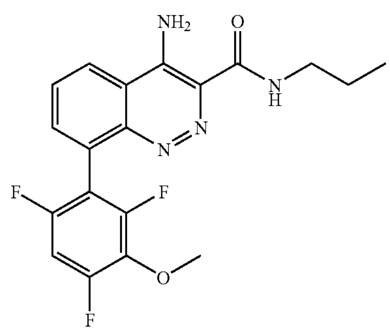 |
| E | 4-amino-8-(2-fluoro-5-methylpyridin-3-yl)-N-propylcinnoline-3-carboxamide | |
| E | 4-amino-8-(1,3-dimethyl-1H-pyrazol-5-yl)-N-propylcinnoline-3-carboxamide | |

TABLE 2-continued
| Synthesis Method | Compound Name | Structure |
|---|---|---|
| E | 4-amino-8-(2-fluoro-4,6-dimethoxyphenyl)-N-propylcinnoline-3-carboxamide | 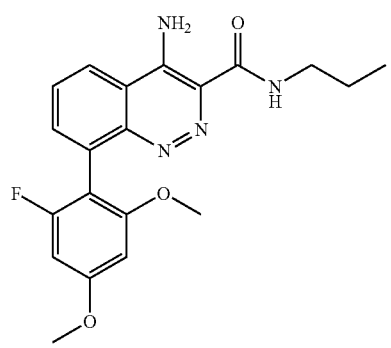 |
| A | 4-amino-8-(3,5-difluoro-2-methoxyphenyl)-N-propylcinnoline-3-carboxamide | 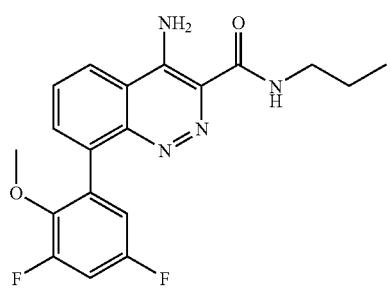 |
| A | 4-amino-8-(2,3-dihydro-1,4-benzodioxin-6-yl)-N-propylcinnoline-3-carboxamide | 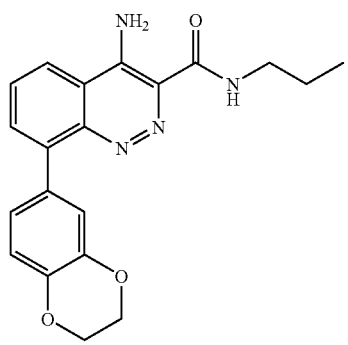 |
| E | 4-amino-8-(4,5-difluoro-2-methoxyphenyl)-N-propylcinnoline-3-carboxamide | 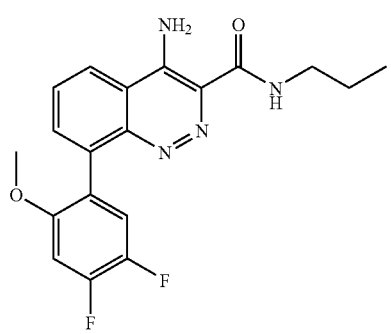 |

TABLE 2-continued

| Synthesis Method | Compound Name | Structure |
|---|---|---|
| E | 4-amino-8-(1,3-benzodioxol-4-yl)-N-propylcinnoline-3-carboxamide | |
| E | 4-amino-8-[5-(azetidin-1-ylcarbonyl)-2-methylphenyl]-N-propylcinnoline-3-carboxamide | |
| E | 4-amino-8-(6-methoxy-4-methylpyridin-3-yl)-N-propylcinnoline-3-carboxamide | |
| A | 4-amino-7-chloro-8-(4-methoxypyridin-3-yl)-N-propylcinnoline-3-carboxamide | |
| A | 4-amino-7-fluoro-8-(4-methoxypyridin-3-yl)-N-propylcinnoline-3-carboxamide | |

TABLE 2-continued

| Synthesis Method | Compound Name | Structure |
|---|---|---|
| A | 4-amino-7-chloro-8-(2-methoxy-5-methylphenyl)-N-propylcinnoline-3-carboxamide | 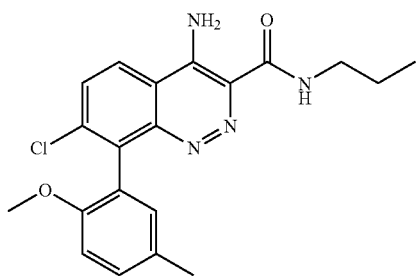 |
| A | 4-amino-7-fluoro-8-(2-methoxy-5-methylphenyl)-N-propylcinnoline-3-carboxamide | 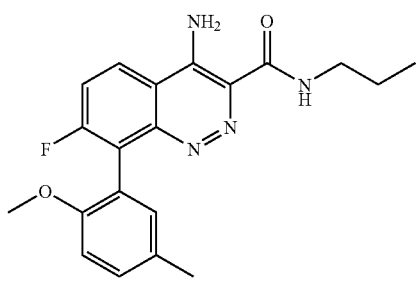 |
| A | 4-amino-8-(2,5-dimethoxyphenyl)-7-chloro-N-propylcinnoline-3-carboxamide | 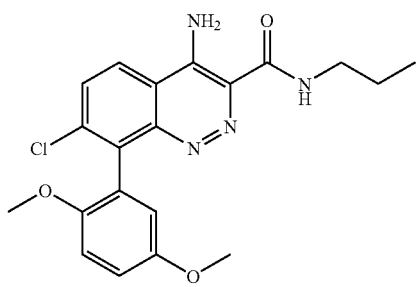 |
| A | 4-amino-8-(2,4-dimethoxy-pyrimidin-5-yl)-7-chloro-N-propylcinnoline-3-carboxamide | 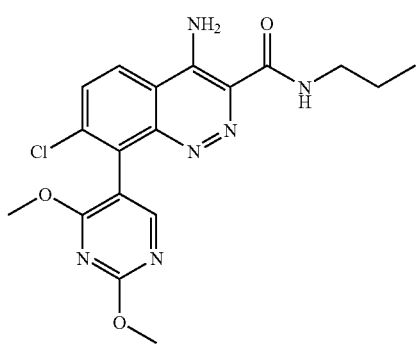 |
| A | 4-amino-N-butyl-8-(4-methoxypyridin-3-yl)cinnoline-3-carboxamide | 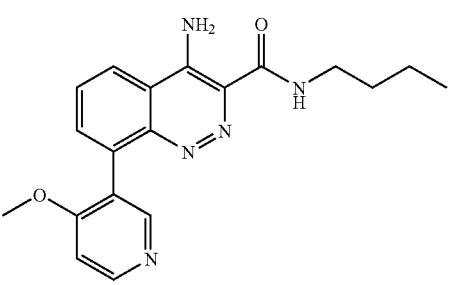 |

TABLE 2-continued

| Synthesis Method | Compound Name | Structure |
|---|---|---|
| A | 4-amino-8-(4-methoxypyridin-3-yl)-N-methylcinnoline-3-carboxamide | 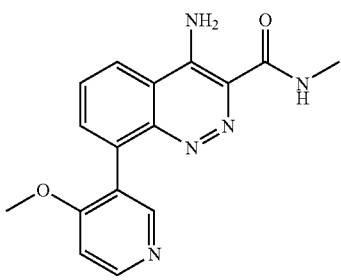 |
| A | 4-amino-N-butyl-8-(2-methoxy-5-methylphenyl)cinnoline-3-carboxamide | 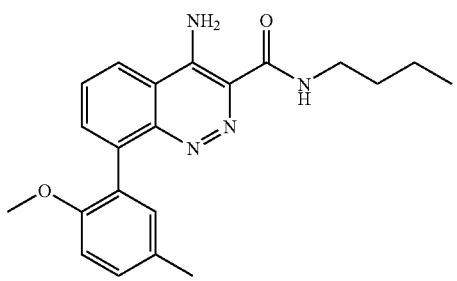 |
| A | 4-amino-N-ethyl-8-(2-methoxy-5-methylphenyl)cinnoline-3-carboxamide | 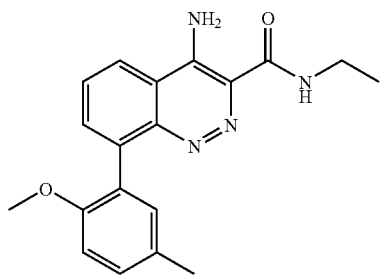 |
| A | 4-amino-8-(2-methoxy-5-methylphenyl)-N-methylcinnoline-3-carboxamide | 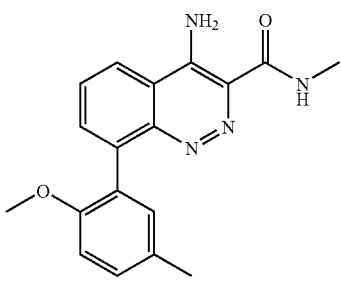 |
| A | 4-amino-8-(2,4-dimethoxypyrimidin-5-yl)-N-methylcinnoline-3-carboxamide | 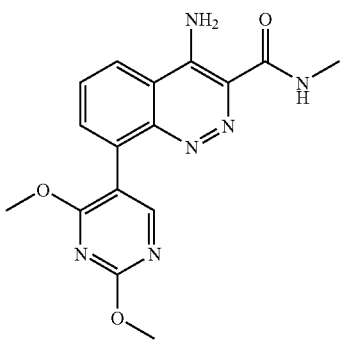 |

TABLE 2-continued

| Synthesis Method | Compound Name | Structure |
|---|---|---|
| A | 4-amino-8-(4-methoxypyridin-3-yl)-N-(tetrahydrofuran-2-yl-methyl)cinnoline-3-carboxamide | 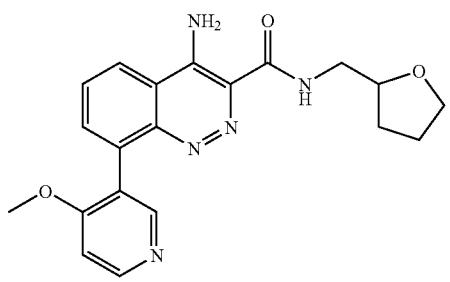 |
| A | 4-amino-N-isobutyl-8-(4-methoxypyridin-3-yl)cinnoline-3-carboxamide | 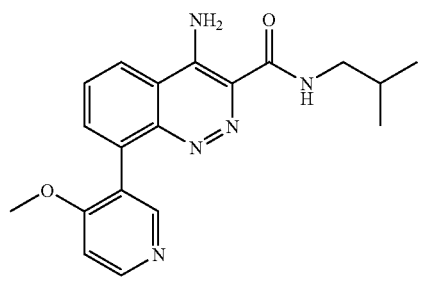 |
| A | 4-amino-N-(2-hydroxypropyl)-8-(4-methoxypyridin-3-yl)cinnoline-3-carboxamide | 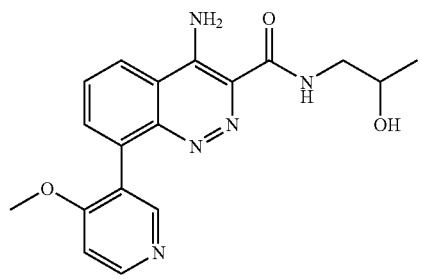 |
| A | 4-amino-8-(2-methoxy-5-methyl-phenyl)-N-(tetrahydrofuran-2-ylmethyl)cinnoline-3-carboxamide | 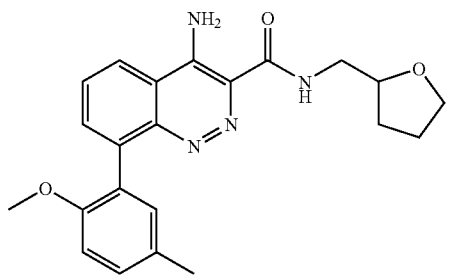 |
| A | 4-amino-N-isobutyl-8-(2-methoxy-5-methylphenyl)cinnoline-3-carboxamide | 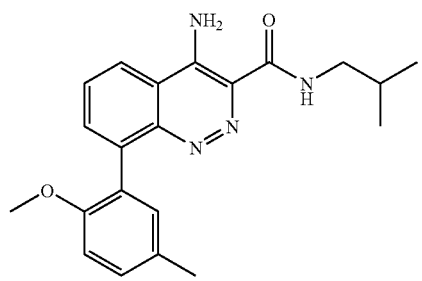 |

TABLE 2-continued

| Synthesis Method | Compound Name | Structure |
|---|---|---|
| A | 4-amino-N-(2-hydroxypropyl)-8-(2-methoxy-5-methylphenyl)cinnoline-3-carboxamide | 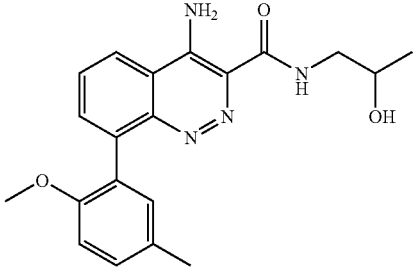 |
| A | 4-amino-8-(2,5-dimethoxyphenyl)-N-(tetrahydrofuran-2-ylmethyl)cinnoline-3-carboxamide | 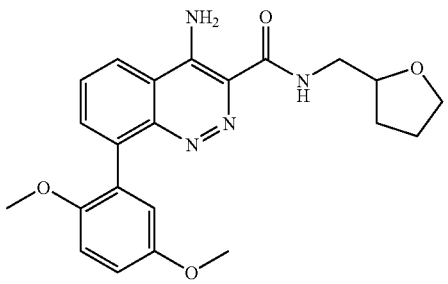 |
| A | 4-amino-8-(2,5-dimethoxyphenyl)-N-isobutylcinnoline-3-carboxamide | 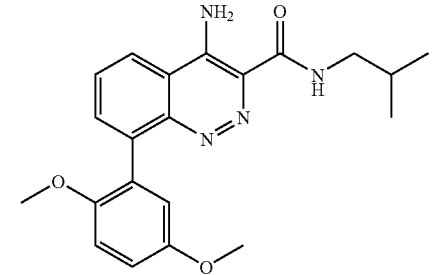 |
| A | 4-amino-8-(2,5-dimethoxyphenyl)-N-(2-hydroxypropyl)cinnoline-3-carboxamide | 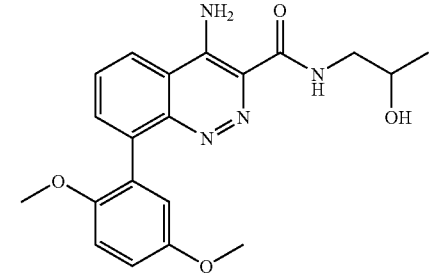 |
| A | 4-amino-8-(2,4-dimethoxypyrimidin-5-yl)-N-(tetrahydrofuran-2-ylmethyl)cinnoline-3-carboxamide | 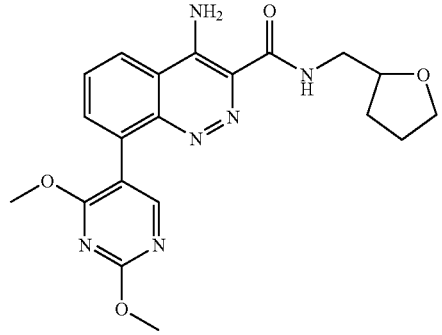 |

TABLE 2-continued

| Synthesis Method | Compound Name | Structure |
|---|---|---|
| A | 4-amino-8-(2,4-dimethoxypyrimidin-5-yl)-N-isobutylcinnoline-3-carboxamide | |
| A | 4-amino-8-(2,4-dimethoxy-pyrimidin-5-yl)-N-(2-hydroxy-propyl)cinnoline-3-carboxamide | |

The compounds in Table 3 were also made according to the methods described herein below.

TABLE 3

| Example Number | Compound Name | Structure |
|---|---|---|
| 114 | 4-amino-8-(2,3-dimethylphenyl)-N-propyl-cinnoline-3-carboxamide | 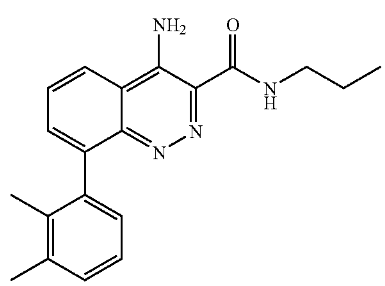 |
| 115 | 4-amino-8-(3,5-dimethylphenyl)-N-propyl-cinnoline-3-carboxamide | 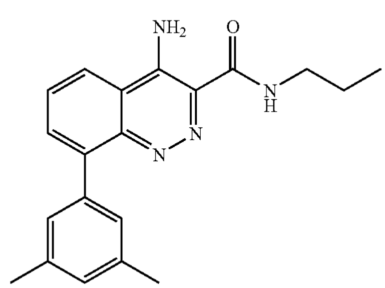 |

TABLE 3-continued
| Example Number | Compound Name | Structure |
|---|---|---|
| 116 | 4-amino-8-(2,4-dimethylphenyl)-N-propyl-cinnoline-3-carboxamide | 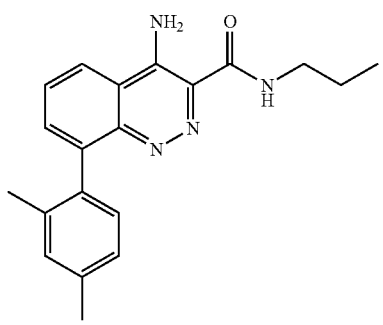 |
| 117 | 4-amino-8-(3,4-dimethylphenyl)-N-propyl-cinnoline-3-carboxamide | 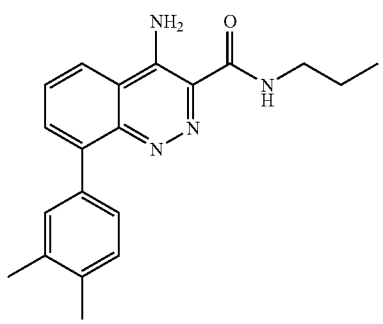 |
| 118 | 4-amino-N-propyl-8-(p-tolyl)cinnoline-3-carboxamide | 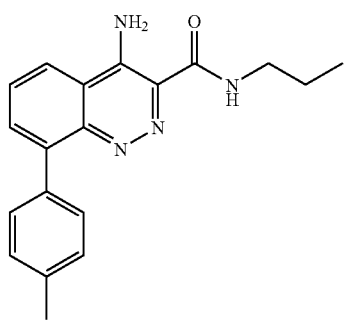 |
| 119 | 4-amino-8-(3-chlorophenyl)-N-propyl-cinnoline-3-carboxamide | 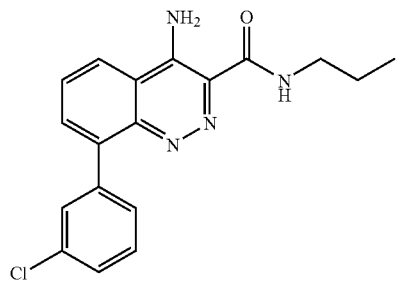 |

TABLE 3-continued
| Example Number | Compound Name | Structure |
|---|---|---|
| 120 | 4-amino-8-(4-chlorophenyl)-N-propyl-cinnoline-3-carboxamide | 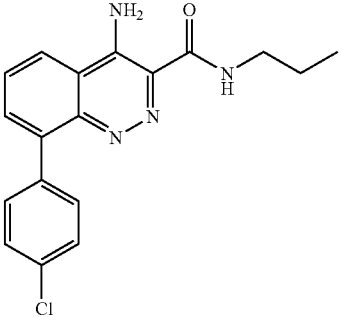 |
| 121 | 4-amino-8-(o-tolyl)-N-propyl-cinnoline-3-carboxamide | 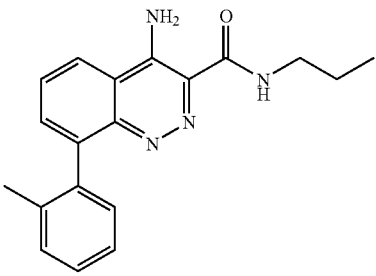 |
| 122 | 4-amino-N-propyl-8-(3-thienyl)cinnoline-3-carboxamide | 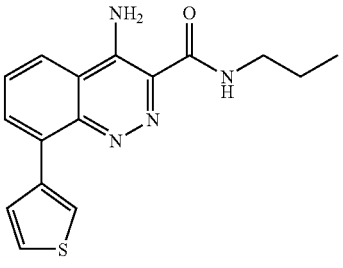 |
| 123 | 4-amino-8-(2,6-dimethylphenyl)-N-propyl-cinnoline-3-carboxamide | 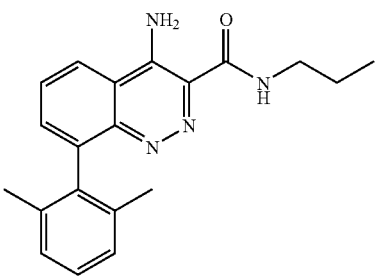 |

Additional example compounds of the invention in table 4 were made according to the methods described herein below.

TABLE 4

| Example No. | Structure | Compound Name | Synthesis Method | Mass Spectrum m/z |
|---|---|---|---|---|
| 124 | 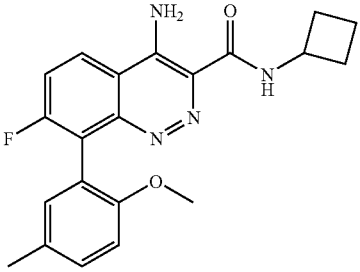 | 4-amino-N-cyclobutyl-7-fluoro-8-(2-ethoxy-5-methyl-phenyl)cinnoline-3-carboxamide | A | 381 |
| 125 | 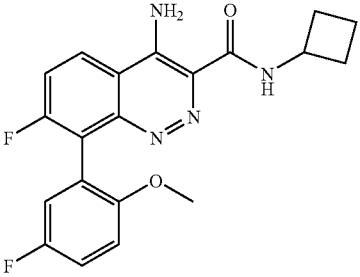 | 4-amino-N-cyclobutyl-7-fluoro-8-(5-fluoro-2-methoxy-phenyl)cinnoline-3-carboxamide | A | 385 |
| 126 | 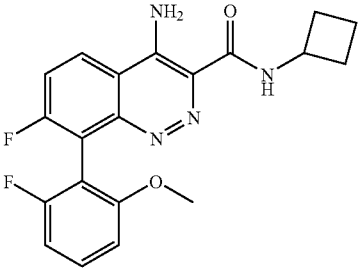 | 4-amino-N-cyclobutyl-7-fluoro-8-(2-fluoro-6-methoxy-phenyl)cinnoline-3-carboxamide | G | 385 |
| 127 | 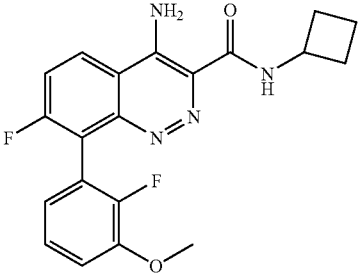 | 4-amino-N-cyclobutyl-7-fluoro-8-(2-fluoro-3-methoxy-phenyl)cinnoline-3-carboxamide | A | 385 |
| 128 | 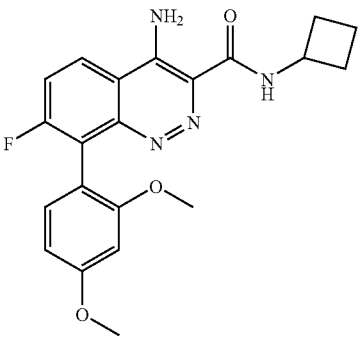 | 4-amino-N-cyclobutyl-8-(2,4-dimethoxyphenyl)-7-fluoro-cinnoline-3-carboxamide | A | 397 |

TABLE 4-continued

| Example No. | Structure | Compound Name | Synthesis Method | Mass Spectrum m/z |
|---|---|---|---|---|
| 129 | 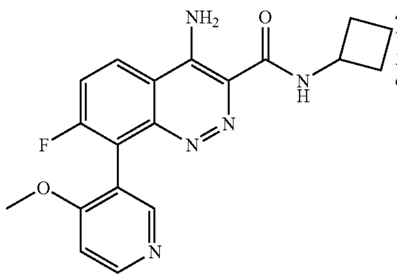 | 4-amino-N-cyclobutyl-7-fluoro-8-(4-methoxypyridin-3-yl)cinnoline-3-carboxamide | A | 368 |
| 130 | 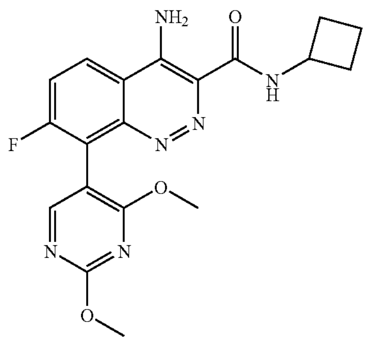 | 4-amino-N-cyclobutyl-8-(2,4-dimethoxypyrimidin-5-yl)-7-fluoro-cinnoline-3-carboxamide | A | 399 |
| 131 | 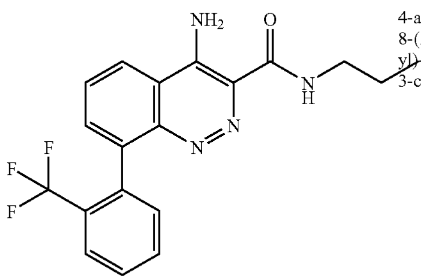 | 4-amino-N-cyclobutyl-8-(2,6-dimethoxypyridin-3-yl)-7-fluoro-cinnoline-3-carboxamide | A | 398 |
| 132 | 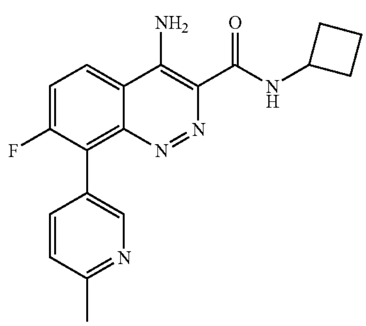 | 4-amino-N-cyclobutyl-7-fluoro-8-(6-methylpyridin-3-yl)cinnoline-3-carboxamide | A | 352 |
| 133 | 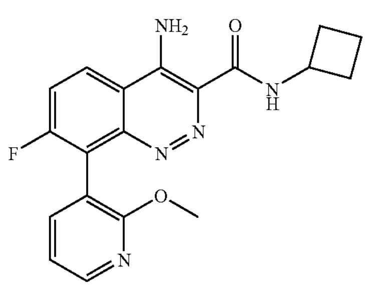 | 4-amino-N-cyclobutyl-7-fluoro-8-(2-methoxypyridin-3-yl)cinnoline-3-carboxamide | A | 368 |

TABLE 4-continued

| Example No. | Structure | Compound Name | Synthesis Method | Mass Spectrum m/z |
|---|---|---|---|---|
| 134 | 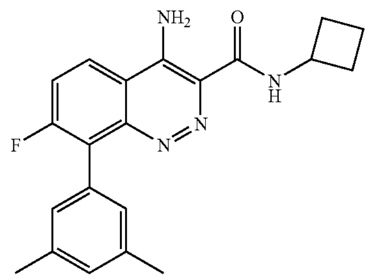 | 4-amino-N-cyclobutyl-8-(3,5-dimethylphenyl)-7-fluoro-cinnoline-3-carboxamide | A | 365 |
| 135 | 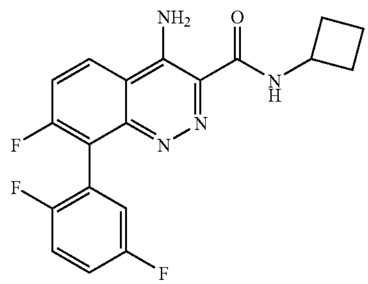 | 4-amino-N-cyclobutyl-8-(2,5-difluorophenyl)-7-fluoro-cinnoline-3-carboxamide | A | 373 |
| 136 | 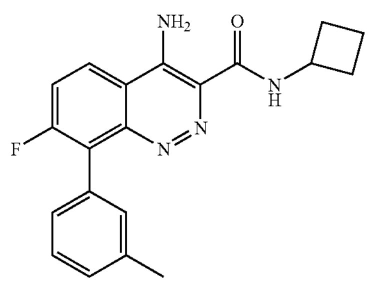 | 4-amino-N-cyclobutyl-7-fluoro-8-(3-methylphenyl)cinnoline-3-carboxamide | A | 351 |
| 137 | 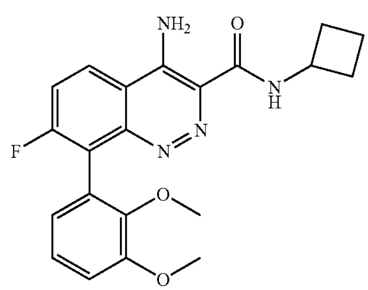 | 4-amino-N-cyclobutyl-8-(2,3-dimethoxyphenyl)-7-fluoro-cinnoline-3-carboxamide | A | 397 |
| 138 | 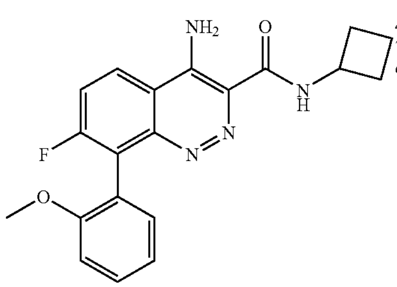 | 4-amino-N-cyclobutyl-7-fluoro-8-(2-methoxyphenyl)cinnoline-3-carboxamide | A | 367 |

TABLE 4-continued

| Example No. | Structure | Compound Name | Synthesis Method | Mass Spectrum m/z |
|---|---|---|---|---|
| 139 | 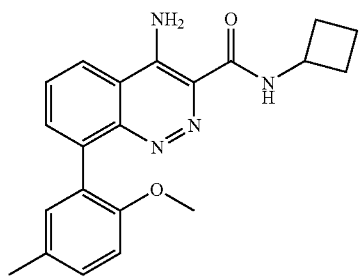 | 4-amino-N-cyclobutyl-8-(2-methoxy-5-methyl-phenyl)cinnoline-3-carboxamide | A | 363 |
| 140 | 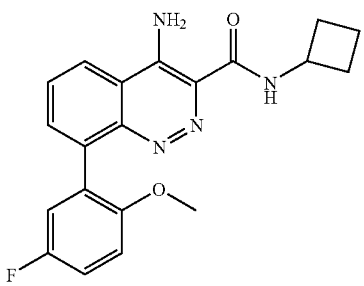 | 4-amino-N-cyclobutyl-8-(5-fluoro-2-methoxy-phenyl)cinnoline-3-carboxamide | A | 367 |
| 141 | 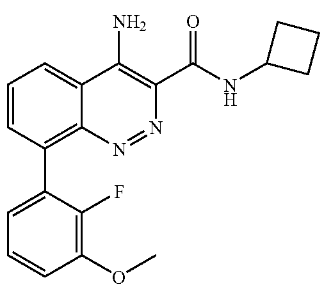 | 4-amino-N-cyclobutyl-8-(2-fluoro-3-methoxy-phenyl)cinnoline-3-carboxamide | A | 367 |
| 142 | 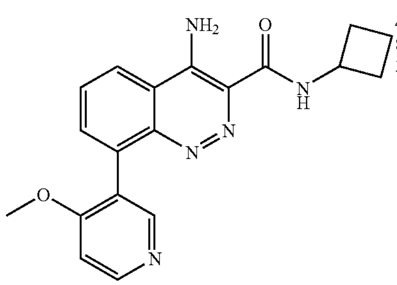 | 4-amino-N-cyclobutyl-8-(4-methoxypyridin-3-yl)cinnoline-3-carboxamide | A | 350 |
| 143 | 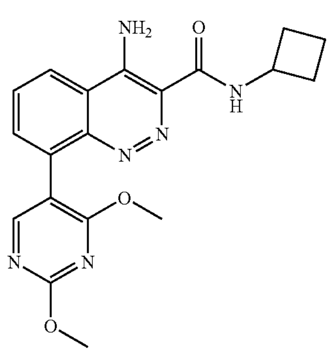 | 4-amino-N-cyclobutyl-8-(2,4-dimethoxypyrimidin-5-yl)cinnoline-3-carboxamide | A | 381 |

TABLE 4-continued

| Example No. | Structure | Compound Name | Synthesis Method | Mass Spectrum m/z |
|---|---|---|---|---|
| 144 | 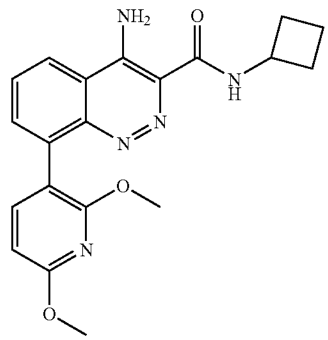 | 4-amino-N-cyclobutyl-8-(2,6-dimethoxypyridin-3-yl)cinnoline-3-carboxamide | A | 380 |
| 145 | | 4-amino-N-cyclobutyl-8-(6-methylpyridin-3-yl)cinnoline-3-carboxamide | A | 334 |
| 145 | | 4-amino-N-cyclobutyl-8-(2-methoxypyridin-3-yl)cinnoline-3-carboxamide | A | 350 |
| 147 | 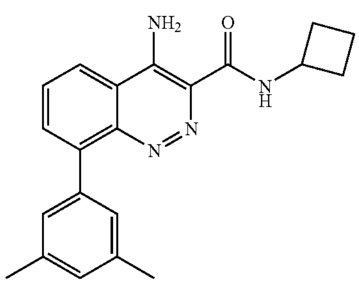 | 4-amino-N-cyclobutyl-8-(3,5-dimethylphenyl)cinnoline-3-carboxamide | A | 347 |
| 148 | 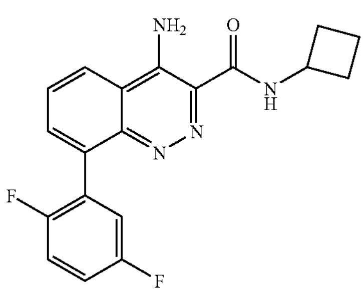 | 4-amino-N-cyclobutyl-8-(2,5-difluorophenyl)cinnoline-3-carboxamide | A | 355 |

TABLE 4-continued

| Example No. | Structure | Compound Name | Synthesis Method | Mass Spectrum m/z |
|---|---|---|---|---|
| 149 | 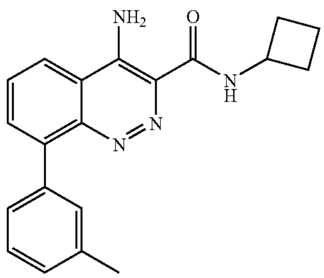 | 4-amino-N-cyclobutyl-methylphenyl)cinnoline-3-carboxamide | A | 333 |
| 150 | 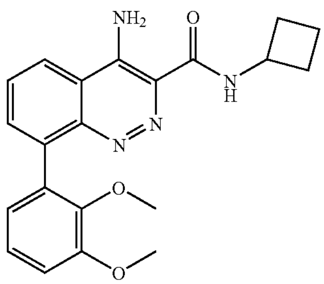 | 4-amino-N-cyclobutyl-8-(2,3-dimethoxyphenyl)cinnoline-3-carboxamide | A | 379 |
| 151 | 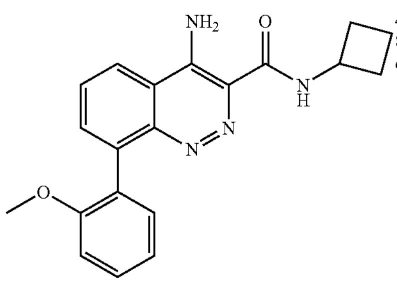 | 4-amino-N-cyclobutyl-8-(2-methoxyphenyl)cinnoline-3-carboxamide | A | 349 |
| 152 | 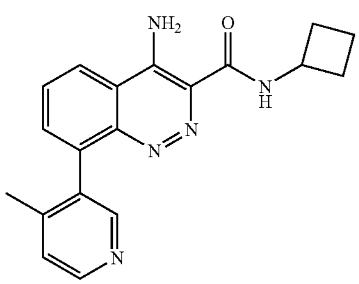 | 4-amino-N-cyclobutyl-8-(4-methylpyridin-3-yl)cinnoline-3-carboxamide | A | 334 |
| 153 | 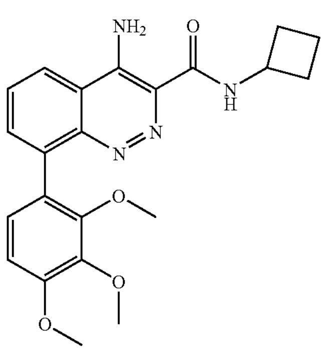 | 4-amino-N-cyclobutyl-8-(2,3,4-trimethoxyphenyl)cinnoline-3-carboxamide | A | 409 |

TABLE 4-continued

| Example No. | Structure | Compound Name | Synthesis Method | Mass Spectrum m/z |
|---|---|---|---|---|
| 154 | 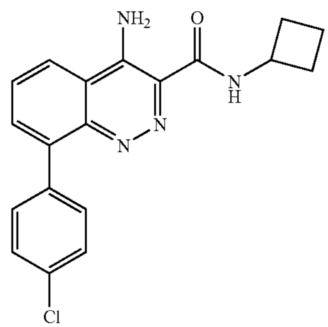 | 4-amino-8-(4-chloro-phenyl)-N-cyclobutyl-cinnoline-3-carboxamide | A | 353 |
| 155 | 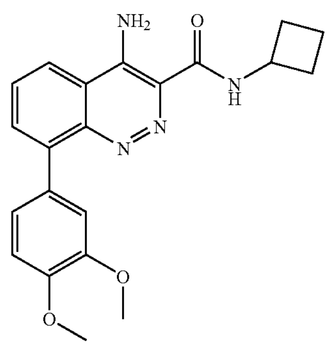 | 4-amino-N-cyclobutyl-8-(3,4-dimethoxyphenyl)cinnoline-3-carboxamide | A | 379 |
| 156 | 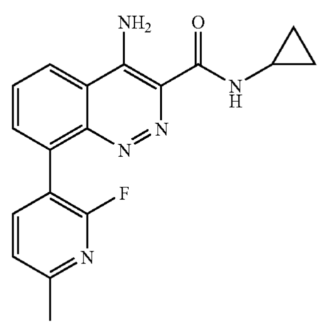 | 4-amino-N-cyclopropyl-8-(2-fluoro-6-methyl-pyridin-3-yl)cinnoline-3-carboxamide | A | 338 |
| 157 | 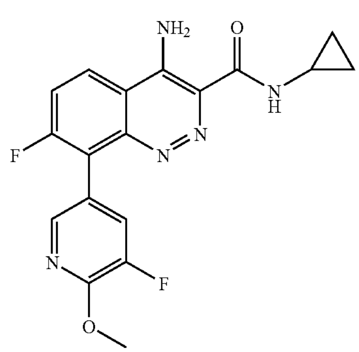 | 4-amino-N-cyclopropyl-7-fluoro-8-(5-fluoro-6-methoxy-pyridin-3-yl)cinnoline-3-carboxamide | A | 372 |

TABLE 4-continued

| Example No. | Structure | Compound Name | Synthesis Method | Mass Spectrum m/z |
|---|---|---|---|---|
| 158 | 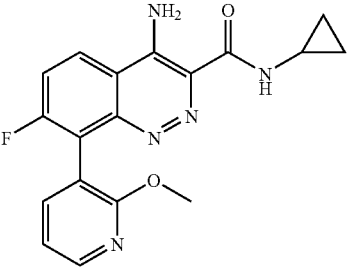 | 4-amino-N-cyclopropyl-7-fluoro-8-(2-methoxypyridin-3-yl)cinnoline-3-carboxamide | A | 354 |
| 159 | 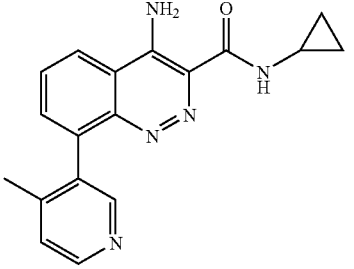 | 4-amino-N-cyclopropyl-8-(4-methylpyridin-3-yl)cinnoline-3-carboxamide | A | 320 |
| 160 | 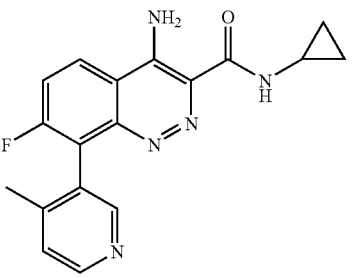 | 4-amino-N-cyclopropyl-7-fluoro-8-(4-methylpyridin-3-yl)cinnoline-3-carboxamide | A | 338 |
| 161 | 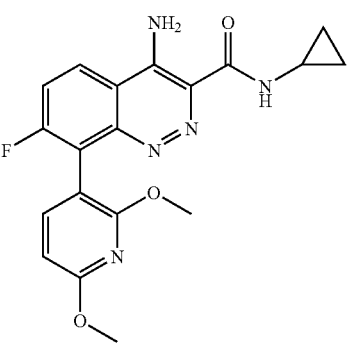 | 4-amino-N-cyclopropyl-8-(2,6-dimethoxypyridin-3-yl)-7-fluoro-cinnoline-3-carboxamide | A | 384 |
| 162 | 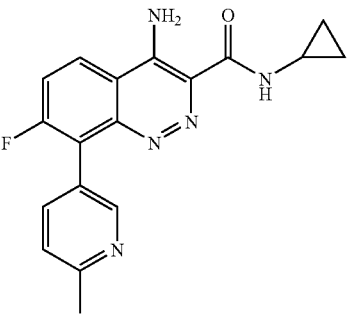 | 4-amino-N-cyclopropyl-7-fluoro-8-(6-methylpyridin-3-yl)cinnoline-3-carboxamide | A | 338 |

TABLE 4-continued

| Example No. | Structure | Compound Name | Synthesis Method | Mass Spectrum m/z |
|---|---|---|---|---|
| 163 | 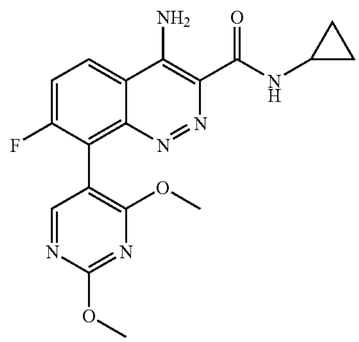 | 4-amino-N-cyclopropyl-8-(2,4-dimethoxypyrimidin-5-yl)-7-fluoro-cinnoline-3-carboxamide | A | 385 |
| 164 | 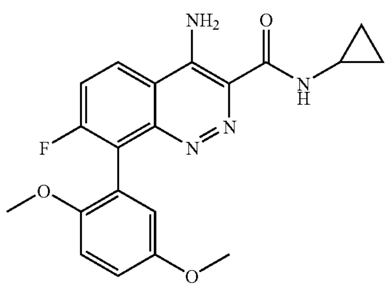 | 4-amino-N-cyclopropyl-8-(2,5-dimethoxyphenyl)-7-fluoro-cinnoline-3-carboxamide | A | 383 |
| 165 | 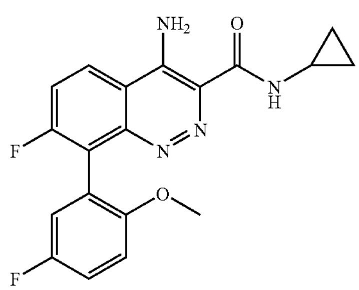 | 4-amino-N-cyclopropyl-7-fluoro-8-(5-fluoro-2-methoxy-phenyl)cinnoline-3-carboxamide | A | 371 |
| 166 | 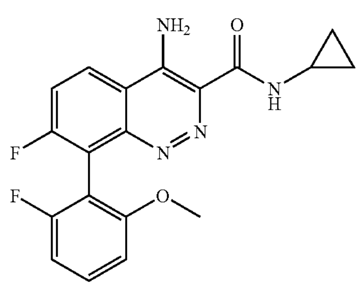 | 4-amino-N-cyclopropyl-7-fluoro-8-(2-fluoro-6-methoxy-phenyl)cinnoline-3-carboxamide | G | 371 |
| 167 | 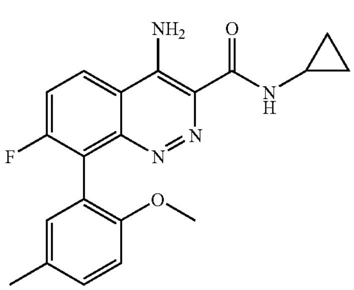 | 4-amino-N-cyclopropyl-7-fluoro-8-(2-methoxy-5-methyl-phenyl)cinnoline-3-carboxamide | A | 367 |

TABLE 4-continued

| Example No. | Structure | Compound Name | Synthesis Method | Mass Spectrum m/z |
|---|---|---|---|---|
| 168 | 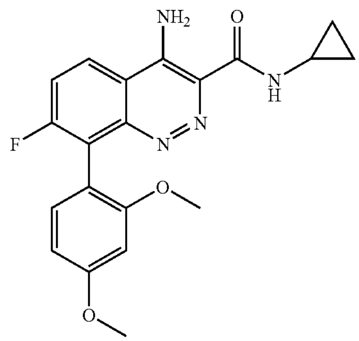 | 4-amino-N-cyclopropyl-8-(2,4-dimethoxyphenyl)-7-fluoro-cinnoline-3-carboxamide | A | 383 |
| 169 | 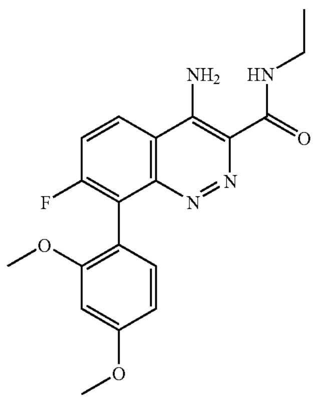 | 4-amino-8-(2,4-dimethoxyphenyl)-N-ethyl-7-fluoro-cinnoline-3-carboxamide | A | 371 |
| 170 | 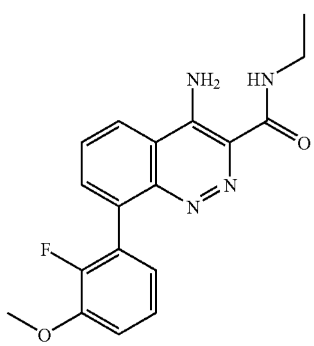 | 4-amino-N-ethyl-8-(2-fluoro-3-methoxy-phenyl)cinnoline-3-carboxamide | A | 341 |
| 171 | 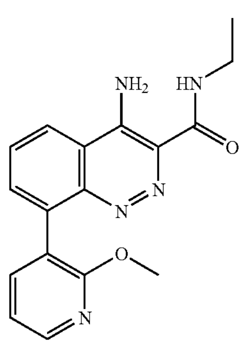 | 4-amino-N-ethyl-8-(2-methoxypyridin-3-yl)cinnoline-3-carboxamide | A | 324 |

TABLE 4-continued

| Example No. | Structure | Compound Name | Synthesis Method | Mass Spectrum m/z |
|---|---|---|---|---|
| 172 | 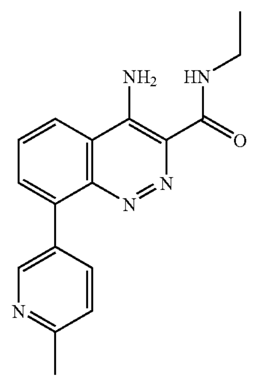 | 4-amino-N-ethyl-8-(6-methylpyridin-3-yl)cinnoline-3-carboxamide | A | 308 |
| 173 | 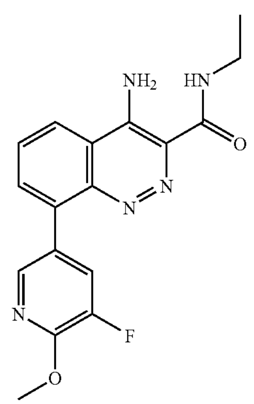 | 4-amino-N-ethyl-8-(5-fluoro-6-methoxy-pyridin-3-yl)cinnoline-3-carboxamide | A | 342 |
| 174 | 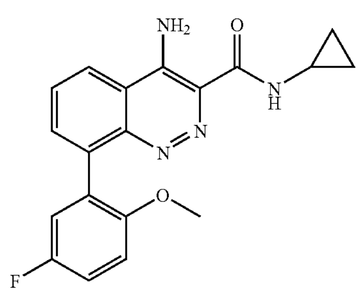 | 4-amino-N-cyclopropyl-8-(5-fluoro-2-methoxy-phenyl)cinnoline-3-carboxamide | A | 353 |
| 175 | 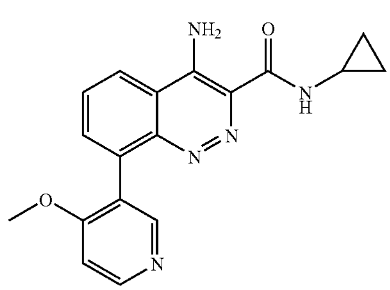 | 4-amino-N-cyclopropyl-8-(4-methoxypyridin-3-yl)cinnoline-3-carboxamide | A | 336 |

TABLE 4-continued
| Example No. | Structure | Compound Name | Synthesis Method | Mass Spectrum m/z |
|---|---|---|---|---|
| 176 | 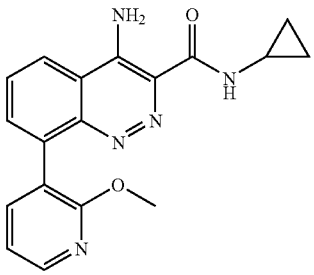 | 4-amino-N-cyclopropyl-8-(2-methoxypyridin-3-yl)cinnoline-3-carboxamide | A | 336 |
| 177 | 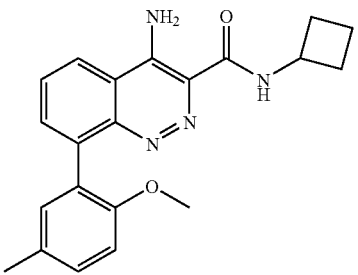 | 4-amino-N-cyclobutyl-8-(2-methoxy-5-methyl-phenyl)cinnoline-3-carboxamide | A | 363 |
| 178 | 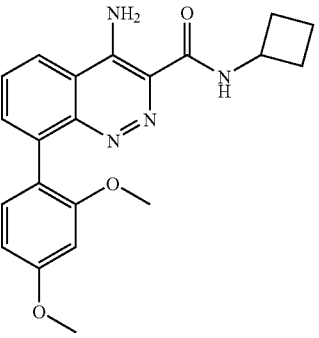 | 4-amino-N-cyclobutyl-8-(2,4-dimethoxyphenyl)cinnoline-3-carboxamide | A | 379 |
| 179 | 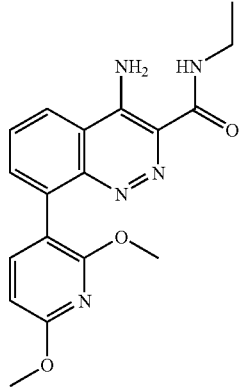 | 4-amino-8-(2,6-dimethoxy-pyridin-3-yl)-N-ethyl-cinnoline-3-carboxamide | A | 354 |

TABLE 4-continued

| Example No. | Structure | Compound Name | Synthesis Method | Mass Spectrum m/z |
|---|---|---|---|---|
| 180 | 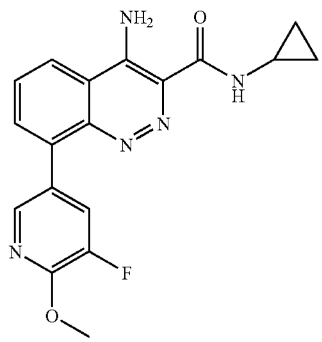 | 4-amino-N-cyclopropyl-8-(5-fluoro-6-methoxy-pyridin-3-yl)cinnoline-3-carboxamide | A | 354 |
| 181 | 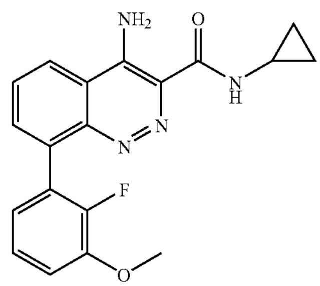 | 4-amino-N-cyclopropyl-8-(2-fluoro-3-methoxy-phenyl)cinnoline-3-carboxamide | A | 353 |
| 182 | 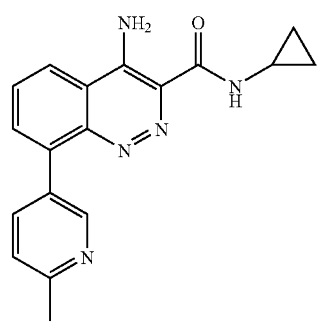 | 4-amino-N-cyclopropyl-8-(6-methylpyridin-3-yl)cinnoline-3-carboxamide | A | 320 |
| 183 | 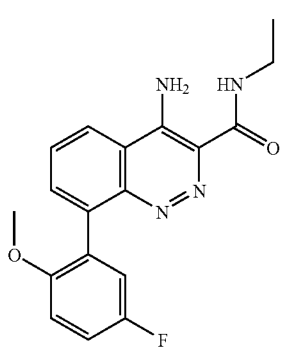 | 4-amino-N-ethyl-8-(5-fluoro-2-methoxy-phenyl)cinnoline-3-carboxamide | A | 341 |

TABLE 4-continued

| Example No. | Structure | Compound Name | Synthesis Method | Mass Spectrum m/z |
|---|---|---|---|---|
| 184 | 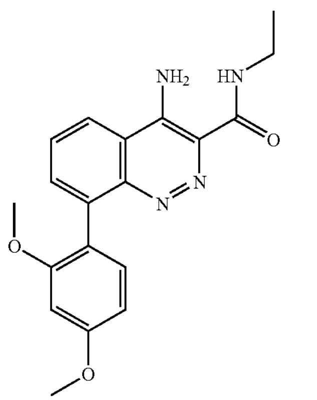 | 4-amino-8-(2,4-dimethoxy-phenyl)-N-ethyl-cinnoline-3-carboxamide | A | 353 |
| 185 | 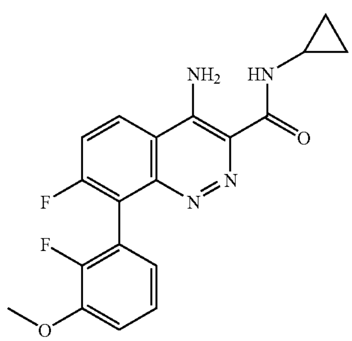 | 4-amino-N-cyclopropyl-7-fluoro-8-(2-fluoro-3-methoxyphenyl)cinnoline-3-carboxamide | A | 371 |
| 186 | 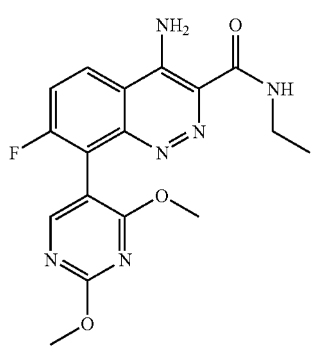 | 4-amino-8-(2,4-dimethoxy-pyrimidin-5-yl)-N-ethyl-7-fluoro-cinnoline-3-carboxamide | A | 373 |
| 187 | 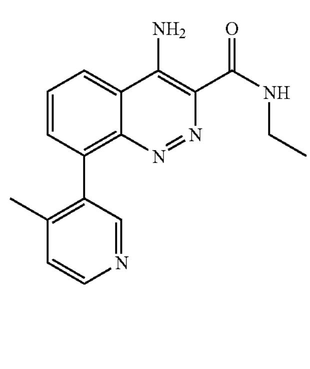 | 4-amino-N-ethyl-8-(4-methyl-pyridin3-yl)cinnoline-3-carboxamide | A | 308 |

TABLE 4-continued

| Example No. | Structure | Compound Name | Synthesis Method | Mass Spectrum m/z |
|---|---|---|---|---|
| 188 | 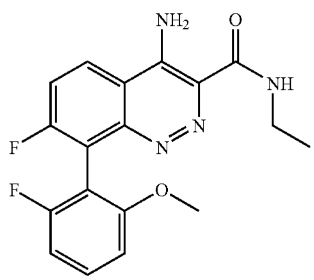 | 4-amino-N-ethyl-7-fluoro-8-(2-fluoro-6-methoxy-phenyl)cinnoline-3-carboxamide | A | 359 |
| 189 | 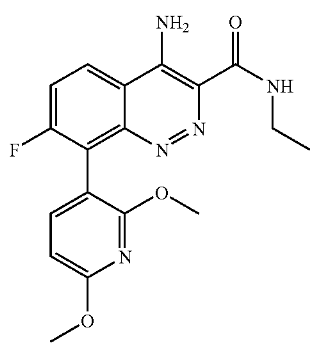 | 4-amino-8-(2,6-dimethoxy-pyridin-3-yl)-N-ethyl-7-fluoro-cinnoline-3-carboxamide | A | 372 |
| 190 | 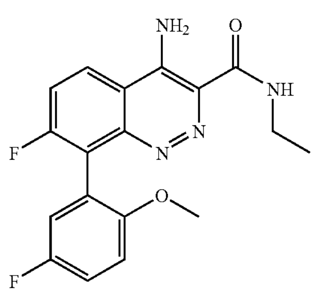 | 4-amino-N-ethyl-7-fluoro-8-(5-fluoro-2-methoxy-phenyl)cinnoline-3-carboxamide | A | 359 |
| 191 | 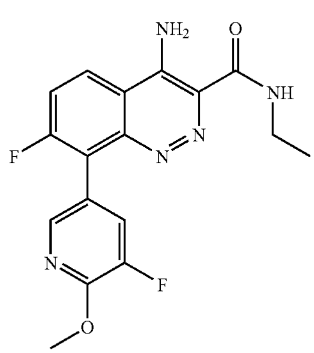 | 4-amino-N-ethyl-7-fluoro-8-(5-fluoro-6-methoxy-pyridin-3-yl)cinnoline-3-carboxamide | A | 360 |

TABLE 4-continued

| Example No. | Structure | Compound Name | Synthesis Method | Mass Spectrum m/z |
|---|---|---|---|---|
| 192 | 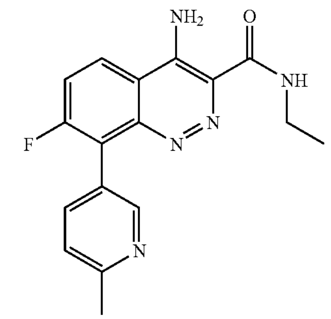 | 4-amino-N-ethyl-7-fluoro-8-(6-methylpyridin-3-yl)cinnoline-3-carboxamide | A | 326 |
| 193 | 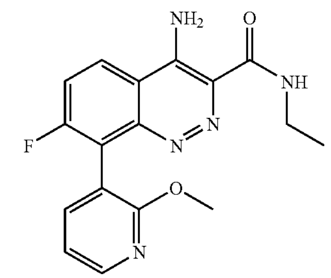 | 4-amino-N-ethyl-7-fluoro-8-(2-methoxypyridin-3-yl)cinnoline-3-carboxamide | A | 342 |
| 194 | 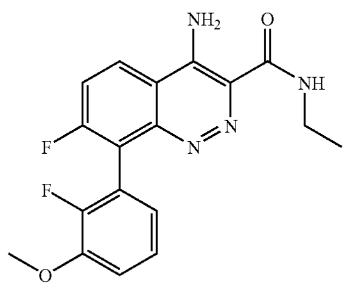 | 4-amino-N-ethyl-7-fluoro-8-(2-fluoro-3-methoxy-phenyl)cinnoline-3-carboxamide | A | 359 |
| 195 | 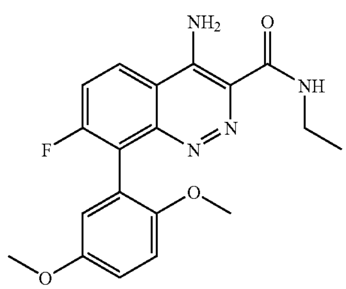 | 4-amino-8-(2,5-dimethoxy-phenyl)-N-ethyl-7-fluoro-cinnoline-3-carboxamide | A | 371 |

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. The starting materials and precursors used in the processes described herein were either commercially available or readily prepared by established organic synthesis methods. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods should then be used.

Chemical abbreviations used in the Examples are defined as follows: "DMSO" denotes dimethylsulfoxide, "THF" denotes tetrahydrofuran, "DMF" denotes N,N-dimethylformamide. Unless otherwise stated reaction progress was monitored by HPLC, LC-MS or TLC. Oven-dried standard laboratory glassware was used and routine manipulations were done at ambient temperature under a blanket of nitrogen unless otherwise indicated. Commercially available reagents and anhydrous solvents were typically used as received.

Evaporations were typically performed under reduced pressure using a rotary evaporator. Preparative chromatography was performed using ICN silica gel 60, 32-63μ or a suitable equivalent. Products were dried under reduced pressure at 40° C. or a suitable temperature.

HPLC-Mass Spectroscopy data were collected utilizing an Agilent Zorbax 5μ SB-C8 column 2.1 mm×5 cm. with a column temperature of 30° C. Solvents: A=98:2 Water:Acetonitrile with 0.1% formic acid added, B=98:2 Acetonitrile:Water with 0.05% formic acid added. Flow rate 1.4 mL/min, injection volume 2.0 μL, initial conditions 5% B, eluting with a linear gradient from 5 to 90% B from time zero to 3 minutes holding at 90% B until 4 minutes. Photodiode array UV detection was used averaging signal from 210 through 400 nm. Mass Spectral data were collected using Full Scan APCI (+), base peak index, 150.0 to 900.0 amu., 30 cone volts with a probe temperature of 450° C.

$^1$H NMR data (δ, ppm) were obtained on a Bruker 300 MHz instrument at 30° C. with tetramethylsilane as an internal standard set at 0.00 ppm. The multiplicities of the NMR spectra absorptions may be abbreviated by: s, singlet; br, broad peak; bs, broad singlet; d, doublet; t, triplet; q, quartet; dd, doublet of doublets; dt, doublet of triplets; m, multiplet. In many cases proton resonances associated with the cinnoline 4-amino group protons were not readily observable in the proton NMR spectra recorded at 30° C. in chloroform-d due to severe broadening into the baseline. These protons can be clearly observed by recording the spectrum at −20° C.

As shown in Scheme 1, a compound 1-3 can be made by coupling of a halogenated cinnoline derivative 1-1 (wherein $X^1$ is halo such as bromo or iodo) to a boron compound 1-2 wherein $R^6$ can be an optionally substituted aryl or heteroaryl (suitable substituents can be alkyl, CN etc.), $R^{101}$ and $R^{102}$ are each, independently, hydrogen or $C_{1-6}$ alkyl; or $R^{101}$ and $R^{102}$, together with the two oxygen atoms to which they are attached and the boron atom to which the two oxygen atoms are attached, form a 4-7 membered heterocyclic ring whose ring-forming atoms comprises B, O and C atoms and which is optionally substituted by 1, 2, 3, or 4 $C_{1-6}$ alkyl (i.e., a moiety shown as 1-2B-R wherein t1 is 0, 1, 2 or 3; t2 is 0, 1, 2, 3 or 4; and $R^{400}$ is each, independently, $C_{1-6}$ alkyl). Two examples of the boron compound 1-2 are 1-2A (a boronic acid derivative) and 1-2B (a 4,4,5,5,-tetramethyl-1,3,2-dioxoborolane derivative). The coupling reaction can be carried out in the presence of a suitable catalyst, such as a metal catalyst. Some exemplary metal catalysts include palladium catalyst, such as bis(triphenylphosphine)palladium(II) dichloride and tetrakis(triphenylphosphine)palladium(0). The coupling reaction can be carried out in the presence of a suitable base such as an inorganic base. Some exemplar suitable inorganic base include cesium carbonate, sodium carbonate, and potassium phosphate. The coupling reaction can be carried out in a suitable solvent such as an organic solvent. Some suitable organic solvent include polar organic solvents, such as an ether and an alcohol. Suitable ethers include 1,2-dimethoxyethane and tetrahydrofuran. Suitable alcohols include ethanol, propanol and isopropanol. A suitable solvent also includes a mixture of two or more individual solvents. Suitable solvents can further contain water. The coupling reaction can be carried out at a suitable temperature to afford the compound 1-3. In some embodiments, the reaction mixture is heated to an elevated temperature (i.e., above the room temperature). In some embodiments, the reaction mixture is heated to a temperature of about 40° C., about 50° C., about 60° C., about 70° C., about 80° C., about 90° C., about 100° C., about 110° C., about 120° C., about 130° C., about 140° C., about 150° C., about 160° C. The reaction progress can be monitored by conventional methods such as TLC or NMR.

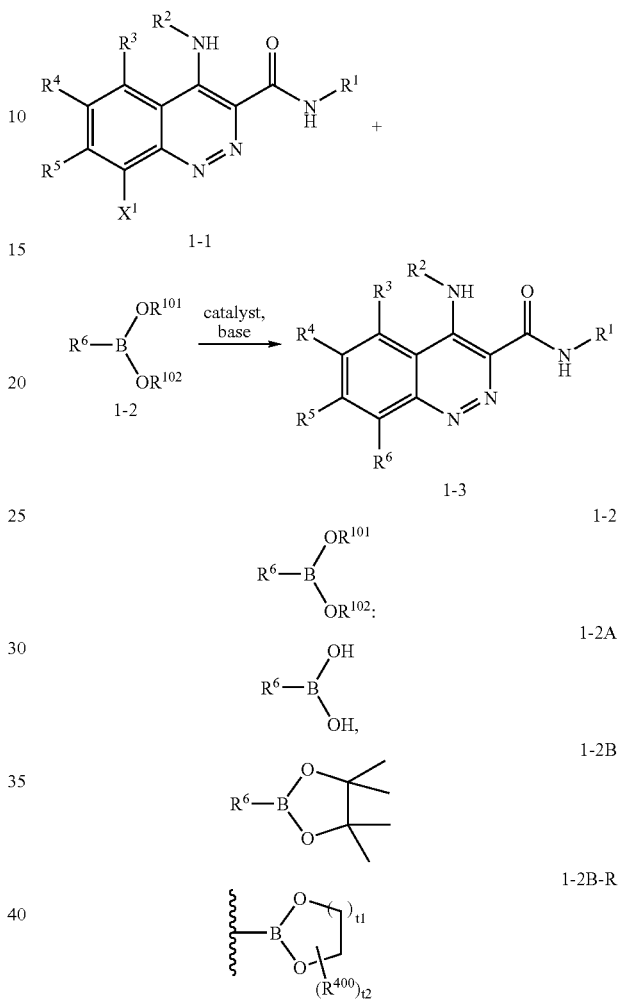

As shown in Scheme 2, a compound 2-3 can be made by coupling of a halogenated crinoline derivative 2-1 (wherein $X^2$ is halo such as broom or iodole) to a tin compound 2-2 wherein $R^6$ can be an optionally substituted aryl or heteroaryl (suitable substituent's can be alkyl, CN etc.), $R^{201}$, $R^{202}$ and $R^{203}$ are each, independently, $C_{1-6}$ alkyl. The coupling reaction can be carried out in the presence of a suitable catalyst, such as a metal catalyst. Some exemplary metal catalysts include palladium catalysts, such as bis(triphenylphosphine) palladium(II) dichloride and tetrakis(triphenylphosphine) palladium(0). The coupling reaction can be carried out in a suitable organic solvent. Some suitable organic solvent include polar organic solvent. Some suitable organic solvent include paretic solvent. Some suitable organic solvent include polar paretic organic solvent such as N,N-dimethylformamide. The coupling reaction can be carried out at a suitable temperature for a time sufficient to afford the compound 2-3. In some embodiments, the reaction mixture is heated to an elevated temperature (i.e., above the room temperature). In some embodiments, the reaction mixture is heated to a temperature of about 40° C., about 50° C., about 60° C., about 70° C., about 80° C., about 90° C., about 100°

C., about 110° C., about 120° C., about 130° C., about 140° C., about 150° C., about 160° C. The reaction progress can be monitored by conventional methods such as TLC or NMR.

palladium catalysts include bis(triphenylphosphine)palladium(II) dichloride and tetrakis(triphenylphosphine)palladium(0).

Scheme 2

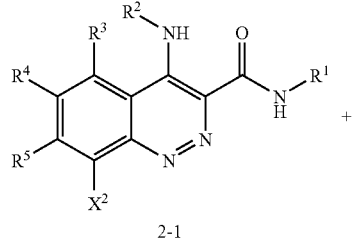

2-1

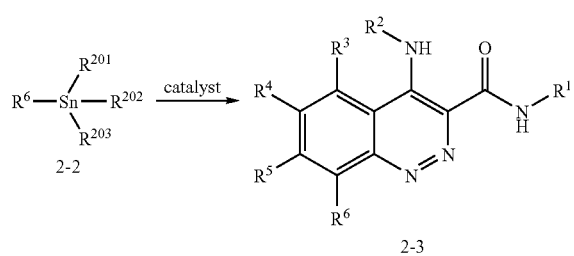

2-2

2-3

Scheme 3

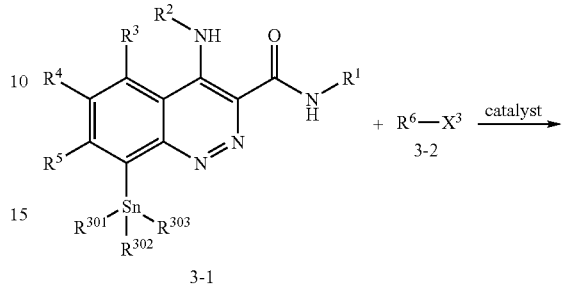

3-1

3-2

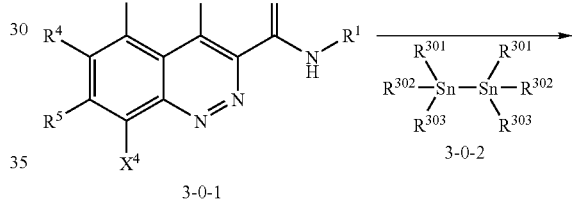

3-3

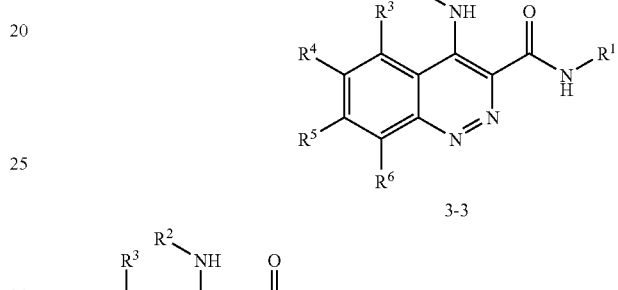

3-0-1

3-0-2

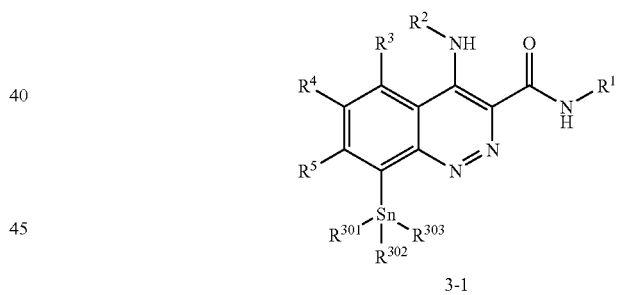

3-1

As shown in Scheme 3 a compound 3-3 can be made by coupling of a Trialkylstannyl-cinnoline derivative 3-1 (wherein $R^{301}$, $R^{302}$ and $R^{303}$ are each, independently, $C_{1-6}$ alkyl) to a halogenated compound $R^6X^3$ 3-2 wherein $X^3$ is halo such as broom or iodole, and wherein $R^6$ can be an optionally substituted aryl or heteroaryl (suitable substituent's can be alkyl, CN etc.). The coupling reaction can be carried out in the presence of a suitable catalyst, such as a metal catalyst. Some exemplary metal catalysts include palladium catalysts, such as bis(triphenylphosphine)palladium (II) dichloride and tetrakis(triphenylphosphine)palladium (0). The coupling reaction can be carried out in a suitable organic solvent. Some suitable organic solvent include polar organic solvent. Some suitable organic solvents include paretic organic solvent. Some suitable organic solvents include polar paretic organic solvents such as N,N-dimethylformamide. The coupling reaction can be carried out at a suitable temperature for a time sufficient to afford the compound 2-3. In some embodiments, the reaction mixture is heated to an elevated temperature (i.e., above the room temperature). In some embodiments, the reaction mixture is heated to a temperature of about 40° C., about 50° C., about 60° C., about 70° C., about 80° C., about 90° C., about 100° C., about 110° C., about 120° C., about 130° C., about 140° C., about 150° C., about 160° C. The reaction progress can be monitored by conventional methods such as TLC or NMR.

Also as shown in Scheme 3, the trialkylstannyl-cinnoline derivative 3-1 can be made by coupling of a halogenated crinoline derivative 3-0-1 (wherein $X^4$ is halo such as broom or iodole) to a di-tin compound 3-0-2 (wherein $R^{301}$, $R^{302}$ and $R^{303}$ are each, independently, $C_{1-6}$ alkyl) in the presence of a suitable catalyst, such as a palladium catalyst. Some exemplar It should noted that in all of the schemes described herein, if there are functional (reactive) groups present on a substituent group such as $R^1$, $R^2$, $R^3$, $R^4$, $R^5$, $R^6$, etc., further modification can be made if appropriate and/or des irked. For example, a CN group can be hydrolyzed to afford an amide group; a carboxylic acid can be converted to an amide; a carboxylic acid can be converted to a ester, which in turn can be reduced to an alcohol, which in turn can be further modified. In another example, an OH group can be converted into a better leaving group such as maculate, which in turn is suitable for nucleophilic substitution, such as by CN. One skilled in the art will recognize further such modifications. Thus, a compound of formula I (such as compound 1-3 of Scheme 1, compound 2-3 in Scheme 2 and compound 3-3 of Scheme 3) having a substituent which contains a function group can be converted to another compound of formula I having a different substituent group.

As used herein, the term "reacting" refers to the bringing together of designated chemical reactants such that a chemical transformation takes place generating a compound different from any initially introduced into the system. Reacting can take place in the presence or absence of solvent.

Some more detailed methods, procedures and precursors as outlined in Schemes 1-3 and additional detailed procedures and characterization data for certain above exemplified compounds are further described herein below.

Precursor 1

4-Amino-7-flour-8-iodo-N-propyl-cinnoline-3-carboxamide

To a 1, 3-necked flask equipped with a mechanical stirrer charged with (2E)-2-cyan-2-[(3-flour-2-indophenols)hydrazono]-N-propylacetamide (43.9 g, 117 mmol) in anhydrous toluene (Aldrich, 600 mL) under $N_2$ was added portion-wise aluminum chloride (Aldrich, 46.8 g, 352 mmol) over 20 minutes. The mixture was heated to 60° C. with vigorous stirring for 2 hours and then cooled to ~15° C. Ethyl acetate (30 mL) was carefully added while maintaining the internal temperature between 20-25° C. Additional ethyl acetate (900 mL) was then added, followed by careful addition of Rochelle's salt (saturated aqueous potassium sodium tart rate, 500 mL). Upon addition of the first 50 mL, the temperature rose from 20 to 36° C. The reaction was heated with stirring at 60° C. for 30 minutes. The aqueous layer contained a thick white precipitate and the organic layer slowly solubilized the brownish yellow solid. Note: If a non-white (brown/yellow) solid still existed at the aqueous/organic interface, the hot extraction was repeated. The mixture was placed in a separator funnel and the aqueous layer was removed. The organic layer was washed with Rochelle's salt (500 mL) and brine, dried over magnesium sulfate, filtered and concentrated to give 38 g of product (86.5%). Further purification by triturating with ethyl acetate/hexanes was carried out when appropriate. An analytically pure sample was obtained by recrystallization from ethyl acetate. $^1$H NMR (300 MHz, CDCl$_3$) δ 8.54 (br, 1H), 7.84 (dd, J=5.3, 9.2 Hz, 1H), 7.39 (dd, J=7.0, 9.2 Hz, 1H), 3.47 (apparent q, J=7.0 Hz, 2H), 1.68 (apparent sextet, J=7.0 Hz, 2H), 1.03 (t, J=7.4 Hz, 3H). MS APCI, m/z=375 (M+H). HPLC 2.13 min.

The intermediate compounds were prepared as follows:

3-Flour-2-iodoaniline hydrochloride

To a 1, 3 necked round bottom flask fitted with a mechanical stirrer was added 3-flour-2-iodonitrobenzene (3B Medical, 47.7 g, 179 mmol) and 500 mL absolute ethanol. To this stirred solution was added iron powder (325 mesh, Aldrich, 30 g, 537 mmol) followed by drop wise addition of concentrated HCl (30 mL, 360 mmol). The internal temperature rose from 23 to ~60° C. over the addition. The flask was fitted with a heating mantle and heated with vigorous stirring for 90 minutes. After cooling to room temperature, 1 N sodium carbonate (300 mL) was added followed by ethyl acetate (200 mL). The mixture was stirred for 30 minutes and then filtered through a pad of elite. The elite was washed with ethyl acetate (3×150 mL). The filtrates were placed in a separator funnel and the water layer was removed. The organic layer was concentrated under reduced pressure to a volume of ~200 mL, placed in a separator funnel, diluted with ethyl acetate (400 mL), washed with brine, dried over sodium sulfate, filtered and concentrated to dryness. The crude product was taken up in ether (300 mL) and made acidic to pH 1 with 2M hydrochloric acid/ether (Aldrich). After 1 hour, the tan solid was isolated by filtration (39.2 g, 80%). The above aqueous layers were extracted with diethyl ether (300 mL), dried over sodium sulfate, combined with the filtrate of the 1$^{st}$ crop, made acidic to pH 1, and isolated as above to give additional tan solid (9.0 g, 18%) for an overall yield of 98%. $^1$H NMR (300 MHz, CDCl$_3$) δ 7.06 (m, 1H), 6.58 (m, 1H), 6.39 (m, 1H), 5.73 (bm, 1H). MS APCI, m/z=238 (M+H). HPLC 2.19 min.

(2E)-2-Cyan-2-[(3-flour-2-indophenols)hydrazono]-N-propylacetamide

Using the procedure outlined in the patent U.S. Pat. No. 4,886,800 example 89b substituting 3-flour-2-iodoaniline hydrochloride (8.8 g, 32.5 mmol) for 2-iodoaniline, the title compound (2E)-2-cyan-2-[(3-flour-2-indophenols)hydrazono]-N-propylacetamide (8.5 g, 70% yield) was obtained as a light brown solid. An analytically pure sample was obtained by recrystallization from ethyl acetate as a yellow crystalline solid. $^1$H NMR (300 MHz, CDCl$_3$) δ 14.39 (s, 1H), 8.67 (bm, 1H), 7.45 (m, 1H), 7.32 (m, 1H), 7.03 (m, 1H), 3.1 (apparent q, J=6.6 Hz, 2H), 1.53 (apparent sextet, J=7.4 Hz, 2H), 0.88 (t, J=7.4 Hz, 3H).

Precursor 2

4-Amino-7-chloral-8-iodo-N-propyl-cinnoline-3-carboxamide

Using a procedure similar to that used in the synthesis of 4-amino-7-flour-8-iodo-N-propyl-cinnoline-3-carboxamide, the title compound 4-amino-7-chloral-8-iodo-N-propyl-cinnoline-3-carboxamide (2.75 g, 67% yield) was obtained from (2E)-2-cyan-2-[(3-chloral-2-indophenols)hydrazono]-N-propylacetamide (4.1 g, 10.5 mmol) as a white solid. $^1$H NMR (300 MHz, CDCl$_3$) δ 8.54 (bs, 1H), 7.76 (d, J=9.0 Hz, 1H), 7.66 (d, J=9.0 Hz, 1H), 3.47 (apparent q, J=7.0 Hz, 2H), 1.68 (apparent sextet, J=7.0 Hz, 2H), 1.03 (t, 7.4 Hz, 3H). MS APCI, m/z=391 (M+H) HPLC 2.38 min.

The intermediate compounds were prepared as follows:

(2E)-2-Cyan-2-[(3-chloral-2-indophenols)hydrazono]-N-propylacetamide

Prepared according to the method described in patent U.S. Pat. No. 4,886,800 example 89b substituting 3-chloral-2-iodoaniline (7.1 g, 28.1 mmol) for 2-iodoaniline, the title compound (2E)-2-cyan-2-[(3-chloral-2-indophenols)hydrazono]-N-propylacetamide (4.2 g, 38% yield) was obtained as a yellow solid. $^1$H NMR (300 MHz, CDCl$_3$) δ 14.30 (s, 1H), 7.48 (m, 1H), 7.24-7.33 (m, 3H), 6.28 (bm, 1H), 3.37 (apparent q, J=7.0 Hz, 2H), 1.64 (apparent sextet, J=7.4 Hz, 2H), 1.00 (t, J=7.4 Hz, 3H) MS APCI, m/z=391 (M+H) HPLC 3.00 min.

3-Chloral-2-iodoaniline

Prepared according to the method described in patent U.S. Pat. No. 4,822,781, process 1, substituting 2-chloral-6-nitro phenol for 2-flour-6-nitro phenol, the title compound, 3-chloral-2-iodoaniline (7.1 g, 3 step overall yield 55% yield) was obtained from 2-chloral-6-nitro phenol as a yellow solid. $^1$H NMR (300 MHz, CDCl$_3$) δ 7.04 (t, J=8.0 Hz, 1H), 6.84 (dd, J=8.0, 1.3 Hz, 1H), 6.60 (dd, J=8.0, 1.3 Hz, 1H), 4.31 (bs, 2H). MS APCI, m/z=254 (M+H) HPLC 2.38 min Precursor 3

4-Amino-8-bromo-N-propyl-cinnoline-3-carboxamide

A 22, 3-necked flask equipped with a mechanical stirrer, thermometer, nitrogen inlet, reflux condenser, and addition funnel was charged with N-propel-2-cyan-2-[(2-bromophenyl)hydrazono]ace amide (195.4 g, 0.632 mol) in toluene (4). Aluminum chloride (295 g, 2.21 mol) was added in three portions. The mixture was heated with a mantle to 90° C. in approximately 30 minutes. After 2.5 hours, the heat was removed and the reaction mixture was allowed to cool to room temperature overnight. The reaction mixture was cooled in an ice bath to $\leq 10°$ C. and elite was added. Water (680 mL) was added drop wise over 1 hr at $\leq 10°$ C. After stirring for 30 minutes, ethylene chloride was added (8). The reaction mixture was cooled to $\leq 10°$ C. and 10% sodium hydroxide (5.8) was added drop wise over 45 minutes at $\leq 10°$ C. After stirring for 30 minutes, tetrahydrofuran (2) was added and the phases were allowed to separate. The aqueous layer was removed, filtered through elite, and the filter cake washed with 2:1 ethylene chloride:tetrahydrofuran (4). Note: Addition of fresh portions of ethylene chloride helped expedite the rather tedious filtration. The phases of the filtrate were separated and the organic phase was transferred to a separator funnel. Separation of the organic phase from the aqueous base as quickly as possible helped avoid undue hydrolysis of the propel amide in the product. The solids remaining in the reaction flask were dissolved with 2:1 tetrahydrofuran:methanol (4) and then 10% methanol in chloroform (4). The layers were separated and the organic layer was washed with brine (500 mL), dried over magnesium sulfate, filtered, and concentrated under reduced pressure to a dark brown solid. The solid was slurred in diethyl ether, collected by filtration and dried. The crude solid (188 g) was then dissolved in hot methanol (6), treated with activated charcoal (19 g), stirred 15 minutes at reflux, filtered through elite while hot, concentrated to approximately 3, and allowed to crystallize overnight. The solids were collected, washed with diethyl ether (400 mL) and dried in a vacuum oven at 50° C. to give a white crystalline solid. The filtrate was concentrated to approximately 1 and a second crop obtained. The mother liquors were stripped and a third and fourth crop were obtained from additional recrystallizations to afford a total of 164.6 g of the desired compound as a white crystalline solid (84%). $^1$H NMR (300.132 MHz, CDCl$_3$) $\delta$ 8.57 (bs, 1H), 8.12 (dd, J=7.6, 1.1 Hz, 1H), 7.83 (dd, J=8.4, 1.0 Hz, 1H), 7.50 (dd, J=8.4, 7.5 Hz, 1H), 3.48 (q, J=6.7 Hz, 2H), 1.69 (sextet, J=7.3 Hz, 2H), 1.03 (t, J=7.4 Hz, 3H). MS APCI, m/z=309/311 (M+H). HPLC 1.66 min.

Precursor 4

4-Amino-8-iodo-N-propyl-cinnoline-3-carboxamide

Prepared according to the method described in the patent U.S. Pat. No. 4,886,800 example 36a.

Precursor 5

4-Amino-8-fluoro-N-propyl-cinnoline-3-carboxamide

To a suspension of N-propel-2-cyan-2-[(2-Fluor phenyl)hydrazono]ace amide (11.1 g, 44.71 mmol) in toluene (275 mL) was added aluminum chloride (20.90 g, 156.74 mmol). The mixture was stirred at 90° C. for 2.5 hours. The reaction mixture was cooled to 0° C., and then diluted with chloroform (1). A small amount of water was added to quench the reaction at 0° C. Aqueous sodium hydroxide (750 mL, 20% w/v solution) was poured into the mixture slowly at 0° C., and the mixture stirred at ambient temperature for one hour. A precipitate was formed gradually. The mixture was diluted with chloroform (2) until all of the precipitate was dissolved, washed twice with water, dried through magnesium sulfate, and concentrated to a volume of approximately 200 mL to leave a suspension of the product. The title compound as a light beige solid (11.06 g) was collected by filtration and washed with ethylene chloride (50 mL×2), methanol (50 mL) and hexane (100 mL×2). The mother liquor was concentrated, and purified by flash chromatography using a gradient of ethyl acetate in hexane to give an additional 400 mg of the title compound as a beige solid. $^1$H NMR (300 MHz, CDCl$_3$) $\delta$ 8.55 (br, 1H), 7.55-7.70 (m, 2H), 3.49 (m, 2H), 1.71 (m, 2H), 1.03 (t, J=7.4 Hz, 3H) MS APCI, m/z=249 (M+H) HPLC 1.30 min.

The intermediate compounds were prepared as follows:

N-propel 2-cyan-2-[(2-Fluor phenyl)hydrazono]ace amide

Solution A: To a mechanically stirred solution of 2-Fluor aniline (11.51 g, 100.34 mmol) in acetic acid (50 mL) was added water (30 mL) at ambient temperature. The mixture was cooled to 0° C., and then concentrated aqueous HCl (25 mL) added. A precipitate was formed as soon as the concentrated HCl was added, and the suspension was stirred at 0° C. for 20 minutes. To this suspension was added drop wise a solution of sodium nitrite (7.72 g, 111.88 mmol) in water (30 mL), maintaining the internal temperature below 5° C. The resulting clear orange solution was stirred at 0° C. for another 30 minutes.

Solution B: To a mechanically stirred solution of N-propel-2-cyanoacetamide (15.69 g, 124.37 mmol) in ethanol (220 mL) was added a solution of sodium acetate (136.00 g, 1.66 moles) in water (600 mL), and chilled to between 0° C. and −5° C.

Solution A was poured into solution B, maintaining the internal temperature below 0° C. An orange precipitate was formed gradually after 10 minutes. The mixture was stirred below 0° C. for another hour, and was then diluted with water (500 mL). After 30 minutes, the orange precipitate was collected by filtration, washed with water (100 mL×3), and dried at 50° C. under high vacuum to remove water. An orange solid (9.50 g) was obtained, which was the "E" isomer, and used for the next step without further purification. $^1$H NMR (300 MHz, CDCl$_3$) $\delta$ 14.18 (br, 1H), 7.68 (td, 1H, J=7.94 Hz, J'=1.47 Hz), 7.00-7.20 (m, 3H), 6.28 (s, 1H), 3.34 (m, 2H), 1.64 (m, 2H), 0.99 (t, 3H, J=7.40 Hz)

Precursor 6

4-amino-8-trimethylstannyl-N-propyl-cinnoline-3-carboxamide

To a stirred solution of 4-amino-8-iodo-N-propyl-cinnoline-3-carboxamide (3.4 g, 9.4 mmol) and tetrakis(triphenylphosphine) palladium(0) (800 mg, 0.69 mmol) in anhydrous N,N-dimethylformamide at ambient temperature under nitrogen was added hexamethylditin (5.0 g, 15.2 mmol). The reaction was heated to 150° C. for 1-1.5 hours. The reaction mixture was filtered through Elite, and the solution evaporated. The residue was dissolved in ethylene chloride, washed with water twice, dried through MgSO$_4$, and then the solvent was evaporated. The residue was purified by flash chromatography using an increasingly polar gradient of ethyl acetate in hexane to give a yellow solid as the title compound (2.4 g, 68.4% yield). $^1$H NMR (300 MHz, CDCl$_3$) δ 8.56 (br, 1H), 7.99 (dd, J=6.6 Hz, J'=1.0 Hz, 1H), 7.83 (dd, J=8.4 Hz, J'=1.1 Hz, 1H), 7.61 (dd, J=8.3 Hz, J'=6.6 Hz, 1H), 3.47 (q, J=6.8 Hz, 2H), 1.70 (m, J=7.3 Hz, 2H), 1.02 (t, 3H, J=7.40 Hz), 0.44 (s, 9H). MS APCI, m/z=391/392/395 (M+H). HPLC 2.75 min.

Precursor 7

4-Amino-8-bromo-N-ethyl-cinnoline-3-carboxamide

To a stirred solution of 2-[(2-bromophenyl)-hydrazono]-N-ethyl-2-cyanoacetamide (260 mg, 0.88 mmol) in anhydrous toluene (10 mL) was added aluminum chloride (370 mg, 2.78 mmol). The reaction was heated with vigorous stirring at 90° C. for 1.5 hours, cooled, diluted with ethyl acetate (40 mL), and treated with Rochelle's salt (saturated aqueous solution). After stirring for 30 minutes, the organic layer was decanted into a separator funnel. (The white precipitate was rinsed with ethyl acetate three times.) The organic layer was washed with 1:1 brine:Rochelle's salt solution, dried over sodium sulfate, and concentrated to a light brown solid. The solid was slurred in ether and filtered to afford the title compound as a brown solid (180 mg, 69%). $^1$H NMR (300.132 MHz, CDCl$_3$) δ 8.52 (s, 1H), 8.13 (dd, J=7.4, 1.1 Hz, 1H), 7.82 (dd, J=8.4, 1.1 Hz, 1H), 7.51 (dd, J=8.4, 7.5 Hz, 1H), 3.56 (dq, J=5.8, 7.3 Hz, 2H), 1.31 (t, J=7.3 Hz, 3H). MS APCI, m/z=395/397 (M+H). HPLC 1.90 min.

The intermediate compounds were prepared as follows:

2-[(2-Bromophenyl)-hydrazono]-N-ethyl-2-cyanoacetamide

To a solution of [(2-bromophenyl)-hydrazono]-cyan acetic acid ethyl ester (1.0 g, 3.4 mmol) in methanol (14 mL) was added 70% ethyl amine in water (16 mL, 20.2 mmol) followed by diethyl amine (468 uL, 3.6 mmol). The reaction was stirred at room temperature overnight, concentrated and dried under high vacuum. The material was routinely used crude. Purification on silica gel using a gradient of 10 to 50% ethyl acetate in hexanes afforded the title compound as a yellow solid. $^1$H NMR (300.132 MHz, CDCl$_3$) δ 14.33 (s, 1H), 7.67 (dd, J=8.3, 1.4 Hz, 1H), 7.53 (dd, J=8.1, 1.3 Hz, 1H), 7.34 (tq, J=7.8, 0.6 Hz, 1H), 7.01 (td, J=7.7, 1.6 Hz, 1H), 3.45 (dq, J=5.9, 7.2 Hz, 2H), 1.26 (t, J=7.3 Hz, 3H). HPLC 4.66 min.

Precursor 8

2-(Biphenyl-2-yl-hydrazono)-2-cyano-N-cyclopropylmethyl-acetamide

To a stirred solution of 2-amino biphenyl (2.95 g, 17.4 mmol) in glacial acetic acid (16 mL) and water (14 mL) with cooling was added drop wise concentrated hydrochloric acid (10 mL). Additional water (10 mL) was added to maintain stirring. The mixture was cooled to 0° C. and a solution of sodium nitrite (1.44 g, 20.7 mmol) in water (10 mL) was added drop wise maintaining an internal temperature of <5° C. Upon complete addition, the reaction was stirred at 0° C. for 30 minutes, poured portion wise into a mechanically stirred 3-necked round bottomed flask charged with a predissolved solution of 2-cyano-N-cyclopropylmethylacetamide (2.8 g, 20.3 mmol), sodium acetate (12.0 g, 146 mmol), and sodium carbonate (12.8 g, 121 mmol) in 2:1 water: ethanol (180 mL). Vigorous CO$_2$(g) evolution was observed. After 1 hour at 0° C., the reaction was diluted with water (200 mL) and extracted with ethyl acetate (400 mL). The organic layer was washed with water (200 mL) and brine (200 mL) and dried over sodium sulfate. The mixture was filtered, concentrated, and purified by recrystallization from ethyl acetate/ hexanes to afford the title compound as a yellow solid (2.0 g, 36%). $^1$H NMR (500.133 MHz, CDCl$_3$) δ 9.23 (t, J=5.3 Hz, 1H), 9.13 (bs, 1H), 8.43 (d, J=8.3 Hz, 1H), 8.17 (bs, 1H), 7.86 (d, J=7.2 Hz, 1H), 7.81 (t, J=7.6 Hz, 1H), 7.71 (d, J=7.5 Hz, 2H), 7.49 (t, J=7.2 Hz, 2H), 7.43 (t, J=7.2 Hz, 1H), 3.30 (s, 0H), 3.23 (t, J=6.1 Hz, 2H), 1.12 (septet, J=6.4 Hz, 1H), 0.45 (d, J=8.0 Hz, 2H), 0.29 (d, J=4.1 Hz, 2H). MS APCI, m/z=319 (M+H). HPLC 1.84 min.

The intermediate compounds were prepared as follows:

2-Cyano-N-cyclopropylmethylacetamide

To an ice-cooled flask charged with cyclopropyl methyl amine (4.25 g, 59.8 mmol) was added ethyl cyan acetate (3.17 mL, 29.7 mmol). The reaction was stirred at 0° C. for 1.75 hour at which point a precipitate had formed and 1:1 ether: hexanes (40 mL) was added. The mixture was stirred for 15 minutes, filtered, and the solids washed with hexanes to give the title compound as a white solid (3.44 g, 84%). $^1$H NMR (300.132 MHz, CDCl$_3$) δ 6.17 (s, 1H), 3.37 (s, 2H), 3.17 (dd, J=7.1, 5.4 Hz, 2H), 1.06-0.92 (m, 1H), 0.62-0.51 (m, 2H), 0.24 (q, J=5.1 Hz, 2H).

Precursor 9

4-Amino-8-bromo-N-butyl-cinnoline-3-carboxamide

To a solution of 2-[(2-bromophenyl)-hydrazono]-N-butyl-2-cyanoacetamide (2.5 g, 7.7 mmol) in anhydrous toluene (Aldrich, 50 mL) under N$_2$ was added portion-wise aluminum chloride (Aldrich, 3.1 g, 23.2 mmol) over 5 minutes. The mixture was heated to 90° C. with vigorous stirring for 1.5 hours then cooled to ~0° C. Water (3 mL) was added drop wise followed by careful addition of Rochelle's salt (saturated aqueous potassium sodium tart rate, 50 mL). The reaction was stirred for 25 minutes and then poured into a separator funnel. The aqueous layer contained a thick white precipitate and was quickly removed. The organic layer was washed with Rochelle's salt and brine, dried over magnesium sulfate, filtered and concentrated to give 2.6 g slightly crude product which was purified on silica gel using a gradient of 20 to 60% ethyl acetate in hexane. Recrystallization from ethyl acetate/hexanes (10 mL each, 0° C. overnight) afforded the title compound as a white solid (650 mg, 26%). $^1$H NMR (300.132 MHz, CDCl$_3$) δ 8.55 (bs, 1H), 8.13 (dd, J=7.4, 1.0 Hz, 1H), 7.82 (dd, J=8.5, 1.0 Hz, 1H), 7.50 (dd, J=8.5, 7.6 Hz, 1H), 3.52 (q, J=6.6 Hz, 2H), 1.65 (quintet, J=7.2 Hz, 2H), 1.47 (sextet, J=7.3 Hz, 2H), 0.97 (t, J=7.3 Hz, 3H). MS APCI, m/z=323/325 (M+H). HPLC 1.93 min.

The intermediate compounds were prepared as follows:

2-[(2-Bromophenyl)-hydrazono]-N-butyl-2-cyanoacetamide

To a microwave vial charged with [(2-bromophenyl)-hydrazono]-cyan acetic acid ethyl ester (387 mg, 1.31 mmol) was added methanol (3 mL) and n-butyl amine (520 uL, 5.24 mmol). The reaction temperature rose approximately 30° C. and everything went into solution. After 25 minutes, additional n-butyl amine (260 uL, mg, 2.6 mmol) and diethyl amine (182 uL, 1.3 mmol) were added. The reaction was stirred at room temperature overnight and then concentrated to afford the title compound which was used without further purification (420 mg, 99%). $^1$H NMR (300.132 MHz, CDCl$_3$)

δ 14.33 (s, 1H), 7.67 (dd, J=8.3, 1.5 Hz, 1H), 7.53 (dd, J=8.1, 1.3 Hz, 1H), 7.34 (td, J=7.8, 1.2 Hz, 1H), 7.01 (dt?ddd, J=6.1 Hz, J=8.0 Hz, J=1.5 Hz, 1H), 6.22 (bs, 1H), 3.40 (dt, J=5.9, 7.2 Hz, 2H), 1.65-1.35 (m, 4H), 0.96 (td, J=7.3, 1.9 Hz, 3H). MS APCI, m/z=323/325 (M+H). HPLC 2.94 min Precursor 10

4-Amino-8-bromo-N-methyl-cinnoline-3-carboxamide hydrochloric acid salt

A 250 mL round-bottomed flask was charged with 2-[(2-bromophenyl)-hydrazono]-N-methyl-2-cyanoacetamide (2.00 g, 7.12 mmol), aluminum chloride (3.46 g, 25.97 mmol), and anhydrous toluene (68 mL). The reaction was gently refluxed for 45 minutes, cooled to room temperature, and slowly treated with 2N HCl (68 mL). A precipitate formed. The mixture was heated to 90° C. for 10 minutes, cooled to room temperature, and filtered. The solids were dried under high vacuum at 50° C. to afford the title compound (2.02 g, 90%). $^1$H NMR (300.132 MHz, DMSO) δ 9.08 (d, J=4.7 Hz, 1H), 8.56 (dd, J=8.4, 0.8 Hz, 1H), 8.28 (dd, J=7.6, 0.7 Hz, 1H), 7.65 (t, J=8.0 Hz, 1H), 2.89 (d, J=4.7 Hz, 3H). MS APCI, m/z=281/283 (M+H). HPLC 1.61 min.

The intermediate compounds were prepared as follows:

2-[(2-Bromophenyl)-hydrazono]-N-methyl-2-cyanoacetamide

[(2-Bromophenyl)-hydrazono]-cyan acetic acid ethyl ester (15.28 g, 51.60 mmol) was dissolved in 40% methylamine in water (67.5 mL) and stirred at room temperature overnight. The reaction mixture was concentrated to dryness, slurred in diethyl ether, and filtered. After drying under high vacuum at 40° C., the title compound was obtained as a yellow solid (11.16 g, 77%). $^1$H NMR (300.132 MHz, CDCl$_3$) δ 7.68 (dd, J=8.2, 1.4 Hz, 1H), 7.54 (dd, J=8.1, 1.3 Hz, 1H), 7.35 (t, J=7.9 Hz, 1H), 7.01 (td, J=7.7, 1.5 Hz, 1H), 6.29 (s, 1H), 2.98 (d, J=4.9 Hz, 3H). MS APCI, m/z=281/283 (M+H). HPLC 4.08 min.

Precursor 11

4-Amino-8-bromo-cinnoline-3-carboxylic acid ally amide

To an ice-cooled suspension of 4-amino-8-bromo-cinnoline-3-carboxylic acid (360 mg, 1.34 mmol) in dimethylformamide (5 mL) was added CDI (370 mg, 2.3 mmol) and the mixture was stirred at room temperature for 1 hour. Additional DMF (14 mL) was added to enable stirring. After an additional 1 hour at room temperature, the mixture was treated with ally amine (120 uL, 91 mg, 1.60 mmol) in one portion. The reaction was stirred at room temperature for 1 hour and then concentrated. Purification on silica gel using a gradient of 20 to 80% ethyl acetate in hexanes afforded the title compound (300 mg, 73%). $^1$H NMR (300.132 MHz, CDCl$_3$) δ 8.14 (dd, J=7.4, 1.0 Hz, 1H), 7.83 (dd, J=8.4, 1.0 Hz, 1H), 7.51 (dd, J=8.4, 7.5 Hz, 1H), 6.04-5.91 (m, 1H), 5.33 (dq, J=17.1, 1.6 Hz, 1H), 5.21 (dq, J=10.4, 1.4 Hz, 1H), 4.15 (ddt, J=6.2, 5.8, 1.6 Hz, 2H). MS APCI, m/z=307/309 (M+H). HPLC 1.59 min.

Precursor 12

2,4-Dimethoxy-5-(4,4,5,5-tetramethyl-[1,3,2]dioxaborolan-2-yl)-pyramiding

To a 100 mL round-bottomed flask charged with 4 Å molecular sieves (approximately 1 g) was added the 2,4-dimethoxypyrimidine-5-moronic acid (5.34 g, 29.0 mmol) and anhydrous tetrahydrofuran (25 mL). The pinochle (2.98 g, 25.3 mmol) was added and the reaction stirred at room temperature for 1.5 hours. Additional 2,4-dimethoxypyrimidine-5-moronic acid (662.2 mg, 3.6 mmol) was added and the reaction stirred overnight. Molecular sieves and 2,4-dimethoxypyrimidine-5-moronic acid (1.53 g, 8.3 mmol) were added and the reaction stirred for 0.5 hours. Pinacol (0.613 g, 5.2 mmol) was then added. After 2 hours, the molecular sieves were removed by filtration and the filtrate was concentrated. After drying under high vacuum, the title compound was obtained as a fine yellow solid (8.61 g, 79%). $^1$H NMR (300.132 MHz, CDCl$_3$) δ 8.56 (s, 1H), 4.01 (d, J=1.5 Hz, 6H), 1.34 (s, 12H).

Precursor 13

4-Amino-8-bromo-N-cyclopropyl-cinnoline-3-carboxamide

A 500 mL, 3-necked flask equipped with a mechanical stirrer, thermometer, nitrogen inlet, reflux condenser, and addition funnel was charged with N-cyclopropyl-2-cyan-2-[(2-bromophenyl)hydrazono]ace amide (1.7 g, 5.6 mmol) in anhydrous toluene (0.2). The reaction mixture was cooled with stirring in an ice bath. Aluminum chloride (1.6 g, 12.0 mmol) was added in three portions. Removed ice bath and heated at 70-75° C. for 60 hours. The reaction mixture was allowed to cool to room temperature, diluted with ethyl acetate (200 mL), added saturated Rochelle's salt (100 mL), stirred vigorously for 1 hour (until purple color dissipated to orange/yellow). Decanted organic layer from thick white aqueous layer, washed with additional Rochelle's salt, brine, dried and concentrated to an orange residue. The residue was slurred in ether (20 mL) to give title compound (930 mg, 52% yield). MS APCI, m/z=307/309 (M+H).

(2E)-2-Cyan-2-[(2-bromoophenyl)hydrazono]-N-cyclopropylacetamide

Using the procedure outlined in the patent U.S. Pat. No. 4,886,800 example 89b substituting 2-bromoaniline for 2-iodoaniline and 2-cyan-N-cyclopropylacetamide for 2-cyan-N-propylacetamide, to give 11.1 g (85% yield) of the title compound as a yellow solid. MS APCI, m/z=307/309 (M+H). $^1$H NMR (300 MHz, CDCl$_3$) δ 14.39 (s, 1H), 8.67 (bm, 1H), 7.45 (m, 1H), 7.32 (m, 1H), 7.03 (m, 1H), 3.1 (apparent q, J=6.6 Hz, 2H), 1.53 (apparent sextet, J=7.4 Hz, 2H), 0.88 (t, J=7.4 Hz, 3H).

The intermediate compounds were prepared as follows:

2-Cyan-N-cyclopropylacetamide

To a flask charged with cyclopropylamine (12.3 g, 215.3 mmol) was added ethyl cyan acetate (9.8 g, 86.1 mmol). The reaction was stirred at 45° C. for 1.5 hour, cooled and concentrated under reduced pressure to give 10.7 g title compound (~100%) as a light yellow solid. $^1$H NMR (300.132 MHz, CDCl$_3$) δ 6.20 (bs, 1H), 3.34 (s, 2H), 2.75 (m, 2H), 0.83 (m, 2H), 0.59 (m, 2H).

Precursor 14

4-Amino-7-flour-8-iodo-N-cyclopropyl-cinnoline-3-carboxamide

Using the procedure outline for 4-Amino-8-bromo-N-cyclopropyl-cinnoline-3-carboxamide (precursor 13) substituting N-cyclopropyl-2-cyan-2-[(3-flour-2-indophenols)hydrazono]ace amide (5.8 g, 15.6 mmol) for N-cyclopropyl-2-cyan-2-[(2-bromophenyl)hydrazono]ace amide to give title compound (3.3 g, 57% yield). MS APCI, m/z=373 (M+H).

(2E)-2-Cyan-2-[(3-flour-2-indophenols)hydrazono]-N-cyclopropylacetamide

Using the procedure outlined in the patent U.S. Pat. No. 4,886,800 example 89b substituting 3-flour-2-iodoaniline for 2-iodoaniline and 2-cyan-N-cyclopropylacetamide for 2-cyan-N-propylacetamide, to give 8.9 g (94% yield) of the title compound as a yellow solid. MS APCI, m/z=373 (M+H)

Detailed Synthesis Methods/Procedures:

Method A: The crinoline-halide, an optionally substituted arylboronic acid, heteroaryl moronic acid, or a boron compound 1-2B of Scheme 2 (typically 2-3 molar equivalents), cesium carbonate (2 molar equivalents) and bis(triphenylphosphine)palladium(II) dichloride (0.025 molar equivalents) were placed in a microwave reaction vessel and dissolved in 7:3:2 (v/v/v) 1,2-dimethoxymethane: water: ethanol (5 mL/mmol crinoline-halide) at ambient temperature. The reaction vessel was capped, the head-space purged with dry nitrogen and the stirred mixture was heated on a Biotope Optimizer (300 W) microwave system maintaining a reaction temperature of 150° C. for 30-90 minutes, reaction pressures of 7 bar were typically observed. The reaction was then cooled to ambient temperature and extracted with ethyl acetate. The residue from the organic extracts was purified by flash chromatography on silica gel eluting with increasingly polar gradient of ethyl acetate in hexanes to afford the desired compound.

Method B: To a solution of the crinoline-halide in 1,2-dimethoxymethane (10 mL/mmol crinoline-halide) under nitrogen at ambient temperature was added tetrakis(triphenylphosphine)palladium (0) (0.05-0.15 molar equivalents). After stirring 10-20 min an arylboronic acid, heteroaryl moronic acid, or a boron compound 1-2B of Scheme 2 (1-4 molar equivalents) was added followed by a solution of sodium carbonate (2.5 molar equivalents) in water (3 mL/mmol halide). The resulting mixture was heated at reflux for 2-24 h. The reaction was then cooled to ambient temperature and extracted with ethyl acetate. The residue from the organic extracts was purified by flash chromatography on silica gel eluting with increasingly polar gradient of ethyl acetate in hexanes to afford the desired compound.

Method C: To a stirred solution of the crinoline-halide in anhydrous N,N-dimethylformamide (2 mL/mmol crinoline-halide) at ambient temperature was added an optionally substituted aryl- or heteroaryl-tin reagent (1.2 molar equivalents) and tetrakis(triphenylphosphine)palladium(0) (0.05 molar equivalents). The mixture was heated at 100° C. for 8-48 h. The reaction was then cooled to ambient temperature and extracted with ethyl acetate. The residue from the organic extracts was purified by flash chromatography on silica gel eluting with an increasingly polar gradient of ethyl acetate in hexanes to afford the desired compound.

Method D: The crinoline-halide, an optionally substituted aryl- or heteroaryl-tin reagent (1.2 molar equivalents) and tetrakis(triphenylphosphine) palladium(0) (0.05-0.10 molar equivalents) were placed in a microwave reaction vessel and dissolved in 2-4 mL of anhydrous N,N-dimethylformamide at ambient temperature. The reaction vessel was purged with nitrogen, capped, and the stirred mixture was heated on a Biotope Optimizer (300 W) microwave system maintaining a reaction temperature of 150° C. for 30 minutes. The reaction was cooled to ambient temperature, diluted with ethylene chloride, washed with water, dried over magnesium sulfate and the solvent was evaporated. The residue was purified by flash chromatography on silica gel eluting with increasingly polar gradient of ethyl acetate in hexanes to afford the desired compound.

Method E: To a stirred solution of 8-trimethylstannyl-cinnoline derivative and tetrakis(triphenylphosphine) palladium (0) (0.05-0.10 molar equivalents) in anhydrous N,N-dimethylformamide at ambient temperature under nitrogen was added an optionally substituted aryl- or heteroaryl bromide (1.2-3 molar equivalents). The reaction was heated to 150° C. for 4-16 hours. The reaction mixture was evaporated under reduced pressure. The residue was dissolved in ethylene chloride, washed with water twice, dried through $MgSO_4$, and then the solvent was evaporated. The residue was purified by flash chromatography on silica gel eluting with an increasingly polar gradient of ethyl acetate in hexane to afford the desired compound.

Method F: To a solution of the crinoline-halide in anhydrous tetrahydrofuran (10 mL/mmol crinoline-halide) under nitrogen at ambient temperature was added (triphenylphosphine)palladium(II) dichloride (0.10 molar equivalents) followed by an optionally substituted arylboronic acid, heteroaryl moronic acid, or a boron compound 1-2B of Scheme 2 (2-4 molar equivalents) followed by freshly ground potassium phosphate (2.0 molar equivalents). The resulting mixture was heated at reflux for 2-40 h. The reaction was then cooled to ambient temperature and diluted with saturated sodium bicarbonate and extracted with ethyl acetate. The residue from the organic extracts was purified by flash chromatography on silica gel eluting with 5% ether in chloroform to afford the desired compound.

Method G: The crinoline-halide, an optionally substituted arylboronic acid, heteroaryl moronic acid, or a boron compound 1-2B of Scheme 2 (4-5 molar equivalents), cesium carbonate (4-5 molar equivalents), 2-dicyclohexylphosphino-2',4',6'-trisopropylbiphenyl (0.24 molar equivalents) and tries(dibenzylidene-acetone)dipalladium(0) (0.06 molar equivalents) were placed in a 3-neck flask under $N_2$ and dissolved in 7:3:2 (v/v/v) THF:water:2-propane (5 mL/mmol crinoline-halide) at ambient temperature. The reaction vessel was fitted with a reflux condenser, capped, vacuum degassed (3×) backfilling with $N_2$ and placed in a preheated oil bath (70° C.) and heated for 20 hours. (* if reaction not complete more moronic acid and cesium carbonate in equal proportions were added with additional heating time). The reaction was then cooled to ambient temperature, decanted organic layer and concentrated under reduced pressure. Residue partitioned between ethyl acetate and 5% sodium bicarbonate (aq). The residue from the organic extracts was purified by flash chromatography on silica gel eluting with increasingly polar gradient of ethyl acetate in hexanes (alternately 1% methanol/dichloromethane) to afford the desired compound.

Method H: The crinoline-halide, an optionally substituted arylboronic acid, heteroaryl moronic acid, or a boron compound 1-2B of Scheme 2 (3-5 molar equivalents), sodium carbonate (4-5 molar equivalents), [1,1'-bis(diphenylphospino)-ferrocene]dichloropalladium(II) complex with dichloromethane (1:1) (0.075 molar equivalents) were placed in a

EXAMPLE 1

4-amino-7-flour-8-phenyl-N-propyl-cinnoline-3-carboxamide

Using method F 4-amino-7-fluoro-8-iodo-N-propyl-cinnoline-3-carboxamide (291 mg, 0.78 mmol) and phenylboronic acid (379 mg, 3.11 mmol) were reacted (reflux 4 hours) to afford the title compound (65 mg, 26% yield) as a white solid. $^1$H NMR (300 MHz, CDCl$_3$) δ 8.52 (bs, 1H), 7.89 (dd, J=9.2, 4.6 Hz, 1H), 7.42-7.60 (m, 6H), 3.45 (apparent q, J=6.6 Hz, 2H), 1.65 (apparent sextet, J=7.2 Hz, 2H), 1.00 (t, J=7.4 Hz, 3H). MS APCI, m/z=325 (M+H) HPLC 1.92 min.

EXAMPLE 2

4-amino-7-chloro-8-phenyl-N-propyl-cinnoline-3-carboxamide

Using Method F, 4-amino-7-chloro-8-iodo-N-propyl-cinnoline-3-carboxamide (184 mg, 0.47 mmol) and phenylboronic acid (229 mg, 1.89 mmol) were reacted (refluxed 40 hours) to afford the title compound (90 mg, 56% yield) as a white solid. $^1$H NMR (300 MHz, CDCl$_3$) δ 8.49 (bs, 1H), 7.82 (d, J=9.0 Hz, 1H), 7.75 (d, J=9.0 Hz, 1H), 7.42-7.55 (m, 5H), 3.43 (apparent q, J=6.6 Hz, 2H), 1.63 (apparent sextet, J=7.2 Hz, 2H), 0.98 (t, J=7.4 Hz, 3H). MS APCI, m/z=341 (M+H) HPLC 2.04 min.

EXAMPLE 3

4-amino-7-metonym-8-phenyl-N-propyl-cinnoline-3-carboxamide

Using Method F, 4-amino-7-metonym-8-iodo-N-propyl-cinnoline-3-carboxamide (311 mg, 0.81 mmol) and phenylboronic acid (394 mg, 3.24 mmol) were reacted (refluxed overnight) to afford the title compound (140 mg, 52% yield) as a white solid. $^1$H NMR (300 MHz, CDCl$_3$) δ 8.51 (bm, 1H), 7.90 (d, J=9.2 Hz, 1H), 7.52 (d, J=9.2 Hz, 1H), 7.36-7.50 (m, 5H), 3.92 (s, 3H), 3.43 (apparent q, J=6.4 Hz, 2H), 1.63 (apparent sextet, J=7.2 Hz, 2H), 0.98 (t, J=7.4 Hz, 3H). MS APCI, m/z=337 (M+H) HPLC 1.76 min.

EXAMPLE 4

4-amino-7-chloro-8-(2,5-dimethylphenyl)-N-propyl-cinnoline-3-carboxamide

Using method A, 4-amino-7-chloro-8-iodo-N-propyl-cinnoline-3-carboxamide (78 mg, 0.20 mmol) and (2,5-dimethylphenyl)moronic acid (63 mg, 0.417 mmol) were reacted to afford the title compound (33 mg, 45% yield) as a white solid. $^1$H NMR (300 MHz, CDCl$_3$) δ 8.48 (bm, 1H), 7.85 (bm, 1H), 7.75 (m, 1H), 7.15-7.24 (m, 2H), 6.98 (s, 1H), 3.43 (apparent q, J=6.7 Hz, 2H), 2.36 (s, 3H), 1.95 (s, 3H), 1.63 (apparent sextet, J=7.2 Hz, 2H), 0.98 (t, J=7.4 Hz, 3H). MS APCI, m/z=369 (M+H) HPLC 2.15 min.

EXAMPLE 5

4-amino-8-(2,4-dimethoxypyrimidin-5-yl)-N-propyl-cinnoline-3-carboxamide

Using method A, 4-amino-8-bromo-N-propyl-cinnoline-3-carboxamide (100 mg, 0.324 mmol) and (2,4-dimethoxypyrimidin-5-yl)moronic acid (125 mg, 0.68 mmol) were reacted to afford the title compound (33 mg, 28% yield) as a white solid. $^1$H NMR (300 MHz, CDCl$_3$) δ 8.52 (bm, 1H), 8.33 (s, 1H), 7.91 (dd, J=7.7, 2.0 Hz, 1H), 7.70-7.77 (m, 2H), 4.06 (s, 3H), 3.93 (s, 3H), 3.46 (apparent q, J=6.5 Hz, 2H), 1.67 (apparent sextet, J=7.2 Hz, 2H), 1.00 (t, J=7.4 Hz, 3H). MS APCI, m/z=369 (M+H) HPLC 1.69 min.

EXAMPLE 6

4-amino-8-(5-metonym-3-perfidy)-N-propyl-cinnoline-3-carboxamide

Using method A, 4-amino-8-bromo-N-propyl-cinnoline-3-carboxamide (100 mg, 0.324 mmol) and 3-metonym-5-(4,4,5,5-tetraethyl-1,3,2-dioxaborolan-2-yl)pyridine (160 mg, 0.68 mmol) were reacted to afford the title compound (84 mg, 77% yield) as a white solid. $^1$H NMR (300 MHz, CDCl$_3$) δ 8.49-8.60 (m, 2H), 8.39 (m, 1H), 7.93 (dd, J=8.2, 1.6 Hz, 1H), 7.73-7.84 (m, 2H), 7.66 (m, 1H), 3.93 (s, 3H), 3.47 (apparent q, J=6.7 Hz, 2H), 1.68 (apparent sextet, J=7.4 Hz, 2H), 0.98 (t, J=7.4 Hz, 3H). MS APCI, m/z=338 (M+H) HPLC 1.52 min.

EXAMPLE 7

4-amino-8-(2-methoxypyrimidin-5-yl)-N-propyl-cinnoline-3-carboxamide

Using method A, 4-amino-8-bromo-N-propyl-cinnoline-3-carboxamide (100 mg, 0.324 mmol) and (2-methoxypyrimidin-5-yl)moronic acid (104 mg, 0.68 mmol) were reacted to afford the title compound (84 mg, 77% yield) as a white solid. $^1$H NMR (300 MHz, DMSO-d6) δ 9.1-9.3 (m, 1.5H), 8.96 (s, 2H), 8.47 (dd, J=8.4, 1.0 Hz, 1H), 8.1-8.4 (bm, 0.5H), 7.99 (dd, J=7.2, 1.0 Hz, 1H), 7.83 (dd, J=8.4, 7.2 Hz, 1H), 4.01 (s, 3H), 3.32 (apparent q, J=7.4 Hz, 2H), 1.60 (apparent sextet, J=7.2 Hz, 2H), 0.91 (t, J=7.4 Hz, 3H). MS APCI, m/z=339 (M+H) HPLC 1.75 min.

EXAMPLE 8

4-amino-8-(3-fluoro-2-metonym-phenyl)-N-propyl-cinnoline-3-carboxamide

Using method A, 4-amino-8-bromo-N-propyl-cinnoline-3-carboxamide (116 mg, 0.375 mmol) and (3-fluoro-2-methoxyphenyl)moronic acid (127 mg, 0.75 mmol) were reacted to afford the title compound (117 mg, 88% yield) as a white solid. $^1$H NMR (300 MHz, DMSO-d6) δ 9.06 (t, J=6.0 Hz, 1H), 8.45 (dd, J=7.5, 2.2 Hz, 1H), 7.74-7.81 (m, 2H), 7.28-7.37 (m, 1 H), 7.12-7.21 (m, 2H), 3.54 (s, 3H), 3.31 (apparent q, J=7.0 Hz, 2H), 1.56 (apparent sextet, J=7.0 Hz, 2H), 0.90 (t, J=7.0 Hz, 3H). MS APCI, m/z=355 (M+H) HPLC 1.86 min.

EXAMPLE 9

4-amino-8-[4-metonym-2-(trifluoromethyl)phenyl]-N-propyl-cinnoline-3-carboxamide Using method A, 4-amino-8-bromo-N-propyl-cinnoline-3-carboxamide (116 mg, 0.375 mmol) and [4-metonym-2-(trifluoromethyl)phenyl]moronic acid (164 mg, 0.75 mmol) were reacted to afford the title compound (124 mg, 82% yield) as a white solid. $^1$H NMR (300 MHz, DMSO-d6) δ 9.02 (t, J=6.0 Hz, 1H), 8.45 (d, J=8.3 Hz, 1H), 7.67-7.78 (m, 2H), 7.26-7.38 (m, 3H), 3.91 (s, 3H), 3.29 (apparent q, J=7.0 Hz, 2H), 1.57 (apparent sextet, J=7.0 Hz, 2H), 0.90 (t, J=7.0 Hz, 3H). MS APCI, m/z=405 (M+H) HPLC 2.11 min.

EXAMPLE 10

4-amino-8-(2,5-dilutor-4-metonym-phenyl)-N-propyl-cinnoline-3-carboxamide

Using method A, 4-amino-8-bromo-N-propyl-cinnoline-3-carboxamide (116 mg, 0.375 mmol) and (2,5-dilutor-4-methoxyphenyl)moronic acid (140 mg, 0.75 mmol) were reacted to afford the title compound (93 mg, 67% yield) as a white solid. $^1$H NMR (300 MHz, DMSO-d6) δ 9.15 (t, J=6.0 Hz, 1H), 8.46 (dd, J=8.0, 1.7 Hz, 1H), 7.76-7.86 (m, 2 H), 7.44 (dd, J=11.8, 6.8 Hz, 1H), 7.22 (dd, J=11.3, 7.4 Hz, 1H), 3.93 (s, 3H), 3.29 (apparent q, J=7.0 Hz, 2H), 1.59 (apparent sextet, J=7.0 Hz, 2H), 0.91 (t, J=7.0 Hz, 3H). MS APCI, m/z=373 (M+H) HPLC 2.03 min.

EXAMPLE 11

4-amino-8-(5-fluoro-6-metonym-3-perfidy)-N-propyl-cinnoline-3-carboxamide

Using method A, 4-amino-8-bromo-N-propyl-cinnoline-3-carboxamide (126 mg, 0.408 mmol) and (5-fluoro-6-methoxypyridin-3-yl)moronic acid (138 mg, 0.81 mmol) were reacted to afford the title compound (70 mg, 48% yield) as a white solid. $^1$H NMR (300 MHz, DMSO-d6) δ 9.22 (t, J=6.0 Hz, 1H), 8.45 (d, J=7.6 Hz, 1H), 8.29 (d, J=1.9 Hz, 1H), 8.13 (dd, J=11.9, 1.9 Hz, 1H), 7.95 (apparent d, J=7.0 Hz, 1H), 7.80 (apparent t, J=8.0 Hz, 1H), 4.03 (s, 3H), 3.31 (apparent q, J=7.0 Hz, 2H), 1.60 (apparent sextet, J=7.0 Hz, 2H), 0.91 (t, J=7.0 Hz, 3H). MS APCI, m/z=356 (M+H) HPLC 1.99 min

EXAMPLE 12

4-amino-8-(5-chloro-6-metonym-3-perfidy)-N-propyl-cinnoline-3-carboxamide

Using method A, 4-amino-8-bromo-N-propyl-cinnoline-3-carboxamide (119 mg, 0.385 mmol) and (5-chloro-6-methoxypyridin-3-yl)moronic acid (144 mg, 0.77 mmol) were reacted to afford the title compound (59 mg, 42% yield) as a white solid. $^1$H NMR (300 MHz, DMSO-d6) δ 9.25 (t, J=6.0 Hz, 1H), 8.43-8.46 (m, 2H), 8.34 (d, J=2.0 Hz, 1H), 7.95 (apparent d, J=7.0 Hz, 1 H), 7.80 (apparent t, J=7.8 Hz, 1H), 4.03 (s, 3H), 3.31 (apparent q, J=7.0 Hz, 2H), 1.59 (apparent sextet, J=7.0 Hz, 2H), 0.91 (t, J=7.0 Hz, 3H). MS APCI, m/z=372(M+H) HPLC 2.17 min

EXAMPLE 13

4-amino-8-(3,5-dichlorophenyl)-N-propyl-cinnoline-3-carboxamide

Using method B, 4-amino-8-bromo-N-propyl-cinnoline-3-carboxamide (100 mg, 0.33 mmol) and 3,5-dichlorophenyl moronic acid (252 mg, 1.32 mmol) were reacted to afford the title compound (65 mg, 52.5% yield) as a pale-yellow solid. $^1$H NMR (300 MHz, DMSO-d6) δ 9.26 (br, 1H), 8.48 (d, J=8.2 Hz, 1H), 7.95 (d, J=7.2 Hz, 2H), 7.74-7.85 (m, 3H), 7.67 (t, J=2.0 Hz, 1H), 3.31 (m, overlapped with H$_2$O), 1.60 (m, J=7.3 Hz, 2H), 0.91 (t, J=7.4 Hz, 3H). MS APCI, m/z=375/377 (M+H). HPLC 2.52 min.

EXAMPLE 14

4-amino-8-(3,5-difluorophenyl)-N-propyl-cinnoline-3-carboxamide

Using method B, 4-amino-8-bromo-N-propyl-cinnoline-3-carboxamide (200 mg, 0.65 mmol), 3,5-difluorophenyl moronic acid (300 mg, 1.90 mmol) and bis(triphenylphosphine) palladium(II) dichloride (24 mg, 0.034 mmol) were reacted to afford the title compound (200 mg, 89.7% yield) as an off-white solid. $^1$H NMR (300 MHz, CDCl$_3$) δ 8.55 (br, 1H), 7.92 (dd, J=8.1 Hz, J'=1.4 Hz, 1H), 7.67-7.82 (m, 2H), 7.22 (m, 2H), 6.88 (m, 1H), 3.47 (q, J=6.7 Hz, 2H), 1.68 (m, J=7.2 Hz, 2H), 1.01 (t, J=7.4 Hz, 3H). MS APCI, m/z=343 (M+H). HPLC 2.14 min.

EXAMPLE 15

4-amino-8-(5-azotizing-1-ylcarbonyl-3-perfidy)-N-propyl-cinnoline-3-carboxamide

Using method D, 4-amino-8-iodo-N-propyl-cinnoline-3-carboxamide (100 mg, 0.28 mmol) and 3-trimethylstannyl-5-(azotizing-1-ylcarbonyl)-pyridine (182 mg, of 80%, 0.45 mmol) were reacted to afford the title compound (48 mg, 44.0% yield) as an off-white solid. $^1$H NMR (300 MHz, CDCl$_3$) δ 9.00 (s, 1H), 8.89 (s, 1H), 8.51 (br, 1H), 8.40 (s, 1H), 7.96 (d, J=7.0 Hz, 1H), 7.72-7.88 (m, 2H), 4.46 (br, 2H), 4.28 (br, 2H), 3.48 (q, J=6.7 Hz, 2H), 2.40 (m, J=7.8 Hz, 2H), 1.69 (m, J=7.3 Hz, 2H), 1.02 (t, J=7.4 Hz, 3H). MS APCI, m/z=391 (M+H). HPLC 1.74 min.

The reagent, 3-trimethylstannyl-5-(azotizing-1-ylcarbonyl)-pyridine, was synthesized by the following method:

To a stirred suspension of 5-bromonicotinic acid (1.0 g, 4.95 mmol) in 15 mL of anhydrous ethylene chloride at 0° C. under nitrogen was added oxalic chloride (817 mg, 6.44 mmol). The reaction mixture was stirred at 0° C. for 30 minutes. Then diethylamide (1.25 g, 12.38 mmol) was added slowly, and followed by the addition of astatine (565 mg, 9.90 mmol) at 0° C. The reaction was warmed to ambient temperature, and stirred for another hour. The reaction mixture was diluted with ethylene chloride, quenched with water, washed with 10% potassium carbonate aqueous solution twice, dried through magnesium sulfate, and the solvent was evaporated to dry. The residue was purified by flash chromatography using a gradient of methanol in ethylene chloride to give a yellow liquid as 3-broom-5-(azotizing-1-ylcarbonyl)-pyridine (846 mg, 70.9% yield). Following, to a stirred solution of 3-broom-5-(azotizing-1-ylcarbonyl)-pyridine (600 mg, 2.50 mmol) and tetrakis(triphenylphosphine) palladium(0) (240 mg, 0.21 mmol) in 40 mL of xylem at ambient temperature under nitrogen was added hexamethylditin (1.58 g, 4.50 mmol). The reaction was heated to 150° C. overnight. The reaction mixture was filtrated through Elite, and the filtrate was vacuumed to dry. The residual was dissolved in ethylene chloride, washed with water twice, dried through $MgSO_4$, and then the solvent was evaporated. The precipitate was purified by flash chromatography using a gradient of ethyl acetate in hexane to give a yellow solid as 3-trimethylstannyl-5-(azotizing-1-ylcarbonyl)-pyridine (846 mg, 83.0% yield). $^1$H NMR (300 MHz, $CDCl_3$) δ 8.65-8.70 (m, 2H), 8.04 (t, J=1.9 Hz, 1H), 4.31 (t, J=7.63 Hz, 2H), 4.00-4.10 (m, overlapped with $H_2O$), 2.27 (m, J=6.2 Hz, 2H MS APCI, m/z=323/325/327 (M+H) HPLC 1.61 min.

EXAMPLE 16

4-amino-8-(2,3-dimethoxyphenyl)-N-propyl-cinnoline-3-carboxamide

Using method A, 4-amino-8-bromo-N-propyl-cinnoline-3-carboxamide (100 mg, 0.33 mmol) and 2,3-dimethoxyphenyl moronic acid (148 mg, 0.97 mmol) were reacted to afford the title compound (106 mg, 89.5% yield) as a pale-yellow solid. $^1$H NMR (300 MHz, $CDCl_3$) δ 8.55 (br, 1H), 7.89 (d, J=8.1 Hz, 1H), 7.78 (dd, J=7.1 Hz, J'=1.5 Hz, 1H), 7.71 (t, J=7.6 Hz, 1H), 7.15 (t, J=7.9 Hz, 1H), 6.99 (m, 2H), 3.92 (s, 3H), 3.53 (s, 3H), 3.45 (q, J=6.7 Hz, 2H), 1.65 (m, J=7.2 Hz, 2H), 0.99 (t, J=7.4 Hz, 3H) MS APCI, m/z=367 (M+H) HPLC 1.86 min.

EXAMPLE 17

4-amino-8-(4-dimethylaminophenyl)-N-propyl-cinnoline-3-carboxamide

Using method A, 4-amino-8-bromo-N-propyl-cinnoline-3-carboxamide (100 mg, 0.33 mmol) and 4-dimethylaminophenyl moronic acid (160 mg, 0.97 mmol) were reacted to afford the title compound (105 mg, 93.0% yield) as a pale-yellow solid. $^1$H NMR (300 MHz, $CDCl_3$) δ 8.61 (br, 1H), 7.58-7.85 (m, 5H), 6.88 (d, J=8.8 Hz, 2H), 3.47 (q, J=6.7 Hz, 2H), 3.02 (s, 6H), 1.67 (m, J=7.3 Hz, 2H), 1.01 (t, J=7.4 Hz, 3H) MS APCI, m/z=350 (M+H) HPLC 2.67 min.

EXAMPLE 18

4-amino-8-(3-methoxyphenyl)-N-propyl-cinnoline-3-carboxamide

Using method A, 4-amino-8-bromo-N-propyl-cinnoline-3-carboxamide (100 mg, 0.33 mmol) and 3-methoxyphenyl moronic acid (147 mg, 0.97 mmol) were reacted to afford the title compound (69 mg, 64.2% yield) as an off-white crystal. $^1$H NMR (300 MHz, $CDCl_3$) δ 8.58 (br, 1H), 7.87 (dd, J=8.3 Hz, J'=1.4 Hz, 1H), 7.81 (dd, J=7.1 Hz, J'=1.4 Hz, 1H), 7.72 (t, J=8.1 Hz, 1H), 7.41 (t, J=8.0 Hz, 1H), 7.15-7.35 (m, overlapped with $CHCl_3$), 6.98 (dd, J=8.1 Hz, J'=1.8 Hz, 1H), 3.86 (s, 3H), 3.46 (q, J=6.7 Hz, 2H), 1.67 (m, J=7.3 Hz, 2H), 1.01 (t, J=7.4 Hz, 3H) MS APCI, m/z=337 (M+H) HPLC 1.89 min.

EXAMPLE 19

4-amino-8-(3,4-dimethoxyphenyl)-N-propyl-cinnoline-3-carboxamide

Using method A, 4-amino-8-bromo-N-propyl-cinnoline-3-carboxamide (100 mg, 0.33 mmol) and 3,4-dimethoxyphenyl moronic acid (148 mg, 0.97 mmol) were reacted to afford the title compound (91 mg, 77.7% yield) as a pale-yellow solid. $^1$H NMR (300 MHz, $CDCl_3$) δ 8.58 (br, 1H), 7.76-7.88 (m, 2H), 7.71 (t, J=7.7 Hz, 1H), 7.29 (m, overlapped with $CHCl_3$), 7.23 (d, J=1.9 Hz, 1H), 7.02 (d, J=8.3 Hz, 1H), 3.95 (s, 3H), 3.93 (s, 3H), 3.47 (q, J=6.7 Hz, 2H), 1.68 (m, J=7.2 Hz, 2H), 1.01 (t, J=7.4 Hz, 3H) MS APCI, m/z=367 (M+H) HPLC 1.78 min.

EXAMPLE 20

4-amino-8-(2,5-dimethoxyphenyl)-N-propyl-cinnoline-3-carboxamide

Using method B, 4-amino-8-bromo-N-propyl-cinnoline-3-carboxamide (13.0 g, 42.1 mmol), 2,5-dimethoxyphenyl moronic acid (15.4 g, 84.6 mmol) and bis(triphenylphosphine) palladium(II) dichloride (886 mg, 1.3 mmol) were reacted to afford the title compound (13.51 g, 87.7% yield) as an off-white needle. $^1$H NMR (300 MHz, $CDCl_3$) δ 8.59 (br, 1H), 7.89 (dd, J=7.8 Hz, J'=1.9 Hz, 1H), 7.65-7.77 (m, 2H), 6.85-7.20 (m, 3H), 3.79 (s, 3H), 3.64 (s, 3H), 3.35-3.55 (m, overlapped with $H_2O$), 1.64 (m, J=7.3 Hz, 2H), 0.99 (t, J=7.4 Hz, 3H) MS APCI, m/z=367 (M+H) HPLC 1.72 min.

EXAMPLE 21

4-amino-8-(3,5-dimethoxyphenyl)-N-propyl-cinnoline-3-carboxamide

Using method A, 4-amino-8-bromo-N-propyl-cinnoline-3-carboxamide (100 mg, 0.33 mmol) and 2-(3,5-dimethoxyphenyl)-4,4,5,5-tetraethyl-(1,3,2)-dioxaborolane (256 mg, 0.97 mmol) were reacted to afford the title compound (110 mg, 93.9% yield) as an off-white solid. $^1$H NMR (300 MHz, $CDCl_3$) δ 8.57 (br, 1H), 7.87 (d, J=8.2 Hz, 1H), 7.79 (dd, J=7.2 Hz, J'=1.3 Hz, 1H), 7.71 (t, J=7.7 Hz, 1H), 6.79 (d, 3H), 3.83 (s, 6H), 3.47 (q, J=6.7 Hz, 2H), 1.67 (m, J=7.3 Hz, 2H), 1.01 (t, J=7.4 Hz, 3H) MS APCI, m/z=367 (M+H) HPLC 1.98 min.

EXAMPLE 22

4-amino-8-(2,4-dimethoxyphenyl)-N-propyl-cinnoline-3-carboxamide

Using method A, 4-amino-8-bromo-N-propyl-cinnoline-3-carboxamide (100 mg, 0.33 mmol) and 2,4-dimethoxyphenyl moronic acid (148 mg, 0.97 mmol) were reacted to afford the title compound (88 mg, 75.1% yield) as an off-white solid. $^1$H NMR (300 MHz, $CDCl_3$) δ 8.57 (br, 1H), 7.84 (dd, J=8.2 Hz, J'=1.4 Hz, 1H), 7.75 (dd, J=7.1 Hz, J'=1.4 Hz, 1H), 7.68 (t, J=7.6 Hz, 1H), 7.29 (m, overlapped with $CHCl_3$), 6.58-6.60 (m, 2H), 3.87 (s, 3H), 3.69 (s, 3H), 3.45 (q, 6.7 Hz, 2H), 1.65 (m, J=7.3 Hz, 2H), 0.99 (t, J=7.4 Hz, 3H) MS APCI, m/z=367 (M+H) HPLC 1.94 min.

EXAMPLE 23

4-amino-8-(2-fluoro-3-perfidy)-N-propyl-cinnoline-3-carboxamide

Using method E, 4-amino-8-trimethylstannyl-N-propyl-cinnoline-3-carboxamide (170 mg of 90% purity, 0.37 mmol) and 3-broom-2-fluoro-3-pyridine (195 mg, 1.11 mmol) were reacted to afford the title compound (45 mg, 37.7% yield) as an off-white solid. $^1$H NMR (300 MHz, DMSO-d6) δ 9.16

(br, 1H), 8.52 (dd, J=8.4 Hz, J'=1.2 Hz, 1H), 8.33 (m, 1H), 8.11 (m, 1H), 7.92 (d, J=6.1 Hz, 1H), 7.83 (t, J=7.7 Hz, 1H), 7.50 (m, 1H), 3.20-3.35 (m, overlapped with $H_2O$), 1.58 (m, J=7.2 Hz, 2H), 0.90 (t, J=7.4 Hz, 3H) MS APCI, m/z=326 (M+H) HPLC 1.74 min

EXAMPLE 24

4-amino-8-(2,3-difluorophenyl)-N-propyl-cinnoline-3-carboxamide

Using method A, 4-amino-8-bromo-N-propyl-cinnoline-3-carboxamide (100 mg, 0.33 mmol) and 2,3-difluorophenyl moronic acid (153 mg, 0.97 mmol) were reacted to afford the title compound (63 mg, 57.6% yield) as a pale-yellow solid. $^1$H NMR (300 MHz, $CDCl_3$) δ 8.55 (br, 1H), 7.95 (dd, J=8.0 Hz, J'=1.7 Hz, 1H), 7.70-7.85 (m, 2H), 7.15-7.30 (m, overlapped with $CHCl_3$), 3.46 (q, J=6.7 Hz, 2H), 1.66 (m, J=7.3 Hz, 2H), 1.00 (t, J=7.4 Hz, 3H) MS APCI, m/z=343 (M+H) HPLC 2.08 min.

EXAMPLE 25

4-amino-8-(2,3-dichlorophenyl)-N-propyl-cinnoline-3-carboxamide

Using method A, 4-amino-8-bromo-N-propyl-cinnoline-3-carboxamide (100 mg, 0.33 mmol) and 2,3-dichlorophenyl moronic acid (185 mg, 0.97 mmol) were reacted to afford the title compound (99.8 mg, 83.1% yield) as a pale-yellow solid. $^1$H NMR (300 MHz, $CDCl_3$) δ 8.52 (br, 1H), 7.96 (dd, J=7.6 Hz, J'=2.1 Hz, 1H), 7.66-7.78 (m, 2H), 7.53 (dd, J=6.3 Hz, J'=3.3 Hz, 1H), 7.28-7.35 (m, 2H), 3.45 (q, J=6.7 Hz, 2H), 1.64 (m, J=7.3 Hz, 2H), 0.99 (t, J=7.4 Hz, 3H) MS APCI, m/z=375/377 (M+H) HPLC 2.19 min.

EXAMPLE 26

4-amino-N-propel-8-(6-quaintly)crinoline-3-carboxamide

Using method A, 4-amino-8-bromo-N-propyl-cinnoline-3-carboxamide (100 mg, 0.33 mmol) and 6-(4,4,5,5-tetraethyl-1,3,2-dioxa-borolane-2-yl)quinoline (247 mg, 0.97 mmol) were reacted to afford the title compound (105 mg, 91.9% yield) as a pale-yellow solid. $^1$H NMR (300 MHz, $CDCl_3$) δ 8.96 (dd, J=4.2 Hz, J'=1.7 Hz, 1H), 8.56 (br, 1H), 8.23 (d, J=8.4 Hz, 2H), 8.05-8.15 (m, 2H), 7.88-7.96 (m, 2H), 7.78 (t, J=7.7 Hz, 1H), 7.44 (dd, J=8.2 Hz, J'=4.2 Hz, 1H), 3.47 (q, J=6.7 Hz, 2H), 1.67 (m, J=7.2 Hz, 2H), 1.00 (t, J=7.4 Hz, 3H) MS APCI, m/z=358 (M+H) HPLC 1.47 min.

EXAMPLE 27

4-amino-N-propel-8-(3-quaintly)crinoline-3-carboxamide

Using method A, 4-amino-8-bromo-N-propyl-cinnoline-3-carboxamide (100 mg, 0.33 mmol) and 3-quinoline moronic acid (168 mg, 0.97 mmol) were reacted to afford the title compound (93 mg, 80.5% yield) as a pale-yellow solid. $^1$H NMR (300 MHz, $CDCl_3$) δ 9.24 (d, J=2.2 Hz, 1H), 8.50-8.60 (m, 2H), 8.18 (d, J=8.6 Hz, 1H), 7.88-7.98 (m, 3H), 7.82 (d, J=8.2 Hz, 1H), 7.76 (m, 1H), 7.59 (m, 1H), 3.47 (q, J=6.7 Hz, 2H), 1.68 (m, J=7.2 Hz, 2H), 1.01 (t, J=7.4 Hz, 3H) MS APCI, m/z=358 (M+H) HPLC 1.88 min.

EXAMPLE 28

4-amino-8-(2-naphthalene)-N-propyl-cinnoline-3-carboxamide

Using method A, 4-amino-8-bromo-N-propyl-cinnoline-3-carboxamide (100 mg, 0.33 mmol) and 2-naphthalene moronic acid (167 mg, 0.97 mmol) were reacted to afford the title compound (99 mg, 86.9% yield) as a pale-yellow solid. $^1$H NMR (300 MHz, $CDCl_3$) δ 8.58 (br, 1H), 8.11 (s, 1H), 7.83-7.99 (m, 6H), 7.76 (dd, J=8.0 Hz, J'=7.1 Hz, 1H), 7.46-7.55 (m, 2H), 3.46 (q, J=6.7 Hz, 2H), 1.66 (m, J=7.2 Hz, 2H), 1.00 (t, J=7.4 Hz, 3H) MS APCI, m/z=357 (M+H) HPLC 2.11 min.

EXAMPLE 29

4-amino-8-(1H-idol-5-yl)-N-propyl-cinnoline-3-carboxamide

Using method A, 4-amino-8-bromo-N-propyl-cinnoline-3-carboxamide (100 mg, 0.33 mmol) and 5-unduly moronic acid (156 mg, 0.97 mmol) were reacted to afford the title compound (105 mg, 95.1% yield) as a pale-yellow solid. $^1$H NMR (300 MHz, $CDCl_3$) δ 8.60 (br, 1H), 8.34 (s, 1H), 7.94 (s, 1H), 7.86 (d, J=7.1 Hz, 1H), 7.81 (d, J=8.4 Hz, 1H), 7.69 (t, J=7,7 Hz, 1H), 7.57 (d, J=8.5 Hz, 1H), 7.47 (d, J=8.5 Hz, 1H), 7.22 (s, 1H), 6.61 (s, 1H), 3.46 (q, J=6.7 Hz, 2H), 1.66 (m, J=7.2 Hz, 2H), 0.99 (t, J=7.4 Hz, 3H) MS APCI, m/z=346 (M+H) HPLC 1.88 min.

EXAMPLE 30

4-amino-8-(4-metonym-3-perfidy)-N-propyl-cinnoline-3-carboxamide

To a stirred solution of 4-amino-8-iodo-N-propyl-cinnoline-3-carboxamide (1.00 g, 2.81 mmol), sodium bicarbonate (473 mg, 5.62 mmol) and tetrakis(triphenylphosphine) palladium(0) (974 mg, 0.84 mmol) in 1,2-dimethoxymethane (180 mL)/water (30 mL) at 85° C. under nitrogen was added the aqueous solution of 4-metonym-pyridine-3-moronic acid (25 mg/mL) drop wise, maintaining the internal temperature between 80° C. and 85° C. The reaction was monitored by HPLC until completed. Upon the completion, 2.42 equivalents of 4-metonym-pyridine-3-moronic acid (1.16 g, 6.80 mmol) were applied. The reaction mixture was diluted with ethylene chloride (300 mL), washed with water twice, dried through $MgSO_4$, and then the solvent was evaporated. The residual was purified by flash chromatography using a gradient of methanol in ethylene chloride to give a yellow solid. The yellow solid was crystallized from ethylene chloride/methanol (2/1) to give an off-white needle crystal as the title compound (570 mg, 60.2% yield). $^1$H NMR (300 MHz, $CDCl_3$) δ 8.58 (d, J=5.8 Hz, 1H), 8.53 (br, 1H), 5.11 (m, 6H), 8.46 (s, 1H), 7.94 (t, J=4.9 Hz, 1H), 7.74 (d, J=4.8 Hz, 2H), 6.96 (d, J=5.8 Hz, 1H), 3.78 (s, 3H), 3.45 (q, J=6.7 Hz, 2H), 1.66 (m, overlapped with $H_2O$), 1.00 (t, J=7.4 Hz, 3H) MS APCI, m/z=338 (M+H) HPLC 1.28 min.

EXAMPLE 31

4-amino-8-(3-dimethylaminophenyl)-N-propyl-cinnoline-3-carboxamide

Using method A, 4-amino-8-bromo-N-propyl-cinnoline-3-carboxamide (100 mg, 0.33 mmol) and 3-dimethylaminophenyl moronic acid (160 mg, 0.97 mmol) were reacted to afford the title compound (99 mg, 88.6% yield) as a pale-yellow solid. $^1$H NMR (300 MHz, CDCl$_3$) δ 8.60 (br, 1H), 7.83 (m, 2H), 7.70 (t, J=7.7 Hz, 1H), 7.35 (t, J=7.9 Hz, 1H), 7.03 (d, J=7.9 Hz, 1H), 6.98 (m, 1H), 6.82 (dd, J=8.3 Hz, J'=2.3 Hz, 1H), 3.46 (q, J=6.7 Hz, 2H), 2.99 (s, 6H), 1.67 (m, J=7.2 Hz, 2H), 1.00 (t, J=7.4 Hz, 3H) MS APCI, m/z=350 (M+H) HPLC 1.60 min.

EXAMPLE 32

4-amino-N-propel-8-(3,4,5-trimethoxyphenyl)-crinoline-3-carboxamide

Using method A, 4-amino-8-bromo-N-propyl-cinnoline-3-carboxamide (100 mg, 0.33 mmol) and 3,4,5-trimethoxyphenyl moronic acid (206 mg, 0.97 mmol) were reacted to afford the title compound (116 mg, 91.5% yield) as a pale-yellow solid. $^1$H NMR (300 MHz, CDCl$_3$) δ 8.56 (br, 1H), 7.88 (d, J=8.2 Hz, 1H), 7.80 (dd, J=7.2 Hz, J'=1.4 Hz, 1H), 7.72 (t, J=7.7Hz, 1H), 6.87 (s, 2H), 3.92 (s, 3H), 3.90 (s, 6H), 3.47 (q, J=6.5 Hz, 2H), 1.68 (m, J=7.2 Hz, 2H), 1.01 (t, J=7.4 Hz, 3H) MS APCI, m/z=397 (M+H) HPLC 1.83 min.

EXAMPLE 33

4-amino-8-(2,4-difluorophenyl)-N-propyl-cinnoline-3-carboxamide

Using method A, 4-amino-8-bromo-N-propyl-cinnoline-3-carboxamide (100 mg, 0.33 mmol) and 2,4-difluorophenyl moronic acid (202 mg, 1.28 mmol) were reacted to afford the title compound (101 mg, 92.3% yield) as a pale-yellow solid. $^1$H NMR (300 MHz, CDCl$_3$) δ 8.55 (br, 1H), 7.92 (dd, J=8.0 Hz, J'=1.7 Hz, 1H), 7.70-7.80 (m, 2H), 7.49 (m, 1H), 6.90-7.05 (m, 2H), 3.46 (q, J=6.7 Hz, 2H), 1.66 (m, J=7.3 Hz, 2H), 1.00 (t, J=7.4 Hz, 3H) MS APCI, m/z=343 (M+H) HPLC 1.84 min.

EXAMPLE 34

4-amino-8-(3,4-difluorophenyl)-N-propyl-cinnoline-3-carboxamide

Using method A, 4-amino-8-bromo-N-propyl-cinnoline-3-carboxamide (100 mg, 0.33 mmol) and 3,4-difluorophenyl moronic acid (202 mg, 1.28 mmol) were reacted to afford the title compound (108 mg, 98.7% yield) as a pale-yellow solid. $^1$H NMR (300 MHz, CDCl$_3$) δ 8.55 (br, 1H), 7.89 (dd, J=7.9 Hz, J'=1.9 Hz, 1H), 7.68-7.80 (m, 2H), 7.48-7.59 (m, 1H), 7.37-7.45 (m, 1H), 7.23-7.33 (m, overlapped with CHCl$_3$), 3.47 (q, J=6.7 Hz, 2H), 1.68 (m, J=7.2 Hz, 2H), 1.01 (t, J=7.4 Hz, 3H) MS APCI, m/z=343 (M+H) HPLC 2.01 min.

EXAMPLE 35

4-amino-N-propel-8-(2,3,4-trimethoxyphenyl)-crinoline-3-carboxamide

Using method A, 4-amino-8-bromo-N-propyl-cinnoline-3-carboxamide (106 mg, 0.34 mmol) and 2,3,4-trimethoxyphenyl moronic acid (206 mg, 0.97 mmol) were reacted to afford the title compound (124 mg, 92.1% yield) as a pale-yellow solid. $^1$H NMR (300 MHz, CDCl$_3$) δ 8.56 (br, 1H), 7.88 (dd, J=8.2 Hz, J'=1.5 Hz, 1H), 7.76 (d, J=6.3 Hz, 1H), 7.69 (t, J=7.6 Hz, 1H), 7.09 (d, J=8.6 Hz, 1H), 6.80 (d, J=8.6 Hz, 1H), 3.94 (s, 3H), 3.92 (s, 3H), 3.62 (s, 3H), 3.45 (q, J=6.7 Hz, 2H), 1.65 (m, J=7.2 Hz, 2H), 0.99 (t, J=7.4 Hz, 3H) MS APCI, m/z=397 (M+H) HPLC 1.70 min.

EXAMPLE 36

4-amino-8-(2-metonym-3-perfidy)-N-propyl-cinnoline-3-carboxamide

Using method A, 4-amino-8-bromo-N-propyl-cinnoline-3-carboxamide (100 mg, 0.33 mmol) and 2-methoxy-pyridyl-3-moronic acid (148 mg, 0.97 mmol) were reacted to afford the title compound (92 mg, 85.3% yield) as an off-white solid. $^1$H NMR (300 MHz, CDCl$_3$) δ 8.53 (br, 1H), 8.26 (dd, J=5.0 Hz, J'=1.9 Hz, 1H), 7.90 (dd, J=8.1 Hz, J'=1.5 Hz, 1H), 7.79 (dd, J=7.1 Hz, J'=1.6 Hz, 1H), 7.74 (d, J=8.0 Hz, 1H), 7.70 (dd, J=7.3 Hz, J'=2.0 Hz, 1H), 7.04 (dd, J=6.8 Hz, J'=5.0 Hz, 1H), 3.88 (s, 3H), 3.45 (q, J=6.7 Hz, 2H), 1.66 (m, J=7.3 Hz, 2H), 1.00 (t, J=7.4 Hz, 3H) MS APCI, m/z=338 (M+H) HPLC 1.49 min.

EXAMPLE 37

4-amino-8-(2,6-dimethoxy-3-perfidy)-N-propyl-cinnoline-3-carboxamide

Using method A, 4-amino-8-bromo-N-propyl-cinnoline-3-carboxamide (100 mg, 0.33 mmol) and 2,6-dimethoxy-perfidy-3-moronic acid (120 mg, 0.64 mmol) were reacted to afford the title compound (110 mg, 92.6% yield) as a pale-yellow solid. $^1$H NMR (300 MHz, CDCl$_3$) δ 8.55 (br, 1H), 7.85 (dd, J=8.3 Hz, J'=1.4 Hz, 1H), 7.79 (d, J=7.2 Hz, 1H), 7.60-7.73 (m, 2H), 6.46 (d, J=8.0 Hz, 1H), 3.98 (s, 3H), 3.88 (s, 3H), 3.45 (q, J=6.7 Hz, 2H), 1.66 (m, J=7.3 Hz, 2H), 1.00 (t, J=7.4 Hz, 3H) MS APCI, m/z=368 (M+H) HPLC 1.77 min.

EXAMPLE 38

4-amino-8-(2,5-dimethylphenyl)-N-propyl-cinnoline-3-carboxamide

Using method B, 4-amino-8-iodo-N-propyl-cinnoline-3-carboxamide (250 mg, 0.702 mmol) and 2,5-dimethylphenyl-boronic acid (150 mg, 1.00 mmol) were reacted to afford the title compound (195 mg, 83% yield) as a white solid. $^1$H NMR (300 MHz, CDCl$_3$) δ 8.55 (br, 1H), 7.87 (m, 1H), 7.75-7.64 (m, 2H), 7.23-7.07 (m, 3H), 3.44 (apparent quartet, J=7.0 Hz, 2H), 2.35 (s, 3H), 2.01 (s, 3H), 1.64 (apparent sextet, J=7.0 Hz, 2H), 0.99 (t, J=7.4 Hz, 3H) MS APCI, m/z=335 HPLC 1.98 min.

EXAMPLE 39

3-[4-amino-3-(propylcarbamoyl)crinoline-8-yl]benzoic acid hydrochloride

Using method B, 4-amino-8-iodo-N-propyl-cinnoline-3-carboxamide (150 mg, 0.421 mmol) and 3-(dihydroxyboryl)benzoic acid (77 mg, 0.464 mmol) were reacted to afford the title compound (117 mg, 79% yield) as a white solid. $^1$H NMR (300 MHz, Methanol-d4) δ 8.58-8.52 (m, 1H), 8.30-8.22 (m, 2H), 8.07-7.92 (m, 2H), 7.86-7.73 (m, 2H), 3.41 (t, J=7.0 Hz, 2H), 1.67 (apparent sextet, J=7.0 Hz, 2H), 0.99 (t, J=7.0 Hz, 3H). MS APCI, m/z=351 (M+H) HPLC 1.65 min.

EXAMPLE 40

4-amino-8-(3-azotizing-1-ylcarbonylphenyl)-N-propyl-cinnoline-3-carboxamide

To a stirred solution of 3-[4-amino-3-(propylcarbamoyl) crinoline-8-yl]benzoic acid (67 mg, 0.191 mmol) dissolved in anhydrous DMF (2 mL) at ambient temperature under argon was added astatine (16.4 mg, 0.287 mmol), N-methylmorpholine (29 mg, 0.287 mmol), 1-hydroxybenzotriazole (44 mg, 0.287 mmol) and N-(3-dimethylaminopropyl)-N'-ethylcabodiimide hydrochloride (55 mg, 0.287 mmol). The mixture was stirred at ambient temperature for 19 hours then diluted with water and extracted with ethyl acetate. The residue from the organic extracts was purified by flash chromatography on silica gel eluting with increasingly polar gradient of ethyl acetate in hexanes to afford the title compound (61 mg, 82% yield) as a white solid. $^1$H NMR (300 MHz, CDCl$_3$) δ 8.54 (br, 1H), 8.03-7.64 (m, 6H), 7.53 (t, J=7.7 Hz, 1H), 4.38 (br, 2H), 4.25 (br, 2H), 3.47 (apparent quartet, J=7.0 Hz, 2H), 2.34 (apparent panted, J=7.5 Hz, 2H), 1.67 (apparent sextet, J=7.0 Hz, 2H), 1.01 (t, J=7.4 Hz, 3H) MS APCI, m/z=390 (M+H) HPLC 1.70 min.

EXAMPLE 41

4-amino-N-propel-8-phrasing-2-yl-crinoline-3-carboxamide

Using method C, 4-amino-8-iodo-N-propyl-cinnoline-3-carboxamide (178 mg, 0.500 mmol) and 2-(tributylstannyl) pyridine (219 mg, 0.600 mmol) were reacted to afford the title compound (70 mg, 45% yield) as an off-white solid. $^1$H NMR (300 MHz, CDCl$_3$) δ 9.41 (m, 1H), 8.74 (m, 1H), 8.61 (d, J=2.5 Hz, 1H), 8.54 (br, 1H), 8.22 (m, 1H), 7.99 (m, 1H), 7.85-7.78 (m, 1H), 3.48 (apparent quartet, J=7.0 Hz, 2H), 1.69 (apparent sextet, J=7.0 Hz, 2H), 1.20 (t, J=7.0 Hz, 3H). MS APCI, m/z=309 (M+H) HPLC 1.49 min.

EXAMPLE 42

4-amino-N-propel-8-(3-perfidy)crinoline-3-carboxamide

Using method A, 4-amino-8-bromo-N-propyl-cinnoline-3-carboxamide (200 mg, 0.647 mmol) and pyridine-3-ylboronic acid (160 mg, 1.301 mmol) were reacted to afford the title compound (153 mg, 74% yield) as an off-white solid. $^1$H NMR (300 MHz, CDCl$_3$) δ 8.89 (m, 1H), 8.68 (m, 1H), 8.54 (br, 1H), 8.13 (m, 1H), 7.93 (m, 1H), 7.85-7.73 (m, 2H), 7.44 (m, 1H), 3.47 (apparent quartet, J=7.0 Hz, 2H), 1.68 (apparent sextet, J=7.0 Hz, 2H), 1.01 (t, J=7.0 Hz, 3H). MS APCI, m/z=308 (M+H) HPLC 1.46 min.

EXAMPLE 43

4-amino-8-(3-methylsulfonylphenyl)-N-propyl-cinnoline-3-carboxamide

Using method A, 4-amino-8-bromo-N-propyl-cinnoline-3-carboxamide (150 mg, 0.485 mmol) and 3-(methylsulfonyl)phenylboronic acid (200 mg, 1.000 mmol) were reacted to afford the title compound (155 mg, 83% yield) as a white solid. $^1$H NMR (300 MHz, CDCl$_3$) δ 8.51 (br, 1H), 8.21 (m, 1H), 8.11-7.67 (m, 6H), 3.45 (apparent quartet, J=7.0 Hz, 2H), 3.12 (s, 3H), 1.67 (apparent sextet, J=7.0 Hz, 2H), 1.01 (t, J=7.0 Hz, 3H). MS APCI, m/z=385 (M+H) HPLC 1.75 min.

EXAMPLE 44

4-amino-8-(3-cyan phenyl)-N-propyl-cinnoline-3-carboxamide

Using method A, 4-amino-8-bromo-N-propyl-cinnoline-3-carboxamide (150 mg, 0.485 mmol) and 3-cyanophenylboronic acid (147 mg, 1.000 mmol) were reacted to afford the title compound (138 mg, 86% yield) as a white solid. $^1$H NMR (300 MHz, CDCl$_3$) δ 8.54 (br, 1H), 8.06-7.89 (m, 3H), 7.85-7.69 (m, 3H), 7.65-7.57 (m, 1H), 3.47 (apparent quartet, J=7.0 Hz, 2H), 1.68 (apparent sextet, J=7.0 Hz, 2H), 1.01 (t, J=7.0 Hz, 3H). MS APCI, m/z=332 (M+H) HPLC 1.93 min.

EXAMPLE 45

4-amino-N-propel-8-(2-perfidy)crinoline-3-carboxamide

Using method C, 4-amino-8-iodo-N-propyl-cinnoline-3-carboxamide (178 mg, 0.500 mmol) and 2-(tributylstannyl) pyridine (220 mg, 0.600 mmol) were reacted to afford the title compound (60 mg, 39% yield) as a yellow solid. $^1$H NMR (300 MHz, CDCl$_3$) δ 8.79 (m, 1H), 8.52 (br, 1H), 8.26-8.21 (m, 1H), 8.14-8.09 (m, 1H), 8.05-7.98 (m, 1H), 7.88-7.75 (m, 2H), 7.34 (m, 1H), 3.47 (apparent quartet, J=7.0 Hz, 2H), 1.68 (apparent sextet, J=7.0 Hz, 2H), 1.01 (t, J=7.0 Hz, 3H). MS APCI, m/z=308 (M+H). HPLC 1.53 min.

EXAMPLE 46

4-amino-8-[3,5-bis(trifluoromethyl)phenyl]-N-propyl-cinnoline-3-carboxamide

Using method A, 4-amino-8-bromo-N-propyl-cinnoline-3-carboxamide (150 mg, 0.485 mmol) and 3,5-bis(trifluromethyl)phenylboronic acid (258 mg, 1.000 mmol) were reacted to afford the title compound 200 mg, 94% yield as an off-white solid. $^1$H NMR (300 MHz, CDCl$_3$) δ 8.50 (br, 1H), 8.13 (s, 2H), 7.99-7.93 (m, 2H), 7.84-7.73 (m, 2H), 3.47 (apparent quartet, J=7.0 Hz, 2H), 1.68 (apparent sextet, J=7.0 Hz, 2H), 1.01 (t, J=7.0 Hz, 3H). MS APCI, m/z=443 (M+H). HPLC 2.85 min.

EXAMPLE 47

4-amino-N-propel-8-(1H-parasol-4-yl)crinoline-3-carboxamide

Using method A, 4-amino-8-bromo-N-propyl-cinnoline-3-carboxamide (150 mg, 0.485 mmol) and 4-(4,4,5,5-tetraethyl-1,3,2-dioxaborolan-2-yl)-1H-parasol (194 mg, 1.000 mmol) were reacted to afford the title compound (35 mg, 25% yield) as an off-white solid. $^1$H NMR (300 MHz, DMSO-d6) δ 12.97 (br, 1H), 9.20 (broad triplet, 1H), 8.48 (br, 2H), 8.23 (d, J=8.3 Hz, 1H), 8.14 (d, J=6.6 Hz, 1H), 7.70 (m, 1H), 3.32 (m, 2H), 1.62 (apparent sextet, J=7.0 Hz, 2H), 0.93 (t, J=7.0 Hz, 3H). MS APCI, m/z=297 (M+H). HPLC 1.43 min.

EXAMPLE 48

4-amino-8-[2-chloro-5-(trifluoromethyl)phenyl]-N-propyl-cinnoline-3-carboxamide Using method A, 4-amino-8-bromo-N-propyl-cinnoline-3-carboxamide (150 mg, 0.485 mmol) and 2-chloro-5-(trifluoromethyl)phenylboronic acid (224 mg, 1.000 mmol) were reacted to afford the title compound (85 mg, 44% yield) as a white solid. ¹H NMR (300 MHz, CDCl₃) δ 8.51 (br, 1H), 7.98 (m, 1H), 7.81-7.63 (m, 5H), 3.45 (apparent quartet, J=7.0 Hz, 2H), 1.65 (apparent sextet, J=7.0 Hz, 2H), 0.99 (t, J=7.0 Hz, 3H). MS APCI, m/z=409 (M+H). HPLC 2.46 min.

EXAMPLE 49

4-amino-8-(2-metonym-5-methyl-phenyl)-N-propyl-cinnoline-3-carboxamide

Using method A, 4-amino-8-bromo-N-propyl-cinnoline-3-carboxamide (150 mg, 0.485 mmol) and 2-metonym-5-methyl-phenylboronic acid (166 mg, 1.000 mmol) were reacted to afford the title compound (141 mg, 83% yield) as a white solid. ¹H NMR (300 MHz, CDCl₃) δ 8.56 (br, 1H), 7.88-7.82 (m, 1H), 7.76-7.65 (m, 2H), 7.22-7.12 (m, 2H), 6.93 (m, 1H), 3.67 (s, 3H), 3.45 (apparent q, J=7.0 Hz, 2H), 2.34 (s, 3H), 1.65 (apparent sextet, J=7.0 Hz, 2H), 0.99 (t, J=7.0 Hz, 3H). MS APCI, m/z=351 (M+H). HPLC 1.96 min.

EXAMPLE 50

4-amino-N-propel-8-[2-(trifluoromethyl)phenyl]-crinoline-3-carboxamide

Using method A, 4-amino-8-bromo-N-propyl-cinnoline-3-carboxamide (150 mg, 0.485 mmol) and 2-triflurorom-ethyl-phenylboronic acid (190 mg, 1.000 mmol) were reacted to afford the title compound (115 mg, 64% yield) as a white solid. ¹H NMR (300 MHz, CDCl₃) δ 8.50 (br, 1H), 7.93 (m, 1H), 7.82 (m, 1H), 7.71 (m, 1H), 7.66-7.50 (m, 2H), 7.41 (m, 1H), 3.43 (apparent quartet, J=7.0 Hz, 2H), 1.63 (apparent sextet, J=7.0 Hz, 2H), 0.98 (t, J=7.0 Hz, 3H). MS APCI, m/z=375 (M+H). HPLC 2.05 min.

EXAMPLE 51

4-amino-8-(5-chloro-2-metonym-phenyl)-N-propyl-cinnoline-3-carboxamide

Using method A, 4-amino-8-bromo-N-propyl-cinnoline-3-carboxamide (150 mg, 0.485 mmol) and 2-metonym-5-chloro-phenylboronic acid (186 mg, 1.000 mmol) were reacted to afford the title compound (137 mg, 77% yield) as a white solid. ¹H NMR (300 MHz, CDCl₃) δ 8.54 (br, 1H), 7.89 (m, 1H), 7.71 (m, 2H), 7.40-7.29 (m, 2H), 6.95 (m, 1H), 3.45 (apparent quartet, J=7.0 Hz, 2H), 1.65 (apparent sextet, J=7.0 Hz, 3H). MS APCI, m/z=371 (M+H). HPLC 2.00 min.

EXAMPLE 52

4-amino-N-propel-8-(4-perfidy)crinoline-3-carboxamide

Using method C, 4-amino-8-iodo-N-propyl-cinnoline-3-carboxamide (178 mg, 0.500 mmol) 4-(tributylstannyl)pyridine (220 mg, 0.600 mmol) were reacted to afford the title compound (47 mg, 30% yield) as a yellow solid. ¹H NMR (300 MHz, CDCl₃) δ 8.75 (m, 2H), 8.54 (br, 1H), 7.95 (m, 1H), 7.86-7.72 (m, 2H), 7.66 (m, 2H), 3.47 (apparent quartet, J=7.0 Hz, 2H), 1.68 (m, 2H), 1.01 (t, J=7.0 Hz, 3H). MS APCI, m/z=308 (M+H) HPLC 1.47 min.

EXAMPLE 53

4-amino-8-(2,5-dichlorophenyl)-N-propyl-cinnoline-3-carboxamide

Using method A, 4-amino-8-bromo-N-propyl-cinnoline-3-carboxamide (150 mg, 0.485 mmol) and 2,5-dichloride-phenylboronic acid (190 mg, 1.00 mmol) were reacted to afford the title compound (85 mg, 47% yield) as a white solid. ¹H NMR (300 MHz, CDCl₃) δ 8.52 (br, 1H), 7.99-7.91 (m, 1H), 7.78-7.67 (m, 2H), 7.48-7.31 (m, 3H), 3.45 (apparent quartet, J=7.0 Hz, 2H), 1.65 (apparent sextet, J=7.0 Hz, 2H), 1.00 (t, J=7.0 Hz, 3H). MS APCI, m/z=375 (M+H). HPLC 2.24 min.

EXAMPLE 54

4-amino-8-(2,5-difluorophenyl)-N-propyl-cinnoline-3-carboxamide

Using method A, 4-amino-8-bromo-N-propyl-cinnoline-3-carboxamide (150 mg, 0.485 mmol) and 2,5-dilutor-phenylboronic acid (160 mg, 1.00 mmol) were reacted to afford the title compound (116 mg, 70% yield) as a white solid. ¹H NMR (300 MHz, CDCl₃) δ 8.54 (br, 1H), 7.97-7.91 (m, 1H), 7.83-7.69 (m, 2H), 7.27-7.05 (m, 3H), 3.46 (apparent quartet, J=7.0 Hz, 2H), 1.74-1.59 (m, 2H), 1.00 (t, J=7.0 Hz, 3H). MS APCI, m/z=343 (M+H). HPLC 2.01 min.

EXAMPLE 55

4-amino-8-(1-methyl-1H-parasol-4-yl)-N-propyl-cinnoline-3-carboxamide

Using method A, 4-amino-8-bromo-N-propyl-cinnoline-3-carboxamide (150 mg, 0.485 mmol) and 1-methyl-4-(4,4,5,5-tetraethyl-1,3,2-dioxaborolan-2-yl)-1H-parasol (212 mg, 1.020 mmol) were reacted to afford the title compound (123 mg, 82% yield) as a white solid. ¹H NMR (300 MHz, CDCl₃) δ 8.55 (br, 1H), 8.50 (s, 1H), 8.05 (s, 1H), 8.02-7.95 (m, 1H), 7.75-0.60 (m, 2H), 4.01 (s, 3H), 3.49 (apparent quartet, J=7.0 Hz, 2H), 1.71 (apparent sextet, J=7.0 Hz, 2H), 1.03 (t, J=7.0 Hz, 3H). MS APCI, m/z=311 (M+H). HPLC 1.56 min.

EXAMPLE 56

4-amino-8-(2-fluoro-3-metonym-phenyl)-N-propyl-cinnoline-3-carboxamide

Using method A, 4-amino-8-bromo-N-propyl-cinnoline-3-carboxamide (150 mg, 0.485 mmol) and 2-fluoro-3-metonym-phenylboronic acid (170 mg, 1.000 mmol) were reacted to afford the title compound (99 mg, 57% yield) as a white solid. ¹H NMR (300 MHz, CDCl₃) δ 8.55 (br, 1H), 7.93 (m, 1H), 7.83-7.69 (m, 2H), 7.22-7.14 (m, 1H), 7.10-7.00 (m, 2H), 3.93 (s, 3H), 3.45 (apparent quartet, J=7.0 Hz, 2H), 1.65 (apparent sextet, J=7.0 Hz, 2H), 0.99 (t, J=7.0 Hz, 3H). MS APCI, m/z=355 (M+H). HPLC 1.74 min.

EXAMPLE 57

4-amino-8-(2,5-diethyl-2H-parasol-3-yl)-N-propyl-cinnoline-3-carboxamide

Using method A, 4-amino-8-bromo-N-propyl-cinnoline-3-carboxamide (200 mg, 0.647 mmol) and 1,3-diethyl-5-(4,4,5,5-tetraethyl-1,3,2-dioxaborolan-2-yl)-1H-parasol (288 mg, 1.297 mmol) were reacted to afford the title compound (45 mg, 21% yield) as a white solid. $^1$H NMR (300 MHz, CDCl$_3$) δ 8.54 (br, 1H), 7.95 (m, 1H), 7.80-7.68 (m, 2H), 6.25 (s, 1H), 3.68 (s, 3H), 3.47 (apparent quartet, J=7.0 Hz, 2H), 2.35 (s, 3H), 1.67 (apparent sextet, J=7.0 Hz, 2H), 1.01 (t, J=7.0 Hz, 3H). MS APCI, m/z=325 (M+H). HPLC 1.55 min.

1,3-diethyl-5-(4,4,5,5-tetraethyl-1,3,2-dioxaborolan-2-yl)-1H-parasol

This precursor was prepared according to the method of A. V. Ivanchatchenko as described in the Journal of Heterocyclic Chemistry (2004) vol. 41 p. 931

EXAMPLE 58

4-amino-8-[2-fluoro-5-(trifluoromethyl)phenyl]-N-propyl-cinnoline-3-carboxamide

Using method A, 4-amino-8-bromo-N-propyl-cinnoline-3-carboxamide (150 mg, 0.485 mmol) and 2-fluoro-5-(trifluoromethyl)phenylboronic acid (208 mg, 1.000 mmol) were reacted to afford the title compound (148 mg, 78% yield) as a white solid. $^1$H NMR (300 MHz, CDCl$_3$) δ 8.52 (br, 1H), 7.97 (m, 1H), 7.83-7.67 (m, 4H), 7.32 (m, 1H), 3.46 (apparent quartet, J=7.0 Hz, 2H), 1.66 (apparent sextet, J=7.0 Hz, 2H), 1.00 (t, J=7.0 Hz, 3H). MS APCI, m/z=393 (M+H). HPLC 2.30 min.

EXAMPLE 59

4-amino-8-(2-fluoro-5-methyl-phenyl)-N-propyl-cinnoline-3-carboxamide

Using method A, 4-amino-8-bromo-N-propyl-cinnoline-3-carboxamide (150 mg, 0.485 mmol) and 2-fluoro-5-methyl-phenylboronic acid (154 mg, 1.000 mmol) were reacted to afford the title compound (127 mg, 77% yield) as a white solid. $^1$H NMR (300 MHz, CDCl$_3$) δ 8.56 (br, 1H), 7.91 (m, 1H), 7.81-7.68 (m, 2H), 7.28 (m, 1H), 7.24-7.17 (m, 1H), 7.13-7.05 (m, 1H), 3.45 (apparent quartet, J=7.0 Hz, 2H), 2.39 (s, 3H), 1.65 (apparent sextet, J=7.0 Hz, 2H), 1.00 (t, J=7.0 Hz, 3H). MS APCI, m/z=339 (M+H). HPLC 1.86 min.

EXAMPLE 60

4-amino-8-(2-fluoro-4-methyl-phenyl)-N-propyl-cinnoline-3-carboxamide

Using method A, 4-amino-8-bromo-N-propyl-cinnoline-3-carboxamide (150 mg, 0.485 mmol) and 2-fluoro-4-methyl-phenylboronic acid (154 mg, 1.000 mmol) were reacted to afford the title compound (141 mg, 86% yield) as a white solid. $^1$H NMR (300 MHz, CDCl$_3$) δ 8.56 (br, 1H), 7.91 (m, 1H), 7.81-7.69 (m, 2H), 7.28 (m, 1H), 7.24-7.16 (m, 1H), 7.13-7.04 (m, 1H), 3.45 (apparent quartet, J=7.0 Hz, 2H), 2.39 (s, 3H), 1.65 (apparent sextet, J=7.0 Hz, 2H), 1.00 (t, J=7.0 Hz, 3H). MS APCI, m/z=339 (M+H). HPLC 1.86 min.

EXAMPLE 61

4-amino-8-(5-fluoro-2-methyl-phenyl)-N-propyl-cinnoline-3-carboxamide

Using method A, 4-amino-8-bromo-N-propyl-cinnoline-3-carboxamide (150 mg, 0.485 mmol) and 5-fluoro-2-methyl-phenylboronic acid (154 mg, 1.000 mmol) were reacted to afford the title compound (142 mg, 86% yield) as a white solid. $^1$H NMR (300 MHz, CDCl$_3$) δ 8.53 (br, 1H), 7.91 (m, 1H), 7.77-7.63 (m, 2H), 7.26 (m, 1H), 7.07-6.97 (m, 2H), 3.45 (apparent quartet, J=7.0 Hz, 2H), 2.01 (s, 3H), 1.65 (apparent sextet, J=7.0 Hz, 2H), 0.99 (t, J=7.0 Hz, 3H). MS APCI, m/z=339 (M+H). HPLC 1.77 min.

EXAMPLE 62

4-amino-8-(4-fluoro-2-metonym-phenyl)-N-propyl-cinnoline-3-carboxamide

Using method A, 4-amino-8-bromo-N-propyl-cinnoline-3-carboxamide (150 mg, 0.485 mmol) and 4-fluoro-2-metonym-phenylboronic acid (170 mg, 1.000 mmol) were reacted to afford the title compound (143 mg, 83% yield) as a white solid. $^1$H NMR (300 MHz, CDCl$_3$) δ 8.55 (br, 1H), 7.87 (m, 1H), 7.74-7.67 (m, 2H), 7.34-7.27 (m, 1H), 6.83-6.72 (m, 2H), 3.69 (s, 3H), 3.45 (apparent quartet, J=7.0 Hz, 2H), 1.65 (apparent sextet, J=7.0 Hz, 2H), 0.99 (t, 3H, J=7.0 Hz). MS APCI, m/z=355 (M+H). HPLC 1.66 min.

EXAMPLE 63

4-amino-8-(3-fluoro-4-metonym-phenyl)-N-propyl-cinnoline-3-carboxamide

Using method A, 4-amino-8-bromo-N-propyl-cinnoline-3-carboxamide (150 mg, 0.485 mmol) and 3-fluoro-4-metonym-phenylboronic acid (170 mg, 1.000 mmol) were reacted to afford the title compound (135 mg, 78% yield) as a white solid. $^1$H NMR (300 MHz, CDCl$_3$) δ 8.57 (br, 1H), 7.88-7.66 (m, 3H), 7.52-7.41 (m, 2H), 7.10 (m, 1H), 3.96 (s, 3H), 3.47 (apparent quartet, J=7.0 Hz, 2H), 1.67 (apparent sextet, J=7.0 Hz, 2H), 1.01 (t, J=7.0 Hz, 3H). MS APCI, m/z=355 (M+H). HPLC 1.76 min.

EXAMPLE 64

4-amino-8-(2-fluoro-6-metonym-phenyl)-N-propyl-cinnoline-3-carboxamide

Using method A, 4-amino-8-bromo-N-propyl-cinnoline-3-carboxamide (150 mg, 0.485 mmol) and 2-fluoro-6-metonym-phenylboronic acid (170 mg, 1.000 mmol) were reacted to afford the title compound (73 mg, 42% yield) as a white solid. $^1$H NMR (300 MHz, CDCl$_3$) δ 8.54 (br, 1H), 7.93 (m, 1H), 7.78-7.69 (m, 2H), 7.42-7.31 (m, 1H), 6.89-6.80 (m, 2H), 3.70 (s, 3H), 3.44 (apparent quartet, J=7.0 Hz, 2H), 1.64 (apparent sextet, J=7.0 Hz, 2H), 0.99 (t, J=7.0 Hz, 3H). MS APCI, m/z=355 (M+H). HPLC 1.68 min.

EXAMPLE 64A

Large Scale Synthesis of 4-Amino-8-(2-fluoro-6-metonym-phenyl)-N-propylcinnoline-3-carboxamide

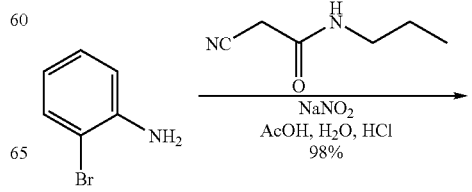

-continued

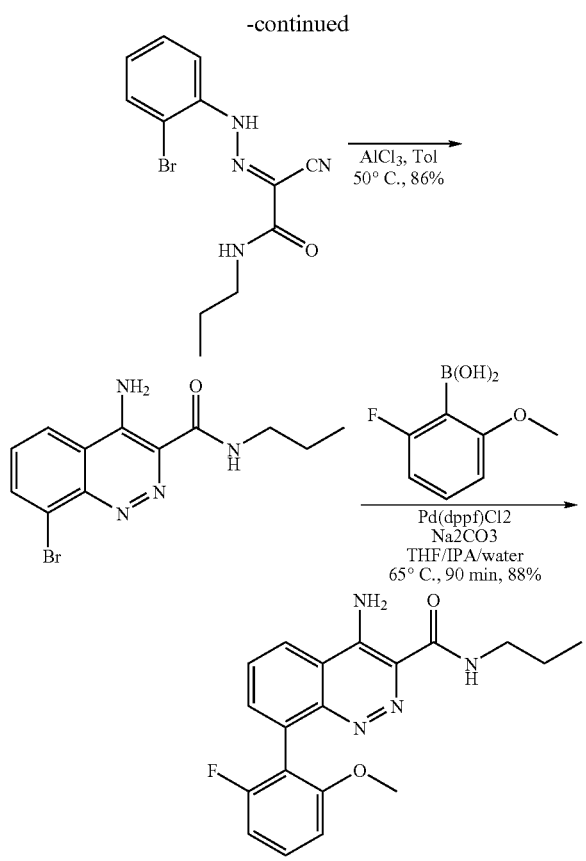

A 2 L, 3-necked flask equipped with a reflux condenser, mechanical stirrer, and 250 mL addition funnel was charged with 4-amino-8-bromo-N-propyl-cinnoline-3-carboxamide (36.80 g, 119.09 mmol), 2-fluoro-6-metonym-phenylboronic acid (60.70 g, 357.06 mmol), and Pd(dppf)Cl$_2$.CH$_2$Cl$_2$ (7.40 g, 9.06 mmol) under Argon at ambient temperature. A gentle vacuum was applied and the apparatus was back-filled with Argon two times. Tetrahydrofuran (515 mL, anhydrous) and isopropanol (147 mL, anhydrous) were added and the resulting red suspension was stirred at room temperature for 15 minutes. A solution of sodium carbonate (57.0 g, 537.7 mmol) in water (220 mL) was added rapidly through the addition funnel and the resulting mixture immediately placed into a pre-heated 80° C. oil bath. After 90 minutes at reflux (observed internal temperature 65° C.), the reaction mixture was cooled to room temperature and filtered though a bed of Elite supported on a sintered glass funnel topped with Norte decolorizing carbon (30 g). The residual salts and filter-cake were washed with 4:1 (v/v) THF: isopropanol until no additional material could be detected in the fluent by TLC (silica gel, 1:1 (v/v) hexanes: ethyl acetate, UV detection, R$_f$=0.25). The dark red solution was concentrated to a small volume under reduced pressure and then diluted with ethyl acetate (250 mL). The organic phase was separated and the aqueous phase extracted with ethyl acetate (2×250 mL). The combined organic layers were washed with brine, dried over sodium sulfate, filtered and then concentrated under reduced pressure. The residues were passed through a small pad of silica gel on a sintered glass funnel washing with ethyl acetate until no more material was detected in the fluent. The solution was evaporated to afford the crude product as a foamy red-brown solid. This material was purified by flash chromatography on silica gel using a gradient of 40 to 50% ethyl acetate in hexanes. Product containing fractions were combined and evaporated. The residue was precipitated from dichloromethane by addition of hexanes at room temperature. Recrystallization of this material from hot 1:1 (v/v) ethanol: water afforded the title compound as off-white white crystals (32.78 g, 78% yield). Additional title compound (4.30 g, 10% yield) was isolated by processing the residues form the crystallization liquors through an acid-base extractive workup. $^1$H NMR (500.3 MHz, CDCl$_3$) δ 8.54 (br, 1H), 7.90 (dd, J=8.1 Hz, 1H), 7.75-7.67 (m, 2H), 7.37-7.31 (m, 1H), 6.86-6.80 (m, 2H), 3.69 (s, 3H), 3.44 (qd, J=7.1 Hz, 2H), 1.64 (apparent sextet, J=7 Hz, 2H), 0.99 (t, J=7 Hz, 3H). The 4-Amino protons were not observable in the reported proton NMR spectra recorded at 30° C. due to severe broadening into the baseline. These protons can be clearly observed by recording the spectrum at −20° C. HRMS (C19H19FN4O2) Cal'd=355.1570, Observed=355.1531. HPLC 1.68 min.

It is found that the titled compound can be separated into two atropisomers using Supercritical Fluid Chromatography. Generally, in supercritical CO$_2$ modified with methanol, these atropisomers are stable and hence are separable on a choral support. However, in aqueous media and acidic aqueous media, in particular, the atropisomers inter-conversion is greatly facilitated.

4-Amino-8-bromo-N-propyl-cinnoline-3-carboxamide

Prepared according to the method described in the patent U.S. Pat. No. 4,886,800 example 35a.

EXAMPLE 65

4-amino-8-(2-fluoro-5-metonym-phenyl)-N-propyl-cinnoline-3-carboxamide

Using method A, 4-amino-8-bromo-N-propyl-cinnoline-3-carboxamide (150 mg, 0.485 mmol) and 2-fluoro-5-metonym-phenylboronic acid (170 mg, 1.000 mmol) were reacted to afford the title compound (142 mg, 83% yield) as a white solid. $^1$H NMR (300 MHz, CDCl$_3$) δ 8.56 (br, 1H), 7.92 (m, 1H), 7.82-7.69 (m, 2H), 7.12 (m, 1H), 7.02-6.89 (m, 2H), 3.81 (s, 3H), 3.45 (apparent quartet, J=7.0 Hz, 2H), 1.66 (apparent sextet, J=7.0 Hz, 2H), 1.00 (t, J=7.0 Hz, 3H). MS APCI, m/z=355 (M+H). HPLC 1.78 min.

EXAMPLE 66

4-amino-8-(5-fluoro-2-metonym-phenyl)-N-propyl-cinnoline-3-carboxamide

Using method A, 4-amino-8-bromo-N-propyl-cinnoline-3-carboxamide (150 mg, 0.485 mmol) and 5-fluoro-2-metonym-phenylboronic acid (170 mg, 1.000 mmol) were reacted to afford the title compound (140 mg, 81% yield) as a white solid. $^1$H NMR (300 MHz, CDCl$_3$) δ 8.54 (br, 1H), 7.89 (m, 1H), 7.75-7.67 (m, 2H), 7.14-7.04 (m, 2H), 6.99-6.92 (m, 1H), 3.67 (s, 3H), 3.45 (apparent quartet, J=7.0 Hz, 2H), 1.65 (apparent sextet, J=7.0 Hz, 2H), 1.00 (t, J=7.0 Hz, 3H). MS APCI, m/z=355 (M+H). HPLC 1.67 min.

EXAMPLE 67

4-amino-8-(4-methoxyphenyl)-N-propyl-cinnoline-3-carboxamide

Using method F, 4-amino-8-iodo-N-propyl-cinnoline-3-carboxamide (178 mg, 0.50 mmol) and 4-methoxyphenylboronic acid (303 mg, 2.00 mmol) were reacted (reflux 14 hours) to afford the title compound (118 mg, 70% yield) as a white solid. $^1$H NMR (300 MHz, CDCl$_3$) δ 8.58 (bm, 1H), 7.69-7.83 (m, 3H), 7.62 (d, J=8.9 Hz, 2H), 7.05 (d, J=8.9 Hz, 2H), 3.87 (s, 3H), 3.45 (apparent q, J=6.6 Hz, 2H), 1.65 (apparent sextet, J=7.4 Hz, 2H), 1.00 (t, J=7.4 Hz, 3H).

MS APCI, m/z=337 (M+H) HPLC 1.71 min.

EXAMPLE 68

4-amino-8-(4-Fluor phenyl)-N-propyl-cinnoline-3-carboxamide

Using method F, 4-amino-8-iodo-N-propyl-cinnoline-3-carboxamide (178 mg, 0.50 mmol) and 4-fluorophenylboronic acid (280 mg, 2.00 mmol) were reacted (reflux 24 hours) to afford the title compound (76 mg, 47% yield) as a white solid. $^1$H NMR (300 MHz, CDCl$_3$) δ 8.56 (bm, 1H), 7.86 (dd, J=7.7 Hz, 1H), 7.65-7.80 (m, 4H), 7.19 (t, J=8.6 Hz, 2H), 3.45 (apparent q, J=6.6 Hz, 2H), 1.67 (apparent sextet, J=7.4 Hz, 2H), 1.01 (t, J=7.4 Hz, 3H).

MS APCI, m/z=325 (M+H) HPLC 1.74 min.

EXAMPLE 69

4-amino-N-propel-8-[4-(trifluoromethoxy)phenyl]-crinoline-3-carboxamide

Using method F, 4-amino-8-iodo-N-propyl-cinnoline-3-carboxamide (178 mg, 0.42 mmol) and 4-trifluoromethylphenylboronic acid (347 mg, 1.68 mmol) were reacted (reflux 16 hours) to afford the title compound (119 mg, 73% yield) as a white solid. $^1$H NMR (300 MHz, CDCl$_3$) δ 8.56 (bs, 1H), 7.90 (dd, J=7.9, 1.5 Hz, 1H), 7.71-7.82 (m, 4H), 7.35 (d, J=8.3 Hz, 2H), 3.45 (apparent q, J=6.8 Hz, 2H), 1.67 (apparent sextet, J=7.3 Hz, 2H), 1.01 (t, J=7.3 Hz, 3H).

MS APCI, m/z=391 (M+H) HPLC 2.21 min.

EXAMPLE 70

4-amino-N-propel-8-[3-(trifluoromethoxy)phenyl]-crinoline-3-carboxamide

Using method F, 4-amino-8-iodo-N-propyl-cinnoline-3-carboxamide (178 mg, 0.42 mmol) and 3-trifluoromethylphenylboronic acid (347 mg, 1.68 mmol) were reacted (reflux 16 hours) to afford the title compound (94 mg, 57% yield) as a white solid. $^1$H NMR (300 MHz, CDCl$_3$) δ 8.56 (bs, 1H), 7.90 (d, J=8.3, 1H), 7.71-7.81 (m, 2H), 7.67 (d, J=7.9, 1H), 7.49-7.57 (m, 2H), 7.28 (m, 1H), 3.47 (apparent q, J=6.7 Hz, 2H), 1.67 (apparent sextet, J=7.3 Hz, 2H), 1.01 (t, J=7.4 Hz, 3H). MS APCI, m/z=391 (M+H) HPLC 2.20 min.

EXAMPLE 71

4-amino-8-(6-metonym-3-perfidy)-N-propyl-cinnoline-3-carboxamide

Using method A, 4-amino-8-bromo-N-propyl-cinnoline-3-carboxamide (150 mg, 0.49 mmol) and (6-methoxypyridin-3-yl)moronic acid (153 mg, 1.00 mmol) were reacted to afford the title compound (117 mg, 72% yield) as a white solid. $^1$H NMR (300 MHz, CDCl$_3$) δ 8.55 (bs, 1H), 8.43 (d, J=1.65 Hz, 1H), 8.05 (dd, J=8.5, 1.9 Hz, 1H), 7.87 (d, J=7.9 Hz, 1H), 7.71-7.81 (m, 2H), 6.89 (d, J=8.5 Hz, 1H), 4.01 (s, 3H), 3.46 (apparent q, J=6.6 Hz, 2H), 1.67 (apparent sextet, J=7.2 Hz, 2H), 1.01 (t, J=7.4 Hz, 3H). MS APCI, m/z=338 (M+H) HPLC 1.73 min.

EXAMPLE 72

4-amino-8-(4-metonym-3,5-diethyl-phenyl)-N-propyl-cinnoline-3-carboxamide

Using method A, 4-amino-8-bromo-N-propyl-cinnoline-3-carboxamide (125 mg, 0.40 mmol) and (4-metonym-3,5-dimethylphenyl)moronic acid (144 mg, 0.80 mmol) were reacted to afford the title compound (121 mg, 82% yield) as a white solid. $^1$H NMR (300 MHz, CDCl$_3$) δ 8.57 (bs, 1H), 7.66-7.85 (m, 3H), 7.32 (s, 2H), 3.78 (s, 3H), 3.46 (apparent q, J=6.6 Hz, 2H), 2.36 (s, 6H), 1.67 (apparent sextet, J=7.2 Hz, 2H), 1.01 (t, J=7.4 Hz, 3H). MS APCI, m/z=365 (M+H) HPLC 2.08 min.

EXAMPLE 73

4-amino-8-(4-metonym-3-methyl-phenyl)-N-propyl-cinnoline-3-carboxamide

Using method A, 4-amino-8-bromo-N-propyl-cinnoline-3-carboxamide (125 mg, 0.40 mmol) and (4-metonym-3-methyl phenyl)moronic acid (133 mg, 0.80 mmol) were reacted to afford the title compound (105 mg, 75% yield) as a white solid. $^1$H NMR (300 MHz, CDCl$_3$) δ 8.59 (bs, 1H), 7.76-7.82 (m, 2H), 7.67-7.72 (m, 1H), 7.53 (dd, J=8.2, 2.2 Hz, 1H), 7.46 (m, 1H), 6.96 (d, J=8.2, 1H), 3.89 (s, 3H), 3.46 (apparent q, J=6.7 Hz, 2H), 2.30 (s, 3H), 1.67 (apparent sextet, J=7.2 Hz, 2H), 1.00 (t, J=7.4 Hz, 3H). MS APCI, m/z'351 (M+H) HPLC 1.88 min.

EXAMPLE 74

4-amino-8-(2-fluoro-4-metonym-phenyl)-N-propyl-cinnoline-3-carboxamide

Using method A, 4-amino-8-bromo-N-propyl-cinnoline-3-carboxamide (125 mg, 0.40 mmol) and (2-fluoro-4-methoxyphenyl)moronic acid (136 mg, 0.80 mmol) were reacted to afford the title compound (93 mg, 66% yield) as a white solid. $^1$H NMR (300 MHz, CDCl$_3$) δ 8.56 (bs, 1H), 7.88 (dd, J=8.2, 1.5 Hz, 1H), 7.69-7.77 (m, 2H), 7.43 (t, J=8.3 Hz, 1H), 6.76-6.86 (m, 2H), 3.86 (s, 3H), 3.45 (apparent q, J=6.6 Hz, 2H), 1.65 (apparent sextet, J=7.2 Hz, 2H), 1.00 (t, J=7.4 Hz, 3H). MS APCI, m/z=355 (M+H) HPLC 1.79 min.

EXAMPLE 75

4-amino-8-(6-methylpyridin-3-yl)-N-propylcinnoline-3-carboxamide

Using method C, 4-amino-8-iodo-N-propyl-cinnoline-3-carboxamide (178 mg, 0.500 mmol) and 2-methyl-5-(trimethylstannyl)pyridine (270 mg, 1.058 mmol) were reacted to afford the title compound (123 mg, 76% yield). $^1$H NMR (300 MHz, CDCl$_3$) δ 8.75 (bs, 1H), 8.55 (br, 1H), 8.03 (m, 1H), 7.91 (m, 1H), 7.84-7.70 (m, 2H), 7.30 (m, 1H), 3.47 (apparent quartet, J=7.0 Hz, 2H), 2.64 (s, 3H), 1.67 (apparent sextet, J=7.0 Hz, 2H), 1.01 (t, J=7.0 Hz, 3H).

MS APCI, m/z=322 (M+H). HPLC 1.41 min.

2-methyl-5-(trimethylstannyl)pyridine

Prepared according to the method described by Li et. al., J. Med. Chem., 1996, 39, 1846-1856.

EXAMPLE 76

4-amino-8-(4-methylpyridin-3-yl)-N-propylcinnoline-3-carboxamide

Using method A, 4-amino-8-bromo-N-propyl-cinnoline-3-carboxamide (150 mg, 0.485 mmol) and (4-methylpyridin-3-yl)moronic acid (274 mg, 2.000 mmol) were reacted to afford the title compound (134 mg, 86% yield). $^1$H NMR (300 MHz, CDCl$_3$) δ 8.59-8.45 (m, 3H), 7.98-7.92 (m , 1H), 7.80-7.66 (m, 2H), 7.27 (m, 1H), 3.44 (m, 2H), 2.11 (s, 3H), 1.65 (m, 2H), 1.00 (t, J=7.0 Hz, 3H). MS APCI, m/z=322 (M+H). HPLC 1.27 min.

EXAMPLE 77

4-amino-8-(5-metonym-2-methyl phenyl)-N-propyl-cinnoline-3-carboxamide

Using method A, 4-amino-8-bromo-N-propyl-cinnoline-3-carboxamide (150 mg, 0.485 mmol) and 5-metonym-2-methyl-phenylboronic acid (125 mg, 1.000 mmol) were reacted to afford the title compound (125 mg, 73% yield). $^1$H NMR (300 MHz, CDCl$_3$) δ 8.55 (br, 1H), 7.88 (m, 1H), 7.76-7.64 (m, 2H), 7.21 (m, 1H), 6.92-6.81 (m, 2H), 3.79 (s, 3H), 3.45 (apparent quartet, J=7.0 Hz, 2H), 1.97 (s, 3H), 1.65 (apparent sextet, J=7.0 Hz, 2H), 0.99 (t, J=7.0 Hz, 3H). MS APCI, m/z=351 (M+H). HPLC 1.77 min.

EXAMPLE 78

4-Amino-8-(2,4-dimethoxyphenyl)-7-fluoro-N-propylcinnoline-3-carboxamide

Synthetic Scheme for Making Compound 78:

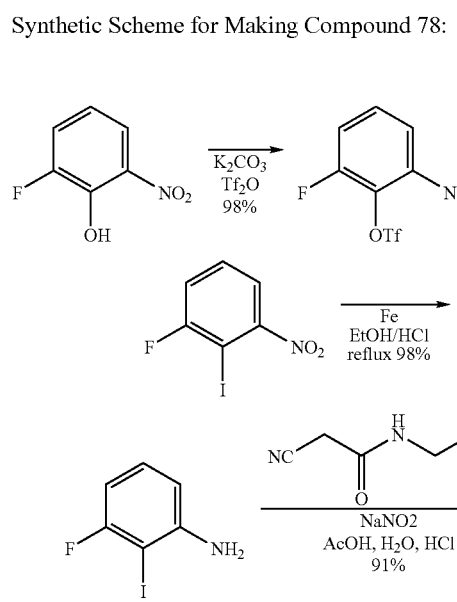

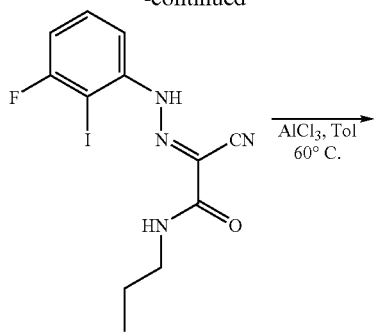

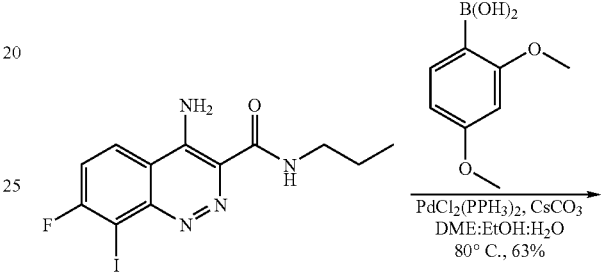

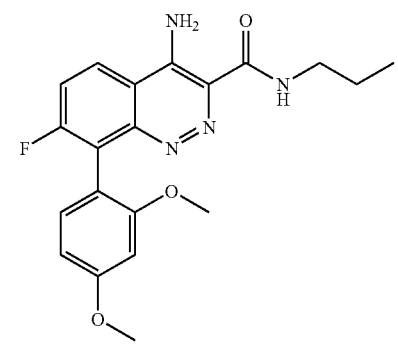

A 2 L, 3-necked flask equipped with a mechanical stirrer was charged with 4-amino7-fluoro-8-iodole-N-propylcinnoline-3-carboxamide (40.5 g, 108.2 mmol), DME (700 mL, anhydrous), and ethanol (200 mL, absolute). A nitrogen dispersion tube was fitted into the suspension and the mixture was stirred until a solution was obtained. Water (300 mL) and PdCl$_2$(PPh$_3$)$_2$ (7.6 g, 10 mol %) were added. After 5 minutes, 2,4-dimethoxyphenyl moronic acid (39.4 g, 216.5 mmol) was added followed by cesium carbonate (70.3 g, 216.5 mmol). Nitrogen was bubbled through the suspension for 5 minutes. The mixture was heated to approximately 80° C. Additional 7:3:2 DME:H$_2$O:EtOH (340 mL) was added as the reflux started. The reaction was refluxed 18 hours and then cooled to room temperature, diluted with ethyl acetate (1.5), and washed with water (3×500 mL). The aqueous layers were extracted with ethyl acetate (3×150 mL). The combined organic layers were stirred for 1 hour with 40 g of DARCO, dried over sodium sulfate, and filtered through Elite. The solids were washed with 5% methanol in chloroform (3×200 mL) and the filtrates concentrated to a dark semisolid. This was taken up in 200 mL 1% methanol in chloroform and warmed to solubilize the material. The solution was divided into two portions. Each portion was filtered through Whitman fluted filter paper onto a 330 g silica gel column and eluted with 5% ethyl acetate in dichloromethane. (Note: Some solid catalyst appeared to be removed via the filter paper.) The purest fractions from each column were combined in 5-10% ethyl acetate in dichloromethane. The solution was concentrated to approximately 200 mL, diluted with hexane (200 mL), and let stand at room temperature overnight. The resulting solids were isolated by filtration, washed with ether (3 times), and dried under vacuum at room temperature to afford the desired product (26.4 g, 63%). $^1$H NMR (500.333 MHz, CDCl$_3$) δ 8.51 (bs, 1H), 7.86 (dd, J=9.4, 5.2 Hz, 1H), 7.50 (t, J=8.8 Hz, 1H), 7.27 (d, J=9.2, 1H), 6.66 (dd, J=8.2, 2.3 Hz, 1H), 6.63 (d, J=2.3 Hz, 1H), 3.87 (s, 3H), 3.71 (s, 3H), 3.44 (q, J=6.7 Hz, 2H), 1.64 (sextet, J=7.3 Hz, 2H), 0.99 (t, J=7.4 Hz, 3H). MS APCI, m/z=385 (M+H). HPLC: 2.61 min.

4-Amino-7-fluoro-8-iodo-N-propyl-cinnoline-3-carboxamide

To a 1L, 3-necked flask equipped with a mechanical stirrer charged with (2E)-2-cyan-2-[(3-fluoro-2-indophenols)hydrazono]-N-propylacetamide (43.9 g, 117 mmol) in anhydrous toluene (Aldrich, 600 mL) under N$_2$ was added portionwise aluminum chloride (Aldrich, 46.8 g, 352 mmol) over 20 minutes. The mixture was heated to 60° C. with vigorous stirring for 2 hours then cooled to 15° C. Ethyl acetate (30 mL) was carefully added while maintaining the internal temperature between 20-25° C. Additional ethyl acetate (900 mL) was then added, followed by careful addition of Rochelle's salt (saturated aqueous potassium sodium tart rate, 500 mL). Upon addition of the first 50 mL, the temperature rose from 20 to 36° C. The reaction was heated with stirring at 60° C. for 30 minutes. The aqueous layer contained a thick white precipitate and the organic layer slowly solubilized the brownish yellow solid. (Note: If a non-white (brown/yellow) solid still existed at the aqueous/organic interface, the hot extraction was repeated). The mixture was placed in a separator funnel and the aqueous layer was removed. The organic layer was washed with Rochelle's salt (500 mL), washed with brine, dried over magnesium sulfate, filtered and concentrated to give 38 g slightly crude product (86.5%). Further purification by triturating with ethyl acetate/hexanes was carried out when appropriate. An analytically pure sample was obtained by recrystallization from ethyl acetate. $^1$H NMR (300 MHz, CDCl$_3$) δ 8.54 (br, 1H), 7.84 (dd, J=5.3, 9.2 Hz, 1H), 7.39 (dd, J=7.0, 9.2 Hz, 1H), 3.47 (apparent q, J=7.0 Hz, 2H), 1.68 (apparent sextet, J=7.0 Hz, 2H), 1.03 (t, J=7.4 Hz, 3H). MS APCI, m/z=375 (M+H). HPLC 2.13 min.

(2E)-2-Cyan-2-[(3-fluoro-2-indophenols)hydrazono]-N-propylacetamide

Using the procedure outlined in the patent U.S. Pat. No. 4,886,800 example 89b substituting 3-fluoro-2-iodoaniline hydrochloride (8.8 g, 32.5 mmol) for 2-iodoaniline, the title compound (2E)-2-cyan-2-[(3-fluoro-2-indophenols)hydrazono]-N-propylacetamide was obtained as a light brown solid (8.5 g, 70% yield). An analytically pure sample was obtained by recrystallization from ethyl acetate as a yellow crystalline solid. $^1$H NMR (300 MHz, CDCl$_3$) δ 14.39, (s, 1H), 8.67 (bm, 1H), 7.45 (m, 1H), 7.32 (m, 1H), 7.03 (m, 1H), 3.1 (apparent q, J=6.6 Hz, 2H), 1.53 (apparent sextet, J=7.4 Hz, 2H), 0.88 (t, J=7.4 Hz, 3H).

3-Fluoro-2-iodoaniline hydrochloride

To a 1L, 3 necked round bottom flask fitted with a mechanical stirrer was added 3-fluoro-2-iodonitrobenzene (3B Medical, 47.7 g, 179 mmol) and 500 mL absolute ethanol. To this stirred solution was added iron powder (325 mesh, Aldrich, 30 g, 537 mmol) followed by drop wise addition of concentrated HCl (30 mL, 360 mmol). The internal temperature rose from 23 to ~60° C. over the addition. The flask was fitted with a heating mantle and heated with vigorous stirring for 90 minutes. After cooling to room temperature, 1 N Na$_2$CO$_3$ (300 mL) was added followed by EtOAc (200 mL). The mixture was stirred for 30 minutes and then filtered through a pad of Elite. The Elite was washed with EtOAc (3×150 mL). The filtrates were placed in a separator funnel and the water layer was removed. The organic layer was concentrated under reduced pressure to reduce volume to ~200 mL, placed in a separator funnel, diluted with EtOAc (400 mL), washed organic with brine, dried over sodium sulfate, filtered and concentrated to dryness. The crude product was taken up in ether (300 mL) and made acidic to pH 1 with 2M HCl/ether (Aldrich). After 1 hour, the tan solid was isolated by filtration (39.2 g, 80%). The above aqueous layers were extracted with diethyl ether (300 mL), dried over sodium sulfate, combined with the filtrate of the 1$^{st}$ crop, made acidic to pH 1, and isolated as above to give additional tan solid (9.0 g, 18%) for an overall yield of 98%. $^1$H NMR (300 MHz, CDCl$_3$) δ 7.06 (m, 1H), 6.58 (m, 1H), 6.39 (m, 1H), 5.73 (bm, 1H). MS APCI, m/z=238 (M+H). HPLC 2.19 min.

It is found that the title compound may form isolable atropisomers in certain organic solvents (e.g. 25-35% methanol) at room temperature. The two atropisomers of the title compound may be isolated using choral LC. However, these isomers will acidize rapidly under neutral or acidic aqueous solutions.

EXAMPLE 79

4-amino-8-(2,5-dimethoxyphenyl)-7-fluoro-N-propylcinnoline-3-carboxamide

The title compound was prepared from 4-amino7-fluoro-8-iodole-N-propylcinnoline-3-carboxamide (200 mg, 0.535 mmol) and 2,5-dimethoxyphenyl moronic acid (194 mg, 1.07 mmol) according to Method A. The off-white solid from chromatography was slurred in ether, filtered and dried under vacuum at room temperature to afford the desired product (147 mg, 71%). $^1$H NMR (300.132 MHz, CDCl$_3$) δ 8.50 (t, J=4.7 Hz, 1H), 7.89 (dd, J=9.3, 5.1 Hz, 1H), 7.52 (t, J=8.8 Hz, 1H), 6.98 (m, 2H), 6.91 (dd, J=2.4, 0.9 Hz, 1H), 3.79 (s, 3H), 3.67 (s, 3H), 3.44 (q, J=6.7 Hz, 2H), 1.64 (sextet, J=7.3 Hz, 2H), 0.99 (t, J=7.4 Hz, 3H). MS APCI, m/z=385 (M+H). HPLC 2.62 min.

EXAMPLE 80

4-Amino-8-(2,4-dimethoxypyrimidin-5-yl)-7-fluoro-N-propylcinnoline-3-carboxamide The title compound was prepared from 4-amino-7-flour-8-iodole-N-propylcinnoline-3-carboxamide (220 mg, 58.8 mmol) and 2,4-dimethoxy-5-(4,4,5,5-tetramethyl-[1,3,2]dioxaborolan-2-yl)-pyramiding (312 mg, 1.62 mmol) according to Method B to afford a white solid (123 mg, 54%). $^1$H NMR (300.132 MHz, CDCl$_3$) δ 8.47 (t, J=5.4 Hz, 1H), 8.32 (s, 1H), 7.93 (dd, J=9.1, 5.2 Hz, 1H), 7.53 (dd, J=9.2, 8.4 Hz, 1H), 4.07 (s, 3H), 3.94 (s, 3H), 3.45 (q, J=6.7 Hz, 2H), 1.66

(sextet, J=7.3 Hz, 2H), 1.00 (t, J=7.4 Hz, 3H). MS APCI, m/z=387 (M+H). HPLC 1.87 min.

EXAMPLE 81

4-Amino-N-ethyl-8-(4-methoxypyridin-3-yl)crinoline-3-carboxamide

The title compound was prepared from 4-amino-8-bromo-N-ethyl-cinnoline-3-carboxamide (70.0 mg, 0.237 mmol) and 4-metonym-3-pyridine moronic acid (153.0 mg, 0.3439 mmol) according to Method A except that the extraction was carried out with ethylene chloride rather than ethyl acetate and the flash column was eluted with a gradient of 10 to 60% methanol in dichloromethane. The concentrated product was then recrystallized from chloroform (with a few drops of methanol) and hexanes to afford the title compound as a yellow solid (19.6 mg, 26% yield). $^1$H NMR (300.132 MHz, CDCl$_3$) δ 8.58 (d, J=5.7 Hz, 1H), 8.52-8.43 (bm, 1H), 8.46 (s, 1 H), 7.92 (app quintet, J=4.0 Hz, 1H), 7.74 (dd, J=4.9, 0.9 Hz, 2H), 6.96 (d, J=5.8 Hz, 1H), 3.78 (s, 3H), 3.53 (dq, J=5.8, 7.3, Hz, 2H), 1.27 (t, J=7.3 Hz, 3H). MS APCI, m/z=324 (M+H). HPLC 1.42 min.

EXAMPLE 82

4-Amino-N-butyl-8-(2,5-dimethoxyphenyl)crinoline-3-carboxamide

The title compound was prepared from 4-amino-8-bromo-N-butyl-cinnoline-3-carboxamide (100 mg, 0.31 mmol) and 2,5-dimethoxyphenyl moronic acid (112.6 mg, 0.62 mmol) according to Method A to afford a white solid (96.3 mg, 82%). $^1$H NMR 300.132 MHz, CDCl$_3$) δ 8.54 (t, J=4.7 Hz, 1H), 7.86 (dd, J=7.6, 2.2 Hz, 1H), 6.96 (t, J=3.0 Hz, 1H), 6.96 (s, 1H), 6.93 (d, J=1.9 Hz, 1H), 7.76-7.68 (m, 2H), 3.79 (s, 3H), 3.64 (s, 3H), 3.48 (q, J=6.6 Hz, 2H), 1.61 (quintet, J=7.2 Hz, 2H), 1.43 (sextet, J=7.3 Hz, 2H), 0.94 (t, J=7.3 Hz, 3H). MS APCI, m/z=381.2 (M+H). HPLC 2.83 min.

EXAMPLE 83

4-Amino-8-(2,5-dimethoxyphenyl)-N-ethylcinnoline-3-carboxamide

The title compound was prepared from 4-amino-8-bromo-N-ethyl-cinnoline-3-carboxamide (100.0 mg, 0.339 mmol) and 2,5-dimethoxyphenyl moronic acid (123.3 mg, 0.678 mmol) according to Method A. The solid obtained after chromatography was washed with diethyl ether and dried overnight at 40° C. to afford the title compound as a fluffy white solid (64.4 mg, 54% yield). HNMR (300.132 MHz, CDCl$_3$) δ 8.51 (bt, J=5.2 Hz, 1H), 7.86 (dd, J=7.5, 2.1 Hz, 1H), 7.76-7.68 (m, 2H), 6.97-6.91 (m, 3H), 3.79 (s, 3H), 3.64 (s, 3H), 3.52 (dq, J=5.7, 7.3 Hz, 2H), 1.26 (t, J=7.3 Hz, 3H). MS APCI, m/z=353 (M+H). HPLC 2.41 min.

EXAMPLE 84

4-Amino-8-(2,5-dimethoxyphenyl)-N-methylcinnoline-3-carboxamide

The title compound was prepared from 4-amino-8-bromo-N-methyl-cinnoline-3-carboxamide (20.0 g, 63.1 mmol) and 2,5-dimethoxyphenyl moronic acid (22.3 g, 122.4 mmol) according to Method B except that potassium carbonate was used as the base and tetrahydrofuran:ethanol:water (1:1:1) was used as the solvent system. The reaction mixture was filtered and the yellow solids were slurred in 10% methanol in chloroform and filtered. The combined filtrates were concentrated to a solid, slurred in hot ethyl acetate, and filtered. The combined solids were further purified on silica gel using 5% methanol in chloroform as the fluent. A final crystallization from refluxing ethyl acetate followed by drying under high vacuum at 45° C. afforded the title compound as a light yellow solid (12.65 g, 59%). $^1$H NMR (500.333 MHz, DMSO) δ 9.07 (d, J=4.6 Hz, 1H), 8.39 (d, J=8.2 Hz, 1H), 7.76-7.70 (m, 2H), 7.03 (d, J=9.1 Hz, 1H), 6.97 (dd, J=8.9, 3.0 Hz, 1H), 6.87 (d, J=3.2 Hz, 1H), 3.73 (s, 3H), 3.55 (s, 3H), 2.86 (d, J=4.8 Hz, 3H). MS APCI, m/z=xx (M+H). HPLC 2.23 min. MP=279.1-279.8.

EXAMPLE 85

4-Amino-N-butyl-8-(2,4-dimethoxypyrimidin-5-yl)crinoline-3-carboxamide

The title compound was prepared from 4-amino-8-bromo-N-butyl-cinnoline-3-carboxamide (200.0 mg, 0.62 mmol) and 2,4-dimethoxy-5-(4,4,5,5-tetramethyl-[1,3,2]dioxaborolan-2-yl)-pyramiding (987.9 mg, 3.72 mmol) according to Method B to afford a white solid (162.1 mg, 69%). $^1$H NMR (300.132 MHz, CDCl$_3$) δ 8.49 (t, J=5.5 Hz, 1H), 8.33 (s, 1H), 7.90 (dd, J=7.6, 2.1 Hz, 1H), 7.77-7.69 (m, 3H), 4.07 (s, 3H), 3.93 (s, 3H), 3.50 (q, J=6.6 Hz, 2H), 1.63 (quintet, J=7.2 Hz, 2H), 1.44 (sextet, J=7.4 Hz, 2H), 0.95 (t, J=7.3 Hz, 3H). MS APCI, m/z=383.1 (M+H). HPLC 2.52 min.

EXAMPLE 86

4-Amino-8-(2,4-dimethoxypyrimidin-5-yl)-N-ethyl-cinnoline-3-carboxamide

The title compound was prepared from 4-amino-8-bromo-N-ethyl-cinnoline-3-carboxamide (200.0 mg, 0.678 mmol) and 2,4-dimethoxyprimidine-5-moronic acid pinnacle ester (363.1 mg, 1.362 mmol) according to Method B except that the reaction was heated at 90° C. to fully dissolve the starting materials. After 4 hours, additional 2,4-dimethoxyprimidine-5-moronic acid pinnacle ester (363.1 mg, 1.362 mmol) was added and the reaction was refluxed overnight. A third addition of 2,4-dimethoxyprimidine-5-moronic acid pinnacle ester (363.1 mg, 1.362 mmol) and an additional 5 mol % tetrakis(triphenylphospine)palladium(0) were required to force the reaction to completion. The reaction was then worked up as described in Method B using dichloromethane rather than ethyl acetate for the extraction and crystallizing the material obtained from the flash column from chloroform/hexanes to afford the title compound as a white solid (89.5 mg, 37%). $^1$H NMR (300.132 MHz, CDCl3) δ 8.47 (s, 1H), 8.32 (s, 1H), 7.90 (dd, J=7.6, 2.1 Hz, 1H), 7.78-7.70 (m, 2H), 4.07 (s, 3H), 3.93 (s, 3H), 3.53 (dq, J=5.7, 7.3 Hz, 2H), 1.28 (t, J=7.3 Hz, 3H). MS APCI, m/z=354 (M+H). HPLC 2.07 min.

EXAMPLE 87

4-Amino-8-(2,5-dimethoxyphenyl)-crinoline-3-carboxylic acid ally amide

The title compound was prepared from 4-amino-8-bromo-cinnoline-3-carboxylic acid ally amide (273 mg, 0.89 mmol) and 2,5-dimethoxyphenyl moronic acid (201.1 mg, 1.11 mmol) according to Method A to afford an off-white solid (105 mg, 32%). $^1$H NMR (300.132 MHz, CDCl$_3$) δ 8.64 (bs, 1H), 7.87 (d, J=7.3 Hz, 1H), 7.77-7.69 (m, 2H), 6.96 (t, J=2.8 Hz, 1H), 6.96 (s, 1H), 6.93 (d, J=1.8 Hz, 1H), 6.00-5.88 (m, 1H), 5.29 (dq, J=17.2, 1.6 Hz, 1H), 5.17 (dq, J=10.2, 1.4 Hz, 1H), 4.12 (tt, J=5.7, 1.6 Hz, 2H), 3.79 (s, 3H), 3.64 (s, 3H). MS APCI, m/z=365 (M+H). HPLC 1.76 min.

EXAMPLE 88

4-Amino-N-(cyclopropylmethyl)-8-phenyl-crinoline-3-carboxamide

To a suspension of 2-(biphenyl-2-yl-hydrazono)-2-cyano-N-cyclopropylmethylacetamide (1.9 g, 6.0 mmol) in anhydrous toluene (30 mL) was added aluminum chloride (1.72 g, 13.0 mmol). The mixture was heated at 70° C. for 1 hour, cooled to room temperature, and diluted with ethyl acetate (150 mL). Water was added drop wise until no further precipitate formed. Aqueous 10% sodium hydroxide (150 mL) was added and the layers were separated. The organic layer was washed with 10% sodium hydroxide (100 mL), water (100 mL), and brine (100 mL) and dried over sodium sulfate, filtered, and concentrated to a semisolid. The material was dissolved in chloroform and purified on silica gel to give 500 mg of material which was then recrystallized from ethyl acetate/hexanes and then from hot toluene (two times) to afford the pure product as a solid (117 mg, 6.2%). $^1$H NMR (500.133 MHz, CDCl$_3$) δ 9.23 (t, J=5.3 Hz, 1H), 9.13 (bs, 1H), 8.43 (d, J=8.4 Hz, 1H), 8.17 (bs, 1H), 7.86 (d, J=7.1 Hz, 1H), 7.81 (td, J=7.7, 1.2 Hz, 1H), 7.71 (d, J=7.5 Hz, 2H), 7.49 (t, J=7.3 Hz, 2H), 7.43 (td, J=7.2, 0.9 Hz, 1H), 3.23 (t, J=6.3 Hz, 2H), 1.12 (t, J=5.6 Hz, 1H), 0.45 (dd, J=6.5, 1.5 Hz, 2H), 0.29 (d, J=4.4 Hz, 2H). MS APCI, m/z=319 (M+H). HPLC 1.83 min.

EXAMPLE 89

4-Amino-8-(m-toll)-N-propyl-cinnoline-3-carboxamide

The title compound was prepared from 4-amino-8-bromo-N-propyl-cinnoline-3-carboxamide (450 mg, 1.46 mmol) and 3-methyl phenyl moronic acid (408 mg, 3.00 mmol) according to Method A to afford an off-white solid (321 mg, 69%). $^1$H NMR (300.132 MHz, CDCl$_3$) δ 8.58 (t, J=5.0 Hz, 1H), 7.85 (dd, J=8.3, 1.4 Hz, 1H), 7.79 (dd, J=7.3, 1.4 Hz, 1H), 7.71 (dd, J=8.1, 7.3 Hz, 1H), 7.50 (s, 1H), 7.48 (s, 2H), 7.39 (t, J=7.9 Hz, 1H), 7.23 (s, 1H), 3.46 (q, J=6.7 Hz, 2H), 2.44 (s, 3H), 1.67 (sextet, J=7.3 Hz, 2H), 1.00 (t, J=7.4 Hz, 3H). MS APCI, m/z=321 (M+H). HPLC 1.90 min.

EXAMPLE 90

4-Amino-8-(2-fluoro-6-methylpyridin-3-yl)-crinoline-3-carboxylic acid polyamide The title compound was prepared from 4-amino-8-bromo-N-propyl-cinnoline-3-carboxamide (300.0 mg, 0.97 mmol) and 2-fluoro-6-methyl pyridine-3-moronic acid (426.7 mg, 2.75 mmol) according to Method A to afford a white solid (124.2 mg, 38%). $^1$H NMR (300.132 MHz, CDCl$_3$) δ 8.53 (bs, 1H), 7.94 (t, J=1.4 Hz, 1H), 7.92 (dt, J=8.6, 1.4 Hz, 1H), 7.89 (d, J=7.6 Hz, 1H), 7.83 (dt, J=7.1, 1.2 Hz, 1H), 7.74 (dd, J=8.8, 7.3 Hz, 1H), 7.19 (dd, J=7.4, 1.3 Hz, 1H), 3.46 (q, J=6.7 Hz, 2H), 2.59 (s, 3H), 1.66 (sextet, J=7.3 Hz, 2H), 1.00 (t, J=7.4 Hz, 3H). MS APCI, m/z=340 (M+H). HPLC 2.28 min.

EXAMPLE 91

4-Amino-7-fluoro-8-(5-fluoro-2-methoxyphenyl)-crinoline-3-carboxylic acid polyamide The title compound was prepared from 4-amino-7-fluoro-8-iodole-N-propylcinnoline-3-carboxamide (200.0 mg, 0.53 mmol) and 2-fluoro-5-methoxyphenyl moronic acid (181.7 mg, 1.07 mmol) according to Method A to afford a yellow crystalline solid (111.0 mg, 56%). $^1$H NMR (300.132 MHz, CDCl$_3$) δ 8.49 (t, J=5.3 Hz, 1H), 7.91 (dd, J=9.3, 5.2 Hz, 1H), 7.52 (t, J=8.8 Hz, 1H), 7.16-7.07 (m, 2H), 6.98 (dd, J=9.1, 4.5 Hz, 1H), 3.70 (s, 3H), 3.44 (q, J=6.7 Hz, 2H), 1.64 (sextet, J=7.3 Hz, 2H), 0.99 (t, J=7.4 Hz, 3H). MS APCI, m/z=373 (M+H). HPLC 2.66 min.

EXAMPLE 92

4-Amino-8-(2-chloro-5-methoxyphenyl)-7-fluoro-crinoline-3-carboxylic acid polyamide The title compound was prepared from 4-amino-7-fluoro-8-iodole-N-propylcinnoline-3-carboxamide (250 mg, 0.67 mmol) and 2-chloro-5-methoxyphenyl moronic acid (279 mg, 1.50 mmol) according to Method A to afford a solid (181 mg, 72%). $^1$H NMR (500.333 MHz, CDCl$_3$) δ 8.41 (s, 1H), 7.90 (dd, J=9.1, 5.1 Hz, 1H), 7.49 (t, J=8.7 Hz, 1H), 7.41 (dd, J=6.9, 2.7 Hz, 1H), 6.94-6.92 (m, 2H), 3.79 (s, 3H), 3.44 (q, J=6.7 Hz, 2H), 1.65 (sextet, J=7.2 Hz, 2H), 0.99 (t, J=7.3 Hz, 3H). MS APCI, m/z=389/391 (M+H). HPLC 2.13 min.

EXAMPLE 93

4-amino-N-cyclopropyl-8-(2,6-dimethoxypyridin-3-yl)crinoline-3-carboxamide

Using Method A, 4-amino-8-bromo-N-cyclopropyl-cinnoline-3-carboxamide (143 mg, 0.47 mmol) and 2,6-dimethoxypyridine-3-moronic acid (170 mg, 0.94 mmol) were reacted. After purification the title compound (132 mg, 77% yield) was obtained as a white solid. $^1$H NMR (500 MHz, DMSO-d6) δ 9.03 (d, J=4.9 Hz, 1H), 8.38 (d, J=8.0 Hz, 1H), 7.76 (m, 2H), 7.67 (d, J=8.0 Hz, 1H), 6.48 (d, J=8.0 Hz, 1H), 3.93 (s, 3H), 3.77 (s, 3H), 2.96 (m, 1H), 0.70(m, 4H). MS APCI, m/z=366.

EXAMPLE 94

4-amino-N-cyclopropyl-8-(2-metonym-5-methyl-phenyl)crinoline-3-carboxamide

Using Method A, 4-amino-8-bromo-N-cyclopropyl-cinnoline-3-carboxamide (143 mg, 0.47 mmol) and 2-metonym-5-methylphenylboronic acid (155 mg, 0.94 mmol) were reacted. After purification the title compound (120 mg, 74% yield) was obtained as a white solid. $^1$H NMR (500 MHz, DMSO-d6) δ 9.00 (d, J=4.9 Hz, 1H), 8.38 (d, J=7.1 Hz, 1H), 7.74 (t, J=7.7 Hz, 1H), 7.68 (d, J=7.1 Hz, 1H), 7.19 (d, J=8.5 Hz, 1H), 7.06 (s, 1H), 6.98 (d, J=8.5 Hz, 1H), 3.57 (s, 3H), 2.96 (m, 1H), 2.28 (s, 3H), 0.70(m, 4H). MS APCI, m/z=349.

EXAMPLE 95

4-amino-N-cyclopropyl-8-(2,4-dimethoxyphenyl) crinoline-3-carboxamide

Using Method A, 4-amino-8-bromo-N-cyclopropyl-cinnoline-3-carboxamide (143 mg, 0.47 mmol) and 2,4-dimethoxyphenylboronic acid (171 mg, 0.94 mmol) were reacted. After purification the title compound (136 mg, 80% yield) was obtained as a white solid. $^1$H NMR (500 MHz, DMSO-d6) δ 9.00 (d, J=4.8 Hz, 1H), 8.35 (d, J=8.4 Hz, 1H), 7.72 (t, J=7.7 Hz, 1H), 7.68 (ad, J=7.1 Hz, 1H), 7.18 (d, J=8.3 Hz, 1H), 6.66 (s, 1H), 6.59 (ad, J=8.3 Hz, 1H), 3.83 (s, 3H), 3.61 (s, 3H), 2.96 (m, 1H), 0.70(m, 4H). MS APCI, m/z=365.

EXAMPLE 96

4-amino-N-cyclopropyl-8-(2,4-dimethoxypyrimidin-5-yl)crinoline-3-carboxamide

Using Method A, 4-amino-8-bromo-N-cyclopropyl-cinnoline-3-carboxamide (143 mg, 0.47 mmol) and 2,4-dimethoxypyrimidine-5-moronic acid (171 mg, 0.94 mmol) were reacted. After purification the title compound (133 mg, 78% yield) was obtained as a white solid. $^1$H NMR (300 MHz, CDCl$_3$) δ 8.51 (bm, 1H), 8.31 (s, 1H), 7.89 (a dd, J=2.3, 7.4 Hz, 1H), 7.75 (m, 2H), 4.06 (s, 3H), 3.92 (s, 3H), 2.96 (m, 1H), 0.88 (m, 2H), 0.65 (m, 2H). MS APCI, m/z=367, HPLC 2.07 min

EXAMPLE 97

4-amino-N-cyclopropyl-8-(2,5-dimethoxyphenyl) crinoline-3-carboxamide

Using Method A, 4-amino-8-bromo-N-cyclopropyl-cinnoline-3-carboxamide (100 mg, 0.33 mmol) and 2,5-dimethoxyphenylboronic acid (118 mg, 0.65 mmol) were reacted. After purification the title compound (101 mg, 85% yield) was obtained as a white solid. $^1$H NMR (300 MHz, CDCl$_3$) δ 8.56 (bm, 1H), 7.85 (a dd, J=2.2, 7.6 Hz, 1H), 7.73 (m, 2H), 6.95 (m, 2H), 6.91 (m, 1H), 3.77 (s, 3H), 3.63 (s, 3H), 2.96 (m, 1H), 0.88 (m, 2H), 0.65 (m, 2H). MS APCI, m/z=365, HPLC 2.42 min.

EXAMPLE 98

4-amino-N-ethyl-8-(2-fluoro-6-metonym-phenyl) crinoline-3-carboxamide

Using Method A, 4-amino-8-bromo-N-ethyl-cinnoline-3-carboxamide and 2-fluoro-6-metonym-phenyl moronic acid were reacted to afford the title compound as a off-white solid. $^1$H NMR (500 MHz, CDCl$_3$) δ 8.50 (br, 1H), 7.90 (m, 1H), 7.74 (m, 2H), 7.36 (m, 1H), 6.84 (m, 2H), 3.70 (s, 3H), 3.52 (m, 2H), 1.25 (t, J=7.0 Hz, 3H). MS APCI, m/z=341 (M+H).

EXAMPLE 99

4-amino-7-fluoro-8-(2-fluoro-6-metonym-phenyl)-N-propyl-cinnoline-3-carboxamide

Using Method G, 4-amino-8-broom-7-fluoro-N-propyl-cinnoline-3-carboxamide and 2-fluoro-6-metonym-phenyl moronic acid were reacted to afford the title compound as a white solid. $^1$HNMR (500 MHz, DMSO-d6) δ 9.16 (br, 1H), 9.06 (m, 1H), 8.58 (m, 1H), 8.32 (br, 1H), 7.76(m, 1H), 7.50 (m, 1H), 7.02(m, 1H), 6.94(m, 1H), 3.68 (s, 3H), 3.31-3.25 (m, 2H), 1.57 (m, 2H), 0.89 (t, J=7.0 Hz, 3H). MS APCI, m/z=373 (M+H).

EXAMPLE 100

4-amino-7-cyan-8-(2,4-dimethoxyphenyl)-N-propyl-cinnoline-3-carboxamide

Using Method G, 4-amino-8-broom-7-cyan-N-propyl-cinnoline-3-carboxamide and 2,4-dimethoxyphenyl moronic acid were reacted to afford the title compound as a white solid. $^1$H NMR (500 MHz, CDCl$_3$) δ 8.51 (br, 1H), 7.87 (m, 2H), 7.27 (m, 1H), 6.66 (m, 2H), 3.88 (s, 3H), 3.74 (s, 3H), 3.45 (m, 2H), 1.64 (apparent sextet, 2H), 0.99 (t, J=7.0 Hz, 3H). MS APCI, m/z=392 (M+H).

EXAMPLE 101

4-amino-N-cyclobutyl-8-(2-fluoro-6-methoxyphenyl)crinoline-3-carboxamide

Using Method A, 4-amino-8-bromo-N-cyclobutyl-cinnoline-3-carboxamide (145 mg) and 2-fluoro-6-metonym-phenyl moronic acid (191 mg) were reacted to afford the title compound (32 mg) as white solid. $^1$H NMR (500 MHz, DMSO-d6) δ 9.20 (d, 1H), 8.44 (m, 1H), 7.76 (m, 2H), 7.44 (m, 1H), 6.99 (d, 1H), 6.90 (t, 1H), 4.49 (m, 1H), 3.65 (s, 3H), 2.26-2.10 (m, 4H), 1.72-1.62 (m, 2H). MS APCI, m/z=367 (M+H).

EXAMPLE 102

4-amino-N-cyclopropyl-8-(2-fluoro-6-methoxyphenyl)crinoline-3-carboxamide

Using Method H, 4-amino-8-bromo-N-cyclopropyl-cinnoline-3-carboxamide (120 mg, 0.39 mmol) and 2-fluoro-6-methoxyphenylboronic acid (250 mg, 1.47 mmol) were reacted (refluxed 2 hours). After purification the title compound (82 mg, 60% yield) was obtained as a white solid. $^1$H NMR (300 MHz, CDCl$_3$) δ 8.52 (bm, 1H), 7.93 (m, 1H), 7.75 (m, 1H), 7.36 (apparent q, J=7.0 Hz, 1H), 6.84 (m, 2H), 3.69 (s, 3H), 2.96 (m, 1H), 0.85 (m, 2H), 0.63 (m, 2H). MS APCI, m/z=353 (M+H) HPLC 1.74 min.

EXAMPLE 103

4-amino-8-(2-chloro-6-metonym-phenyl)-N-propyl-cinnoline-3-carboxamide

Using Method G, 4-amino-8-bromo-N-propyl-cinnoline-3-carboxamide (600 mg) and 2-chloro-6-metonym-phenyl-boronic acid (1051 mg) were reacted to afford the title compound (263 mg) as a off-white solid. $^1$H NMR (300 MHz, CDCl$_3$) δ 8.55(br, 1H), 7.94-7.88 (m, 1H), 7.79-7.65 (m, 2H), 7.37-7.29 (m, 1H), 7.15 (m, 1H), 6.94 (m, 1H), 3.65 (s, 3H), 3.44 (apparent quartet, J=7.0 Hz, 2H), 1.64 (apparent sextet, J=7.0 Hz, 2H), 0.99 (t, J=7.0 Hz, 3H). MS APCI, m/z=371 (M+H) HPLC 1.86 min.

EXAMPLE 104

4-amino-7-fluoro-8-(2-fluoro-3-methoxyphenyl)-N-propyl-cinnoline-3-carboxamide Using method A, 4-amino-7-fluoro-8-iodo-N-propyl-cinnoline-3-carboxamide (250 mg, 0.67 mmol) and (2-fluoro-3-methoxyphenyl)moronic acid (193.4 mg, 1.136 mmol) were reacted to afford the title compound (72.0 mg, 29% yield) as an off-white solid. $^1$H NMR (500 MHz, CDCl$_3$) δ 8.49 (bs, 1H), 7.94 (dxd, J=4.9 Hz, J=9.2 Hz, 1H), 7.55 (t, J=8.5 Hz, 1H), 7.21 (m, 1H), 7.03-7.10 (m, 2H), 3.94 (s, 3H), 3.44 (q, J=6.7 Hz, J=13.4 Hz, 2H), 1.64 (apparent sextet, J=7.3 Hz, 2H), 0.98 (t, J=7.3 Hz, 3H). MS APCI, m/z=373 (M+H) HPLC 2.72 min.

EXAMPLE 107

4-amino-7-fluoro-8-(4-fluoro-2-metonym-phenyl)-N-propyl-cinnoline-3-carboxamide Using method A, 4-amino-7-fluoro-8-iodo-N-propyl-cinnoline-3-carboxamide (250 mg, 0.67 mmol) and (2-metonym-4-Fluor phenyl)moronic acid (227.1 mg, 1.336 mmol) were reacted to afford the title compound (131.7 mg, 53% yield) as an off-white solid. $^1$H NMR (500 MHz, CDCl$_3$) δ 8.49 (bs, 1H), 7.89 (dxd, J=5.5 Hz, J=9.2 Hz, 1H), 7.52 (apparent triplet, J=8.9 Hz, 1H), 7.30 (m, 1H), 6.82 (dxd, J=2.4 Hz, J=8.5 Hz, 1H), 6.79 (dxd, J=2.4 Hz, J=12.8 Hz, 1H), 3.72 (s, 3H), 3.44 (q, J=6.7 Hz, J=13.4 Hz, 2H), 1.64 (apparent sextet, J=7.3 Hz, 2H), 0.99 (t, J=7.6 Hz, 3H). MS APCI, m/z=373 (M+H) HPLC 2.70 min.

EXAMPLE 108

4-amino-7-fluoro-8-(2-fluoro-4-methoxyphenyl)-N-propyl-cinnoline-3-carboxamide Using method A, 4-amino-7-fluoro-8-iodo-N-propyl-cinnoline-3-carboxamide (250.0 mg, 0.67 mmol) and (2-fluoro-4-methoxyphenyl)moronic acid (227.1 mg, 1.336 mmol) were reacted to afford the title compound (165.4 mg, 67% yield) as a white solid. $^1$H NMR (500 MHz, CDCl$_3$) δ 8.51 (bs, 1H), 7.90 (dxd, J=5.5 Hz, J=9.2 Hz, 1H), 7.53 (apparent triplet, J=8.9 Hz, 1H), 7.41 (t, J=8.5 Hz, 1H), 6.86 (dxd, J=2.4 Hz, J=8.5 Hz, 1H), 6.80 (dxd, J=2.4 Hz, J=11.6 Hz, 1H), 3.87 (s, 3H), 3.44 (q, J=6.7 Hz, J=12.8 Hz, 2H), 1.65 (apparent sextet, J=7.3 Hz, 2H), 1.00 (t, J=7.3 Hz, 3H). MS APCI, m/z=373 (M+H) HPLC 2.78 min.

EXAMPLE 110

4-amino-7-fluoro-8-(2-methyl-5-Fluor phenyl)-N-propyl-cinnoline-3-carboxamide Using method A, 4-amino-7-fluoro-8-iodo-N-propyl-cinnoline-3-carboxamide (300 mg, 0.80 mmol) and (2-methyl-5-Fluor phenyl)moronic acid (246.8 mg, 1.60 mmol) were reacted to afford the title compound (164.7 mg, 58% yield) as a white solid. $^1$H NMR (300 MHz, CDCl$_3$) δ 8.48 (bs, 1H), 7.93 (dxd, J=5.3 Hz, J=9.4 Hz, 1H), 7.54 (apparent t, J=8.6 Hz, 1H), 7.30 (dxd, J=5.6 Hz, J=8.3 Hz, 1H), 6.99-7.09 (m, 2H), 3.44 (apparent q, J=7.0 Hz, 2H), 2.03 (s, 3H), 1.64 (apparent sextet, J=7.4 Hz, 2H), 0.99 (t, J=7.4 Hz, 3H). MS APCI, m/z=357 (M+H) HPLC 2.78 min.

EXAMPLE 113

4-amino-7-fluoro-8-(2,5-difluorophenyl)-N-propyl-cinnoline-3-carboxamide

Using method B, 4-amino-7-fluoro-8-iodo-N-propyl-cinnoline-3-carboxamide (150 mg, 0.40 mmol) and (2,5-difluorophenyl)moronic acid (519.0 mg, 3.29 mmol) were reacted to afford the title compound (50.5 mg, 35% yield) as an off-white solid. $^1$H NMR (300 MHz, CDCl$_3$) δ 8.48 (bs, 1H), 7.96 (dxd, J=5.3 Hz, J=9.3 Hz, 1H), 7.55 (t, J=9.1 Hz, 1H), 7.13-7.23 (m, 3H), 3.45 (apparent q, J=6.9 Hz, J=13.1 Hz, 2H), 1.65 (apparent sextet, J=7.3 Hz, 2H), 1.00 (t, J=7.4 Hz, 3H). MS APCI, m/z=361 (M+H) HPLC 2.98 min.

EXAMPLE 124

4-amino-N-cyclobutyl-7-fluoro-8-(2-metonym-5-methyl-phenyl)crinoline-3-carboxamide Using Method A, 4-amino-8-broom-7-fluoro-N-cyclobutyl-crinoline-3-carboxamide (175 mg) and 2-metonym-5-methyl-phenyl moronic acid (187 mg) were reacted to afford the title compound (128 mg) as white solid. $^1$H NMR (500 MHz, DMSO-d6) δ 9.18 (d, 1H), 8.50 (m, 1H), 7.71 (m, 1H), 7.24 (m, 1H), 7.07 (m, 1H), 7.03 (m, 1H), 4.49 (m, 1H), 3.61 (s, 3H), 2.29 (s, 3H), 2.26-2.10 (m, 4H), 1.72-1.62 (m, 2H). MS APCI, m/z=381 (M+H).

EXAMPLE 125

4-amino-N-cyclobutyl-7-fluoro-8-(5-fluoro-2-metonym-phenyl)crinoline-3-carboxamide Using Method A, 4-amino-8-broom-7-fluoro-N-cyclobutyl-crinoline-3-carboxamide (175 mg) and 5-fluoro-2-metonym-phenyl moronic acid (191 mg) were reacted to afford the title compound (141 mg) as white solid. $^1$H NMR (500 MHz, DMSO-d6) δ 9.21 (d, 1H), 8.53 (m, 1H), 7.74 (m, 1H), 7.28 (m, 1H), 7.17 (m, 2H), 4.49 (m, 1H), 3.64 (s, 3H), 2.26-2.10 (m, 4H), 1.72-1.62 (m, 2H). MS APCI, m/z=385 (M+H).

EXAMPLE 128

4-amino-N-cyclobutyl-8-(2,4-dimethoxyphenyl)-7-fluoro-crinoline-3-carboxamide Using Method A, 4-amino-8-broom-7-fluoro-N-cyclobutyl-crinoline-3-carboxamide (175 mg) and 2,4-dimethoxyphenyl moronic acid (205 mg) were reacted to afford the title compound (133 mg) as white solid. $^1$H NMR (500 MHz, DMSO-d6) δ 9.20 (d, 1H), 8.47 (m, 1H), 7.70 (m, 1H), 7.18 (m, 1H), 6.70 (m, 1H), 6.64 (m, 1H), 4.49 (m, 1H), 3.85 (s, 3H), 3.65 (s, 3H), 2.26-2.10 (m, 4H), 1.72-1.62 (m, 2H). MS APCI, m/z=397 (M+H).

EXAMPLE 130

4-amino-N-cyclobutyl-8-(2,4-dimethoxypyrimidin-5-yl)-7-fluoro-crinoline-3-carboxamide Using Method A, 4-amino-8-broom-7-fluoro-N-cyclobutyl-crinoline-3-carboxamide (175 mg) and 2,4-dimethoxypyrimidin-5-yl moronic acid (207 mg) were reacted to afford the title compound (88 mg) as white solid. $^1$H NMR (500 MHz, DMSO-d6) δ 9.24 (d, 1H), 8.57 (m, 1H), 8.38 (s, 1H), 7.77

(m, 1H), 4.49 (m, 1H), 4.00 (s, 3H), 3.84 (s, 3H), 2.26-2.10 (m, 4H), 1.72-1.62 (m, 2H). MS APCI, m/z=399 (M+H).

EXAMPLE 131

4-amino-N-cyclobutyl-8-(2,6-dimethoxypyridin-3-yl)-7-fluoro-crinoline-3-carboxamide Using Method A, 4-amino-8-broom-7-fluoro-N-cyclobutyl-crinoline-3-carboxamide (175 mg) and 2,6-dimethoxypyridin-3-yl moronic acid (206 mg) were reacted to afford the title compound (122 mg) as white solid. $^1$H NMR (500 MHz, DMSO-d6) δ 9.22 (d, 1H), 8.50 (m, 1H), 7.73 (t, 1H), 7.67 (d, 1H), 6.53 (d, 1H), 4.49 (m, 1H), 3.95 (s, 3H), 3.80 (s, 3H), 2.26-2.10 (m, 4H), 1.72-1.62 (m, 2H). MS APCI, m/z=398 (M+H).

EXAMPLE 139

4-amino-N-cyclobutyl-8-(2-metonym-5-methyl-phenyl)crinoline-3-carboxamide

Using Method A, 4-amino-8-bromo-N-cyclobutyl-cinnoline-3-carboxamide (145 mg) and 2-metonym-5-methyl-phenyl moronic acid (186 mg) were reacted to afford the title compound (94 mg) as white solid. $^1$H NMR (500 MHz, DMSO-d6) δ 9.20 (d, 1H), 8.38 (d, 1H), 7.76-7.66 (m, 2H), 7.20 (m, 1H), 7.07 (m, 1H), 7.00 (m, 1H), 4.50 (m, 1H), 3.58 (s, 3H), 2.29 (s, 3H), 2.26-2.10 (m, 4H), 1.72-1.62 (m, 2H). MS APCI, m/z=363 (M+H).

EXAMPLE 142

4-amino-N-cyclobutyl-8-(4-methoxypyridin-3-yl)crinoline-3-carboxamide

Using Method A, 4-amino-8-bromo-N-cyclobutyl-cinnoline-3-carboxamide (145 mg) and 4-methoxypyridin-3-yl moronic acid (172 mg) were reacted to afford the title compound (31 mg) as white solid. $^1$H NMR (500 MHz, DMSO-d6) δ 9.24 (d, 1H), 8.52 (m, 1H), 8.44 (m, 1H), 8.33 (s, 1H), 7.78 (m, 2H), 7.18 (d, 1H), 4.49 (m, 1H), 3.72 (s, 3H), 2.26-2.10 (m, 4H), 1.72-1.62 (m, 2H). MS APCI, m/z=350 (M+H).

EXAMPLE 147

4-amino-N-cyclobutyl-8-(3,5-dimethylphenyl)crinoline-3-carboxamide

Using Method A, 4-amino-8-bromo-N-cyclobutyl-cinnoline-3-carboxamide (145 mg) and 3,5-dimethylphenyl moronic acid (169 mg) were reacted to afford the title compound (59 mg) as white solid. $^1$H NMR (500 MHz, DMSO-d6) δ 9.31 (d, 1H), 8.38 (d, 1H), 7.78 (m, 2H), 7.28 (s, 2H), 7.06 (s, 1H), 4.52 (m, 1H), 2.35 (s, 6H), 2.26-2.10 (m, 4H), 1.72-1.62 (m, 2H). MS APCI, m/z=347 (M+H).

EXAMPLE 154

4-amino-8-(4-chloroprene)-N-cyclobutyl-crinoline-3-carboxamide

Using Method A, 4-amino-8-bromo-N-cyclobutyl-cinnoline-3-carboxamide (145 mg) and 4-chloroprene moronic acid (176 mg) were reacted to afford the title compound (112 mg) as white solid. $^1$H NMR (500 MHz, DMSO-d6) δ 9.31 (d, 1H), 8.43 (d, 1H), 7.86 (m, 1H), 7.79 (m, 1H), 7.73 (m, 2H), 7.54 (m, 2H), 4.52 (m, 1H), 2.26-2.10 (m, 4H), 1.72-1.62 (m, 2H). MS APCI, m/z=353 (M+H).

EXAMPLE 156

4-amino-N-cyclopropyl-8-(2-fluoro-6-methylpyridin-3-yl)crinoline-3-carboxamide

Using Method A, 4-amino-8-bromo-N-cyclopropyl-cinnoline-3-carboxamide (61 mg, 0.20 mmol) and 2-fluoro-6-methyl pyridine-3-moronic acid (62 mg, 0.36 mmol) were reacted. After purification the title compound (41 mg, 60% yield) was obtained as a white solid. $^1$H NMR (300 MHz, CDCl$_3$) δ 8.52 (bm, 1H), 7.92 (a t, J=7.5 Hz, 2H), 7.85 (m, 1H), 7.75 (a t, J=7.7 Hz, 1H), 7.18 (a d, J=7.5 Hz, 1H), 2.96 (m, 1H), 2.58 (s, 3H), 0.88 (m, 2H), 0.65 (m, 2H). MS APCI, m/z=338, HPLC 2.17 min.

EXAMPLE 157

4-amino-N-cyclopropyl-7-fluoro-8-(5-fluoro-6-methoxypyridin-3-yl)crinoline-3-carboxamide Using Method A, 4-amino-7-fluoro-8-iodo-N-cyclopropyl-cinnoline-3-carboxamide (175 mg, 0.48 mmol) and 5-fluoro-6-methoxypyridine-3-moronic acid (162 mg, 0.96 mmol) were reacted. After purification the title compound (106 mg, 61% yield) was obtained as a white solid. $^1$H NMR (300 MHz, CDCl$_3$) δ 8.48 (bm, 1H), 8.15 (m, 1H), 7.92 (a dd, J=5.2, 9.0 Hz, 1H), 7.65 (a d, J=10.7 Hz, 1H), 7.56 (a t, J=9.0 Hz, 1H), 4.10 (s, 3H), 2.96 (m, 1H), 0.88 (m, 2H), 0.65 (m, 2H). MS APCI, m/z=372, HPLC 2.59 min.

EXAMPLE 158

4-amino-N-cyclopropyl-7-fluoro-8-(2-methoxypyridin-3-yl)crinoline-3-carboxamide

Using Method A, 4-amino-7-fluoro-8-iodo-N-cyclopropyl-cinnoline-3-carboxamide (188 mg, 0.50 mmol) and 2-methoxypyridine-3-moronic acid (155 mg, 1.01 mmol) were reacted. After purification the title compound (110 mg, 62% yield) was obtained as a white solid. $^1$H NMR (300 MHz, CDCl$_3$) δ 8.48 (bm, 1H), 8.29 (ad, J=5.0 Hz, 1H), 7.91 (a dd, J=5.2, 9.2 Hz, 1H), 7.67 (a d, J=7.3 Hz, 1H), 7.56 (a t, J=8.9 Hz, 1H), 7.05 (a dd, J=5.0, 7.3 Hz, 1H), 3.88 (s, 3H), 2.96 (m, 1H), 0.88 (m, 2H), 0.65 (m, 2H). MS APCI, m/z=354, HPLC 2.23 min.

EXAMPLE 159

4-amino-N-cyclopropyl-8-(4-methylpyridin-3-yl)crinoline-3-carboxamide

Using Method A, 4-amino-8-bromo-N-cyclopropyl-cinnoline-3-carboxamide (143 mg, 0.47 mmol) and 4-methyl pyridine-3-moronic acid (128 mg, 0.94 mmol) were reacted. After purification the title compound (96 mg, 64% yield) was obtained as a white solid. $^1$H NMR (300 MHz, CDCl$_3$) δ 8.53 (d, J=5.0 Hz, 1H), 8.50 (bm, 1H), 8.47 (s, 1H), 7.95 (a d, J=8.3 Hz, 1H), 7.77 (t, J=7.7 Hz, 1H), 7.69 (apparent d, J=7.0 Hz, 1H), 2.96 (m, 1H), 2.10 (s, 3H), 0.88 (m, 2H), 0.62 (m, 2H). MS APCI, m/z=320, HPLC 1.55 min.

EXAMPLE 160

4-amino-N-cyclopropyl-7-fluoro-8-(4-methylpyridin-3-yl)crinoline-3-carboxamide Using Method A, 4-amino-7-fluoro-8-iodo-N-cyclopropyl-cinnoline-3-carboxamide (178 mg, 0.48 mmol) and 4-methyl pyridine-3-moronic acid (150 mg, 0.96 mmol) were reacted. After purification the title compound (100 mg, 62% yield) was obtained as a white solid. $^1$H NMR (300 MHz, CDCl$_3$) δ 8,56 (d, J=5.1 Hz, 1H), 8.47 (s, 1H), 8.46 (bm, 1H), 7.99 (a dd, J=5.2, 9.2 Hz, 1H), 7.58 (t, J=8.7 Hz, 1H), 7.30 (d, J=5.0 Hz, 1H), 2.96 (m, 1H), 2.11 (s, 3H), 0.88 (m, 2H), 0.65 (m, 2H). MS APCI, m/z=338, HPLC 1.68 min.

EXAMPLE 161

4-amino-N-cyclopropyl-7-fluoro-8-(2,6-dimethoxypyridin-3-yl)crinoline-3-carboxamide Using Method A, 4-amino-7-fluoro-8-iodo-N-cyclopropyl-cinnoline-3-carboxamide (178 mg, 0.48 mmol) and 2,6-dimethoxypyridine-3-moronic acid (176 mg, 0.96 mmol) were reacted. After purification the title compound (124 mg, 67% yield) was obtained as a white solid. $^1$H NMR (500 MHz, DMSO-d6) δ 9.02 (d, J=4.8 Hz, 1H), 8.51 (m, 1H), 7.73 (t, J=9.1 Hz, 1H), 7.66 (d, J=8.0 Hz, 1H), 6.51 (d, J=8.0 Hz, 1H), 3.94 (s, 3H), 3.78 (s, 3H), 2.93 (m, 1H), 0.70(m, 4H). MS APCI, m/z=384.

EXAMPLE 162

4-amino-N-cyclopropyl-7-fluoro-8-(6-dimethylpyridin-3-yl)crinoline-3-carboxamide Using Method A, 4-amino-7-fluoro-8-iodo-N-cyclopropyl-cinnoline-3-carboxamide (178 mg, 0.48 mmol) and 6-methyl pyridine-3-moronic acid (150 mg, 0.96 mmol) were reacted. After purification the title compound (18 mg, 11% yield) was obtained as a white solid. $^1$H NMR (500 MHz, DMSO-d6) δ 9.05 (d, J=4.8 Hz, 1H), 8.58 (s, 1H), 8.56 (dd, J=5.6, 9.3 Hz, 1H), 7.86 (ad, J=8.1 Hz, 1H), 7.80 (t, J=9.3 Hz, 1H), 7.39 (d, J=8.0 Hz, 1H), 2.96 (m, 1H), 2.56 (s, 3H), 0.70(m, 4H). MS APCI, m/z=338.

EXAMPLE 163

4-amino-N-cyclopropyl-7-fluoro-8-(2,4-dimethoxypyrimidin-5-yl)crinoline-3-carboxamide Using Method A, 4-amino-7-fluoro-8-iodo-N-cyclopropyl-cinnoline-3-carboxamide (178 mg, 0.48 mmol) and 2,4-dimethoxypyrimidin-5-moronic acid (176 mg, 0.96 mmol) were reacted. After purification the title compound (73 mg, 39% yield) was obtained as a white solid. $^1$H NMR (500 MHz, DMSO-d6) δ 9.04 (d, J=4.9 Hz, 1H), 8.57 (dd, J=5.6, 9.3 Hz, 1H), 8.37 (s, 1H) 7.77 (t, J=9.1 Hz, 1H), 3.99 (s, 3H), 3.84 (s, 3H), 2.93 (m, 1H), 0.70(m, 4H). MS APCI, m/z=385.

EXAMPLE 164

4-amino-N-cyclopropyl-7-fluoro-8-(2,5-dimethoxyphenyl)crinoline-3-carboxamide Using Method A, 4-amino-7-fluoro-8-iodo-N-cyclopropyl-cinnoline-3-carboxamide (178 mg, 0.48 mmol) and 2,5-dimethoxyphenylboronic acid (174 mg, 0.96 mmol) were reacted. After purification the title compound (142 mg, 77% yield) was obtained as a white solid. $^1$H NMR (500 MHz, DMSO-d6) δ 8.99 (d, J=4.8 Hz, 1H), 8.51 (a dd, J=5.5, 9.3 Hz, 1H), 7.72 (t, J=9.0 Hz, 1H), 7.06 (a d, J=9.0 Hz, 1H), 7.00 (m, 1H), 6.86 (a d, J=3.0 Hz, 1 H), 3.72 (s, 3H), 3.58 (s, 3H), 2.93 (m, 1H), 0.68 (m, 4H). MS APCI, m/z=383.

EXAMPLE 165

4-amino-N-cyclopropyl-7-fluoro-8-(5-fluoro-2-methoxyphenyl)crinoline-3-carboxamide Using Method A, 4-amino-7-fluoro-8-iodo-N-cyclopropyl-cinnoline-3-carboxamide (178 mg, 0.48 mmol) and 2,5-dimethoxyphenylboronic acid (162 mg, 0.96 mmol) were reacted. After purification the title compound (150 mg, 84% yield) was obtained as a white solid. $^1$H NMR (500 MHz, DMSO-d6) δ 9.02 (d, J=4.8 Hz, 1H), 8.54 (a dd, J=5.5, 9.3 Hz, 1H), 7.74 (t, J=9.1 Hz, 1H), 7.27 (at, J=8.7 Hz, 1H), 7.15 (m, 2H), 3.64 (s, 3H), 2.95 (m, 1H), 0.67 (m, 4H). MS APCI, m/z=371.

EXAMPLE 166

4-amino-N-cyclopropyl-7-fluoro-8-(2-fluoro-6-methoxyphenyl)crinoline-3-carboxamide Using Method G, 4-amino-7-fluoro-8-iodo-N-cyclopropyl-cinnoline-3-carboxamide (372 mg, 1.00 mmol) and 2-fluoro-6-methoxyphenylboronic acid (1.40 g, 8.24 mmol) were reacted. After purification the title compound (117 mg, 33% yield) was obtained as a white solid. $^1$H NMR (300 MHz, CDCl$_3$) δ 8.50 (bm, 1H), 7.94 (dd, J=5.2, 9.2 Hz, 1H), 7.53 (a t, J=8.7 Hz, 1H), 7.40 (apparent q, J=7.8 Hz, 1H), 6.86 (m, 2H), 3.72 (s, 3H), 2.96 (m, 1H), 0.88 (m, 2H), 0.62 (m, 2H). MS APCI, m/z=371.

EXAMPLE 167

4-amino-N-cyclopropyl-7-fluoro-8-(2-methoxy-5-methylphenyl)crinoline-3-carboxamide Using Method A, 4-amino-7-fluoro-8-iodo-N-cyclopropyl-cinnoline-3-carboxamide (178 mg, 0.48 mmol) and 2-metonym-5-methylphenylboronic acid (160 mg, 0.96 mmol) were reacted. After purification the title compound (134 mg, 76% yield) was obtained as a white solid. $^1$H NMR (500 MHz, DMSO-d6) δ 8.98 (d, J=4.8 Hz, 1H), 8.50 (a dd, J=5.5, 9.3 Hz, 1H), 7.71 (t, J=9.1 Hz, 1H), 7.23 (m, 1H), 7.106 (s, 1H), 7.02 (d, J=8.4 Hz, 1H), 3.60 (s, 3H), 2.95 (m, 1H), 2.28 (s, 3H), 0.67 (m, 4H). MS APCI, m/z=367.

EXAMPLE 168

4-amino-N-cyclopropyl-7-fluoro-8-(2,4-dimethoxyphenyl)crinoline-3-carboxamide Using Method A, 4-amino-7-fluoro-8-iodo-N-cyclopropyl-cinnoline-3-carboxamide (178 mg, 0.48 mmol) and 2,4-dimethoxyphenylboronic acid (175 mg, 0.96 mmol) were reacted. After purification the title compound (110 mg, 60% yield) was obtained as a white solid. $^1$H NMR (500 MHz, DMSO-d6) δ 8.98 (d, J=4.8 Hz, 1H), 8.47 (a dd, J=5.6, 9.3 Hz, 1H), 7.70 (t, J=9.0 Hz, 1H), 7.17 (d, J=8.0 Hz, 1H), 6.70 (s, 1H), 6.63 (a d, J=8.3 Hz, 1H), 3.84 (s, 3H), 3.64 (s, 3H), 2.95 (m, 1H), 0.67 (m, 4H). MS APCI, m/z=383.

EXAMPLE 174

4-amino-N-cyclopropyl-8-(5-fluoro-2-methoxyphenyl)crinoline-3-carboxamide

Using Method A, 4-amino-8-bromo-N-cyclopropyl-cinnoline-3-carboxamide (143 mg, 0.47 mmol) and 5-fluoro-2-methoxyphenylboronic acid (158 mg, 0.94 mmol) were reacted. After purification the title compound (125 mg, 76% yield) was obtained as a white solid. $^1$H NMR (300 MHz, CDCl$_3$) δ 8.54 (bm, 1H), 7.87 (a dd, J=3.1, 6.6 Hz, 1H), 7.73 (m, 2H), 7.10 (m, 2H), 6.95 (m, 1H), 3.66 (s, 3H), 2.96 (m, 1H), 0.86 (m, 2H), 0.64 (m, 2H). MS APCI, m/z=353.

EXAMPLE 175

4-amino-N-cyclopropyl-8-(4-methoxypyridin-3-yl)crinoline-3-carboxamide

Using Method A, 4-amino-8-bromo-N-cyclopropyl-cinnoline-3-carboxamide (143 mg, 0.47 mmol) and 4-methoxypyridine-3-moronic acid (640 mg, 4.20 mmol) were reacted. After purification the title compound (52 mg, 33% yield) was obtained as a white solid. $^1$H NMR (500 MHz, CDCl$_3$) δ 8.58 (d, J=5.8 Hz, 1H), 8.57 (bm, 1H), 8.44 (s, 1H), 7.91 (m, 1H), 7.74 (m, 2H), 6.94 (d, J=5.8 Hz, 1H), 3.77 (s, 3H), 2.96 (m, 1H), 0.86 (m, 2H), 0.64 (m, 2H). MS APCI, m/z=336.

EXAMPLE 176

4-amino-N-cyclopropyl-8-(2-methoxypyridin-3-yl)crinoline-3-carboxamide

Using Method A, 4-amino-8-bromo-N-cyclopropyl-cinnoline-3-carboxamide (143 mg, 0.47 mmol) and 2-methoxypyridine-3-moronic acid (142 mg, 0.94 mmol) were reacted. After purification the title compound (118 mg, 76% yield) was obtained as a white solid. $^1$H NMR (500 MHz, DMSO-d6) δ 9.04(d, J=4.9 Hz, 1H), 8.43 (m, 1H), 8.24 (d, J=5.0 Hz, 1H), 7.77 (m, 2H), 7.71 (a d, J=7.2 Hz, 1H), 7.71 (a dd, J=5.1, 7.2 Hz, 1H), 3.73 (s, 3H), 2.95 (m, 1H), 0.67 (m, 4H). MS APCI, m/z=336.

EXAMPLE 180

4-amino-N-cyclopropyl-8-(5-fluoro-6-methoxypyridin-3-yl)crinoline-3-carboxamide

Using Method A, 4-amino-8-bromo-N-cyclopropyl-cinnoline-3-carboxamide (143 mg, 0.47 mmol) and 5-fluoro-6-methoxypyridine-3-moronic acid (159 mg, 0.94 mmol) were reacted. After purification the title compound (146 mg, 88% yield) was obtained as a white solid. $^1$H NMR (500 MHz, DMSO-d6) δ 9.13(d, J=4.9 Hz, 1H), 8.45 (d, J=7.4 Hz, 1H), 8.29 (s, 1H), 8.11 (a d, J=13.8 Hz, 1H), 7.95 (a d, J=7.2 Hz, 1H), 7.81 (a t, J=7.8 Hz, 1H), 4.03 (s, 3H), 2.95 (m, 1H), 0.67 (m, 4H). MS APCI, m/z=354.

EXAMPLE 181

4-amino-N-cyclopropyl-8-(2-fluoro-3-methoxyphenyl)crinoline-3-carboxamide

Using Method A, 4-amino-8-bromo-N-cyclopropyl-cinnoline-3-carboxamide (143 mg, 0.47 mmol) and 2-fluoro-3-methoxyphenylboronic acid (158 mg, 0.94 mmol) were reacted. After purification the title compound (128 mg, 78% yield) was obtained as a white solid. $^1$H NMR (500 MHz, DMSO-d6) δ 9.04(d, J=4.9 Hz, 1H), 8.48 (dd, J=2.6, 7.2 Hz, 1H), 7.79 (m, 2H), 7.23 (m, 2H), 7.02 (m, 1H), 3.90 (s, 3H), 2.95 (m, 1H), 0.67 (m, 4H). MS APCI, m/z=353.

EXAMPLE 182

4-amino-N-cyclopropyl-8-(6-methylpyridin-3-yl)crinoline-3-carboxamide

Using Method A, 4-amino-8-bromo-N-cyclopropyl-cinnoline-3-carboxamide (143 mg, 0.47 mmol) and 6-methyl pyridine-3-moronic acid (128 mg, 0.94 mmol) were reacted. After purification the title compound (119 mg, 80% yield) was obtained as a white solid. MS APCI, m/z=320.

EXAMPLE 185

4-amino-N-cyclopropyl-7-fluoro-8-(2-fluoro-3-methoxyphenyl)crinoline-3-carboxamide Using Method A, 4-amino-7-fluoro-8-iodo-N-cyclopropyl-cinnoline-3-carboxamide (178 mg, 0.48 mmol) and 2-fluoro-3-methoxyphenylboronic acid (162 mg, 0.96 mmol) were reacted. After purification the title compound (100 mg, 56% yield) was obtained as a white solid. $^1$H NMR (500 MHz, DMSO-d6) δ 9.04(d, J=4.8 Hz, 1H), 8.59 (m, 1H), 7.26 (m, 2H), 7.02 (m,1H), 3.90 (s, 3H), 2.93 (m, 1H), 0.69 (m, 4H). MS APCI, m/z=371.

Method AA

Preparation of *Xenopus* oocytes

*Xenopus laevis* frogs (*Xenopus* I, Kalamazoo, MI) were anesthetized using 0.15% trichina. Surgically removed ovarian lobes were teased out in OR2 solution (82 NaCl, 2.5 KCl, 5 HEPES, 1.5 NaH$_2$PO$_4$, 1 MgCl$_2$, 0.1 EDTA, in mM, pH 7.4). The acolytes were deflocculated by incubation in 25 mL OR2 containing 0.2% collagens 1A (SIGMA) two times for about 60 minutes on a platform shaker and stored in Leibovitz's L-15 medium. Acolytes were injected the following day in 0.5× Leibovitz's L-15 medium containing 50 mg/ml gentamycin, 10 units/ml penicillin, and 10 mg/ml streptomycin.

Method BB

Preparation and Injection of cRNA

Capped cRNAs from the linear zed vectors containing human $α_1$, $β_2$ and $γ_2$ subunits of the GABAA receptor genes were mixed in ratio of 1:1:30. Acolytes were injected with 25-50 nL of mixed RNA with an appx molar ratio for $α_1$, $β_2$ and $γ_2$ as 1:1:10. Acolyte recordings were done 2-10 days after injection. The same methods apply to subtypes derived from $α_2β_3γ_2$, $α_3β_3γ_2$, and $α_5β_3γ_2$, except for 1:1:1 ratio was used for α, β, and γ subunits.

Method CC

Two-Electrode Voltage-Clamping Measurements

All measurements were done in a medium containing ND-96 (96 NaCl, 2 KCl, 1.8 CaCl$_2$.2H$_2$O, 1 MgCl$_2$.6H$_2$O, 5 HEPES, in mM, pH 7.5). Two-electrode voltage-clamp recording was carried out using Opus press amplifier (Axon Instruments, Foster City, Calif.), which allows simultaneous recording from 8 acolytes. Acolytes were impaled with two electrodes of 1-2 MΩ tip resistance when filled with 3M KCl. Recordings were begun when membrane potential became stable at potentials negative to −50-−60 mV. Membrane potential was held at −60 mV. Typical leak currents were between 0-40 nA, and rarely if a few cells did have a relatively high leak (>100 nA) they were not used. For the determination of the GABA EC10, a series of 30 s pulses with increasing concentrations of GABA were applied to the cells every 5 minutes. After calculating EC10 for GABA for each acolyte, a series of 30 s GABA pulses were applied at 5 minutes interval, with increasing doses of the modulator. The concentration of GABA corresponded to the EC10 value calculated for each acolyte. The modulator pulses started 30 s before the GABA pulse so as to allow preoccupation with the modulator. A set of 3 pulses with just GABA without modulator was given prior to the modulator-containing pulses to define the baseline GABA response. Two acolytes per each experiment were dedicated to observe the effect of diazepam on GABA response to ensure the presence of γ subunit in the GABAA pantomimic complex, which imparts diazepam sensitivity to the complex.

Method DD

Calculation of Current Amplitude and Curve Fitting

Current amplitude (i) was measured from baseline to peak using Clamp fit (Axon Inst., Foster City, Calif.). Potentiating was calculated as percent change from the baseline GABA current flux $100 \times (i_{mod}/i_{control}) - 1$ where $i_{mod}$=current mediated by modulator+GABA and $i_{control}$=current mediated by GABA alone. A value of 100% potentiating means that modulator has caused the control current to double. Similarly, a value of −50% potentiating means the presence of modulator caused a 50% decrease in the control current. Various other data shown here were fitted and plotted using Graph Pad Prism (Graph Pad Software, Inc. San Diego, Calif.). The percentage potentiating was converted to relative potentiating by dividing it with percentage potentiating value obtained from the same assay with diazepam as a control.

Method EE

GABAA1 Binding Method

Reagents

Assay and Wash Buffer: 50 mM Tris-Citrate, 200 mM NaCl, pH 7.8

Compounds at 10 mM in DMSO: Put 75 µl in column 1 of compound plate.

Flumazenil, 10 mM (for NSB)

Membranes (α1, β2, γ2 receptor subunits transected into Sf9 cells and harvested; prepared by Cell Trends, stored at −80° C.) Sonic ate thawed membranes for about 5-10 seconds at setting 3 on Brinkman solicitor, then dilute membranes 1:71 in assay buffer (working conc.=100 ug/ml protein). Keep on ice.

[$^3$H]-Flunitrazepam (Cat #NET567): Prepare 10× stock=30 nM, [F] in assay=~3 nM Assay (See Below for Automation Programs.)

1. On Plate Mate, prepare 1:3 serial dilutions (30 µl+60 µl) in DMSO for final assay concentrations of 10 µM to 170 pM (Automation Programs 1 and 2). Add 5 ul of 30 uM flumazenil to wells 12 D-E for 50% control wells.

2. Spot 2 µl of compound dilutions into dry plate (Automation Program 3). Manually spot 2 µl 10 mM flumazenil into wells 12 F-H for nonspecific control.

3. Make 1:100 dilution in assay buffer (2 µl into 200 µl) and dispense 25 µl compound into assay plates (Automation Program 4).

4. Dispense 200 µl membranes into assay plate (Automation Program 5).

5. Add 25 µl [$^3$H]-Flunitrazepam (Automation Program 6). Incubate for 1 hr at 4° C.

6. Collect membranes on a cell harvester onto GF/B filter plates (pre-wet with dH$_2$O and wash 5×400 µl/well, with cold assay buffer. (First 3 washes are considered hot; last two are cold.)

7. Dry plates for 2-3 hours at RT.

8. Add 40 µl Microsecond 40/well (Automation Program 7); seal plates. Count on a Top Count.

Automation Programs

1. Plate Mate add 60 ul DMSO for dilutions 96 w: 96/300 ul head, 5516 tips in columns 2-12, compound plate in left stacker A, DMSO reservoir on stage 2

2. Plate Mate 11 pt-dilute one-third GABAA: 96/300 ul head, 5516 tips in column 1 of serial dilution magazine, compound plate in left stacker A 3. Plate Mate 2 ul addition of cmpd dry new wash: 96/30 ul head, 5506 tips, compound plate in left stacker A, dilution plate in right stacker A, 100% DMSO in reservoir on stage 2, must change to fresh DMSO every 4-6 plates.

4. Plate Mate tip chg mix and dips 25 ul to assay plate 96 w: 96/300 ul head, 5516 tips, dilution plate in left stacker A, assay plates in right stacker A, auto fill assay buffer reservoir on stage 2, need to change tips after every plate.

5. Plate Mate add 200 ul membranes 96 w: 96/300 ul head, 5516 tips, assay plates in left stacker A, membrane reservoir on stage 2.

6. Rapid Plate add 25 ul hot (number of plates): 100 ul (yellow box) tips in position 1, hot reservoir in position 2, plates beginning in position 3

7. Rapid Plate add microsecond 40 ul (number of plates): 200 ul (burgundy box) tips in position 1, Microsecond 40 reservoir in position 2, plates beginning in position 3.

Data Analysis

Data is analyzed by calculating percent of control, IC50, and Kid in an Lift template. The following formula is used in the templates:

$$Ki = \frac{IC50}{1 + [\text{ligand}]/K_D}$$

Method FF

GABAA2 Binding Method

Reagents

Assay and Wash Buffer: 50 mM Tris-Citrate, 200 mM NaCl, pH 7.8

Compounds at 10 mM in DMSO: Put 75 µl in column 1 of compound plate.

Flumazenil, 10 mM (for NSB)

Membranes (α2, β3, γ2 receptor subunits transected into Sf9 cells and harvested; prepared by Paragon at 12.5 mg/ml, stored at −80° C.) Sonic ate thawed membranes for about 5-10 seconds at setting 3 on Brinkman solicitor, then dilute membranes 1:50 in assay buffer (working conc.=250 ug/ml protein). Keep on ice.

[$^3$H]-Flunitrazepam (Cat #NET567): Prepare 10× stock=20 nM, [F} in assay=~2 nM Assay (See Below for Automation Programs.)

1. On Plate Mate, prepare 1:3 serial dilutions (30 µl+60 µl) in DMSO for final assay concentrations of 10 µM to 170 pM (Automation Programs 1 and 2). Add 5 ul of 30 uM flumazenil to wells 12 D-E for 50% control wells.

2. Spot 2 μl of compound dilutions into dry plate (Automation Program 3). Manually spot 2 μl 10 mM flumazenil into wells 12 F-H for nonspecific control.

3. Make 1:100 dilution in assay buffer (2 μl into 200 μl) and dispense 25 μl compound into assay plates (Automation Program 4).

4. Dispense 200 μl membranes into assay plate (Automation Program 5).

5. Add 25 μl [$^3$H]-Flunitrazepam (Automation Program 6). Incubate for 1 hr at 4° C.

6. Collect membranes on a cell harvester onto GF/B filter plates (pre-wet with dH$_2$O and wash 5×400 μl/well, with cold assay buffer. (First 3 washes are considered hot; last two are cold.)

7. Dry plates for 2-3 hours at RT.

8. Add 40 μl Microsecond 40/well (Automation Program 7); seal plates. Count on a Top Count.

Automation Programs

1. Plate Mate add 60 ul DMSO for dilutions 96 w: 96/300 ul head, 5516 tips in columns 2-12, compound plate in left stacker A, DMSO reservoir on stage 2.

2. Plate Mate 11 pt-dilute one-third GABAA: 96/300 ul head, 5516 tips in column 1 of serial dilution magazine, compound plate in left stacker A.

3. Plate Mate 2 ul addition of cmpd dry new wash: 96/30 ul head, 5506 tips, compound plate in left stacker A, dilution plate in right stacker A, 100% DMSO in reservoir on stage 2, must change to fresh DMSO every 4-6 plates.

4. Plate Mate tip chg mix and dips 25 ul to assay plate 96 w: 96/300 ul head, 5516 tips, dilution plate in left stacker A, assay plates in right stacker A, auto fill assay buffer reservoir on stage 2, need to change tips after every plate.

5. Plate Mate add 200 ul membranes 96 w: 96/300 ul head, 5516 tips, assay plates in left stacker A, membrane reservoir on stage 2.

6. Rapid Plate add 25 ul hot (number of plates): 100 μl (yellow box) tips in position 1, hot reservoir in position 2, plates beginning in position 3.

7. Rapid Plate add microsecond 40 ul (number of plates): 200 μl (burgundy box) tips in position 1, Microsecond 40 reservoir in position 2, plates beginning in position 3.

Data Analysis

Data is analyzed by calculating percent of control, IC50, and Kid in an Lift template. The following formula is used in the templates:

$$Ki = \frac{IC50}{1 + [\text{ligand}]/K_D}$$

Method GG

GABAA3 Binding Method

Reagents

Assay and Wash Buffer: 50 mM Tris-Citrate, 200 mM NaCl, pH 7.8

Compounds at 10 mM in DMSO: Put 75 ul in column 1 of compound plate.

Flumazenil, 10 mM (for NSB)

Membranes (α3, β3, γ2 receptor subunits transected into Sf9 cells and harvested; prepared by Cell Trends, stored at −80° C.) Sonic ate thawed membranes for about 5-10 seconds at setting 3 on Brinkman solicitor, then dilute membranes 1:125 to make a solution of 200 ug/mL in assay buffer. Keep on ice.

[3H]-Flunitrazepam (Cat #NET567): Prepare 10× stock=30 nM, [F} in assay=~3 nM

Assay (See Below for Automation Programs.)

1. On Plate Mate, prepare 1:3 serial dilutions (30 μl+60 μl) in DMSO for final assay concentrations of 10 μM to 170 μM (Automation Programs 1 and 2). Add 5 μl of 30 μM flumazenil to wells 12 D-E for 50% control wells.

2. Spot 2 μl of compound dilutions into dry plate (Automation Program 3). Manually spot 2 μl 10 mM flumazenil into wells 12 F-H for nonspecific control.

3. Make 1:100 dilution in assay buffer (2 μl into 200 μl) and dispense 25 μl compound into assay plates (Automation Program 4).

4. Dispense 200 μl membranes into assay plate (Automation Program 5).

5. Add 25 μl [$^3$H]-Flunitrazepam (Automation Program 6). Incubate for 1 hr at 4° C.

6. Collect membranes on a cell harvester onto GF/B filter plates (pre-wet with dH$_2$O and wash 5×400 μl/well, with cold assay buffer. (First 3 washes are considered hot; last two are cold.)

7. Dry plates for 2-3 hours at RT.

8. Add 40 μl Microsecond 40/well (Automation Program 7); seal plates. Count on a Top Count.

Automation Programs

1. Plate Mate add 60 μl DMSO for dilutions 96 w: 96/300 μl head, 5516 tips in columns 2-12, compound plate in left stacker A, DMSO reservoir on stage 2.

2. Plate Mate 11 pt-dilute one-third GABAA: 96/300 μl head, 5516 tips in column 1 of serial dilution magazine, compound plate in left stacker A.

3. Plate Mate 2 μl addition of cmpd dry new wash: 96/30 μl head, 5506 tips, compound plate in left stacker A, dilution plate in right stacker A, 100% DMSO in reservoir on stage 2, must change to fresh DMSO every 4-6 plates.

4. Plate Mate tip chg mix and dips 25 μl to assay plate 96 w: 96/300 μl head, 5516 tips, dilution plate in left stacker A, assay plates in right stacker A, auto fill assay buffer reservoir on stage 2, need to change tips after every plate.

5. Plate Mate add 200 μl membranes 96 w: 96/300 μl head, 5516 tips, assay plates in left stacker A, membrane reservoir on stage 2.

6. Rapid Plate add 25 μl hot (number of plates): 100 μl (yellow box) tips in position 1, hot reservoir in position 2, plates beginning in position 3.

7. Rapid Plate add microsecond 40 ul (number of plates): 200 μl (burgundy box) tips in position 1, Microsecond 40 reservoir in position 2, plates beginning in position 3.

Data Analysis

Data is analyzed by calculating percent of control, IC50, and Kid in an Lift template. The following formula is used in the templates:

$$Ki = \frac{IC50}{1 + [\text{ligand}]/K_D}$$

Method HH

GABAA5 Binding Method

Reagents

Assay and Wash Buffer: 50 mM Tris-Citrate, 200 mM NaCl, pH 7.8

Compounds at 10 mM in DMSO: Put 75 μl in column 1 of compound plate.

Flumazenil, 10 mM (for NSB)

Membranes (α5, β3, γ2 receptor subunits transected into Sf9 cells and harvested; prepared by Cell Trends, stored at −80° C.) Sonicate thawed membranes for about 5-10 seconds at setting 3 on Brinkman solicitor, then dilute membranes 1:31 in assay buffer (working conc.=500 ug/ml protein). Keep on ice.

[$^3$H]-Flunitrazepam (Cat #NET567): Prepare 10× stock=20 nM, [F] in assay=~2 nM Assay (See Below for Automation Programs.)

1. On Plate Mate, prepare 1:3 serial dilutions (30 μl+60 μl) in DMSO for final assay concentrations of 10 μM to 170 μM (Automation Programs 1 and 2). Add 5 ul of 30 uM flumazenil to wells 12 D-E for 50% control wells.

2. Spot 2 μl of compound dilutions into dry plate (Automation Program 3). Manually spot 2 μl 10 mM flumazenil into wells 12 F-H for nonspecific control.

3. Make 1:100 dilution in assay buffer (2 μl into 200 μl) and dispense 25 μl compound into assay plates (Automation Program 4).

4. Dispense 200 μl membranes into assay plate (Automation Program 5).

5. Add 25 μl [$^3$H]-Flunitrazepam (Automation Program 6). Incubate for 1 hr at 4° C.

6. Collect membranes on a cell harvester onto GF/B filter plates (pre-wet with dH$_2$O and wash 5×400 μl/well, with cold assay buffer. (First 3 washes are considered hot; last two are cold.)

7. Dry plates for 2-3 hours at RT.

8. Add 40 μl Microsecond 40/well (Automation Program 7); seal plates. Count on a Top Count.

Automation Programs

1. Plate Mate add 60 ul DMSO for dilutions 96 w: 96/300 ul head, 5516 tips in columns 2-12, compound plate in left stacker A, DMSO reservoir on stage 2.

2. Plate Mate 11 pt-dilute one-third GABAA: 96/300 ul head, 5516 tips in column 1 of serial dilution magazine, compound plate in left stacker A.

3. Plate Mate 2 ul addition of cmpd dry new wash: 96/30 ul head, 5506 tips, compound plate in left stacker A, dilution plate in right stacker A, 100% DMSO in reservoir on stage 2, must change to fresh DMSO every 4-6 plates.

4. Plate Mate tip chg mix and dips 25 ul to assay plate 96 w: 96/300 ul head, 5516 tips, dilution plate in left stacker A, assay plates in right stacker A, auto fill assay buffer reservoir on stage 2, need to change tips after every plate.

5. Plate Mate add 200 ul membranes 96w: 96/300 ul head, 5516 tips, assay plates 5 in left stacker A, membrane reservoir on stage 2.

6. Rapid Plate add 25 ul hot (number of plates): 100 μl (yellow box) tips in position 1, hot reservoir in position 2, plates beginning in position 3.

7. Rapid Plate add microsecond 40 ul (number of plates): 200 μl (burgundy box) tips in position 1, Microsecond 40 reservoir in position 2, plates beginning in position 3.

Data Analysis

Data is analyzed by calculating percent of control, IC50, and Kid in an Lift template. The following formula is used in the templates:

$$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| 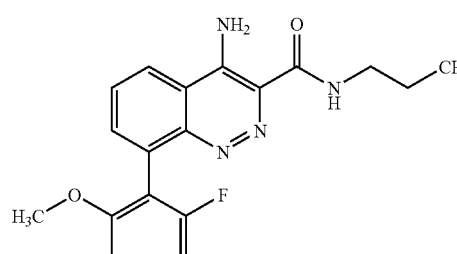<br>ISOMER 2 | 1.44E−10 | −0.015 | 0.15 |
| 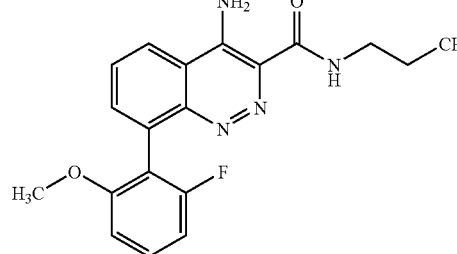 | 2.66E−10 | −0.008 | 0.18 |

-continued
$$Ki = \frac{IC50}{1 + [ligand]/K_D}$$
| Compound | GABAA2 Binding Ki (M) | Relative Potentiation for GABAA1 | Relative Potentiation for GABAA2 |
|---|---|---|---|
| 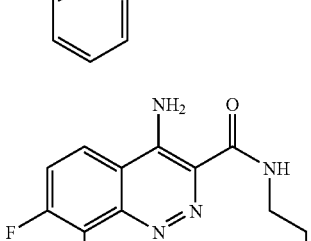 | 3.01E−10 | | |
| 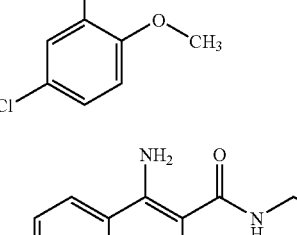 | 3.27E−10 | 0.25 | |
| 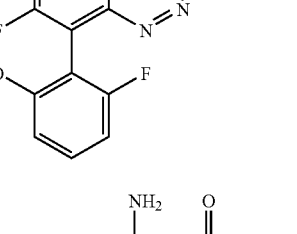 | 3.41E−10 | | |
| 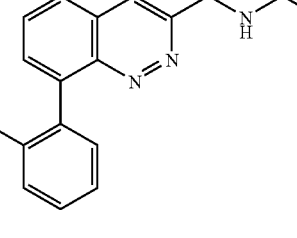 | 3.64E−10 | 0.12 | 0.063 |
| 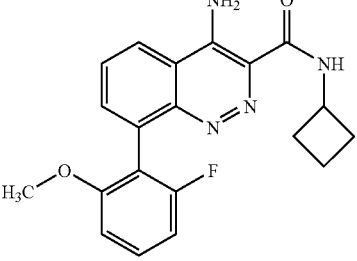 | 3.87E−10 | 0.0017 | 0.12 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| (4-amino-7-fluoro-8-(2,4-dimethoxyphenyl)cinnoline-3-carboxylic acid propylamide) | 4.03E−10 | 0.063 | 0.13 |
| (4-amino-7-chloro-8-(4-methoxypyridin-3-yl)cinnoline-3-carboxylic acid propylamide) | 5.05E−10 | 0.15 | 0.14 |
| (4-amino-7-fluoro-8-(3,5-dimethoxyphenyl)cinnoline-3-carboxylic acid propylamide) | 5.52E−10 | 0.38 | |
| (4-amino-8-(2,6-difluorophenyl)cinnoline-3-carboxylic acid propylamide) | 5.58E−10 | −0.11 | 0.17 |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| (4-amino-8-(2,6-dimethoxypyridin-3-yl)cinnoline-3-carboxylic acid N-propylamide) | 5.60E−10 | 0.17 | 0.25 |
| (4-amino-7-fluoro-8-(4-fluoro-2-methoxyphenyl)cinnoline-3-carboxylic acid N-propylamide) | 5.65E−10 | −0.028 | 0.18 |
| (4-amino-7-fluoro-8-(2,3,4-trimethoxyphenyl)cinnoline-3-carboxylic acid N-propylamide) | 6.00E−10 | 0.51 | |
| (4-amino-7-fluoro-8-(2-fluoro-4-methoxyphenyl)cinnoline-3-carboxylic acid N-propylamide) | 6.13E−10 | 0.053 | 0.18 |

-continued
$$Ki = \frac{IC50}{1 + [\text{ligand}]/K_D}$$
| Compound | GABAA2 Binding Ki (M) | Relative Potentiation for GABAA1 | Relative Potentiation for GABAA2 |
|---|---|---|---|
| 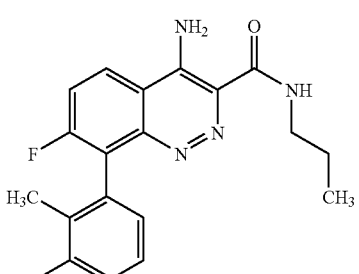 | 6.15E−10 | 0.11 | 0.13 |
| 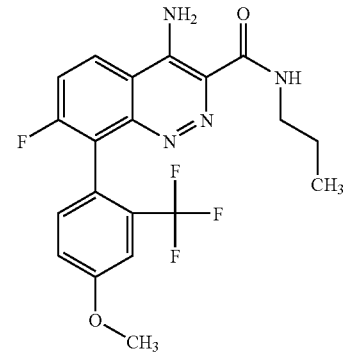 | 6.24E−10 | 0.28 | |
| 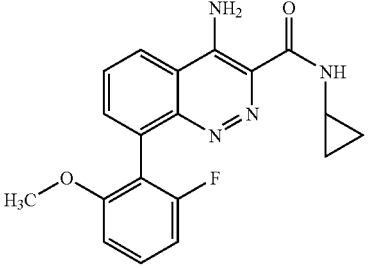 | 6.98E−10 | −0.048 | 0.16 |
| 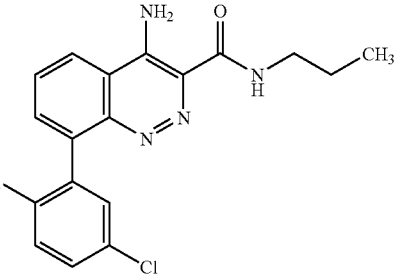 | 7.10E−10 | 0.12 | 0.21 |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| (structure) | 7.35E−10 | 0.032 | 0.12 |
| (structure) | 8.52E−10 | 0.095 | 0.37 |
| (structure) | 9.18E−10 | 0.12 | 0.39 |
| (structure) | 9.37E−10 | 0.23 | 0.37 |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| (4-amino-7-fluoro-8-(2-fluoro-3-methoxyphenyl)cinnoline-3-carboxamide N-propyl) | 9.41E−10 | 0.05 | 0.23 |
| (4-amino-7-fluoro-8-(5-fluoro-2-methoxyphenyl)cinnoline-3-carboxamide N-propyl) | 9.80E−10 | 0.085 | 0.22 |
| (4-amino-8-(2,5-difluorophenyl)cinnoline-3-carboxamide N-propyl) | 9.96E−10 | −0.078 | 0.29 |
| (4-amino-7-fluoro-8-phenylcinnoline-3-carboxamide N-propyl) | 1.00E−09 | −0.093 | 0.02 |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| (structure: 4-amino-8-(2,6-dimethoxypyridin-3-yl)-cinnoline-3-carboxylic acid cyclopropylamide) | 1.00E−09 | | |
| (structure: 4-amino-7-fluoro-8-(2-ethoxy-4-fluorophenyl)-cinnoline-3-carboxylic acid propylamide) | 1.03E−09 | 0.27 | |
| (structure: 4-amino-8-(2-methoxy-5-chlorophenyl)-cinnoline-3-carboxylic acid propylamide) | 1.11E−09 | 0.38 | 0.4 |
| (structure: 4-amino-8-(2-fluoropyridin-3-yl)-cinnoline-3-carboxylic acid propylamide) | 1.13E−09 | −0.083 | 0.17 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| (4-amino-8-(3-cyanophenyl)cinnoline-3-carboxamide, N-propyl) | 1.18E−09 | 0.088 | 0.31 |
| (4-amino-7-fluoro-8-(2-chloro-5-methoxyphenyl)cinnoline-3-carboxamide, N-propyl) | 1.25E−09 | 0.14 | 0.19 |
| (4-amino-7-fluoro-8-(2,5-dimethylphenyl)cinnoline-3-carboxamide, N-propyl) | 1.31E−09 | 0.21 | 0.28 |
| (4-amino-7-fluoro-8-(2,5-dichlorophenyl)cinnoline-3-carboxamide, N-propyl) | 1.34E−09 | 0.21 | |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
| --- | --- | --- | --- |
| (4-amino-8-(2-chloro-5-(trifluoromethyl)phenyl)cinnoline-3-carboxamide, N-propyl) | 1.36E−09 | 0.47 | 0.59 |
| (4-amino-8-(2,5-difluoro-4-methoxyphenyl)cinnoline-3-carboxamide, N-propyl) | 1.49E−09 | 0.016 | 0.21 |
| (4-amino-7-fluoro-8-(2,5-dimethoxyphenyl)cinnoline-3-carboxamide, N-propyl) | 1.62E−09 | 0.014 | 0.23 |
| (4-amino-8-(pyridin-4-yl)cinnoline-3-carboxamide, N-propyl) | 1.67E−09 | −0.038 | 0.1 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| (4-amino-8-(2-fluoro-6-methylpyridin-3-yl)cinnoline-3-carboxylic acid propylamide) | 1.67E−09 | 0.053 | 0.27 |
| (4-amino-8-(4-methylpyridin-3-yl)cinnoline-3-carboxylic acid propylamide) | 1.68E−09 | 0.083 | 0.11 |
| (4-amino-8-(2,4-difluorophenyl)cinnoline-3-carboxylic acid propylamide) | 1.72E−09 | −0.088 | 0.12 |
| (4-amino-8-(2-fluoro-5-methoxyphenyl)cinnoline-3-carboxylic acid propylamide) | 1.73E−09 | 0.26 | 0.32 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| (4-amino-8-(2,3-dichlorophenyl)cinnoline-3-carboxamide, N-propyl) | 1.82E−09 | 0.067 | 0.053 |
| (4-amino-8-(4-methoxypyridin-3-yl)cinnoline-3-carboxamide, N-butyl) | 1.84E−09 | 0.2 | 0.52 |
| (4-amino-8-(2-methylphenyl)cinnoline-3-carboxamide, N-propyl) | 1.93E−09 | 0.06 | 0.033 |
| (4-amino-8-(2,4-dimethoxyphenyl)cinnoline-3-carboxamide, N-cyclopropyl) | 2.07E−09 | | |

-continued
$$Ki = \frac{IC50}{1 + [\text{ligand}]/K_D}$$
| Compound | GABAA2 Binding Ki (M) | Relative Potentiation for GABAA1 | Relative Potentiation for GABAA2 |
|---|---|---|---|
| 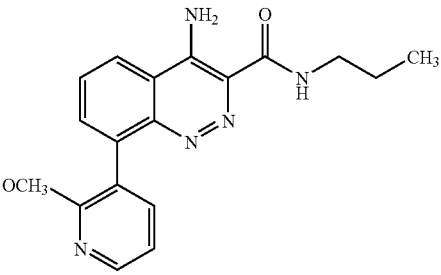 | 2.10E−09 | 0.2 | 0.097 |
| 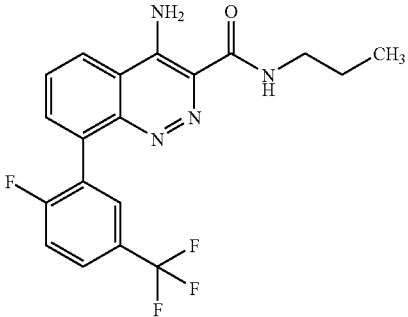 | 2.17E−09 | 0.41 | 0.59 |
| 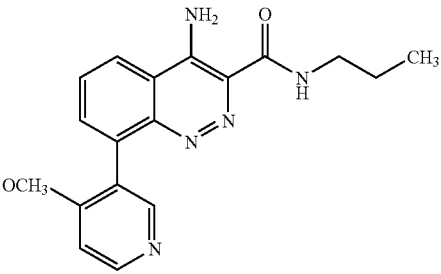 | 2.23E−09 | 0.18 | 0.29 |
| 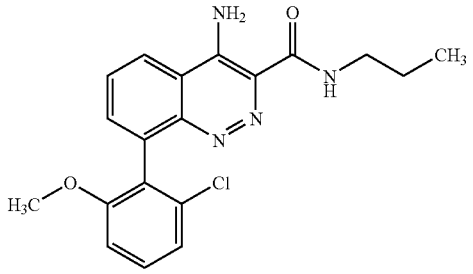 | 2.30E−09 | 0.004 | 0.063 |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| | 2.34E−09 | −0.11 | −0.033 |
| | 2.42E−09 | 0.12 | 0.16 |
| | 2.50E−09 | 0.18 | 0.15 |
| | 2.60E−09 | −0.11 | 0.054 |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| (structure) | 2.69E−09 | | |
| (structure) | 2.73E−09 | 0.19 | 0.29 |
| (structure) | 2.88E−09 | 0.1 | 0.16 |
| (structure) | 2.89E−09 | 0.47 | |

-continued
$$Ki = \frac{IC50}{1 + [ligand]/K_D}$$
| Compound | GABAA2 Binding Ki (M) | Relative Potentiation for GABAA1 | Relative Potentiation for GABAA2 |
|---|---|---|---|
| 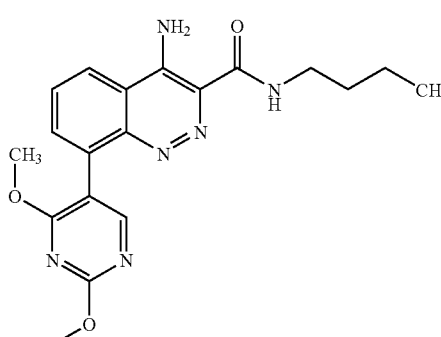 | 2.89E−09 | 0.16 | 0.45 |
| 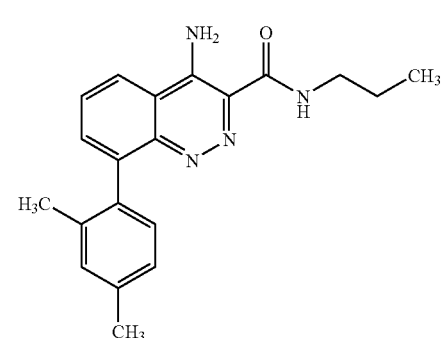 | 3.22E−09 | 0.28 | 0.11 |
| 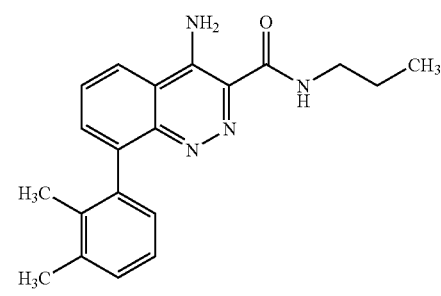 | 3.22E−09 | 0.0058 | 0.18 |
| 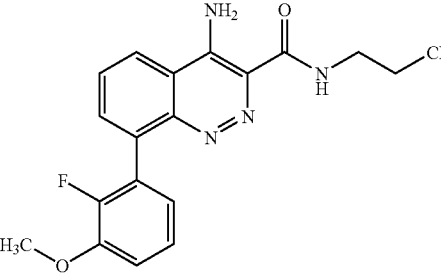 | 3.41E−09 | 0.045 | 0.26 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| | 3.44E−09 | 0.19 | −0.0075 |
| | 3.88E−09 | 0.33 | 0.28 |
| | 4.11E−09 | −0.16 | 0.14 |
| | 4.17E−09 | 0 | 0.12 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| (structure) | 4.21E-09 | 0.07 | 0.34 |
| (structure) | 4.34E-09 | 0.13 | 0.22 |
| (structure) | 4.34E-09 | 0.12 | 0.38 |
| (structure) | 4.36E-09 | -0.02 | 0.28 |
| (structure) | 5.00E-09 | 0.28 | 0.57 |

-continued
$$Ki = \frac{IC50}{1 + [\text{ligand}]/K_D}$$
| Compound | GABAA2 Binding Ki (M) | Relative Potentiation for GABAA1 | Relative Potentiation for GABAA2 |
|---|---|---|---|
| 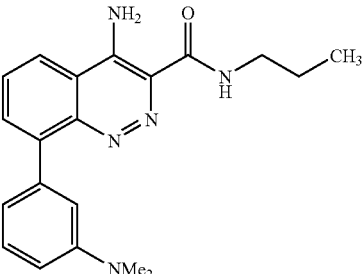 | 5.06E−09 | 0.17 | 0.19 |
| 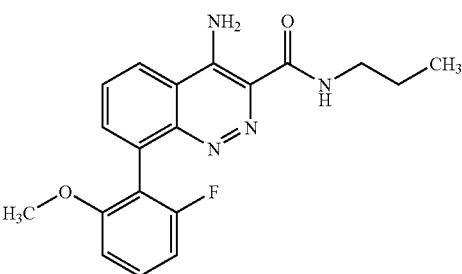<br>ISOMER 1 | 5.11E−09 | 0.09 | 0.16 |
| 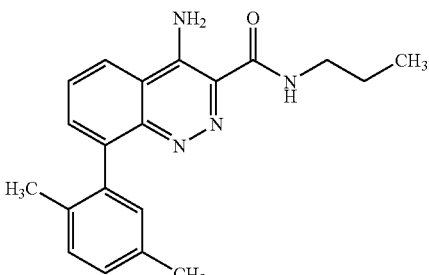 | 5.51E−09 | 0.28 | 0.38 |
| 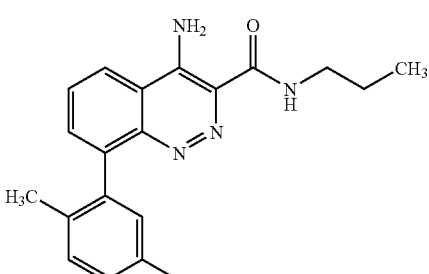 | 5.56E−09 | 0.02 | 0.22 |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| (4-amino-7-chloro-8-(2,4-dimethoxyphenyl)cinnoline-3-carboxamide, N-propyl) | 5.71E−09 | 0.87 | |
| (4-amino-7-fluoro-8-(2-methoxy-3,5-difluorophenyl)cinnoline-3-carboxamide, N-propyl) | 5.78E−09 | 0.1 | 0.14 |
| (4-amino-7-chloro-8-phenylcinnoline-3-carboxamide, N-propyl) | 5.82E−09 | 0.25 | 0.16 |
| (4-amino-8-(4-methoxy-2-methoxypyrimidin-5-yl)cinnoline-3-carboxamide, N-cyclopropyl) | 5.98E−09 | | |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| 4-amino-8-(2-methoxy-5-methylphenyl)-N-propylcinnoline-3-carboxamide | 6.13E−09 | 0.13 | 0.52 |
| 4-amino-8-(quinolin-6-yl)-N-propylcinnoline-3-carboxamide | 6.40E−09 | 0.1 | 0.23 |
| 4-amino-8-(2,3,4-trimethoxyphenyl)-N-propylcinnoline-3-carboxamide | 6.75E−09 | 0.47 | 0.33 |
| 4-amino-8-(1,3-dimethyl-1H-pyrazol-5-yl)-N-propylcinnoline-3-carboxamide | 7.24E−09 | 0.23 | 0.18 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| (structure) | 7.24E−09 | 0.17 | 0.23 |
| (structure) | 7.38E−09 | −0.063 | 0.1 |
| (structure) | 7.41E−09 | 0.1 | 0.22 |
| (structure) | 7.45E−09 | 0.098 | 0.54 |

| | | | |
|---|---|---|---|
| $$Ki = \frac{IC50}{1 + [ligand]/K_D}$$ | | | |
| Compound | GABAA2 Binding Ki (M) | Relative Potentiation for GABAA1 | Relative Potentiation for GABAA2 |
| 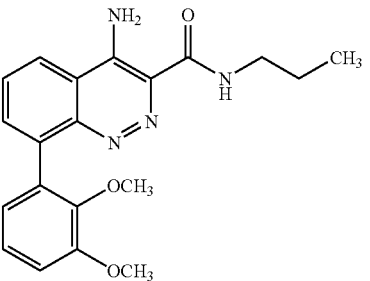 | 7.49E−09 | −0.065 | 0.013 |
| 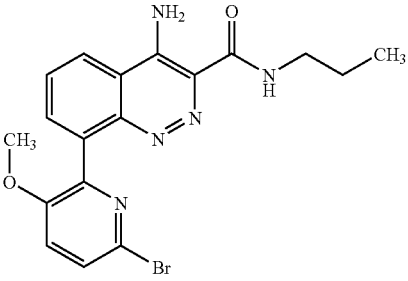 | 7.51E−09 | 0.34 | |
| 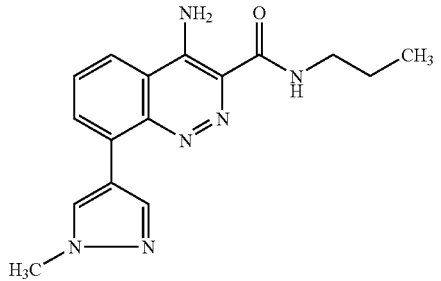 | 8.14E−09 | −0.16 | 0.16 |
| 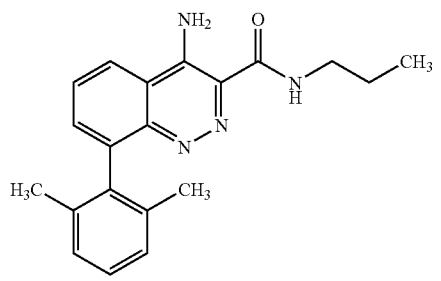 | 8.49E−09 | −0.26 | −0.004 |
| 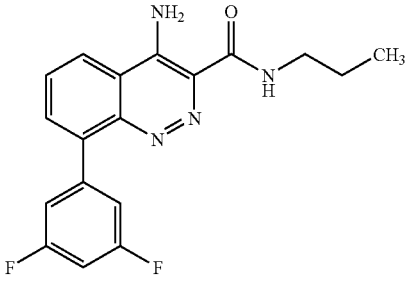 | 8.60E−09 | −0.018 | 0.26 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| (4-amino-7-fluoro-8-(4-chlorophenyl)cinnoline-3-carboxylic acid N-propylamide) | 8.72E-09 | 0.02 | 0.19 |
| (4-amino-8-(6-methoxypyridin-3-yl)cinnoline-3-carboxylic acid N-propylamide) | 8.77E-09 | −0.08 | 0.16 |
| (4-amino-8-(3,5-dimethylphenyl)cinnoline-3-carboxylic acid N-propylamide) | 8.84E-09 | 0.4 | 0.46 |
| (4-amino-8-(2,5-dimethoxyphenyl)cinnoline-3-carboxylic acid N-allylamide) | 8.91E-09 | 0.0075 | 0.33 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| (4-amino-8-(4-fluorophenyl)cinnoline-3-carboxamide, N-propyl) | 9.58E−09 | −0.046 | 0.08 |
| (4-amino-8-(3-methylsulfonylphenyl)cinnoline-3-carboxamide, N-propyl) | 1.04E−08 | 0.34 | 0.26 |
| (4-amino-8-(2-methoxy-5-fluorophenyl)cinnoline-3-carboxamide, N-propyl) | 1.05E−08 | 0.026 | 0.4 |
| (4-amino-8-(2-methoxy-5-methylphenyl)cinnoline-3-carboxamide, N-ethyl) | 1.05E−08 | 0.23 | |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| (structure: 4-amino-8-(3-fluoro-2-methoxyphenyl)cinnoline-3-carboxylic acid N-propyl amide) | 1.09E−08 | 0.11 | 0.11 |
| (structure: 4-amino-7-chloro-8-(2,5-dimethylphenyl)cinnoline-3-carboxylic acid N-propyl amide) | 1.12E−08 | 0.24 | 0.22 |
| (structure: 4-amino-8-(3-chlorophenyl)cinnoline-3-carboxylic acid N-propyl amide) | 1.23E−08 | 0.18 | 0.53 |
| (structure: 4-amino-8-(quinolin-3-yl)cinnoline-3-carboxylic acid N-propyl amide) | 1.23E−08 | −0.15 | 0.11 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| (structure) | 1.33E−08 | 0.32 | |
| (structure) | 1.39E−08 | 0.32 | |
| (structure) | 1.44E−08 | 0.005 | 0.35 |
| (structure) | 1.51E−08 | 0.14 | 0.33 |

-continued
$$Ki = \frac{IC50}{1 + [ligand]/K_D}$$
| Compound | GABAA2 Binding Ki (M) | Relative Potentiation for GABAA1 | Relative Potentiation for GABAA2 |
|---|---|---|---|
| 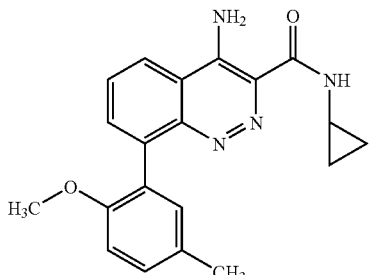 | 1.52E−08 | | |
| 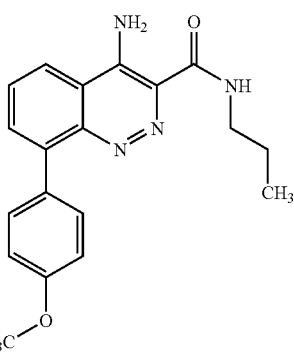 | 1.54E−08 | −0.11 | 0.06 |
| 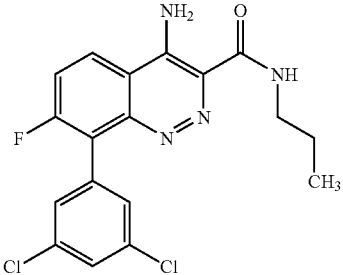 | 1.61E−08 | 0.36 | |
| 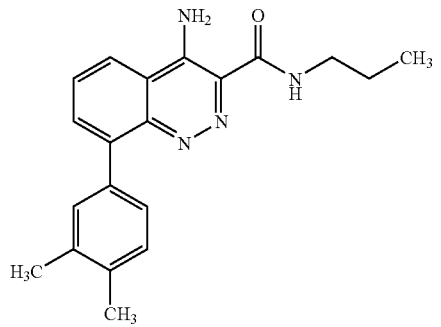 | 1.68E−08 | 0.23 | 0.35 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| | 1.76E−08 | 0.21 | 0.27 |
| | 1.84E−08 | 0.48 | |
| | 1.86E−08 | −0.26 | 0.038 |
| | 1.86E−08 | 0.11 | 0.24 |

-continued
$$Ki = \frac{IC50}{1 + [ligand]/K_D}$$
| Compound | GABAA2 Binding Ki (M) | Relative Potentiation for GABAA1 | Relative Potentiation for GABAA2 |
|---|---|---|---|
| 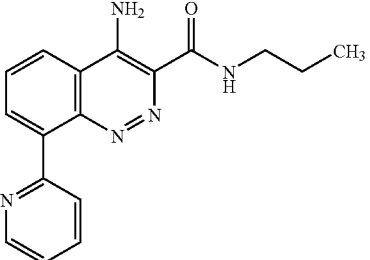 | 1.94E−08 | 0.027 | −0.032 |
| 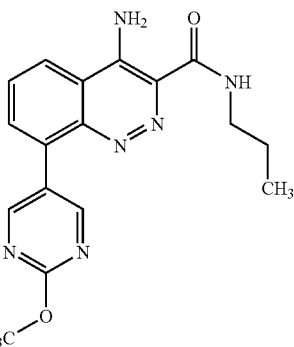 | 1.95E−08 | −0.066 | 0.11 |
| 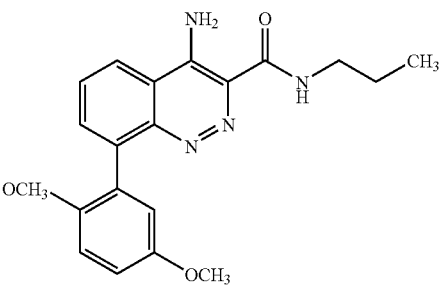 | 1.98E−08 | 0.087 | 0.45 |
| 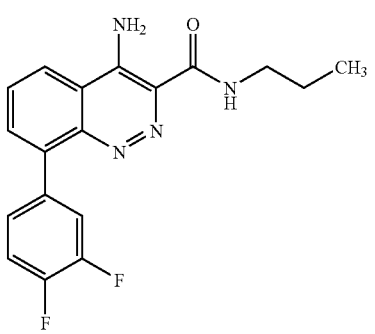 | 2.00E−08 | −0.14 | 0.12 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| 4-amino-8-(3-fluoro-4-methoxyphenyl)-N-propylcinnoline-3-carboxamide | 2.02E−08 | 0.03 | 0.19 |
| 4-amino-8-(pyrazin-2-yl)-N-propylcinnoline-3-carboxamide | 2.04E−08 | −0.067 | −0.01 |
| 4-amino-8-(3,5-dichlorophenyl)-N-propylcinnoline-3-carboxamide | 2.20E−08 | 0.28 | 0.48 |
| 4-amino-8-(5-fluoro-6-methoxypyridin-3-yl)-N-propylcinnoline-3-carboxamide | 2.21E−08 | −0.012 | 0.14 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| (structure: 4-amino-8-(5-chloro-6-methoxypyridin-3-yl)cinnoline-3-carboxylic acid N-propyl amide) | 2.54E−08 | 0.086 | 0.04 |
| (structure: 4-amino-8-(4-dimethylaminophenyl)cinnoline-3-carboxylic acid N-propyl amide) | 2.66E−08 | 0.07 | 0.18 |
| (structure: 4-amino-8-(4-methylphenyl)cinnoline-3-carboxylic acid N-propyl amide) | 2.90E−08 | 0.013 | 0.11 |
| (structure: 4-amino-8-(2,5-dimethoxyphenyl)cinnoline-3-carboxylic acid N-ethyl amide) | 2.98E−08 | 0.013 | 0.25 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| (4-amino-8-(1H-indol-5-yl)cinnoline-3-carboxylic acid propylamide) | 3.50E−08 | 0.15 | 0.16 |
| (4-amino-8-(2-methoxy-5-methylphenyl)cinnoline-3-carboxylic acid methylamide) | 3.58E−08 | 0.19 | 0.43 |
| (4-amino-8-(4-methoxy-3,5-dimethylphenyl)cinnoline-3-carboxylic acid propylamide) | 3.58E−08 | 0.79 | 0.32 |
| (4-amino-8-(4-chlorophenyl)cinnoline-3-carboxylic acid propylamide) | 3.72E−08 | −0.14 | 0.12 |

-continued
$$Ki = \frac{IC50}{1 + [ligand]/K_D}$$
| Compound | GABAA2 Binding Ki (M) | Relative Potentiation for GABAA1 | Relative Potentiation for GABAA2 |
|---|---|---|---|
| 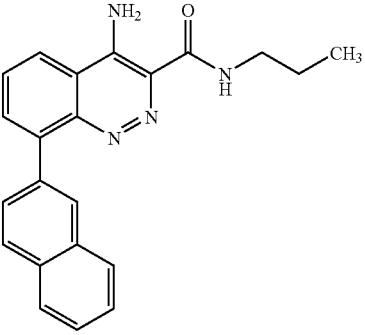 | 4.33E−08 | 0.22 | 0.09 |
| 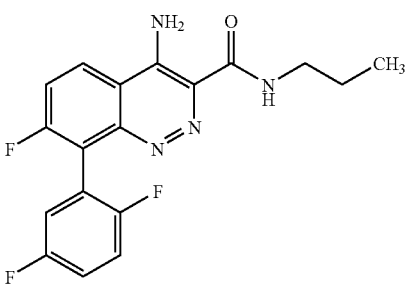 | 4.58E−08 | 0.013 | 0.098 |
| 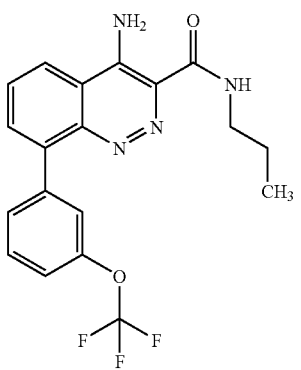 | 4.78E−08 | 0.87 | 0.48 |
| 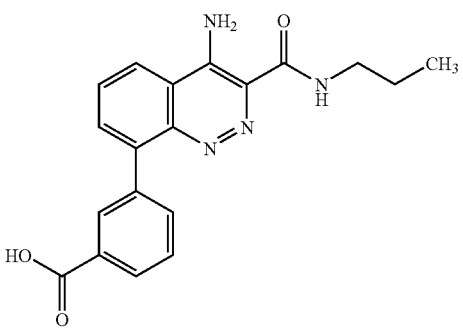 | 5.38E−08 | −0.038 | 0.08 |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| (4-amino-8-(3,4,5-trimethoxyphenyl)cinnoline-3-carboxylic acid N-propyl amide) | 5.65E−08 | 0.4 | 0.67 |
| (4-amino-7-methoxy-8-phenylcinnoline-3-carboxylic acid N-propyl amide) | 9.14E−08 | 0.12 | 0.08 |
| (4-amino-8-(2,5-dimethoxyphenyl)cinnoline-3-carboxylic acid N-(3,3,3-trifluoropropyl)amide) | 9.15E−08 | 0.13 | 0.26 |
| (4-amino-8-(2,5-dimethoxyphenyl)cinnoline-3-carboxylic acid N-(3-hydroxypropyl)amide) | 1.09E−07 | | |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| (4-amino-8-(4-(trifluoromethoxy)phenyl)cinnoline-3-carboxylic acid propylamide) | 1.15E−07 | 0.32 | 0.04 |
| (4-amino-8-(2,5-dimethoxyphenyl)cinnoline-3-carboxylic acid methylamide) | 1.29E−07 | 0.15 | 0.33 |
| (4-amino-8-(2'-cyano-4',6-difluorobiphenyl-3-yl)cinnoline-3-carboxylic acid propylamide) | 1.50E−07 | 0.09 | 0.023 |
| (4-amino-8-(3,5-bis(trifluoromethyl)phenyl)cinnoline-3-carboxylic acid propylamide) | 3.56E−07 | 0.44 | 0.13 |

-continued
$$Ki = \frac{IC50}{1 + [ligand]/K_D}$$
| Compound | GABAA2 Binding Ki (M) | Relative Potentiation for GABAA1 | Relative Potentiation for GABAA2 |
|---|---|---|---|
| 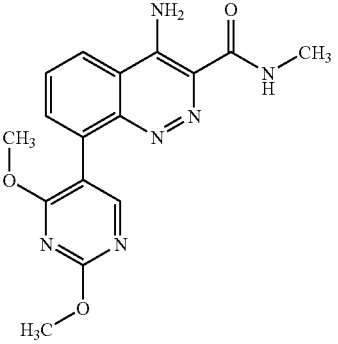 | 5.14E−07 | | |
| 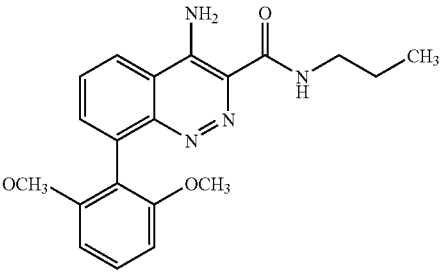 | 6.24E−07 | | |
| 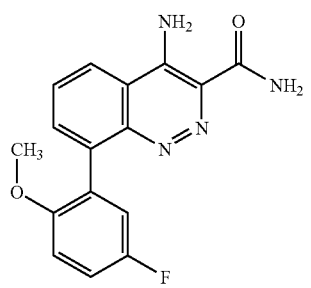 | 5.50E−06 | | |
| 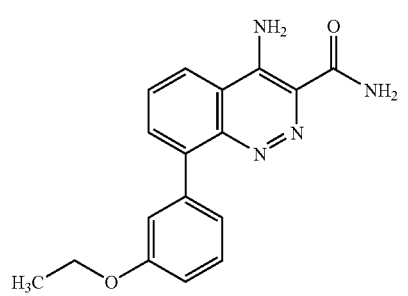 | 5.50E−06 | | |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| (structure) | 5.50E−06 | | |
| (structure) | 5.50E−06 | | |
| (structure) | 5.50E−06 | | |
| (structure) | 5.50E−06 | | |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| 4-amino-8-(3-methoxyphenyl)cinnoline-3-carboxamide | 5.50E−06 | | |
| 4-amino-8-(2-methylphenyl)cinnoline-3-carboxamide | 5.50E−06 | | |
| 4-amino-8-(pyridin-3-yl)cinnoline-3-carboxamide | 5.50E−06 | | |
| 4-amino-8-(4-formylphenyl)cinnoline-3-carboxamide | 5.50E−06 | | |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| 4-amino-8-(2,6-dimethylphenyl)cinnoline-3-carboxamide | 5.50E−06 | | |
| 4-amino-8-(3-acetamidophenyl)cinnoline-3-carboxamide | 5.50E−06 | | |
| 4-amino-8-(5-chloro-2-methoxyphenyl)cinnoline-3-carboxamide | 5.50E−06 | | |
| 4-amino-8-(naphthalen-2-yl)cinnoline-3-carboxamide | 5.50E−06 | | |

-continued $$Ki = \frac{IC50}{1 + [\text{ligand}]/K_D}$$

| Compound | GABAA2 Binding Ki (M) | Relative Potentiation for GABAA1 | Relative Potentiation for GABAA2 |
|---|---|---|---|
| (4-amino-8-(5-fluoro-6-methoxypyridin-3-yl)cinnoline-3-carboxylic acid ethylamide) | 9.00E−09 | −0.010 | 0.223 |
| (4-amino-8-(2-chloro-6-methoxyphenyl)cinnoline-3-carboxylic acid propylamide) ISOMER 2 | 3.00E−10 | −0.040 | 0.119 |
| (4-amino-8-(5-fluoro-2-methoxyphenyl)cinnoline-3-carboxylic acid cyclopropylamide) | 8.22E−09 | −0.028 | 0.357 |
| (4-amino-8-(4-methoxypyridin-3-yl)cinnoline-3-carboxylic acid cyclopropylamide) | 7.85E−10 | 0.077 | 0.337 |

-continued $$Ki = \frac{IC50}{1 + [ligand]/K_D}$$

| Compound | GABAA2 Binding Ki (M) | Relative Potentiation for GABAA1 | Relative Potentiation for GABAA2 |
|---|---|---|---|
| 4-amino-8-(2-methoxypyridin-3-yl)-N-cyclopropylcinnoline-3-carboxamide | 5.01E−10 | −0.054 | 0.247 |
| 4-amino-8-(2,4-dimethoxyphenyl)-N-cyclobutylcinnoline-3-carboxamide | 9.27E−10 | 0.091 | 0.243 |
| 4-amino-8-(6-methylpyridin-3-yl)-N-cyclopropylcinnoline-3-carboxamide | 4.02E−09 | −0.166 | 0.074 |
| 4-amino-8-(2,4-dimethoxyphenyl)-N-ethylcinnoline-3-carboxamide | 4.54E−09 | −0.006 | 0.104 |

Method II

MT1 GTPγ³⁵S-SPA Assay

Test Validation Standards

2-Iodomelatonin and 6-Chloromelatonin with known activities were used as validation standard during the assay development. The EC50 of 2-Iodomelatonin and 6-Chloromelatonin were ~3E-11 M and ~1.5E-10 M respectively in GTPγS assay of hMT1 recombinant cell membranes.

Cells and/or Microorganisms

HEK293F (human embryonic kidney 293 floating cell line) was suspension cultured in Free Style 293 Expression Medium, and expanded in house and stored in liquid nitrogen in cell freezing medium.

Buffers, Solutions, Cell Media

| Lazareno GTPγS Assay Buffer: | | Make 2 Liters Buffer |
|---|---|---|
| 20 mM HEPES | Sigma H-4034, FW 238.3 | 9.532 g |
| 100 mM NaCl | Sigma S-9625, FW 58.44 | 11.688 g |
| 10 mM MgCl$_2$•6H$_2$O | Sigma M-2670, FW 203.3 | 4.066 g |
| pH 7.4 | | Adjust with NaOH |

| Membrane Prepration Buffer: | | Make 2 Liters Buffer |
|---|---|---|
| 20 mM HEPES | Sigma H-4034, FW 238.3 | 9.532 g |
| 3 mM MgCl$_2$•6H$_2$O | Sigma M-2670, FW 203.3 | 1.220 g |
| 1 mM EGTA | Sigma E-3889, FW 380.4 | 0.761 g |
| pH 7.4 | | Adjust with NaOH |

Test Compound Preparation

Test compounds were synthesized in house. Solid compounds were solubilized at 10 mM in DMSO; then 1:3 further diluted in DMSO in 96-well U-bottom plates using Plate Mate on the assay day. 2 μl of diluted compounds were transferred to Optic-assay-plates.

Reference Compounds Preparation

Reference compound, 2-Iodomelatonin, was prepared the way same as test compound.

Compounds Used to Normalize Experimental Results

2-Iodomelatonin for normalization was diluted in DMSO at concentration 50×3 nM (its EC100 concentration=3 nM). 2 μl of 150 nM 2-Iodomelatonin was then transferred to Optic-assay-plates.

Cell Lines and Microorganisms

HEK293F (human embryonic kidney 293 floating cell line) cells transiently expressed human Melatonin receptor 1 (MT1) were harvested 48 hours post-transfection. The cell pellets were homogenized using Polytron; and the cell membranes were prepared fro GTPYS assay.

Preparation of Protein/Membranes Containing Target

The cell pellets were homogenized with Polytron in ice-cold buffer: 20 mM HEPES, 3 mM MgCl2, 1 mM EGTA, pH7.4. (Freshly add protease inhibitor cocktail tables from Roche). The samples were centrifuged at 18,500 rpm for 30 mins at 4° C. in Sorvall SS-34 rotor. The membrane pellets were collected and washed with the ice-cold buffer. The samples were centrifuged at 18,500 rpm for 30 mins at 4° C. again. The membranes were resuspended in the ice-cold buffer with protease inhibitors. The protein concentration of the membrane was determined. The membranes were aliquoted and stored at −80° C.

Test Method

Plate format (if plates are used, as shown in the following table)

*Numbers denote "Compound #, Dilution #, Replicate #"
*Plate direction moves from highest concentration to lowest concentration Number of compounds per plate: 8
Number of replicates per compound: 1
Number of dilutions per compound: 11
Test Plate: DR96_02_C12[LR.1]

| | 1 | 2 | 3 | 4 | 5 | 6 | 7 | 8 | 9 | 10 | 11 | 12 |
|---|---|---|---|---|---|---|---|---|---|---|---|---|
| A | 1, 1, 1 | 1, 2, 1 | 1, 3, 1 | 1, 4, 1 | 1, 5, 1 | 1, 6, 1 | 1, 7, 1 | 1, 8, 1 | 1, 9, 1 | 1, 10, 1 | 1, 11, 1 | MAX |
| B | 2, 1, 1 | 2, 2, 1 | 2, 3, 1 | 2, 4, 1 | 2, 5, 1 | 2, 6, 1 | 2, 7, 1 | 2, 8, 1 | 2, 9, 1 | 2, 10, 1 | 2, 11, 1 | MAX |
| C | 3, 1, 1 | 3, 2, 1 | 3, 3, 1 | 3, 4, 1 | 3, 5, 1 | 3, 6, 1 | 3, 7, 1 | 3, 8, 1 | 3, 9, 1 | 3, 10, 1 | 3, 11, 1 | MAX |
| D | 4, 1, 1 | 4, 2, 1 | 4, 3, 1 | 4, 4, 1 | 4, 5, 1 | 4, 6, 1 | 4, 7, 1 | 4, 8, 1 | 4, 9, 1 | 4, 10, 1 | 4, 11, 1 | MAX |
| E | 5, 1, 1 | 5, 2, 1 | 5, 3, 1 | 5, 4, 1 | 5, 5, 1 | 5, 6, 1 | 5, 7, 1 | 5, 8, 1 | 5, 9, 1 | 5, 10, 1 | 5, 11, 1 | MIN |
| F | 6, 1, 1 | 6, 2, 1 | 6, 3, 1 | 6, 4, 1 | 6, 5, 1 | 6, 6, 1 | 6, 7, 1 | 6, 8, 1 | 6, 9, 1 | 6, 10, 1 | 6, 11, 1 | MIN |
| G | 7, 1, 1 | 7, 2, 1 | 7, 3, 1 | 7, 4, 1 | 7, 5, 1 | 7, 6, 1 | 7, 7, 1 | 7, 8, 1 | 7, 9, 1 | 7, 10, 1 | 7, 11, 1 | MIN |
| H | 8, 1, 1 | 8, 2, 1 | 8, 3, 1 | 8, 4, 1 | 8, 5, 1 | 8, 6, 1 | 8, 7, 1 | 8, 8, 1 | 8, 9, 1 | 8, 10, 1 | 8, 11, 1 | MIN |

MAX response (100% effect) was determined as the effect of 3 nM of 2-Iodomelatonin.

MIN response (0% effect) was determined as the effect of vehicle control.

Description of Experimental Procedure

Human MT1/HEK293F membrane (10 μg/well) was mixed with WGA-SPA beads (300 μg/well) and GDP (10 μM) in certain volume of Lazareno assay buffer (20 mM HEPES, 100 mM NaCl, 10 mM MgCl2, pH7.4). The membrane combo was kept on ice for 30-60 mins. Test compounds were 1:3 diluted in DMSO from 10 mM stock, and transferred 2 μl of diluted compounds to Opti assay plates-96 using PlateMate. GTPγ³⁵S was added to the membrane mixture prior to dispensing 100 μl the membrane combo to the assay plates-96. The final concentration of GTPγ³⁵S was 200 pM. The assay plates were shaking on a plate shaker for 1.5 hours at room temperature. The assay plates were spun at 2000 rpm for 5 mins in bench top centrifuge. The assay plates were measured in TopCount to capture the data within 4 hours.

Summary of the Different Experimental Conditions (the Role of Various Results Types) Final Concentrations of the Constituents

| | |
|---|---|
| 10 µg/well | hMT1/HEK293F membranes |
| 300 µg/well | WGA-SPA beads |
| 10 µM | GDP |
| 200 pM | GTPγ$^{35}$S |
| 10 µM | Start concentration of test compound |
| 2% | DMSO |
| 20 mM | HEPES |
| 100 mM | NaCl |
| 10 mM | MgCl$_2$ |
| pH7.4 | |

Treatments Used in Different Experimental Conditions

The test compounds would be heated to 65° C. if they were not soluble at 10 mM in DMSO. The start concentration in general was 10 µM, but could be adjusted based on its potency. Every single batch of membranes had to be validated for its optimal assay conditions, such as, define the optimal GDP concentration, SPA beads amount and EC100 concentration of normalization compound.

Calculation of Results

Compounds were evaluated for their agonist potency (EC50) and efficacy (Emax). Concentration-response curves were analyzed to determine the EC50 by ActivityBase using equation model #205. Compound's % activity was calculated according to the 100% and 0% activities defined on the same plate as the sample data. Wells A12-C12 were used to define 100% activity, and D12-G12 for 0% activity. More details could be found from the Plate Format above.

Results (Dependent Variables, Dependent Measurements) and Their Calculation Method The raw values for the replicates in the Minimum Control experimental condition were averaged. The raw values for the replicates in the Maximum Control experimental condition were averaged. The average Minimum Control was subtracted from the average Maximum Control resulting in the Data Window. The average for the Minimum Control was subtracted from each raw value in the Compound Data experimental condition resulting in the Specific Response for each data value in the Compound Data condition. Each Specific Response in the Compound Data condition was divided by the Data Window then multiplied by 100 resulting in the Percent Response. The EC50 and SlopeFactor were determined by fitting the Percent Inhibition and the concentrations of test compound to model 205 in XLfit—$y=A+((B-A)/(1+((C/x)^D))$—with parameter A constrained to 0 and parameter B constrained to 100.

Certain compounds of the invention have been tested using the above-identified assay (Method II). The results are shown in the following table.

| | MT1 Receptor | | | |
|---|---|---|---|---|
| | Binding | | GTPgS | |
| | % Inhibition at 1 µM | Ki (M) | EC50 (M) | Emax |
| 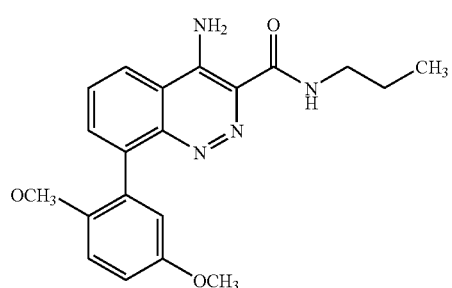 | 86 | 6.00E−08 | 3.75E−08 | 100 |
| 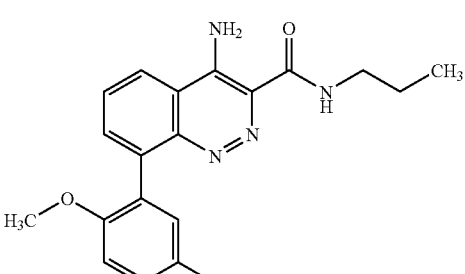 | 96 | 5.60E−08 | 5.60E−08 | 61 |

| | MT1 Receptor | | | |
|---|---|---|---|---|
| | Binding | | GTPgS | |
| | % Inhibition at 1 μM | Ki (M) | EC50 (M) | Emax |
| 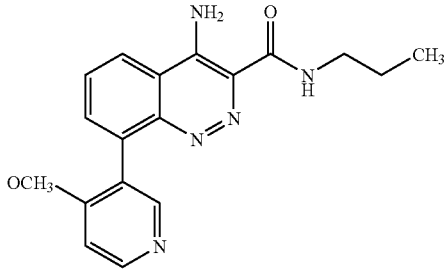 | 82 | 9.20E−08 | 9.20E−08 | 64 |
| 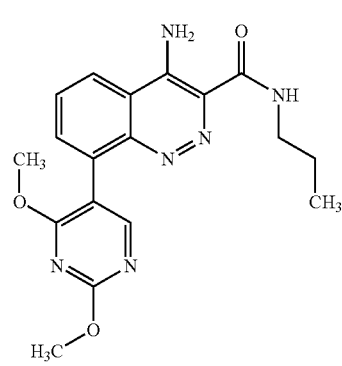 | 93 | 2.76E−07 | 2.76E−07 | 70 |
| 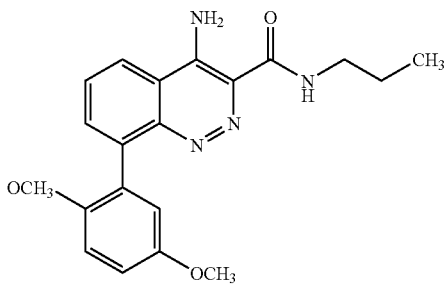 | 91 | 3.6E−08 | 2.67E−08 | 61 |
| 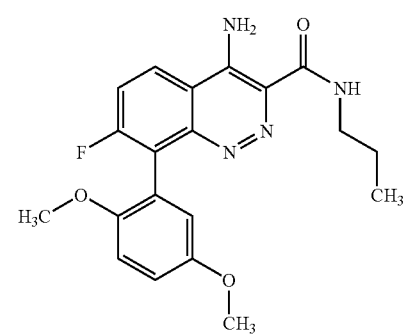 | 93 | 3.1E−08 | 2.36E−08 | 64 |

| | MT1 Receptor | | | |
|---|---|---|---|---|
| | Binding | | GTPgS | |
| | % Inhibition at 1 μM | Ki (M) | EC50 (M) | Emax |
| [structure: 4-amino-8-(2-fluoro-6-methoxyphenyl)-N-propylcinnoline-3-carboxamide] | 89 | 4.9E−08 | 3.43E−08 | 60 |
| [structure: 4-amino-8-(2,4-dimethoxyphenyl)-7-fluoro-N-propylcinnoline-3-carboxamide] | 88 | 9.0E−08 | 1.55E−08 | 54 |

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, and the like) cited in the present application is incorporated herein by reference in its entirety.

What is claimed is:

1. A compound selected from:

4-amino-8-(3,5-dimethyl-1H-pyrazol-4-yl)-N-propylcinnoline-3-carboxamide;
4-amino-8-(3,5-difluoro-2-methoxyphenyl)-N-propylcinnoline-3-carboxamide;
4-amino-8-[5-(azetidin-1-ylcarbonyl)-2-methoxyphenyl]-N-propylcinnoline-3-carboxamide;
4-amino-8-(6-methoxy-2-methylpyridin-3-yl)-N-propylcinnoline-3-carboxamide;
4-amino-N-propyl-8-(1,3,5-trimethyl-1H-pyrazol-4-yl)cinnoline-3-carboxamide;
4-amino-N-propyl-8-(2,4,6-trifluoro-3-methoxyphenyl)cinnoline-3-carboxamide;
4-amino-8-(2-fluoro-5-methylpyridin-3-yl)-N-propylcinnoline-3-carboxamide;
4-amino-8-(1,3-dimethyl-1H-pyrazol-5-yl)-N-propylcinnoline-3-carboxamide;
4-amino-8-(2-fluoro-4,6-dimethoxyphenyl)-N-propylcinnoline-3-carboxamide;
4-amino-8-(3,5-difluoro-2-methoxyphenyl)-N-propylcinnoline-3-carboxamide;
4-amino-8-(2,3-dihydro-1,4-benzodioxin-6-yl)-N-propylcinnoline-3-carboxamide;
4-amino-8-(4,5-difluoro-2-methoxyphenyl)-N-propylcinnoline-3-carboxamide;
4-amino-8-(1,3-benzodioxol-4-yl)-N-propylcinnoline-3-carboxamide;
4-amino-8-[5-(azetidin-1-ylcarbonyl)-2-methylphenyl]-N-propylcinnoline-3-carboxamide;
4-amino-8-(6-methoxy-4-methylpyridin-3-yl)-N-propylcinnoline-3-carboxamide;
4-amino-7-chloro-8-(4-methoxypyridin-3-yl)-N-propylcinnoline-3-carboxamide;
4-amino-7-fluoro-8-(4-methoxypyridin-3-yl)-N-propylcinnoline-3-carboxamide;
4-amino-7-chloro-8-(2-methoxy-5-methylphenyl)-N-propylcinnoline-3-carboxamide;
4-amino-7-fluoro-8-(2-methoxy-5-methylphenyl)-N-propylcinnoline-3-carboxamide;
4-amino-8-(2,5-dimethoxyphenyl)-7-chloro-N-propylcinnoline-3-carboxamide;
4-amino-8-(2,4-dimethoxypyrimidin-5-yl)-7-chloro-N-propylcinnoline-3-carboxamide;
4-amino-N-butyl-8-(4-methoxypyridin-3-yl)cinnoline-3-carboxamide;
4-amino-8-(4-methoxypyridin-3-yl)-N-methylcinnoline-3-carboxamide;
4-amino-N-butyl-8-(2-methoxy-5-methylphenyl)cinnoline-3-carboxamide;
4-amino-N-ethyl-8-(2-methoxy-5-methylphenyl)cinnoline-3-carboxamide;

4-amino-8-(2-methoxy-5-methylphenyl)-N-methylcinnoline-3-carboxamide;
4-amino-8-(2,4-dimethoxypyrimidin-5-yl)-N-methylcinnoline-3-carboxamide;
4-amino-8-(4-methoxypyridin-3-yl)-N-(tetrahydrofuran-2-ylmethyl)cinnoline-3-carboxamide;
4-amino-N-isobutyl-8-(4-methoxypyridin-3-yl)cinnoline-3-carboxamide;
4-amino-N-(2-hydroxypropyl)-8-(4-methoxypyridin-3-yl)cinnoline-3-carboxamide;
4-amino-8-(2-methoxy-5-methylphenyl)-N-(tetrahydrofuran-2-ylmethyl)cinnoline-3-carboxamide;
4-amino-N-isobutyl-8-(2-methoxy-5-methylphenyl)cinnoline-3-carboxamide;
4-amino-N-(2-hydroxypropyl)-8-(2-methoxy-5-methylphenyl)cinnoline-3-carboxamide;
4-amino-8-(2,5-dimethoxyphenyl)-N-(tetrahydrofuran-2-ylmethyl)cinnoline-3-carboxamide;
4-amino-8-(2,5-dimethoxyphenyl)-N-isobutylcinnoline-3-carboxamide;
4-amino-8-(2,5-dimethoxyphenyl)-N-(2-hydroxypropyl)cinnoline-3-carboxamide;
4-amino-8-(2,4-dimethoxypyrimidin-5-yl)-N-(tetrahydrofuran-2-ylmethyl)cinnoline-3-carboxamide;
4-amino-8-(2,4-dimethoxypyrimidin-5-yl)-N-isobutyl-cinnoline-3-carboxamide;
4-amino-8-(2,4-dimethoxypyrimidin-5-yl)-N-(2-hydroxypropyl)cinnoline-3-carboxamide;
and a pharmaceutically acceptable salt thereof.

2. A compound selected from:
4-amino-8-(2,3-dimethylphenyl)-N-propyl-cinnoline-3-carboxamide;
4-amino-8-(3,5-dimethylphenyl)-N-propyl-cinnoline-3-carboxamide;
4-amino-8-(2,4-dimethylphenyl)-N-propyl-cinnoline-3-carboxamide;
4-amino-8-(3,4-dimethylphenyl)-N-propyl-cinnoline-3-carboxamide;
4-amino-N-propyl-8-(p-tolyl)cinnoline-3-carboxamide;
4-amino-8-(3-chlorophenyl)-N-propyl-cinnoline-3-carboxamide;
4-amino-8-(4-chlorophenyl)-N-propyl-cinnoline-3-carboxamide;
4-amino-8-(o-tolyl)-N-propyl-cinnoline-3-carboxamide;
4-amino-N-propyl-8-(3-thienyl)cinnoline-3-carboxamide;
4-amino-8-(2,6-dimethylphenyl)-N-propyl-cinnoline-3-carboxamide;
and a pharmaceutically acceptable salt thereof.

3. (4-amino-8-(2,5-dimethoxyphenyl)-N-propyl-cinnoline-3-carboxamide) or a pharmaceutically acceptable salt thereof.

4. A compound selected from:
4-amino-N-cyclobutyl-7-fluoro-8-(2-methoxy-5-methylphenyl)cinnoline-3-carboxamide;
4-amino-N-cyclobutyl-7-fluoro-8-(5-fluoro-2-methoxyphenyl)cinnoline-3-carboxamide;
4-amino-N-cyclobutyl-7-fluoro-8-(2-fluoro-6-methoxyphenyl)cinnoline-3-carboxamide;
4-amino-N-cyclobutyl-7-fluoro-8-(2-fluoro-3-methoxyphenyl)cinnoline-3-carboxamide;
4-amino-N-cyclobutyl-8-(2,4-dimethoxyphenyl)-7-fluoro-cinnoline-3-carboxamide;
4-amino-N-cyclobutyl-7-fluoro-8-(4-methoxypyridin-3-yl)cinnoline-3-carboxamide;
4-amino-N-cyclobutyl-8-(2,4-dimethoxypyrimidin-5-yl)-7-fluoro-cinnoline-3-carboxamide;
4-amino-N-cyclobutyl-8-(2,6-dimethoxypyridin-3-yl)-7-fluoro-cinnoline-3-carboxamide;
4-amino-N-cyclobutyl-7-fluoro-8-(6-methylpyridin-3-yl)cinnoline-3-carboxamide;
4-amino-N-cyclobutyl-7-fluoro-8-(2-methoxypyridin-3-yl)cinnoline-3-carboxamide;
4-amino-N-cyclobutyl-8-(3,5-dimethylphenyl)-7-fluoro-cinnoline-3-carboxamide;
4-amino-N-cyclobutyl-8-(2,5-difluorophenyl)-7-fluoro-cinnoline-3-carboxamide;
4-amino-N-cyclobutyl-7-fluoro-8-(3-methylphenyl)cinnoline-3-carboxamide;
4-amino-N-cyclobutyl-8-(2,3-dimethoxyphenyl)-7-fluoro-cinnoline-3-carboxamide;
4-amino-N-cyclobutyl-7-fluoro-8-(2-methoxyphenyl)cinnoline-3-carboxamide;
4-amino-N-cyclobutyl-8-(2-methoxy-5-methyl-phenyl)cinnoline-3-carboxamide;
4-amino-N-cyclobutyl-8-(5-fluoro-2-methoxy-phenyl)cinnoline-3-carboxamide;
4-amino-N-cyclobutyl-8-(2-fluoro-3-methoxy-phenyl)cinnoline-3-carboxamide;
4-amino-N-cyclobutyl-8-(4-methoxypyridin-3-yl)cinnoline-3-carboxamide;
4-amino-N-cyclobutyl-8-(2,4-dimethoxypyrimidin-5-yl)cinnoline-3-carboxamide;
4-amino-N-cyclobutyl-8-(2,6-dimethoxypyridin-3-yl)cinnoline-3-carboxamide;
4-amino-N-cyclobutyl-8-(6-methylpyridin-3-yl)cinnoline-3-carboxamide;
4-amino-N-cyclobutyl-8-(2-methoxypyridin-3-yl)cinnoline-3-carboxamide;
4-amino-N-cyclobutyl-8-(3,5-dimethylphenyl)cinnoline-3-carboxamide;
4-amino-N-cyclobutyl-8-(2,5-difluorophenyl)cinnoline-3-carboxamide;
4-amino-N-cyclobutyl-8-(3-methylphenyl)cinnoline-3-carboxamide;
4-amino-N-cyclobutyl-8-(2,3-dimethoxyphenyl)cinnoline-3-carboxamide;
4-amino-N-cyclobutyl-8-(2-methoxyphenyl)cinnoline-3-carboxamide;
4-amino-N-cyclobutyl-8-(4-methylpyridin-3-yl)cinnoline-3-carboxamide;
4-amino-N-cyclobutyl-8-(2,3,4-trimethoxyphenyl)cinnoline-3-carboxamide;
4-amino-8-(4-chlorophenyl)-N-cyclobutyl-cinnoline-3-carboxamide;
4-amino-N-cyclobutyl-8-(3,4-dimethoxyphenyl)cinnoline-3-carboxamide;
4-amino-N-cyclopropyl-8-(2-fluoro-6-methyl-pyridin-3-yl)cinnoline-3-carboxamide;
4-amino-N-cyclopropyl-7-fluoro-8-(5-fluoro-6-methoxypyridin-3-yl)cinnoline-3-carboxamide;
4-amino-N-cyclopropyl-7-fluoro-8-(2-methoxypyridin-3-yl)cinnoline-3-carboxamide;
4-amino-N-cyclopropyl-8-(4-methylpyridin-3-yl)cinnoline-3-carboxamide;
4-amino-N-cyclopropyl-7-fluoro-8-(4-methylpyridin-3-yl)cinnoline-3-carboxamide;
4-amino-N-cyclopropyl-8-(2,6-dimethoxypyridin-3-yl)-7-fluoro-cinnoline-3-carboxamide;
4-amino-N-cyclopropyl-7-fluoro-8-(6-methylpyridin-3-yl)cinnoline-3-carboxamide;
4-amino-N-cyclopropyl-8-(2,4-dimethoxypyrimidin-5-yl)-7-fluoro-cinnoline-3-carboxamide;

4-amino-N-cyclopropyl-8-(2,5-dimethoxyphenyl)-7-fluoro-cinnoline-3-carboxamide;
4-amino-N-cyclopropyl-7-fluoro-8-(5-fluoro-2-methoxy-phenyl)cinnoline-3-carboxamide;
4-amino-N-cyclopropyl-7-fluoro-8-(2-fluoro-6-methoxy-phenyl)cinnoline-3-carboxamide;
4-amino-N-cyclopropyl-7-fluoro-8-(2-methoxy-5-methyl-phenyl)cinnoline-3-carboxamide;
4-amino-N-cyclopropyl-8-(2,4-dimethoxyphenyl)-7-fluoro-cinnoline-3-carboxamide;
4-amino-8-(2,4-dimethoxyphenyl)-N-ethyl-7-fluoro-cinnoline-3-carboxamide;
4-amino-N-ethyl-8-(2-fluoro-3-methoxy-phenyl)cinnoline-3-carboxamide;
4-amino-N-ethyl-8-(2-methoxypyridin-3-yl)cinnoline-3-carboxamide;
4-amino-N-ethyl-8-(6-methylpyridin-3-yl)cinnoline-3-carboxamide;
4-amino-N-ethyl-8-(5-fluoro-6-methoxy-pyridin-3-yl)cinnoline-3-carboxamide;
4-amino-N-cyclopropyl-8-(5-fluoro-2-methoxy-phenyl)cinnoline-3-carboxamide;
4-amino-N-cyclopropyl-8-(4-methoxypyridin-3-yl)cinnoline-3-carboxamide;
4-amino-N-cyclopropyl-8-(2-methoxypyridin-3-yl)cinnoline-3-carboxamide;
4-amino-N-cyclobutyl-8-(2-methoxy-5-methyl-phenyl)cinnoline-3-carboxamide;
4-amino-N-cyclobutyl-8-(2,4-dimethoxyphenyl)cinnoline-3-carboxamide;
4-amino-8-(2,6-dimethoxypyridin-3-yl)-N-ethyl-cinnoline-3-carboxamide;
4-amino-N-cyclopropyl-8-(5-fluoro-6-methoxy-pyridin-3-yl)cinnoline-3-carboxamide;
4-amino-N-cyclopropyl-8-(2-fluoro-3-methoxy-phenyl)cinnoline-3-carboxamide;
4-amino-N-cyclopropyl-8-(6-methylpyridin-3-yl)cinnoline-3-carboxamide;
4-amino-N-ethyl-8-(5-fluoro-2-methoxy-phenyl)cinnoline-3-carboxamide;
4-amino-8-(2,4-dimethoxyphenyl)-N-ethyl-cinnoline-3-carboxamide;
4-amino-N-cyclopropyl-7-fluoro-8-(2-fluoro-3-methoxyphenyl)cinnoline-3-carboxamide;
4-amino-8-(2,4-dimethoxypyrimidin-5-yl)-N-ethyl-7-fluoro-cinnoline-3-carboxamide;
4-amino-N-ethyl-8-(4-methylpyridin-3-yl)cinnoline-3-carboxamide;
4-amino-N-ethyl-7-fluoro-8-(2-fluoro-6-methoxy-phenyl)cinnoline-3-carboxamide;
4-amino-8-(2,6-dimethoxypyridin-3-yl)-N-ethyl-7-fluoro-cinnoline-3-carboxamide;
4-amino-N-ethyl-7-fluoro-8-(5-fluoro-2-methoxy-phenyl)cinnoline-3-carboxamide;
4-amino-N-ethyl-7-fluoro-8-(5-fluoro-6-methoxy-pyridin-3-yl)cinnoline-3-carboxamide;
4-amino-N-ethyl-7-fluoro-8-(6-methylpyridin-3-yl)cinnoline-3-carboxamide;
4-amino-N-ethyl-7-fluoro-8-(2-methoxypyridin-3-yl)cinnoline-3-carboxamide;
4-amino-N-ethyl-7-fluoro-8-(2-fluoro-3-methoxy-phenyl)cinnoline-3-carboxamide;
4-amino-8-(2,5-dimethoxyphenyl)-N-ethyl-7-fluoro-cinnoline-3-carboxamide;
and a pharmaceutically acceptable salt thereof.

5. A pharmaceutical composition comprising a compound of claim 3 and a pharmaceutically acceptable carrier, diluent or excipent.

* * * * *